United States Patent
Inoue et al.

(10) Patent No.: US 9,184,398 B2
(45) Date of Patent: Nov. 10, 2015

(54) LIGHT-EMITTING ELEMENTS COMPRISING IRIDIUM ORGANOMETALLIC COMPLEXES COMPRISING 4-ARYLPYRIMIDINES

(71) Applicant: Semiconductor Energy Laboratory Co., Ltd., Kanagawa-ken (JP)

(72) Inventors: Hideko Inoue, Kanagawa (JP); Tomoya Yamaguchi, Kanagawa (JP); Satoko Shitagaki, Kanagawa (JP); Takahiro Ushikubo, Kanagawa (JP); Satoshi Seo, Kanagawa (JP); Yui Yamada, Kanagawa (JP); Hiromi Nowatari, Kanagawa (JP)

(73) Assignee: Semiconductor Energy Laboratory Co., Ltd. (JP)

( * ) Notice: Subject to any disclaimer, the term of this patent is extended or adjusted under 35 U.S.C. 154(b) by 0 days.

(21) Appl. No.: 14/584,362

(22) Filed: Dec. 29, 2014

(65) Prior Publication Data

US 2015/0108462 A1    Apr. 23, 2015

Related U.S. Application Data

(62) Division of application No. 13/277,603, filed on Oct. 20, 2011, now Pat. No. 8,921,548.

(30) Foreign Application Priority Data

Oct. 22, 2010  (JP) ................................. 2010-238001
Dec. 28, 2010  (JP) ................................. 2010-291881

(51) Int. Cl.
| | | |
|---|---|---|
| C07D 239/24 | (2006.01) |
| C01G 55/00 | (2006.01) |
| H01L 51/00 | (2006.01) |
| C07F 15/00 | (2006.01) |
| C09K 11/06 | (2006.01) |
| H05B 33/14 | (2006.01) |
| H01L 27/32 | (2006.01) |
| H01L 51/50 | (2006.01) |
| H01L 51/52 | (2006.01) |
| H01L 27/18 | (2006.01) |

(52) U.S. Cl.
CPC ........ *H01L 51/0085* (2013.01); *C07F 15/0033* (2013.01); *C09K 11/06* (2013.01); *H01L 51/009* (2013.01); *H05B 33/14* (2013.01); *C09K 2211/1007* (2013.01); *C09K 2211/1011* (2013.01); *C09K 2211/1044* (2013.01); *C09K 2211/185* (2013.01); *H01L 27/18* (2013.01); *H01L 27/3244* (2013.01); *H01L 27/3283* (2013.01); *H01L 51/5016* (2013.01); *H01L 51/5044* (2013.01); *H01L 51/5278* (2013.01); *H01L 2251/5361* (2013.01)

(58) Field of Classification Search
CPC .............................. C01G 55/00; C07D 239/24
USPC ............................................ 423/22; 544/242
See application file for complete search history.

(56) References Cited

U.S. PATENT DOCUMENTS

| | | | |
|---|---|---|---|
| 6,097,147 A | 8/2000 | Baldo et al. |
| 6,830,828 B2 | 12/2004 | Thompson et al. |
| 6,902,830 B2 | 6/2005 | Thompson et al. |
| 6,974,639 B2 | 12/2005 | Tsuboyama et al. |
| 7,001,536 B2 | 2/2006 | Thompson et al. |
| 7,220,495 B2 | 5/2007 | Tsuboyama et al. |
| 7,291,406 B2 | 11/2007 | Thompson et al. |

(Continued)

FOREIGN PATENT DOCUMENTS

| | | |
|---|---|---|
| CN | 101270133 A | 9/2008 |
| EP | 1 239 526 A2 | 9/2002 |

(Continued)

OTHER PUBLICATIONS

Taiwanese Office Action re Application No. TW 102103293, dated Feb. 10, 2015.

(Continued)

*Primary Examiner* — Douglas M Willis
(74) *Attorney, Agent, or Firm* — Husch Blackwell LLP

(57) ABSTRACT

Provided is a novel substance that can emit phosphorescence. Alternatively, provided is a novel substance with high emission efficiency. An organometallic complex in which a 4-arylpyrimidine derivative is a ligand and iridium is a central metal is provided. Specifically, an organometallic complex having a structure represented by a general formula (G1) is provided. In the general formula (G1), $R^1$ represents a substituted or unsubstituted alkyl group having 1 to 4 carbon atoms or a substituted or unsubstituted aryl group having 6 to 10 carbon atoms, $R^2$ represents any of hydrogen, a substituted or unsubstituted alkyl group having 1 to 4 carbon atoms, and a substituted or unsubstituted phenyl group, $R^3$ represents hydrogen or a substituted or unsubstituted alkyl group having 1 to 4 carbon atoms, and $Ar^1$ represents a substituted or unsubstituted arylene group having 6 to 10 carbon atoms.

(G1)

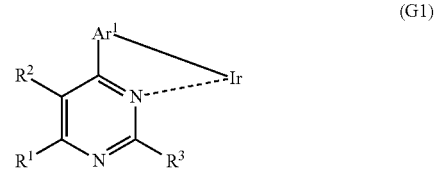

18 Claims, 91 Drawing Sheets

(56) References Cited

U.S. PATENT DOCUMENTS

| | | |
|---|---|---|
| 7,354,662 B2 | 4/2008 | Tsuboyama et al. |
| 7,537,844 B2 | 5/2009 | Thompson et al. |
| 7,883,787 B2 | 2/2011 | Thompson et al. |
| 8,227,975 B2 | 7/2012 | Inoue et al. |
| 8,247,086 B2 | 8/2012 | Inoue et al. |
| 8,598,785 B2 | 12/2013 | Inoue et al. |
| 8,889,266 B2 | 11/2014 | Inoue et al. |
| 8,999,520 B2 | 4/2015 | Inoue et al. |
| 9,012,036 B2 | 4/2015 | Inoue et al. |
| 2005/0221123 A1 | 10/2005 | Inoue et al. |
| 2007/0129545 A1 | 6/2007 | Inoue et al. |
| 2007/0244320 A1 | 10/2007 | Inoue et al. |
| 2008/0305361 A1 | 12/2008 | Inoue et al. |
| 2009/0015143 A1 | 1/2009 | Inoue et al. |
| 2009/0039776 A1 | 2/2009 | Yamada et al. |
| 2010/0105902 A1 | 4/2010 | Inoue et al. |
| 2010/0145044 A1 | 6/2010 | Inoue et al. |
| 2011/0082296 A1 | 4/2011 | Inoue et al. |
| 2011/0112296 A1 | 5/2011 | Thompson et al. |
| 2012/0061707 A1 | 3/2012 | Seo et al. |
| 2012/0208999 A1 | 8/2012 | Konno |
| 2013/0165653 A1 | 6/2013 | Inoue et al. |

FOREIGN PATENT DOCUMENTS

| | | |
|---|---|---|
| EP | 1 873 163 A1 | 1/2008 |
| EP | 2 254 173 A1 | 11/2010 |
| EP | 2 429 008 A1 | 3/2012 |
| JP | 2002-332292 A | 11/2002 |
| JP | 2003-109758 A | 4/2003 |
| JP | 2006-120905 A | 5/2006 |
| JP | 2007-176917 A | 7/2007 |
| JP | 2007-182429 A | 7/2007 |
| JP | 2007-284432 A | 11/2007 |
| JP | 2008-222635 A | 9/2008 |
| JP | 2009-001546 A | 1/2009 |
| JP | 2009-013167 A | 1/2009 |
| JP | 2010-174035 A | 8/2010 |
| JP | 2010-189376 A | 9/2010 |
| JP | 2012-149030 A | 8/2012 |
| TW | I231157 | 4/2005 |
| TW | 200601888 | 1/2006 |
| WO | WO 00/70655 A2 | 11/2000 |
| WO | WO 2006/098460 A1 | 9/2006 |
| WO | WO 2007/066556 A1 | 6/2007 |
| WO | WO 2008/143113 A1 | 11/2008 |
| WO | WO 2008/149828 A1 | 12/2008 |
| WO | WO 2011/024737 A1 | 3/2011 |
| WO | WO 2012/053627 A1 | 4/2012 |

OTHER PUBLICATIONS

Niu, Y.-H. et al., "Highly Efficient Red Electrophosphorescent Devices Based on an Iridium Complex with Trifluoromethyl-Substituted Pyrimidine Ligand," Applied Physics Letter, Aug. 30, 2004, vol. 85, No. 9, pp. 1619-1621.

Caygill, G.B. et al., "Cyclometallated Compounds IV. Cyclopalladation of Phenylpyrimidines and X-ray Structure of a Doubly Cyclopalladated Derivative of 4,6-diphenylpyrimidine," Journal of Organometallic Chemistry, Feb. 13, 1990, vol. 383, No. 3, pp. 455-469.

Kawanishi, Y. et al., "Dependence of Spectroscopic, Electrochemical, and Excited-State Properties of tris Chelate Ruthenium(II) Complexes on Ligand Structure," Inorganic Chemistry, 1989, vol. 28, No. 15, pp. 2968-2975.

Kozhevnikov, V.N. et al., "Highly Luminescent Mixed-Metal Pt(II)/Ir(III) Complexes: Bis-Cyclometalation of 4,6-Diphenylpyrimidine as a Versatile Route to Rigid Multimetallic Assemblies," Inorganic Chemistry, 2011, vol. 50, No. 13, pp. 6304-6313.

International Search Report re Application No. PCT/JP2011/074243, dated Jan. 17, 2012.

Written Opinion re Application No. PCT/JP2011/074243, dated Jan. 17, 2012.

Bredereck, H. et al., "Formamide Reactions, VIII. A New Pyrimidine-Synthesis," Chemische Berichte, 1957, vol. 90, pp. 942-952.

Taiwanese Office Action re Application No. TW 100138309, dated Jun. 26, 2013.

Korean Office Action re Application No. KR 2014-7000221, dated Apr. 24, 2014.

German Office Action re Application No. DE 112011103544.6, dated Jun. 23, 2014.

Chinese Office Action re Application No. CN 201180046029.8, dated Oct. 10, 2014.

LIGHT-EMITTING ELEMENTS COMPRISING IRIDIUM ORGANOMETALLIC COMPLEXES COMPRISING 4-ARYLPYRIMIDINES

This application is a divisional of copending U.S. application Ser. No. 13/277,603, filed on Oct. 20, 2011 which is incorporated herein by reference.

TECHNICAL FIELD

The present invention relates to an organometallic complex. In particular, the present invention relates to an organometallic complex that is capable of converting a triplet excited state into luminescence. In addition, the present invention relates to a light-emitting element, a light-emitting device, an electronic device, and a lighting device each using the organometallic complex.

BACKGROUND ART

In recent years, a light-emitting element using a light-emitting organic compound or inorganic compound as a light-emitting material has been actively developed. In particular, a light-emitting element called an EL (electroluminescence) element has attracted attention as a next-generation flat panel display element because it has a simple structure in which a light-emitting layer containing a light-emitting material is provided between electrodes, and characteristics such as feasibility of being thinner and more lightweight and responsive to input signals and capability of driving with direct current at a low voltage. In addition, a display using such a light-emitting element has a feature that it is excellent in contrast and image quality, and has a wide viewing angle. Further, since such a light-emitting element is a plane light source, it is considered that the light-emitting element is applied as a light source such as a backlight of a liquid crystal display and an illumination device.

In the case where the light-emitting substance is an organic compound having a light-emitting property, the emission mechanism of the light-emitting element is a carrier-injection type. Specifically, by application of a voltage to electrodes between which the light-emitting layer is interposed, electrons and holes injected from the electrodes recombine to raise the light-emitting substance to an excited state, and light is emitted when the substance in the excited state returns to the ground state. There are two types of the excited states which are possible: a singlet excited state (S*) and a triplet excited state (T*). In addition, the statistical generation ratio thereof in a light-emitting element is considered to be $S^*:T^*=1:3$.

In general, the ground state of a light-emitting organic compound is a singlet state. Light emission from a singlet excited state (S*) is referred to as fluorescence where electron transition occurs between the same multiplicities. On the other hand, light emission from a triplet excited state (T*) is referred to as phosphorescence where electron transition occurs between different multiplicities. Here, in a compound emitting fluorescence (hereinafter referred to as a fluorescent compound), in general, phosphorescence is not observed at room temperature, and only fluorescence is observed. Accordingly, the internal quantum efficiency (the ratio of generated photons to injected carriers) in a light-emitting element using a fluorescent compound is assumed to have a theoretical limit of 25% based on $S^*:T^*=1:3$.

On the other hand, the use of a phosphorescent compound can increase the internal quantum efficiency to 100% in theory. In other words, emission efficiency can be 4 times as much as that of the fluorescence compound. For these reasons, in order to achieve a highly efficient light-emitting element, a light-emitting element using a phosphorescent compound has been developed actively recently. As the phosphorescent compound, an organometallic complex that has iridium or the like as a central metal have particularly attracted attention because of their high phosphorescence quantum yield; for example, an organometallic complex that has iridium as a central metal is disclosed as a phosphorescent material in Patent Document 1.

An advantage of the use of the highly efficient light-emitting element is that power consumption of an electronic device using the light-emitting element can be reduced, for example. Energy issues have been discussed recently, and power consumption is becoming a major factor which affects consumer buying patterns; thus, power consumption is a very important element.

REFERENCE

Patent Document

[Patent Document 1] PCT International Publication No. WO 00/70655

DISCLOSURE OF INVENTION

An object of one embodiment of the present invention is to provide a novel substance that can emit phosphorescence. Another object is to provide a novel substance with high emission efficiency. Another object is to provide a light-emitting element, a light-emitting device, an electronic device, or a lighting device using the novel substance.

Another object is to provide a light-emitting element, a light-emitting device, an electronic device, or a lighting device with high emission efficiency. Another object is to provide a light-emitting element, a light-emitting device, an electronic device, or a lighting device with high reliability. Another object is to provide a light-emitting element, a light-emitting device, an electronic device, or a lighting device with low power consumption.

One embodiment of the present invention is an organometallic complex in which a 4-arylpyrimidine derivative is a ligand and iridium is a central metal. In addition, one embodiment of the present invention is an organometallic complex in which a 4-arylpyrimidine derivative having a substituent at the 6-position (in some cases, it can be named a 6-arylpyrimidine derivative having a substituent at the 4-position depending on the type of the substituent) is a ligand and iridium is a central metal. Further, one embodiment of the present invention is an organometallic complex in which a 4-arylpyrimidine derivative having an alkyl group or an aryl group at the 6-position (in some cases, it can be named a 6-arylpyrimidine derivative having an alkyl group or an aryl group at the 4-position depending on the type of the substituent) is a ligand and iridium is a central metal. In particular, the 4-arylpyrimidine derivative is preferably a 4,6-diphenylpyrimidine derivative.

Specific embodiment of the present invention is an organometallic complex having a structure represented by a general formula (G1).

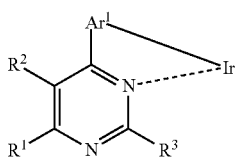

(G1)

In the formula, $R^1$ represents a substituted or unsubstituted alkyl group having 1 to 4 carbon atoms or a substituted or unsubstituted aryl group having 6 to 10 carbon atoms, $R^2$ represents any of hydrogen, a substituted or unsubstituted alkyl group having 1 to 4 carbon atoms, and a substituted or unsubstituted phenyl group, $R^3$ represents hydrogen or a substituted or unsubstituted alkyl group having 1 to 4 carbon atoms, and $Ar^1$ represents a substituted or unsubstituted arylene group having 6 to 10 carbon atoms.

Another embodiment of the present invention is an organometallic complex having a structure represented by a general formula (G2).

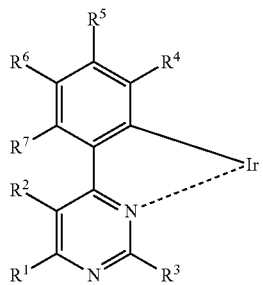

(G2)

In the formula, $R^1$ represents a substituted or unsubstituted alkyl group having 1 to 4 carbon atoms or a substituted or unsubstituted aryl group having 6 to 10 carbon atoms, $R^2$ represents any of hydrogen, a substituted or unsubstituted alkyl group having 1 to 4 carbon atoms, and a substituted or unsubstituted phenyl group, $R^3$ represents hydrogen or a substituted or unsubstituted alkyl group having 1 to 4 carbon atoms, and $R^4$ to $R^7$ individually represent any of hydrogen, a substituted or unsubstituted alkyl group having 1 to 4 carbon atoms, a substituted or unsubstituted alkoxy group having 1 to 4 carbon atoms, a substituted or unsubstituted alkylthio group having 1 to 4 carbon atoms, a halogen group, a substituted or unsubstituted haloalkyl group having 1 to 4 carbon atoms, and a substituted or unsubstituted aryl group having 6 to 10 carbon atoms.

Another embodiment of the present invention is an organometallic complex having a structure represented by a general formula (G3).

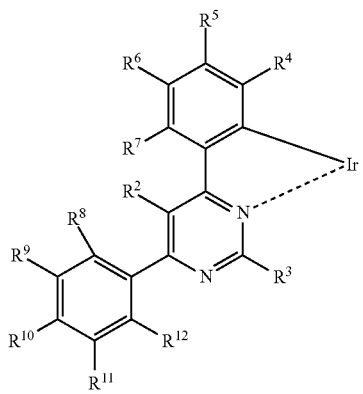

(G3)

In the formula, $R^2$ represents any of hydrogen, a substituted or unsubstituted alkyl group having 1 to 4 carbon atoms, and a substituted or unsubstituted phenyl group, $R^3$ represents hydrogen or a substituted or unsubstituted alkyl group having 1 to 4 carbon atoms, and $R^4$ to $R^{12}$ individually represent any of hydrogen, a substituted or unsubstituted alkyl group having 1 to 4 carbon atoms, a substituted or unsubstituted alkoxy group having 1 to 4 carbon atoms, a substituted or unsubstituted alkylthio group having 1 to 4 carbon atoms, a halogen group, a substituted or unsubstituted haloalkyl group having 1 to 4 carbon atoms, and a substituted or unsubstituted aryl group having 6 to 10 carbon atoms.

Another embodiment of the present invention is an organometallic complex represented by a general formula (G4).

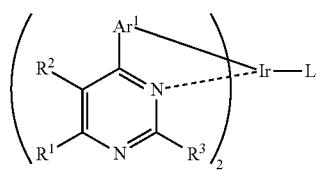

(G4)

In the formula, L represents a monoanionic ligand. In addition, $R^1$ represents a substituted or unsubstituted alkyl group having 1 to 4 carbon atoms or a substituted or unsubstituted aryl group having 6 to 10 carbon atoms, $R^2$ represents any of hydrogen, a substituted or unsubstituted alkyl group having 1 to 4 carbon atoms, and a substituted or unsubstituted phenyl group, $R^3$ represents hydrogen or a substituted or unsubstituted alkyl group having 1 to 4 carbon atoms, and $Ar^1$ represents a substituted or unsubstituted arylene group having 6 to 10 carbon atoms.

Another embodiment of the present invention is an organometallic complex represented by a general formula (G5).

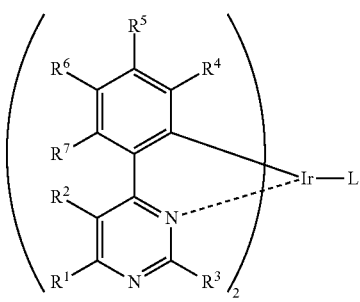

(G5)

In the formula represents a monoanionic ligand. $R^1$ represents a substituted or unsubstituted alkyl group having 1 to 4 carbon atoms or a substituted or unsubstituted aryl group having 6 to 10 carbon atoms, $R^2$ represents any of hydrogen, a substituted or unsubstituted alkyl group having 1 to 4 carbon atoms, and a substituted or unsubstituted phenyl group, $R^3$ represents hydrogen or a substituted or unsubstituted alkyl group having 1 to 4 carbon atoms, and $R^4$ to $R^7$ individually represent any of hydrogen, a substituted or unsubstituted alkyl group having 1 to 4 carbon atoms, a substituted or unsubstituted alkoxy group having 1 to 4 carbon atoms, a substituted or unsubstituted alkylthio group having 1 to 4 carbon atoms, a halogen group, a substituted or unsubstituted haloalkyl group having 1 to 4 carbon atoms, and a substituted or unsubstituted aryl group having 6 to 10 carbon atoms.

Another embodiment of the present invention is an organometallic complex represented by a general formula (G6).

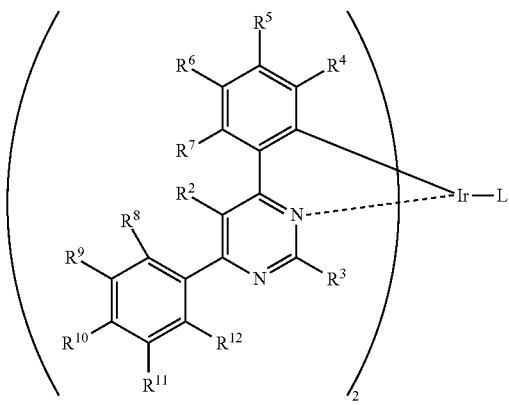

(G6)

In the formula, L represents a monoanionic ligand. $R^2$ represents any of hydrogen, a substituted or unsubstituted alkyl group having 1 to 4 carbon atoms, and a substituted or unsubstituted phenyl group, $R^3$ represents hydrogen or a substituted or unsubstituted alkyl group having 1 to 4 carbon atoms, and $R^4$ to $R^{12}$ individually represent any of hydrogen, a substituted or unsubstituted alkyl group having 1 to 4 carbon atoms, a substituted or unsubstituted alkoxy group having 1 to 4 carbon atoms, a substituted or unsubstituted alkylthio group having 1 to 4 carbon atoms, a halogen group, a substituted or unsubstituted haloalkyl group having 1 to 4 carbon atoms, and a substituted or unsubstituted aryl group having 6 to 10 carbon atoms.

Another embodiment of the present invention is an organometallic complex represented by a general formula (G7).

(G7)

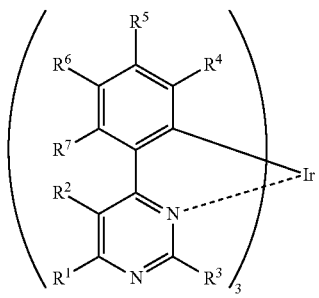

In the formula, $R^1$ represents a substituted or unsubstituted alkyl group having 1 to 4 carbon atoms or a substituted or unsubstituted aryl group having 6 to 10 carbon atoms, $R^2$ represents any of hydrogen, a substituted or unsubstituted alkyl group having 1 to 4 carbon atoms, and a substituted or unsubstituted phenyl group, $R^3$ represents hydrogen or a substituted or unsubstituted alkyl group having 1 to 4 carbon atoms, and $Ar^1$ represents a substituted or unsubstituted arylene group having 6 to 10 carbon atoms.

Another embodiment of the present invention is an organometallic complex represented by a general formula (G8).

(G8)

In the formula, $R^1$ represents a substituted or unsubstituted alkyl group having 1 to 4 carbon atoms or a substituted or unsubstituted aryl group having 6 to 10 carbon atoms, $R^2$ represents any of hydrogen, a substituted or unsubstituted alkyl group having 1 to 4 carbon atoms, and a substituted or unsubstituted phenyl group, $R^3$ represents hydrogen or a substituted or unsubstituted alkyl group having 1 to 4 carbon atoms, and $R^4$ to $R^7$ individually represent any of hydrogen, a substituted or unsubstituted alkyl group having 1 to 4 carbon atoms, a substituted or unsubstituted alkoxy group having 1 to 4 carbon atoms, a substituted or unsubstituted alkylthio group having 1 to 4 carbon atoms, a halogen group, a substituted or unsubstituted haloalkyl group having 1 to 4 carbon atoms, and a substituted or unsubstituted aryl group having 6 to 10 carbon atoms.

Another embodiment of the present invention is an organometallic complex represented by a general formula (G9).

(G9)

In the formula, $R^2$ represents any of hydrogen, a substituted or unsubstituted alkyl group having 1 to 4 carbon atoms, and a substituted or unsubstituted phenyl group, $R^3$ represents hydrogen or a substituted or unsubstituted alkyl group having 1 to 4 carbon atoms, and $R^4$ to $R^{12}$ individually represent any of hydrogen, a substituted or unsubstituted alkyl group having 1 to 4 carbon atoms, a substituted or unsubstituted alkoxy group having 1 to 4 carbon atoms, a substituted or unsubstituted alkylthio group having 1 to 4 carbon atoms, a halogen group, a substituted or unsubstituted haloalkyl group having 1 to 4 carbon atoms, and a substituted or unsubstituted aryl group having 6 to 10 carbon atoms.

In the organometallic complexes represented by the general formulas (G4) to (G6), the monoanionic ligand is preferably any of a monoanionic bidentate chelate ligand having a beta-diketone structure, a monoanionic bidentate chelate ligand having a carboxyl group, a monoanionic bidentate chelate ligand having a phenolic hydroxyl group, and a monoanionic bidentate chelate ligand in which two ligand elements are both nitrogen. A monoanionic bidentate chelate ligand having a beta-diketone structure is particularly preferable.

The monoanionic ligand is preferably a ligand represented by any of general formulas (L1) to (L7).

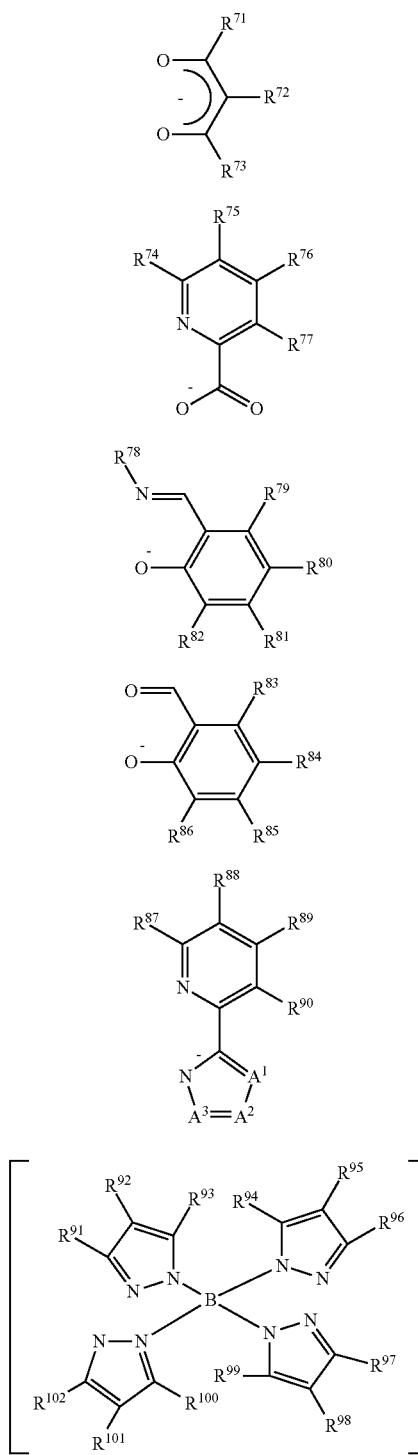

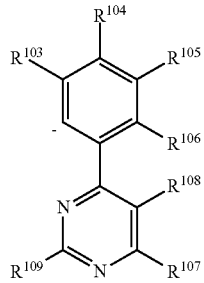

In the formula, $R^{71}$ to $R^{109}$ individually represent any of hydrogen, a substituted or unsubstituted alkyl group having 1 to 4 carbon atoms, a halogen group, a vinyl group, a substituted or unsubstituted haloalkyl group having 1 to 4 carbon atoms, a substituted or unsubstituted alkoxy group having 1 to 4 carbon atoms, and a substituted or unsubstituted alkylthio group having 1 to 4 carbon atoms. In addition, $A^1$ to $A^3$ individually represent any of nitrogen, $sp^2$ hybridized carbon bonded to hydrogen, and $sp^2$ carbon bonded to a substituent R. The substituent R represents any of an alkyl group having 1 to 4 carbon atoms, a halogen group, a haloalkyl group having 1 to 4 carbon atoms, and a phenyl group.

Another embodiment of the present invention is a light-emitting element including, between a pair of electrodes, any organometallic complex described above. In particular, any organometallic complex described above is preferably contained in a light-emitting layer.

A light-emitting device, an electronic device, and a lighting device each using the above light-emitting element also belong to the category of the present invention. Note that the light-emitting device in this specification includes an image display device and a light source. In addition, the light-emitting device includes, in its category, all of a module in which a connector such as a flexible printed circuit (FPC), a tape automated bonding (TAB) tape or a tape carrier package (TCP) is connected to a panel, a module in which a printed wiring board is provided on the tip of a TAB tape or a TCP, and a module in which an integrated circuit (IC) is directly mounted on a light-emitting element by a chip on glass (COG) method.

With one embodiment of the present invention, it is possible to provide a novel substance that can emit phosphorescence. It is also possible to provide a novel substance with high emission efficiency. It is also possible to provide a light-emitting element, a light-emitting device, an electronic device, or a lighting device using the novel substance.

Alternatively, it is possible to provide a light-emitting element, a light-emitting device, an electronic device, or a lighting device with high emission efficiency. Alternatively, it is possible to provide a light-emitting element, a light-emitting device, an electronic device, or a lighting device with high reliability. Further alternatively, it is possible to provide a light-emitting element, a light-emitting device, an electronic device, or a lighting device with low power consumption.

BEST MODE FOR CARRYING OUT THE INVENTION

Figure 1A:
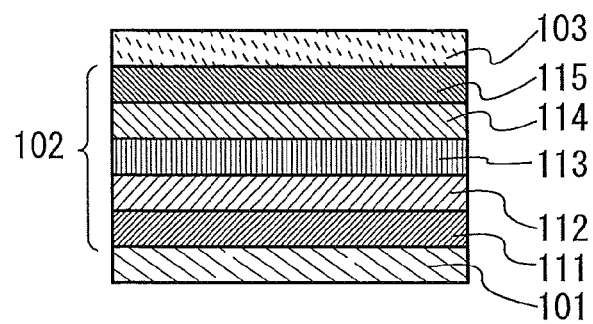
FIGS. 1A to 1C each illustrate a light-emitting element which is one embodiment of the present invention.

Embodiments are described in detail with reference to drawings. Note that the invention is not limited to the following description, and it will be easily understood by those skilled in the art that various changes and modifications can be made without departing from the spirit and scope of the invention. Therefore, the invention should not be construed as being limited to the description in the following embodiments. Note that in the structures of the invention described below, the same portions or portions having similar functions are denoted by the same reference numerals in different drawings, and description of such portions is not repeated.

(Embodiment 1)

In Embodiment 1, an organometallic complex which is one embodiment of the present invention is described.

One embodiment of the present invention is an organometallic complex in which a 4-arylpyrimidine derivative is a ligand and iridium is a central metal. In addition, one embodiment of the present invention is an organometallic complex in which a 4-arylpyrimidine derivative having a substituent at the 6-position (in some cases, it can be named a 6-arylpyrimidine derivative having a substituent at the 4-position depending on the type of the substituent) is a ligand and iridium is a central metal. Further, one embodiment of the present invention is an organometallic complex in which a 4-arylpyrimidine derivative having an alkyl group or an aryl group at the 6-position (in some cases, it can be named a 6-arylpyrimidine derivative having an alkyl group or an aryl group at the 4-position depending on the type of the substituent) is a ligand and iridium is a central metal. In particular, the 4-arylpyrimidine derivative is preferably a 4,6-diphenylpyrimidine derivative.

Specific embodiment of the present invention is an organometallic complex having a structure represented by a general formula (G1).

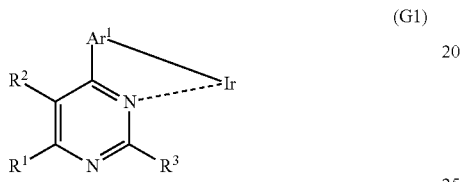

(G1)

In the general formula (G1), $R^1$ represents a substituted or unsubstituted alkyl group having 1 to 4 carbon atoms or a substituted or unsubstituted aryl group having 6 to 10 carbon atoms, $R^2$ represents any of hydrogen, a substituted or unsubstituted alkyl group having 1 to 4 carbon atoms, and a substituted or unsubstituted phenyl group, $R^3$ represents hydrogen or a substituted or unsubstituted alkyl group having 1 to 4 carbon atoms, and $Ar^1$ represents a substituted or unsubstituted arylene group having 6 to 10 carbon atoms.

Here, specific examples of $Ar^1$ include a phenylene group, a phenylene group substituted by one or more alkyl groups each having 1 to 4 carbon atoms, a phenylene group substituted by one or more alkoxy groups each having 1 to 4 carbon atoms, a phenylene group substituted by one or more alkylthio groups each having 1 to 4 carbon atoms, a phenylene group substituted by one or more aryl groups each having 6 to 10 carbon atoms, a phenylene group substituted by one or more halogen groups, a phenylene group substituted by one or more haloalkyl groups each having 1 to 4 carbon atoms, a substituted or unsubstituted biphenyl-diyl group, and a substituted or unsubstituted naphthalene-diyl group.

Specific examples of the alkyl group having 1 to 4 carbon atoms in $R^1$ to $R^3$ include a methyl group, an ethyl group, a propyl group, an isopropyl group, a butyl group, a sec-butyl group, an isobutyl group, a tert-butyl group, and the like. Specific examples of the aryl group having 6 to 10 carbon atoms include a phenyl group, a phenyl group substituted by one or more alkyl groups each having 1 to 4 carbon atoms, a phenyl group substituted by one or more alkoxy groups each having 1 to 4 carbon atoms, a phenyl group substituted by one or more alkylthio groups each having 1 to 4 carbon atoms, a phenyl group substituted by one or more aryl groups each having 6 to 10 carbon atoms, a phenyl group substituted by one or more halogen groups, a phenyl group substituted by one or more haloalkyl groups each having 1 to 4 carbon atoms, a naphthalene-yl group, and the like.

In addition, the alkyl group having 1 to 4 carbon atoms in $R^1$ is preferably an alkyl group having 2 or more carbon atoms. An alkyl group having 2 or more carbon atoms suppresses interaction between molecules due to steric hindrance. Therefore, side reaction in synthesis reaction of an organometallic complex which is one embodiment of the present invention is suppressed and the yield is increased.

Considering that, the alkyl group having 1 to 4 carbon atoms in $R^1$ is more preferably an ethyl group, a propyl group, an isopropyl group, a butyl group, a sec-butyl group, an isobutyl group, or a tert-butyl group.

A substituted or unsubstituted phenylene group is preferably used in $Ar^1$ above for easier synthesis. Therefore, another embodiment of the present invention is an organometallic complex having a structure represented by a general formula (G2).

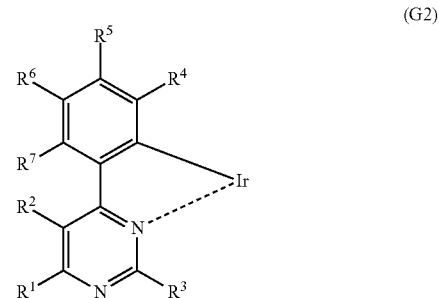

(G2)

In the general formula (G2), $R^1$ represents a substituted or unsubstituted alkyl group having 1 to 4 carbon atoms or a substituted or unsubstituted aryl group having 6 to 10 carbon atoms, $R^2$ represents any of hydrogen, a substituted or unsubstituted alkyl group having 1 to 4 carbon atoms, and a substituted or unsubstituted phenyl group, $R^3$ represents hydrogen or a substituted or unsubstituted alkyl group having 1 to 4 carbon atoms, and $R^4$ to $R^7$ individually represent any of hydrogen, a substituted or unsubstituted alkyl group having 1 to 4 carbon atoms, a substituted or unsubstituted alkoxy group having 1 to 4 carbon atoms, a substituted or unsubstituted alkylthio group having 1 to 4 carbon atoms, a halogen group, a substituted or unsubstituted haloalkyl group having 1 to 4 carbon atoms, and a substituted or unsubstituted aryl group having 6 to 10 carbon atoms.

Here, specific examples of $R^1$ to $R^3$ include the same examples as those in the general formula (G1). Specific examples of $R^4$ to $R^7$ individually include, hydrogen, a methyl group, an ethyl group, a propyl group, an isopropyl group, a butyl group, a sec-butyl group, an isobutyl group, a tert-butyl group, a methoxy group, an ethoxy group, a propoxy group, an isopropoxy group, a butoxy group, a sec-butoxy group, an isobutoxy group, a test-butoxy group, a methylsulfinyl group, an ethylsulfinyl group, a propylsulfinyl group, an isopropylsulfinyl group, a butylsulfinyl group, an isobutylsulfinyl group, a sec-butylsulfinyl group, a tert-butylsulfinyl group, a fluoro group, a fluoromethyl group, a difluoromethyl group, a trifluoromethyl group, a chloromethyl group, a dichloromethyl group, a trichloromethyl group, a bromomethyl group, a 2,2,2-trifluoroethyl group, a 3,3,3-trifluoropropyl group, a 1,1,1,3,3,3-hexafluoroisopropyl group, a phenyl group, a phenyl group substituted by one or more alkyl groups each having 1 to 4 carbon atoms, a phenyl group substituted by one or more alkoxy groups each having 1 to 4 carbon atoms, a phenyl group substituted by one or more alkylthio groups each having 1 to 4 carbon atoms, a phenyl group substituted by one or more aryl groups each having 6 to 10 carbon atoms, a phenyl group substituted by one or more halogen groups, a phenyl group substituted by one or more haloalkyl groups each having 1 to 4 carbon atoms, a substituted or unsubstituted naphthalene-yl group, and the like.

Another embodiment of the present invention is preferably an organometallic complex in which a 4,6-diphenylpyrimidine derivative is a ligand and iridium is a central metal. Specifically, another embodiment of the present invention is an organometallic complex having a structure represented by a general formula (G3). As in the structure represented by the general formula (G3), the 6-position of a pyrimidine skeleton preferably includes a phenyl group (i.e., $R^1$ above is preferably a substituted or unsubstituted phenyl group) for higher yield of the organometallic complex. It is preferable also for extremely high emission efficiency in the case where the organometallic complex is applied to a light-emitting element.

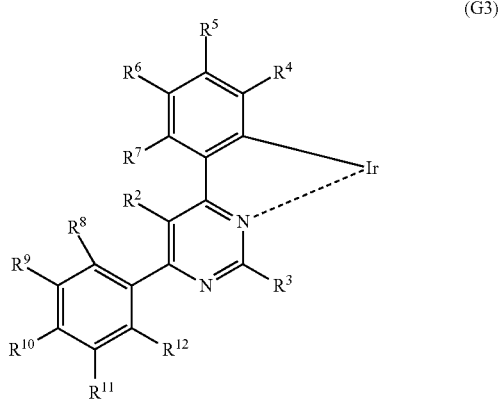

(G3)

In the general formula (G3), $R^2$ represents any of hydrogen, a substituted or unsubstituted alkyl group having 1 to 4 carbon atoms, and a substituted or unsubstituted phenyl group, $R^3$ represents hydrogen or a substituted or unsubstituted alkyl group having 1 to 4 carbon atoms, and $R^4$ to $R^{12}$ individually represent any of hydrogen, a substituted or unsubstituted alkyl group having 1 to 4 carbon atoms, a substituted or unsubstituted alkoxy group having 1 to 4 carbon atoms, a substituted or unsubstituted alkylthio group having 1 to 4 carbon atoms, a halogen group, a substituted or unsubstituted haloalkyl group having 1 to 4 carbon atoms, and a substituted or unsubstituted aryl group having 6 to 10 carbon atoms.

Here, specific examples of $R^2$ to $R^7$ include the same examples as those in the general formulas (G1) and (G2). Specific examples of $R^8$ to $R^{12}$ individually include, hydrogen, a methyl group, an ethyl group, a propyl group, an isopropyl group, a butyl group, a sec-butyl group, an isobutyl group, a tert-butyl group, a methoxy group, an ethoxy group, a propoxy group, an isopropoxy group, a butoxy group, a sec-butoxy group, an isobutoxy group, a tert-butoxy group, a methylsulfinyl group, an ethylsulfinyl group, a propylsulfinyl group, an isopropylsulfinyl group, a butylsulfinyl group, an isobutylsulfinyl group, a sec-butylsulfinyl group, a tert-butylsulfinyl group, a fluoro group, a fluoromethyl group, a difluoromethyl group, a trifluoromethyl group, a chloromethyl group, a dichloromethyl group, a trichloromethyl group, a bromomethyl group, a 2,2,2-trifluoroethyl group, a 3,3,3-trifluoropropyl group, a 1,1,1,3,3,3-hexafluoroisopropyl group, a phenyl group, a phenyl group substituted by one or more alkyl groups each having 1 to 4 carbon atoms, a phenyl group substituted by one or more alkoxy groups each having 1 to 4 carbon atoms, a phenyl group substituted by one or more alkylthio groups each having 1 to 4 carbon atoms, a phenyl group substituted by one or more aryl groups each having 6 to 10 carbon atoms, a phenyl group substituted by one or more halogen groups, a phenyl group substituted by one or more haloalkyl groups each having 1 to 4 carbon atoms, a substituted or unsubstituted naphthalene-yl group, and the like.

Another embodiment of the present invention is an organometallic complex represented by a general formula (G4).

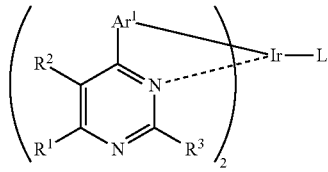

(G4)

In the general formula (G4), L represents a monoanionic ligand. In addition, $R^1$ represents a substituted or unsubstituted alkyl group having 1 to 4 carbon atoms or a substituted or unsubstituted aryl group having 6 to 10 carbon atoms, $R^2$ represents any of hydrogen, a substituted or unsubstituted alkyl group having 1 to 4 carbon atoms, and a substituted or unsubstituted phenyl group, $R^3$ represents hydrogen or a substituted or unsubstituted alkyl group having 1 to 4 carbon atoms, and $Ar^1$ represents a substituted or unsubstituted arylene group having 6 to 10 carbon atoms. Note that specific examples of $Ar^1$ and $R^1$ to $R^3$ include the same examples as those in the general formula (G1).

A phenylene group is preferably used in $Ar^1$ for easier synthesis. Therefore, another embodiment of the present invention is an organometallic complex represented by a general formula (G5).

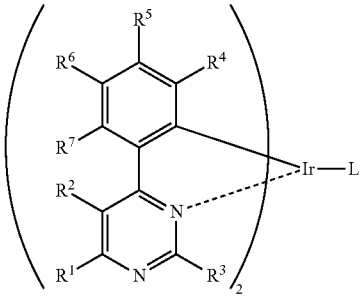

(G5)

In the general formula (G5), L represents a monoanionic ligand. $R^1$ represents a substituted or unsubstituted alkyl group having 1 to 4 carbon atoms or a substituted or unsubstituted aryl group having 6 to 10 carbon atoms, $R^2$ represents any of hydrogen, a substituted or unsubstituted alkyl group having 1 to 4 carbon atoms, and a substituted or unsubstituted phenyl group, $R^3$ represents hydrogen or a substituted or unsubstituted alkyl group having 1 to 4 carbon atoms, and $R^4$ to $R^7$ individually represent any of hydrogen, a substituted or unsubstituted alkyl group having 1 to 4 carbon atoms, a substituted or unsubstituted alkoxy group having 1 to 4 carbon atoms, a substituted or unsubstituted alkylthio group having 1 to 4 carbon atoms, a halogen group, a substituted or unsubstituted haloalkyl group having 1 to 4 carbon atoms, and a substituted or unsubstituted aryl group having 6 to 10 carbon atoms. Note that specific examples of $R^1$ to $R^7$ include the same examples as those in the general formula (G2).

Another embodiment of the present invention is an organometallic complex represented by a general formula (G6). As in the structure represented by the general formula (G6), the 6-position of a pyrimidine skeleton preferably includes a phenyl group for higher yield of the organometallic complex.

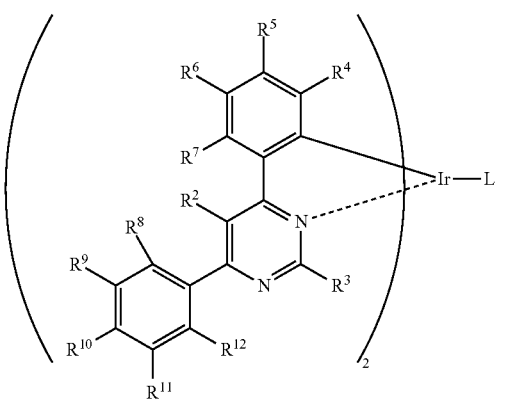
(G6)

In the general formula (G6), L represents a monoanionic ligand. $R^2$ represents any of hydrogen, a substituted or unsubstituted alkyl group having 1 to 4 carbon atoms, and a substituted or unsubstituted phenyl group, $R^3$ represents hydrogen or a substituted or unsubstituted alkyl group having 1 to 4 carbon atoms, and $R^4$ to $R^{12}$ individually represent any of hydrogen, a substituted or unsubstituted alkyl group having 1 to 4 carbon atoms, a substituted or unsubstituted alkoxy group having 1 to 4 carbon atoms, a substituted or unsubstituted alkylthio group having 1 to 4 carbon atoms, a halogen group, a substituted or unsubstituted haloalkyl group having 1 to 4 carbon atoms, and a substituted or unsubstituted aryl group having 6 to 10 carbon atoms. Note that specific examples of $R^2$ to $R^{12}$ include the same examples as those in the general formula (G3).

Another embodiment of the present invention is an organometallic complex represented by a general formula (G7).

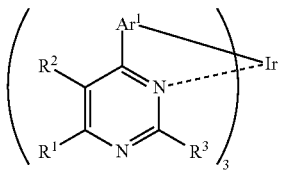
(G7)

In the general formula (G7), $R^1$ represents a substituted or unsubstituted alkyl group having 1 to 4 carbon atoms or a substituted or unsubstituted aryl group having 6 to 10 carbon atoms, $R^2$ represents any of hydrogen, a substituted or unsubstituted alkyl group having 1 to 4 carbon atoms, and a substituted or unsubstituted phenyl group, $R^3$ represents hydrogen or a substituted or unsubstituted alkyl group having 1 to 4 carbon atoms, and $Ar^1$ represents a substituted or unsubstituted arylene group having 6 to 10 carbon atoms. Note that specific examples of $Ar^1$ and $R^1$ to $R^3$ include the same examples as those in the general formula (G1).

A phenylene group is preferably used in $Ar^1$ for easier synthesis. Therefore, another embodiment of the present invention is an organometallic complex represented by a general formula (G8).

(G8)

In the general formula (G8), $R^1$ represents a substituted or unsubstituted alkyl group having 1 to 4 carbon atoms or a substituted or unsubstituted aryl group having 6 to 10 carbon atoms, $R^2$ represents any of hydrogen, a substituted or unsubstituted alkyl group having 1 to 4 carbon atoms, and a substituted or unsubstituted phenyl group, $R^3$ represents hydrogen or a substituted or unsubstituted alkyl group having 1 to 4 carbon atoms, and $R^4$ to $R^7$ individually represent any of hydrogen, a substituted or unsubstituted alkyl group having 1 to 4 carbon atoms, a substituted or unsubstituted alkoxy group having 1 to 4 carbon atoms, a substituted or unsubstituted alkylthio group having 1 to 4 carbon atoms, a halogen group, a substituted or unsubstituted haloalkyl group having 1 to 4 carbon atoms, and a substituted or unsubstituted aryl group having 6 to 10 carbon atoms. Note that specific examples of $R^1$ to $R^7$ include the same examples as those in the general formula (G2).

Another embodiment of the present invention is an organometallic complex represented by a general formula (G9). As in the structure represented by the general formula (G9), the 6-position of a pyrimidine skeleton preferably includes a phenyl group for higher yield of the organometallic complex.

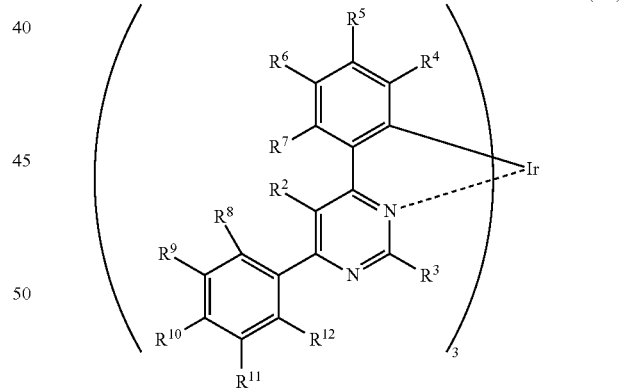
(G9)

In the general formula (G9), $R^2$ represents any of hydrogen, a substituted or unsubstituted alkyl group having 1 to 4 carbon atoms, and a substituted or unsubstituted phenyl group, $R^3$ represents hydrogen or a substituted or unsubstituted alkyl group having 1 to 4 carbon atoms, and $R^4$ to $R^{12}$ individually represent any of hydrogen, a substituted or unsubstituted alkyl group having 1 to 4 carbon atoms, a substituted or unsubstituted alkoxy group having 1 to 4 carbon atoms, a substituted or unsubstituted alkylthio group having 1 to 4 carbon atoms, a halogen group, a substituted or unsubstituted haloalkyl group having 1 to 4 carbon atoms, and a substituted or unsubstituted aryl group having 6 to 10 carbon atoms. Note that specific examples of $R^2$ to $R^{12}$ include the same examples as those in the general formula (G3).

In the organometallic complexes represented by the general formulas (G4) to (G6), the monoanionic ligand is preferably any of a monoanionic bidentate chelate ligand having a beta-diketone structure, a monoanionic bidentate chelate ligand having a carboxyl group, a monoanionic bidentate chelate ligand having a phenolic hydroxyl group, and a monoanionic bidentate chelate ligand in which two ligand elements are both nitrogen. A monoanionic bidentate chelate ligand having a beta-diketone structure is particularly preferable. A beta-diketone structure is preferably included for higher solubility of an organometallic complex in an organic solvent and easier purification. A beta-diketone structure is preferably included for realization of an organometallic complex with high emission efficiency. Inclusion of a beta-diketone structure has advantages such as a higher sublimation property and excellent evaporativity.

In the organometallic complexes represented by the general formulas (G4) to (G6), the monoanionic ligand is preferably a ligand represented by any of general formulas (L1) to (L7).

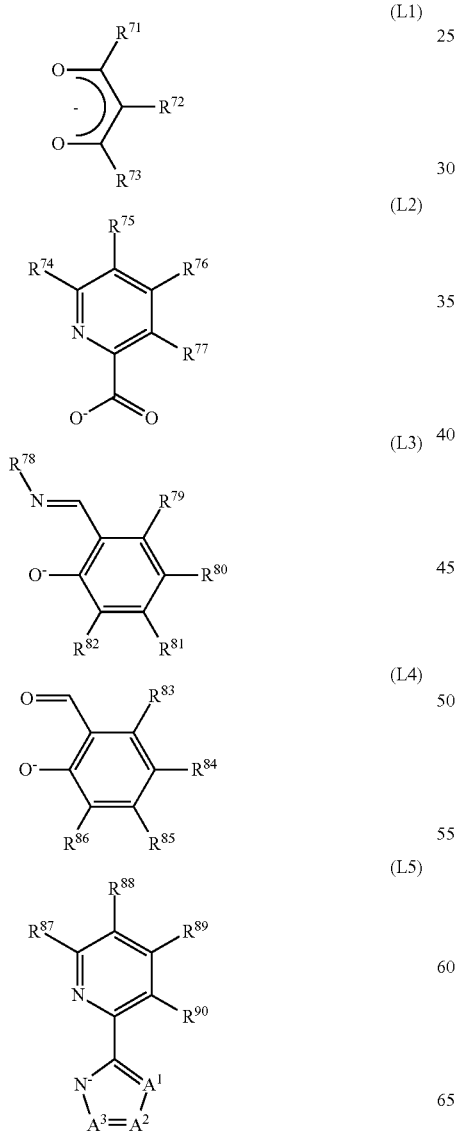

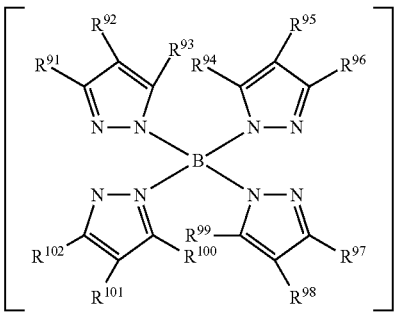

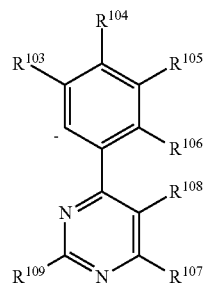

In the general formulas (L1) to (L7), $R^{71}$ to $R^{109}$ individually represent any of hydrogen, a substituted or unsubstituted alkyl group having 1 to 4 carbon atoms, a halogen group, a vinyl group, a substituted or unsubstituted haloalkyl group having 1 to 4 carbon atoms, a substituted or unsubstituted alkoxy group having 1 to 4 carbon atoms, and a substituted or unsubstituted alkylthio group having 1 to 4 carbon atoms. In addition, $A^1$ to $A^3$ individually represent any of nitrogen, sp$^2$ hybridized carbon bonded to hydrogen, and sp$^2$ carbon bonded to a substituent R. The substituent R represents any of an alkyl group having 1 to 4 carbon atoms, a halogen group, a haloalkyl group having 1 to 4 carbon atoms, and a phenyl group.

<<Method of synthesizing a 4-arylpyrimidine derivative represented by a general formula (G0)>>

An example of a method of synthesizing a 4-arylpyrimidine derivative represented by a general formula (G0) below is described. The 4-arylpyrimidine derivative represented by the general formula (G0) below can be synthesized by any of synthesis schemes (a), (a'), and (a"), which are simple as illustrated below.

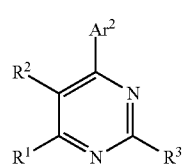

In the general formula (G0), $R^1$ represents a substituted or unsubstituted alkyl group having 1 to 4 carbon atoms or a substituted or unsubstituted aryl group having 6 to 10 carbon atoms, $R^2$ represents any of hydrogen, a substituted or unsubstituted alkyl group having 1 to 4 carbon atoms, and a substituted or unsubstituted phenyl group, $R^3$ represents hydrogen or a substituted or unsubstituted alkyl group having 1 to 4 carbon atoms, and $Ar^2$ represents a substituted or unsubstituted aryl group having 6 to 10 carbon atoms.

For example, as illustrated in the synthesis scheme (a), arylboronic acid (A1) is coupled with a halogenated pyrimidine compound (A2), whereby the 4-arylpyrimidine derivative represented by the general formula (G0) is obtained.

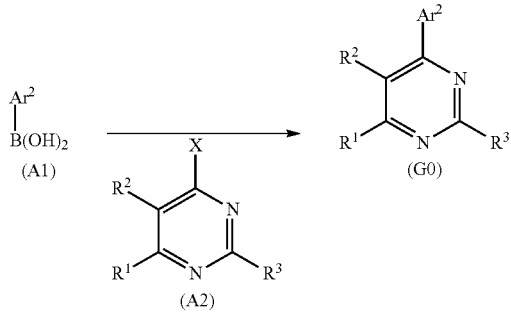

In the synthesis scheme (a), X represents halogen, $R^1$ represents a substituted or unsubstituted alkyl group having 1 to 4 carbon atoms or a substituted or unsubstituted aryl group having 6 to 10 carbon atoms, $R^2$ represents any of hydrogen, a substituted or unsubstituted alkyl group having 1 to 4 carbon atoms, and a substituted or unsubstituted phenyl group, $R^3$ represents hydrogen or a substituted or unsubstituted alkyl group having 1 to 4 carbon atoms, and $Ar^2$ represents a substituted or unsubstituted aryl group having 6 to 10 carbon atoms.

Alternatively, as illustrated in the synthesis scheme (a'), an aryllithium compound or a Grignard reagent illustrated in (A1') is reacted with a pyrimidine compound (A2'), whereby the 4-arylpyrimidine derivative represented by the general formula (G0) is obtained.

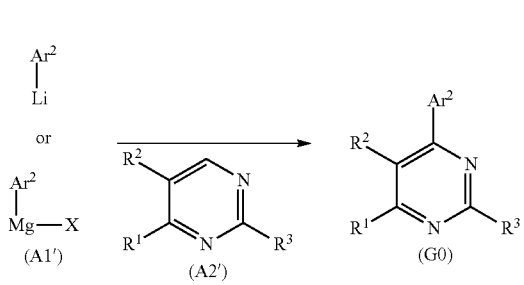

In the synthesis scheme (a'), X represents halogen, $R^1$ represents a substituted or unsubstituted alkyl group having 1 to 4 carbon atoms or a substituted or unsubstituted aryl group having 6 to 10 carbon atoms, $R^2$ represents any of hydrogen, a substituted or unsubstituted alkyl group having 1 to 4 carbon atoms, and a substituted or unsubstituted phenyl group, $R^3$ represents hydrogen or a substituted or unsubstituted alkyl group having 1 to 4 carbon atoms, and $Ar^2$ represents a substituted or unsubstituted aryl group having 6 to 10 carbon atoms.

Further alternatively, as illustrated in the synthesis scheme (a"), 1,3-diketone (A1") of aryl is reacted with amidine (A2"), whereby the 4-arylpyrimidine derivative represented by the general formula (G0) is obtained.

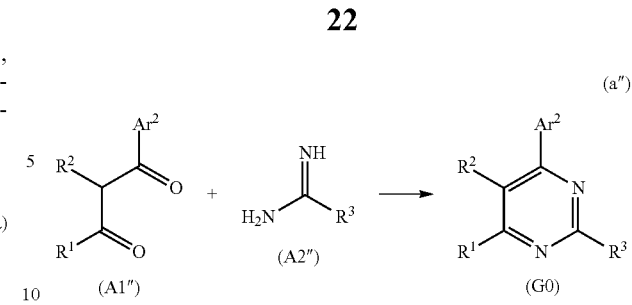

Note that in the case where $R^3$ is hydrogen in the general formula (G0), as shown in Non-Patent Document (H. Bredereck, R. Gompper, G. Morlock, "Chemische Berichte," 90, 942 (1957)), 1,3-diketone (A1") of aryl is reacted with formamide by heating them in the presence of an acid catalyst, whereby the 4-arylpyrimidine derivative represented by the general formula (G0) is obtained.

In the synthesis scheme (a"), $R^1$ represents a substituted or unsubstituted alkyl group having 1 to 4 carbon atoms or a substituted or unsubstituted aryl group having 6 to 10 carbon atoms, $R^2$ represents any of hydrogen, a substituted or unsubstituted alkyl group having 1 to 4 carbon atoms, and a substituted or unsubstituted phenyl group, $R^3$ represents hydrogen or a substituted or unsubstituted alkyl group having 1 to 4 carbon atoms, and $Ar^2$ represents a substituted or unsubstituted aryl group having 6 to 10 carbon atoms.

Since the above-described compounds (A1), (A2), (A1'), (A2'), (A1"), and (A2") are commercially available as a wide variety of compounds or their synthesis is feasible, a great variety of the 4-arylpyrimidine, derivative can be synthesized as the 4-arylpyrimidine derivative represented by the general formula (G0). Thus, a feature of the organometallic complex which is one embodiment of the present invention is the abundance of ligand variations.

<<Method of synthesizing organometallic complexes, each of which is one embodiment of the present invention, represented by general formulas (G4) and (G7)>>

Next, described are methods of synthesizing organometallic complexes represented by general formulas (G4) and (G7) below, which are specific preferable examples of an organometallic complex which is one embodiment of the present invention formed by ortho-metallation of the 4-arylpyrimidine derivative represented by the general formula (G0).

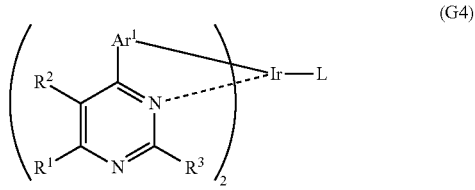

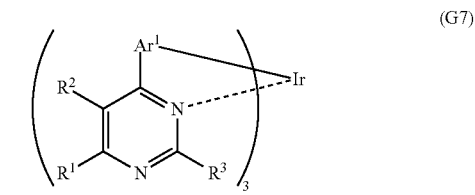

In the general formula (G4) and the general formula (G7), L represents a monoanionic ligand. In addition, $R^1$ represents a substituted or unsubstituted alkyl group having 1 to 4 carbon atoms or a substituted or unsubstituted aryl group having 6 to 10 carbon atoms, $R^2$ represents any of hydrogen, a substituted or unsubstituted alkyl group having 1 to 4 carbon atoms, and a substituted or unsubstituted phenyl group, $R^3$ represents hydrogen or a substituted or unsubstituted alkyl group having 1 to 4 carbon atoms, and $Ar^1$ represents a substituted or unsubstituted arylene group having 6 to 10 carbon atoms.

<Method of synthesizing an organometallic complex which is one embodiment of the present invention represented by the general formula (G4)>

First, as illustrated in a synthesis scheme (b) below, a 4-arylpyrimidine derivative represented by the general formula (G0) and a halogenated iridium compound (e.g., iridium chloride, iridium bromide, or iridium iodide, preferably iridium trichloride hydrate) are heated in an inert gas atmosphere by using no solvent, an alcohol-based solvent (e.g., glycerol, ethylene glycol, 2-metoxyethanol, or 2-ethoxyethanol) alone, or a mixed solvent of water and one or more of the alcohol-based solvents, whereby a Binuclear complex (B), which is one type of an organometallic complex including a halogen-bridged structure and is a novel substance, can be obtained. Although there is no particular limitation on a heating means, an oil bath, a sand bath, or an aluminum block may be used. Alternatively, microwaves can be used as a heating means.

ment of the present invention represented by the general formula (G4) can be obtained. Although there is no particular limitation on a heating means, an oil bath, a sand bath, or an aluminum block may be used. Alternatively, microwaves can be used as a heating means.

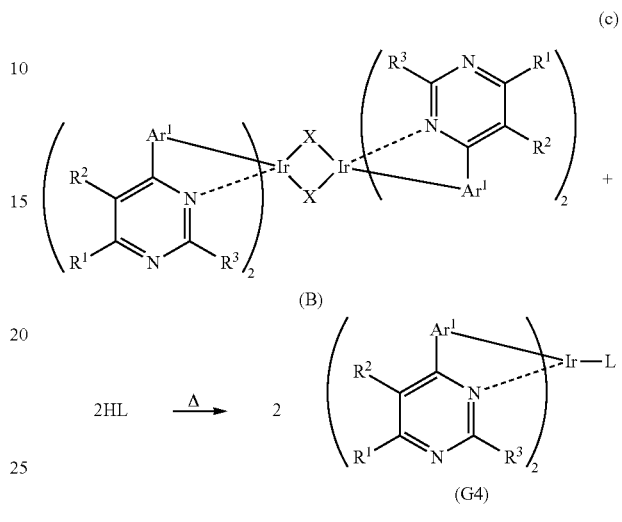

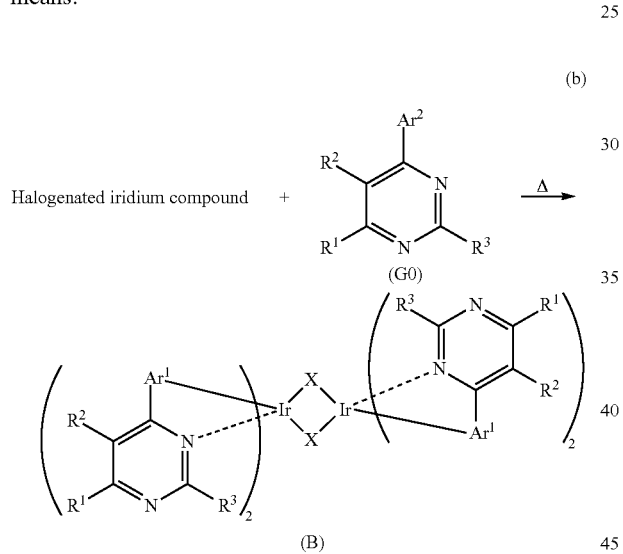

In the synthesis scheme (b), X represents halogen, $R^1$ represents a substituted or unsubstituted alkyl group having 1 to 4 carbon atoms or a substituted or unsubstituted aryl group having 6 to 10 carbon atoms, $R^2$ represents any of hydrogen, a substituted or unsubstituted alkyl group having 1 to 4 carbon atoms, and a substituted or unsubstituted phenyl group, and $R^3$ represents hydrogen or a substituted or unsubstituted alkyl group having 1 to 4 carbon atoms. In addition, $Ar^1$ represents a substituted or unsubstituted arylene group having 6 to 10 carbon atoms, and $Ar^2$ represents a substituted or unsubstituted aryl group having 6 to 10 carbon atoms.

Furthermore, as illustrated in a synthesis scheme (c) below, the dinuclear complex (B) obtained in the above synthesis scheme (b) is reacted with HL which is a material of a monoanionic ligand in an inert gas atmosphere, whereby a proton of HL is separated and coordinated to the central metal Ir. Thus, the organometallic complex which is one embodi- In the synthesis scheme (c), L represents a monoanionic ligand, X represents halogen, $R^1$ represents a substituted or unsubstituted alkyl group having 1 to 4 carbon atoms or a substituted or unsubstituted aryl group having 6 to 10 carbon atoms, $R^2$ represents any of hydrogen, a substituted or unsubstituted alkyl group having 1 to 4 carbon atoms, and a substituted or unsubstituted phenyl group, $R^3$ represents hydrogen or a substituted or unsubstituted alkyl group having 1 to 4 carbon atoms, and $Ar^1$ represents a substituted or unsubstituted arylene group having 6 to 10 carbon atoms.

In the present invention, as described above, a substituent is introduced to the 6-position of pyrimidine (i.e., R') in order to obtain an ortho-metallated complex in which the 4-arylpyrimidine derivative is a ligand. In particular, a substituted or unsubstituted alkyl group having 1 to 4 carbon atoms or a substituted or unsubstituted aryl group having 6 to 10 carbon atoms is used in $R^1$. Therefore, as compared to the case where hydrogen is used in $R^1$, decomposition of the halogen-bridged dinuclear metal complex synthesized in the synthesis scheme (b) is suppressed during reaction represented by the synthesis scheme (c), and a drastically high yield can be obtained.

Note that the monoanionic ligand L in the general formula (G4) is preferably any of a monoanionic bidentate chelate ligand having a beta-diketone structure, a monoanionic bidentate chelate ligand having a carboxyl group, a monoanionic bidentate chelate ligand having a phenolic hydroxyl group, and a monoanionic bidentate chelate ligand in which two ligand elements are both nitrogen. A monoanionic bidentate chelate ligand having a beta-diketone structure is particularly preferable. A beta-diketone structure is preferably included for higher solubility of an organometallic complex in an organic solvent and easier purification. A beta-diketone structure is preferably included for realization of an organometallic complex with high emission efficiency. Inclusion of a beta-diketone structure has advantages such as a higher sublimation property and excellent evaporativity.

The monoanionic ligand is preferably a ligand represented by any of general formulas (L1) to (L7). Since these ligands have high coordinative ability and can be obtained at low price, they are useful.

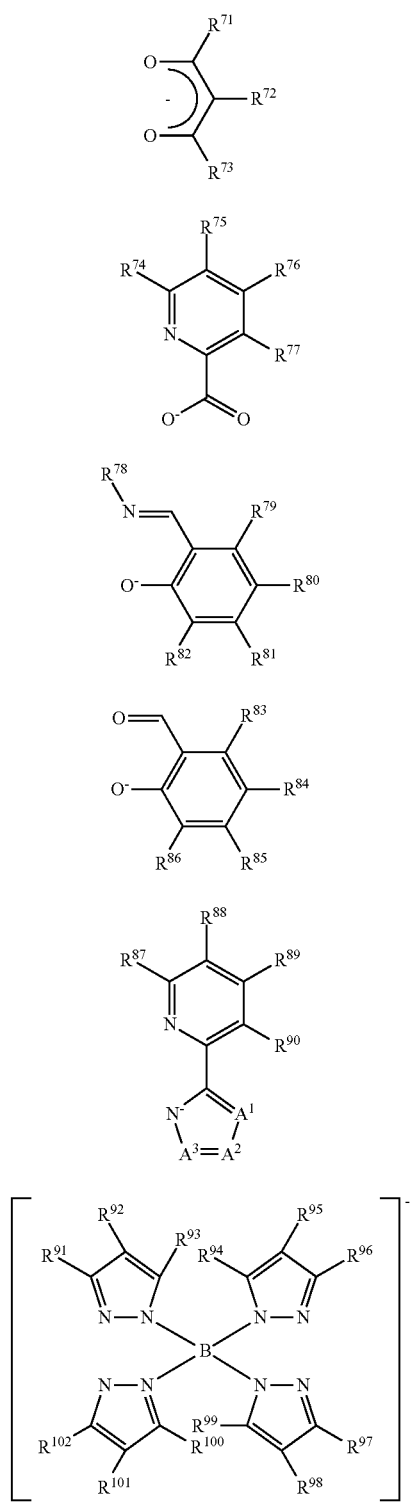

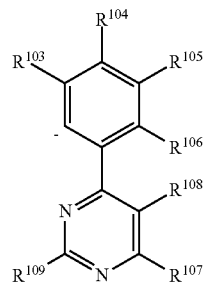

In the general formulas (L1) to (L7), $R^{71}$ to $R^{109}$ individually represent any of hydrogen, a substituted or unsubstituted alkyl group having 1 to 4 carbon atoms, a halogen group, a vinyl group, a substituted or unsubstituted haloalkyl group having 1 to 4 carbon atoms, a substituted or unsubstituted alkoxy group having 1 to 4 carbon atoms, and a substituted or unsubstituted alkylthio group having 1 to 4 carbon atoms. In addition, $A^1$ to $A^3$ individually represent any of nitrogen, sp$^2$ hybridized carbon bonded to hydrogen, and sp$^2$ carbon bonded to a substituent R. The substituent R represents any of an alkyl group having 1 to 4 carbon atoms, a halogen group, a haloalkyl group having 1 to 4 carbon atoms, and a phenyl group.

<Method of Synthesizing an Organometallic Complex which is One Embodiment of the Present Invention Represented by the General Formula (G7)>

The organometallic complex represented by the general formula (G7), which is one embodiment of the present invention, can be synthesized by a synthesis scheme (d) below. That is, a 4-arylpyrimidine derivative represented by the general formula (G0) is mixed with a halogenated iridium compound (e.g., iridium chloride, iridium bromide, or iridium iodide, preferably iridium trichloride hydrate) or an iridium organometallic complex compound (e.g., an acetylacetonate complex or a diethylsulfide complex) and then they are heated, whereby the organometallic complex having a structure represented by the general formula (G7) can be obtained. This heating process may be performed after dissolving the 4-arylpyrimidine derivative represented by the general formula (G0) and the halogenated iridium compound or the iridium organometallic complex compound in an alcohol-based solvent (e.g., glycerol, ethylene glycol, 2-metoxyethanol, or 2-ethoxyethanol). Although there is no particular limitation on a heating means, an oil bath, a sand bath, or an aluminum block may be used. Alternatively, microwaves can be used as a heating means.

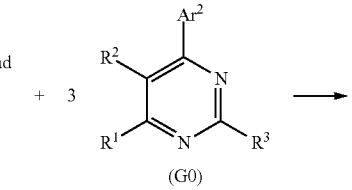

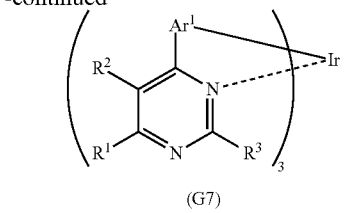

(G7)

In the synthesis scheme (d), $R^1$ represents a substituted or unsubstituted alkyl group having 1 to 4 carbon atoms or a substituted or unsubstituted aryl group having 6 to 10 carbon atoms, $R^2$ represents any of hydrogen, a substituted or unsubstituted alkyl group having 1 to 4 carbon atoms, and a substituted or unsubstituted phenyl group, and $R^3$ represents hydrogen or a substituted or unsubstituted alkyl group having 1 to 4 carbon atoms. In addition, $Ar^1$ represents a substituted or unsubstituted arylene group having 6 to 10 carbon atoms, and $Ar^2$ represents a substituted or unsubstituted aryl group having 6 to 10 carbon atoms.

In the present invention, as described above, a substituent is introduced to the 6-position of pyrimidine (i.e., $R^1$) in order to obtain an ortho-metallated complex in which the 4-arylpyrimidine derivative is a ligand. In particular, a substituted or unsubstituted alkyl group having 1 to 4 carbon atoms or a substituted or unsubstituted aryl group having 6 to 10 carbon atoms is used in R'. Therefore, as compared to the case where hydrogen is used in $R^1$, the yield in the synthesis scheme (d) can be higher.

Although examples of the synthesis methods are described above, organometallic complexes which are disclosed embodiments of the present invention may be synthesized by any other synthesis method.

Specific structural formulas of an organometallic complex which is one embodiment of the present invention are illustrated in structural formula (100) to (201) below. However, the present invention is not limited thereto.

(100)

(101)

(102)

(103)

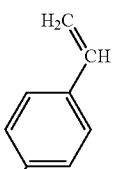

(104)

(105)

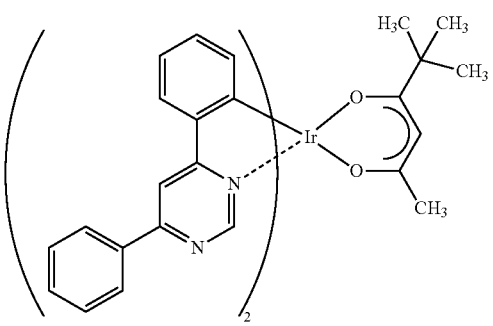

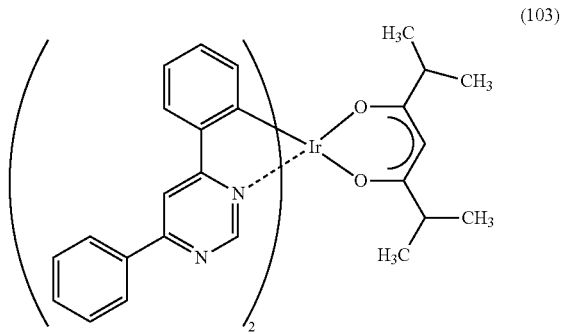

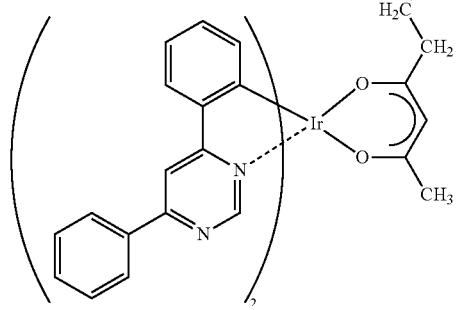

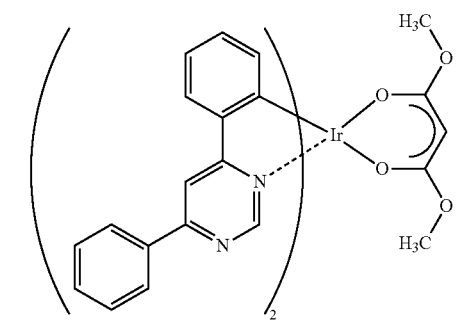

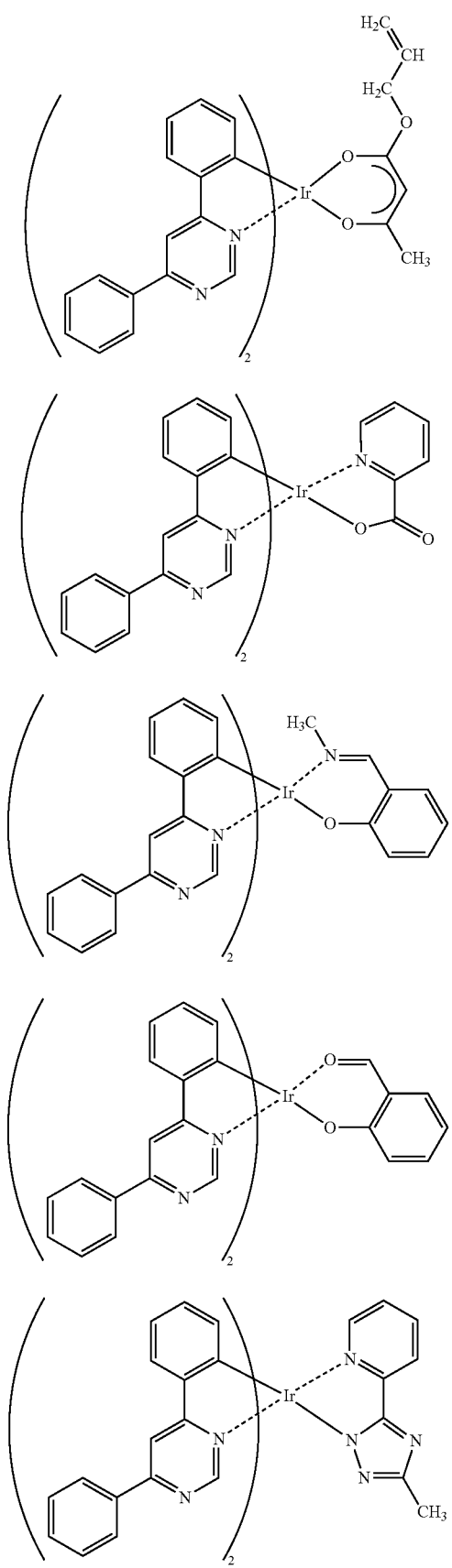

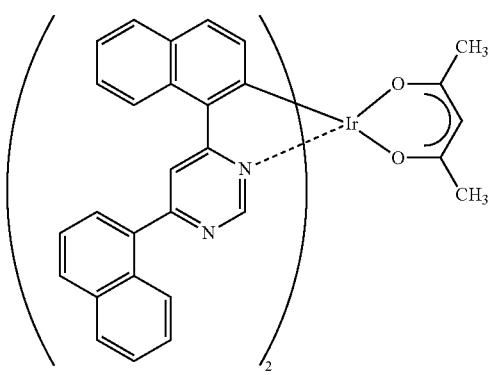 (115)
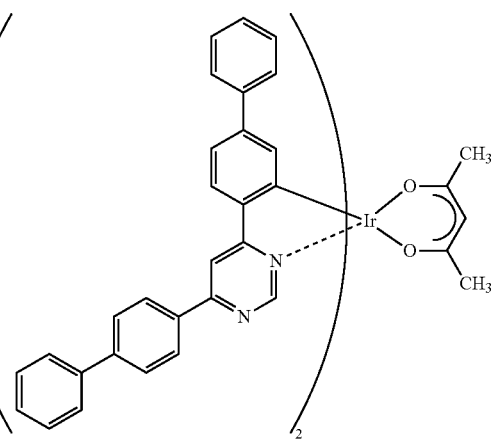 (118)
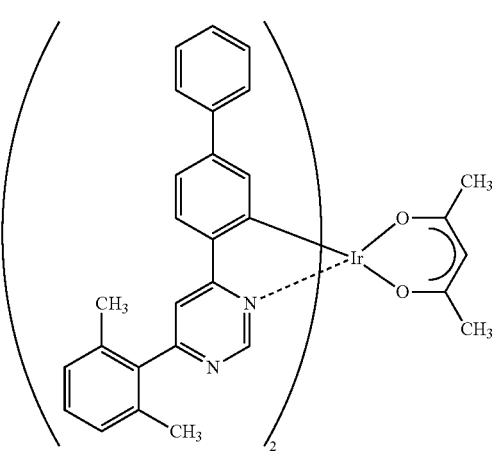 (116)
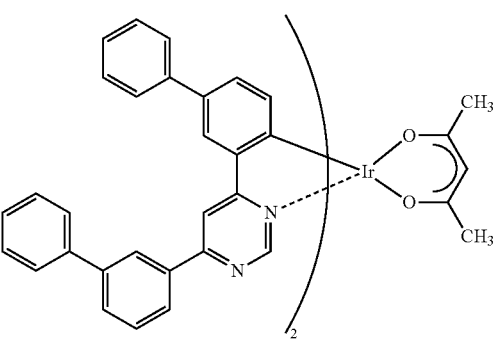 (119)
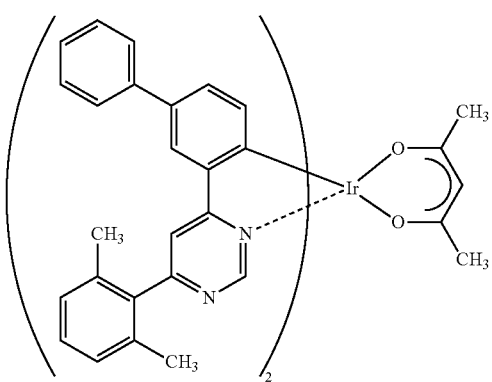 (117)
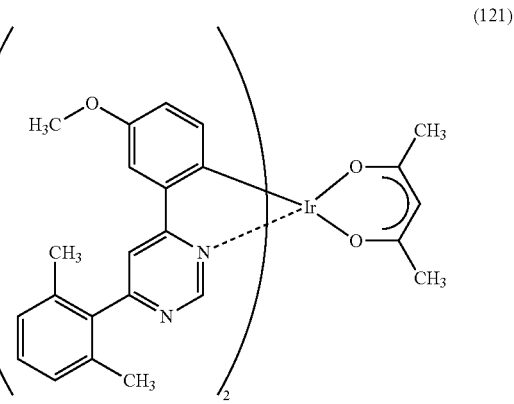 (120)
(121)

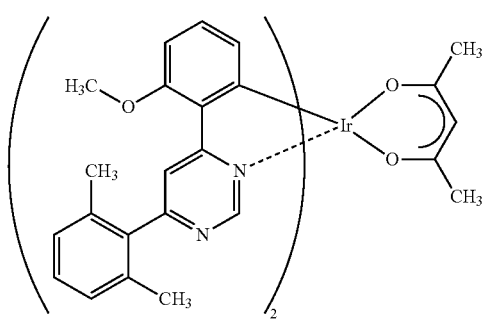
(122)
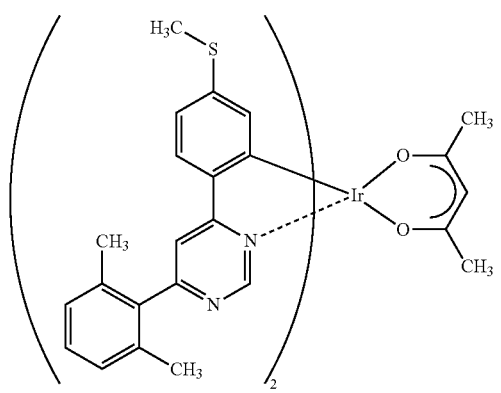
(126)
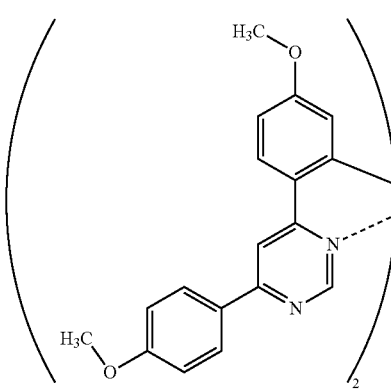
(123)
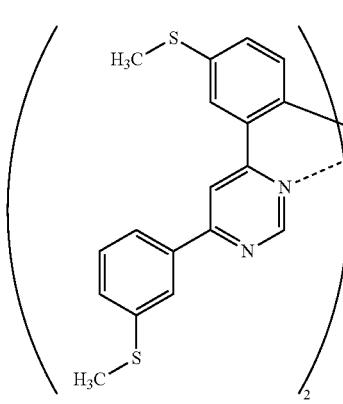
(127)
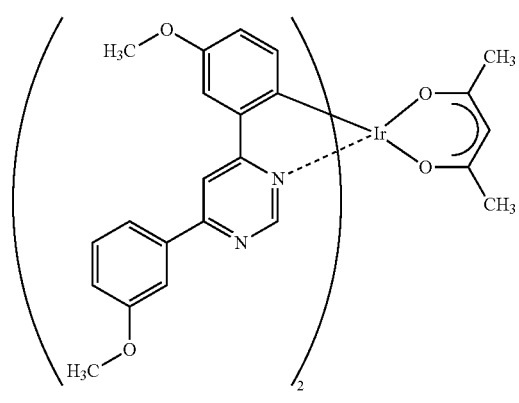
(124)
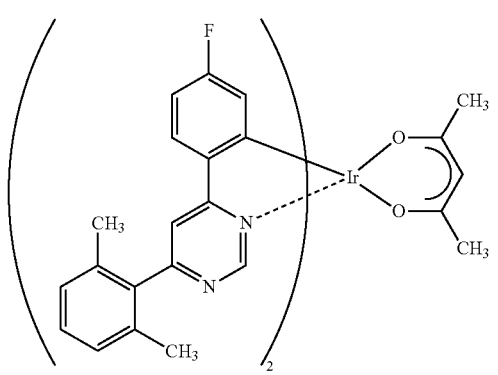
(128)
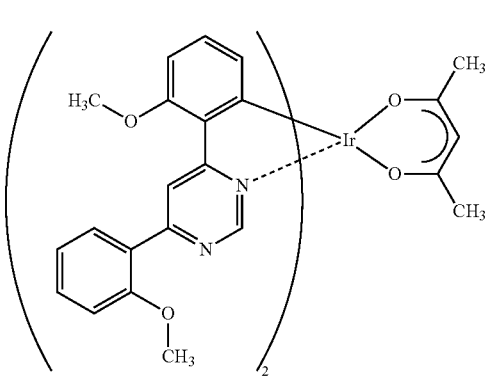
(125)
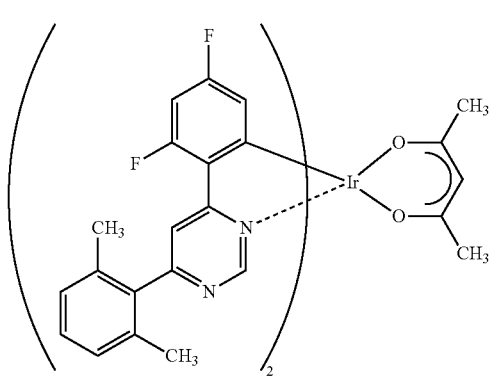
(129)

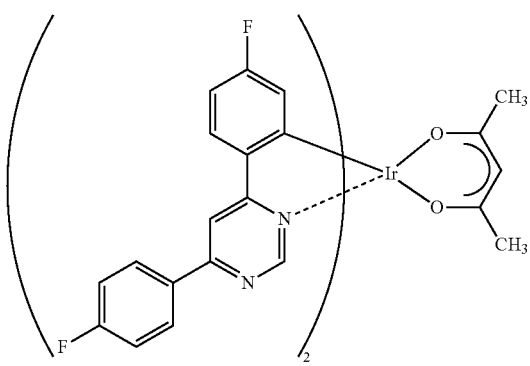
(130)
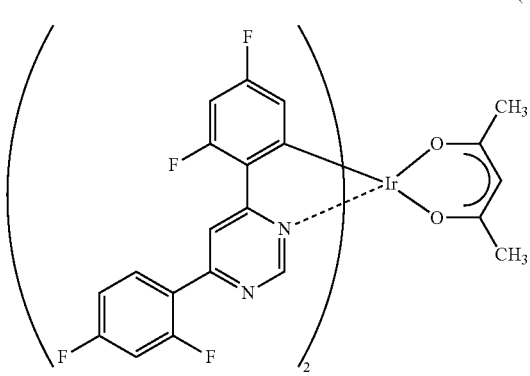
(131)
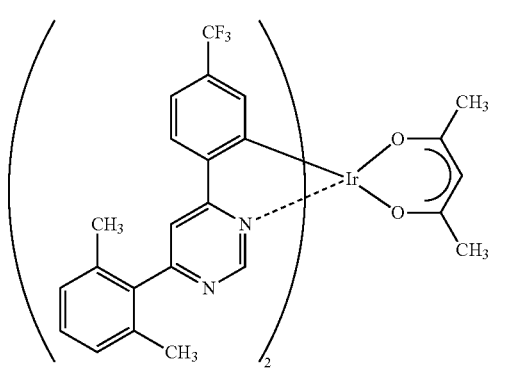
(132)
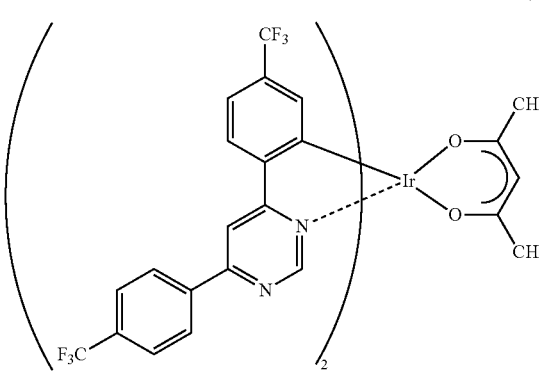
(133)
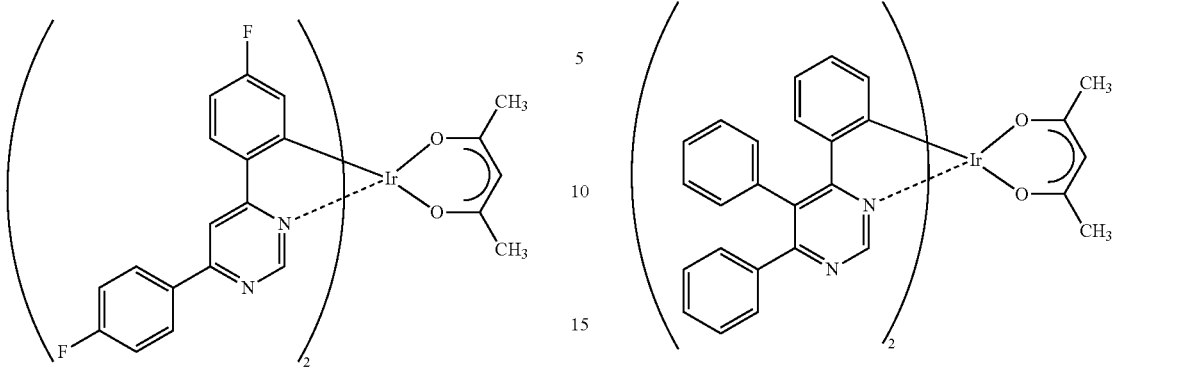
(134)
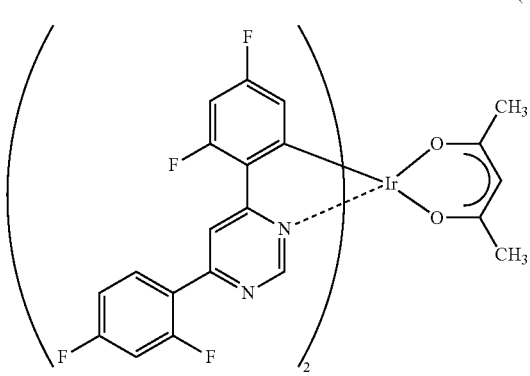
(135)
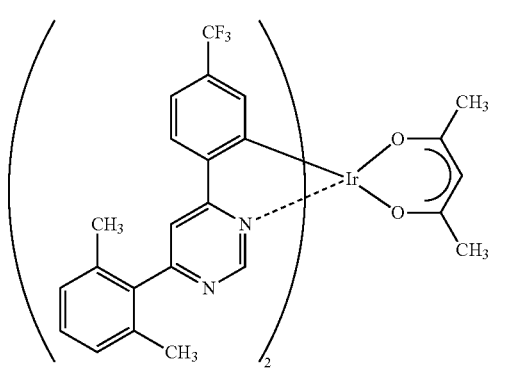
(136)
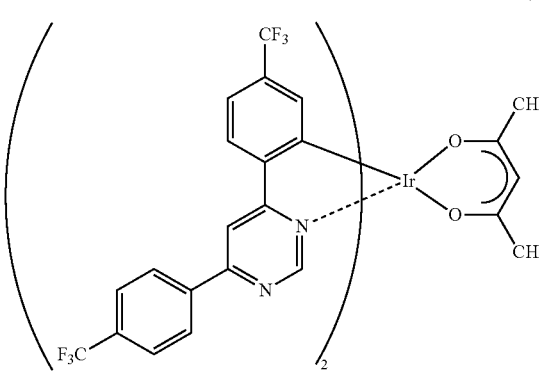
(137)
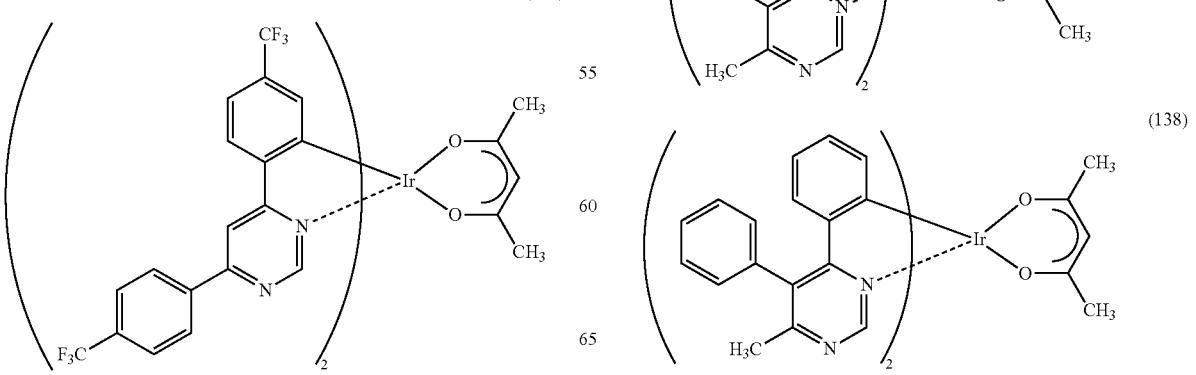
(138)

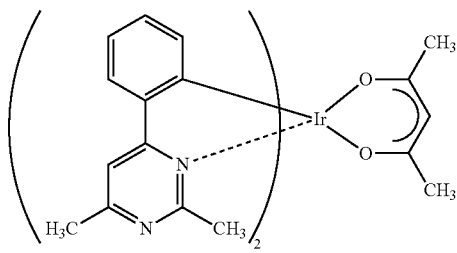
(139)
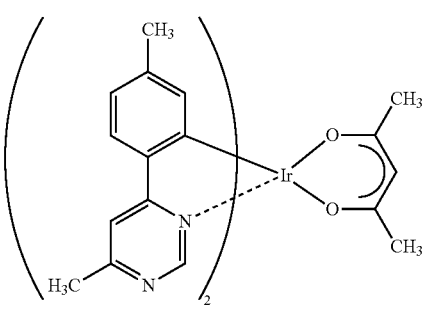
(144)
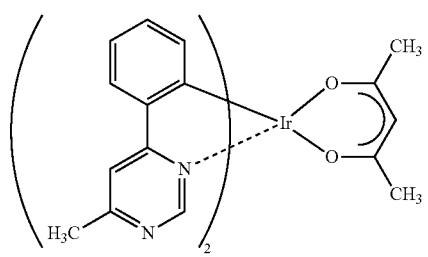
(140)
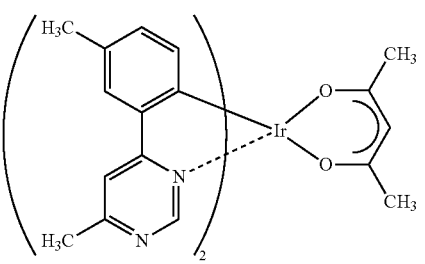
(145)
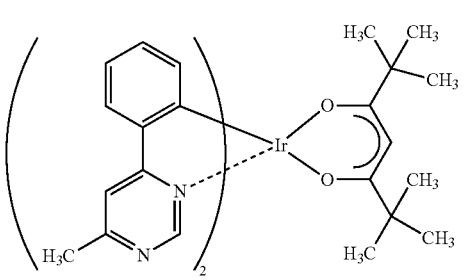
(141)
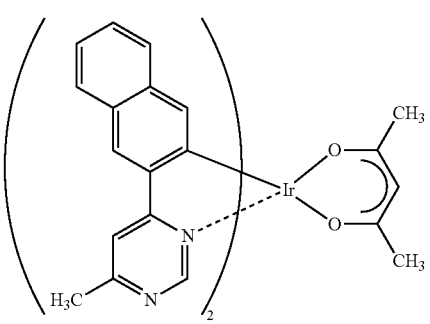
(146)
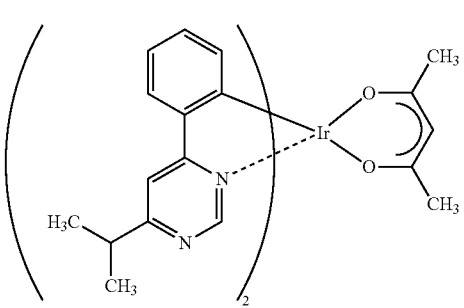
(142)
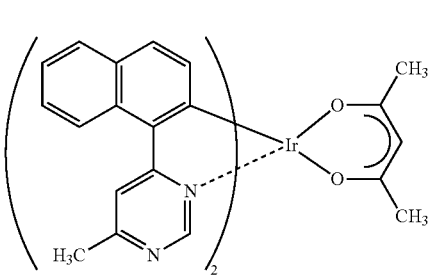
(147)
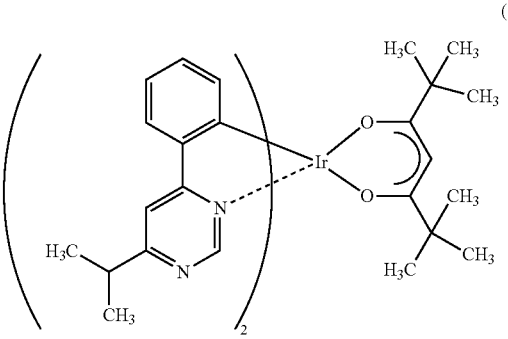
(143)
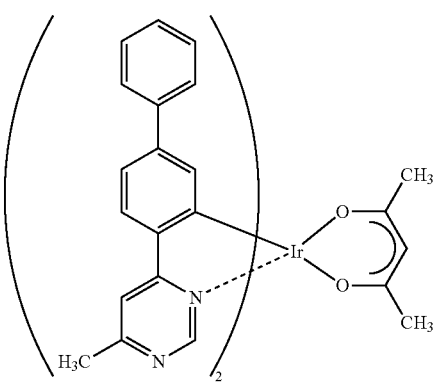
(148)

(149)
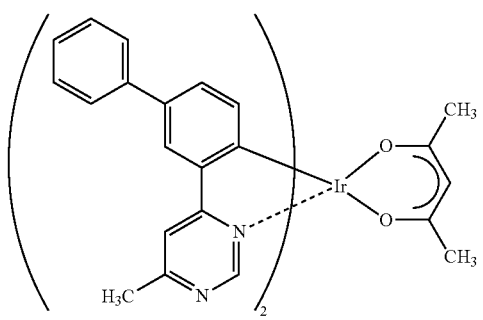
(150)
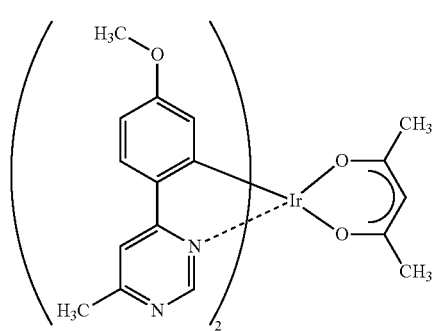
(151)
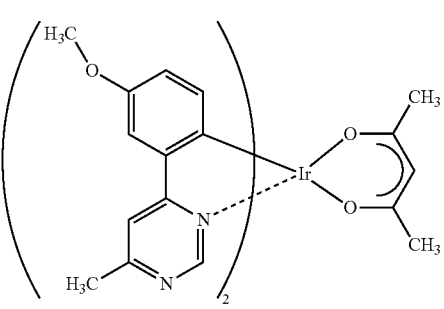
(152)
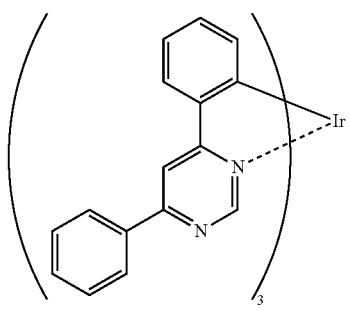
(153)
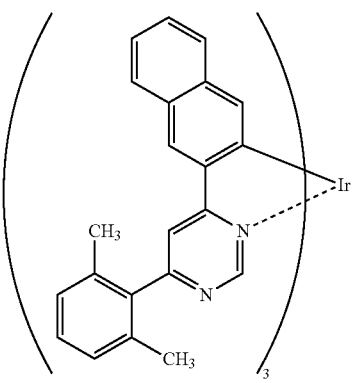
(154)
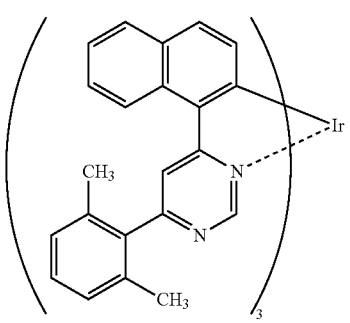
(155)
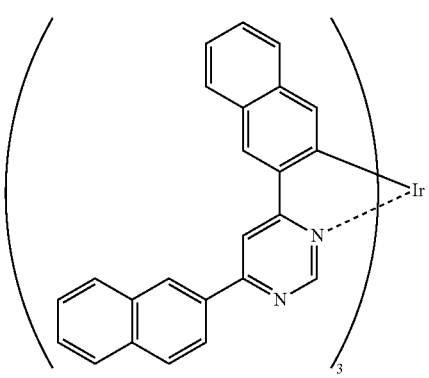
(156)
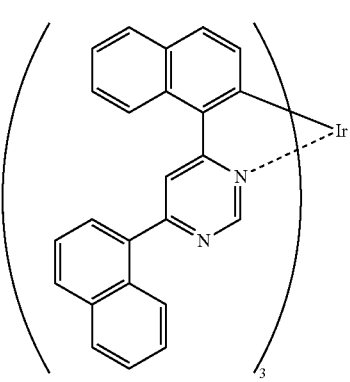
(157)
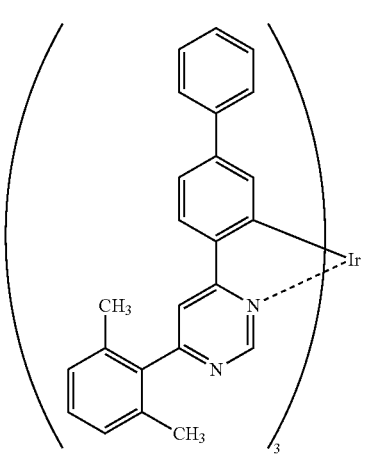

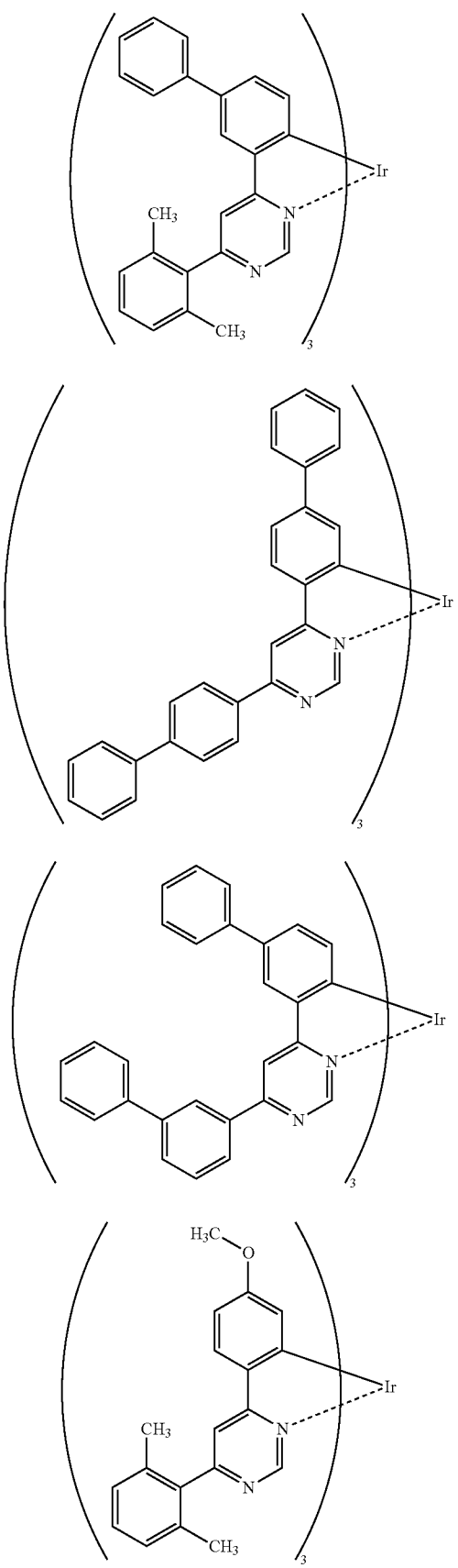
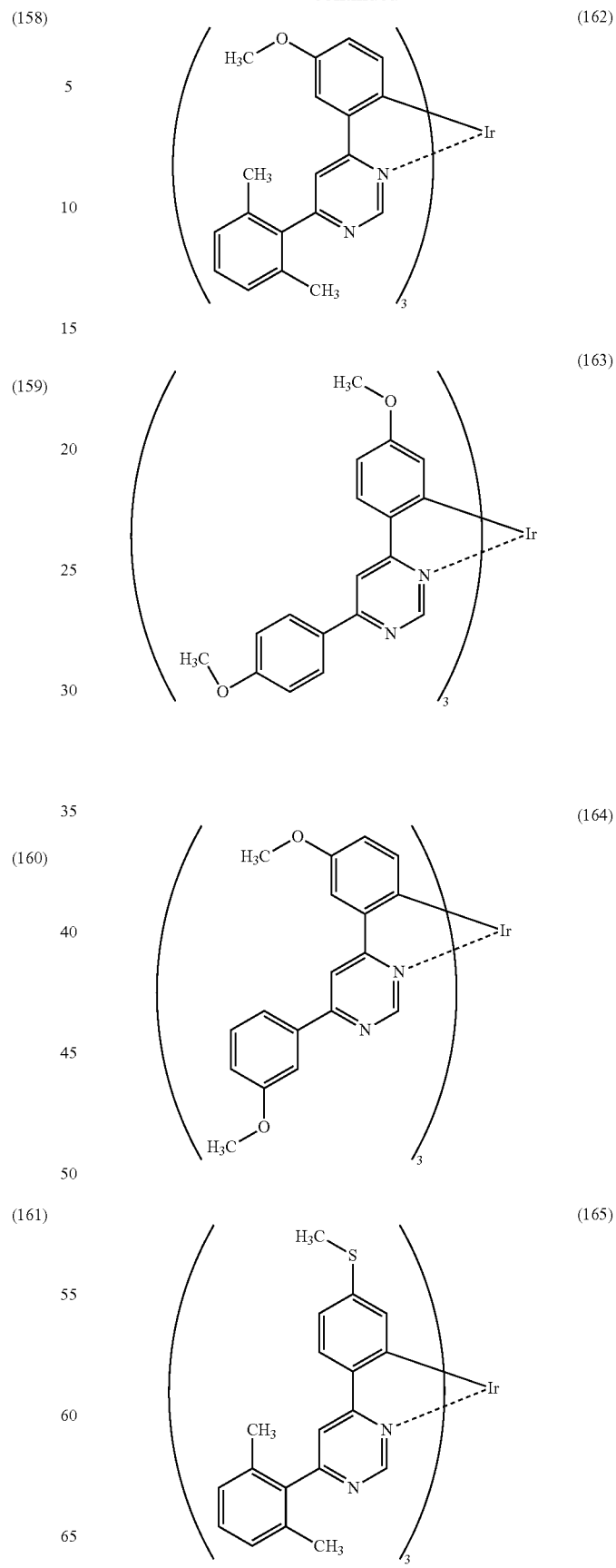

(166) 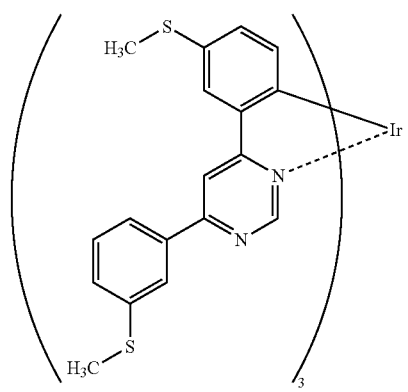
(167) 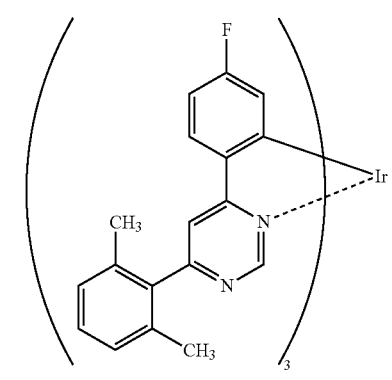
(168) 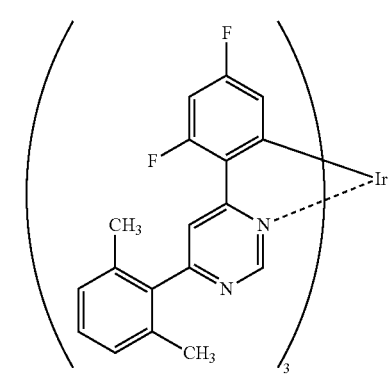
(169) 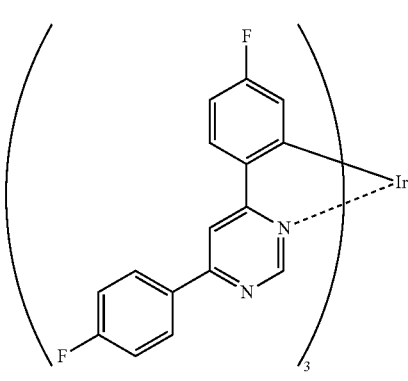
(170) 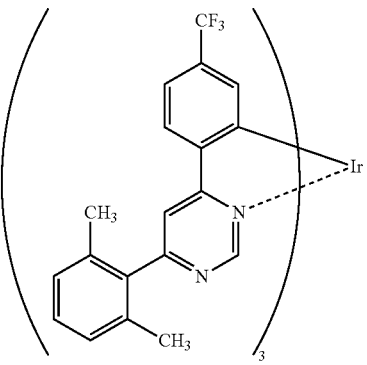
(171) 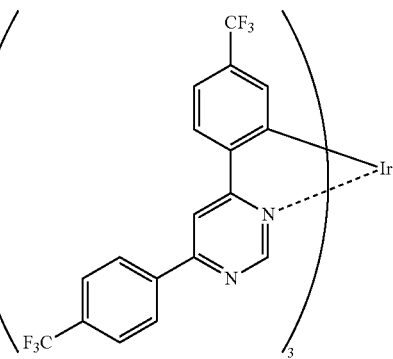
(172) 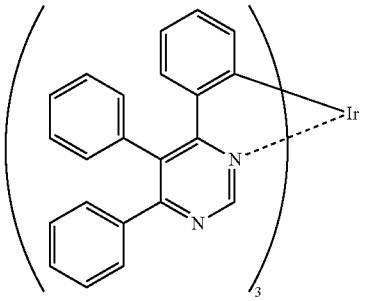
(173) 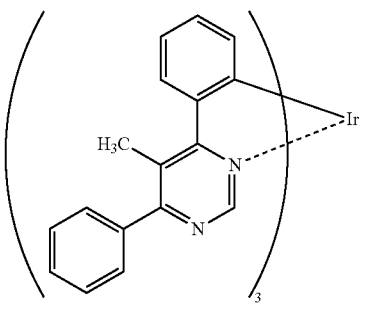
(174) 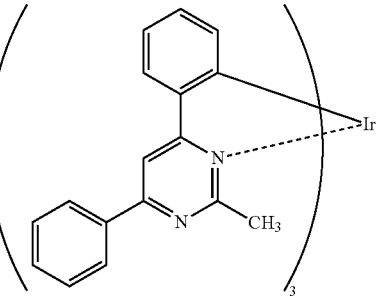

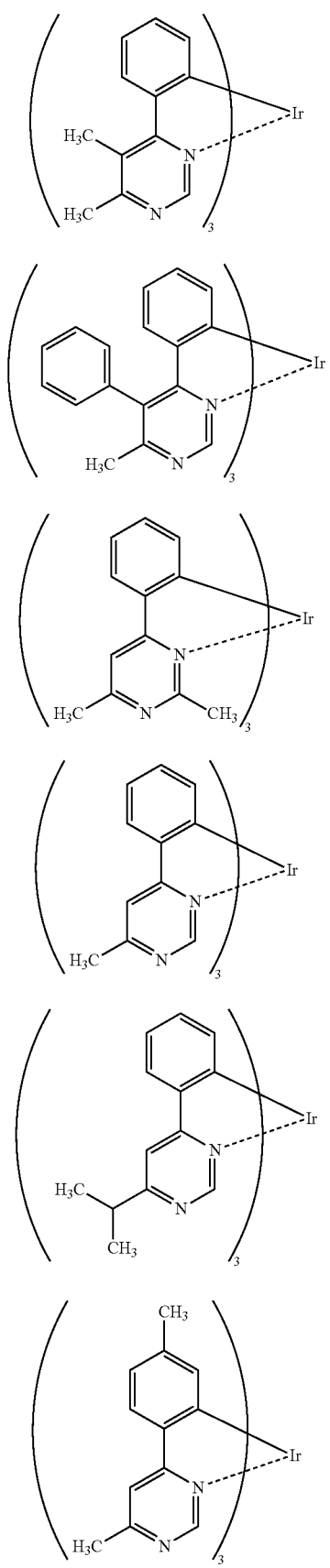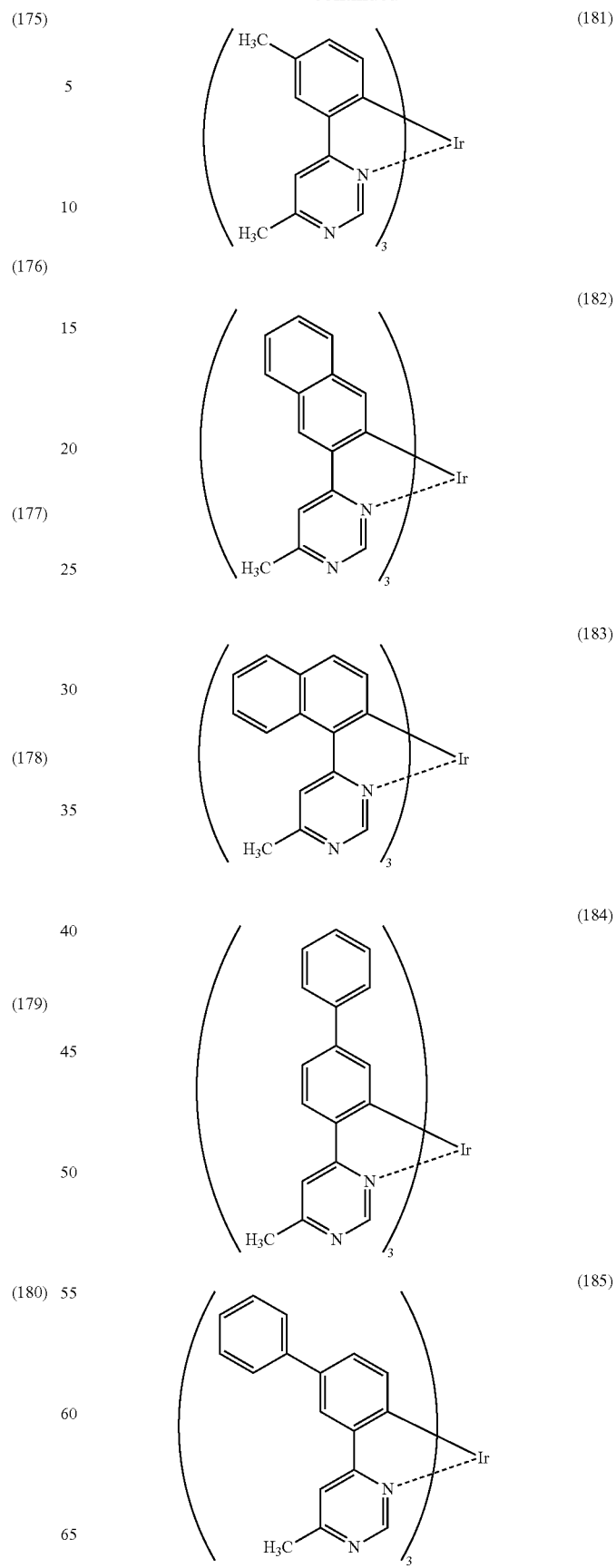

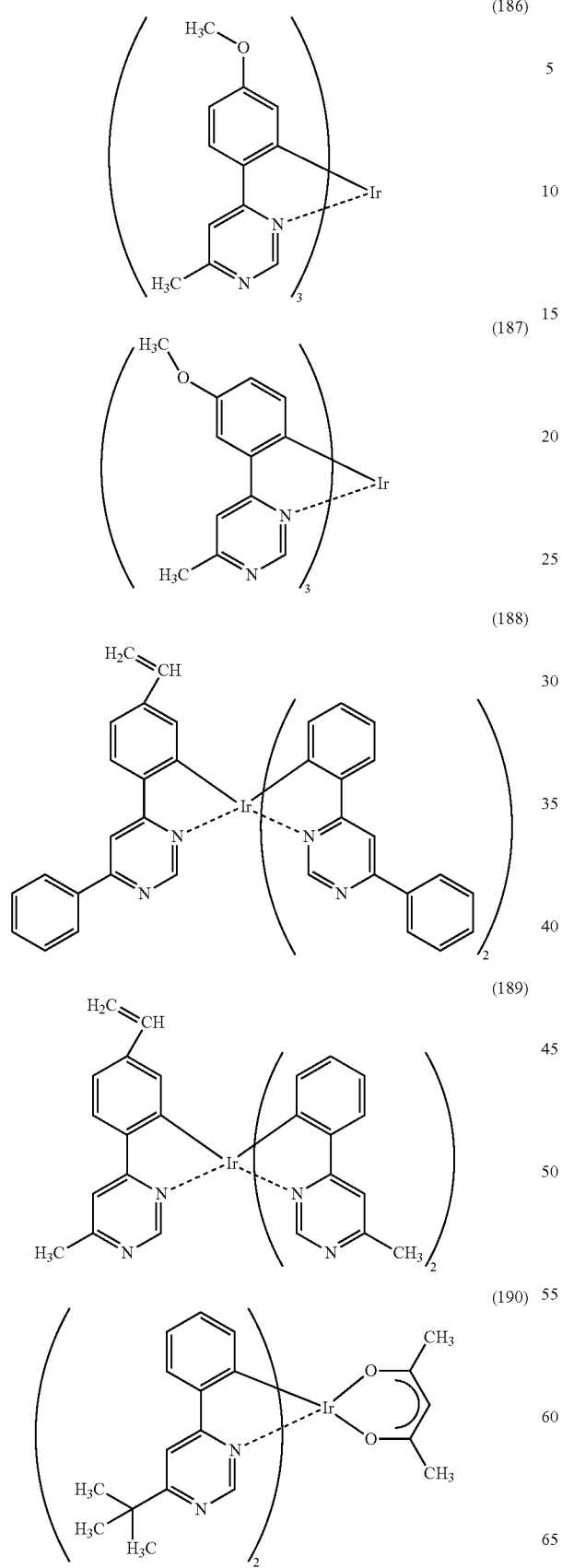
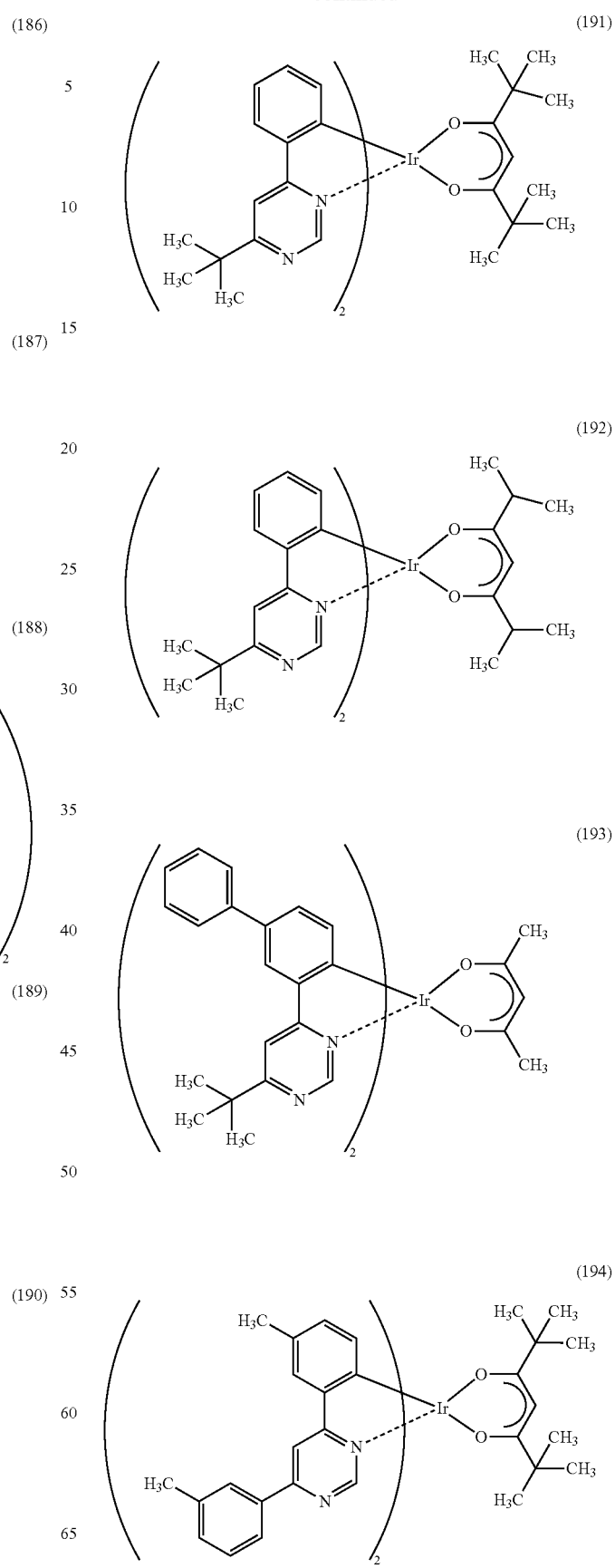

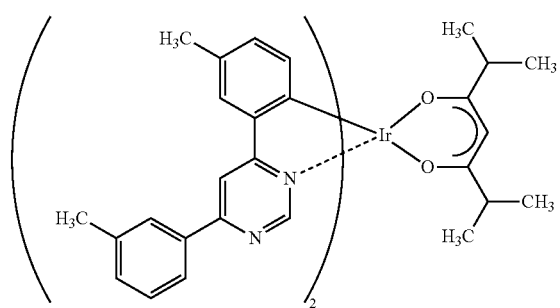

(195)

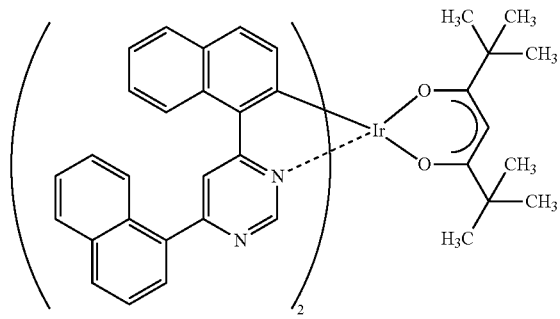

(196)

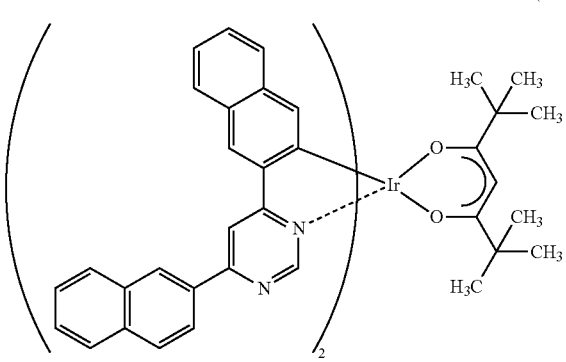

(197)

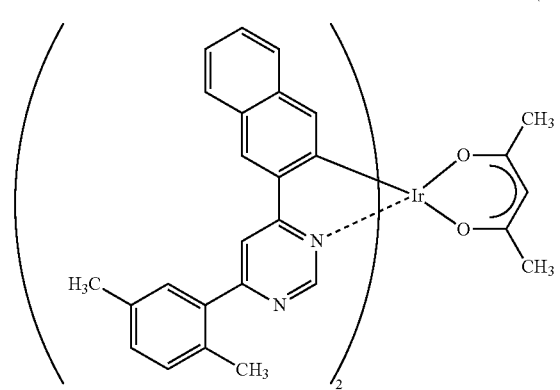

(198)

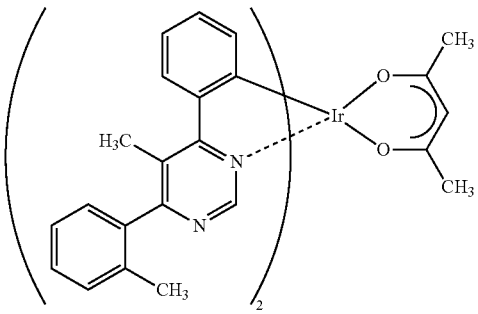

(199)

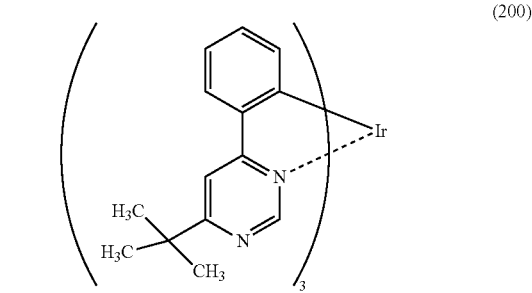

(200)

(201)

Depending on the type of the ligand, there can be stereoisomers of the organometallic complexes represented by the structural formulas (100) to (201) above, and such isomers are included in the category of organometallic complexes which are embodiments of the present invention.

Any above-described organometallic complex which is one embodiment of the present invention can emit phosphorescence and has a broad emission spectrum in the wavelength range of red to green, and thus can be used as a light-emitting material or a light-emitting substance of a light-emitting element.

With the use of the organometallic complex which is one embodiment of the present invention, a light-emitting element, a light-emitting device, an electronic device, or a lighting device with high emission efficiency can be realized. Alternatively, a light-emitting element, a light-emitting device, an electronic device, or a lighting device with low power consumption can be realized.

With the use of the organometallic complex which is one embodiment of the present invention, a light-emitting element, a light-emitting device, an electronic device, or a lighting device with high reliability can be realized.

In Embodiment 1, any of the structures described in another embodiment can be used in appropriate combination.

(Embodiment 2)

In Embodiment 2, as one embodiment of the present invention, a light-emitting element in which any of the organometallic complexes described in Embodiment 1 is used for a light-emitting layer is described with reference to FIG. 1A.

FIG. 1A illustrates a light-emitting element having an EL layer 102 between a first electrode 101 and a second electrode 103. The EL layer 102 includes a light-emitting layer 113. The light-emitting layer 113 contains any of the organometallic complexes each of which is one embodiment of the present invention described in Embodiment 1.

By application of a voltage to such a light-emitting element, holes injected from the first electrode 101 side and electrons injected from the second electrode 103 side recombine in the light-emitting layer 113 to raise the organometallic complex to an excited state. Light is emitted when the organometallic complex in the excited state returns to the ground state. Thus, the organometallic complex which is one embodiment of the present invention functions as a light-emitting substance in the light-emitting element. Note that in the light-emitting element described in this embodiment, the first electrode 101 functions as an anode and the second electrode 103 functions as a cathode.

For the first electrode 101 functioning as an anode, any of metals, alloys, electrically conductive compounds, mixtures thereof, and the like which has a high work function (specifically, a work function of 4.0 eV or more) is preferably used. Specific examples are given below: indium oxide-tin oxide (ITO: indium tin oxide), indium oxide-tin oxide containing silicon or silicon oxide, indium oxide-zinc oxide (IZO: indium zinc oxide), indium oxide containing tungsten oxide and zinc oxide, and the like. Besides, gold, platinum, nickel, tungsten, chromium, molybdenum, iron, cobalt, copper, palladium, titanium, or the like can be used.

Note that, in the EL layer 102, when a layer in contact with the first electrode 101 is formed using a composite material in which an organic compound and an electron acceptor (acceptor) described below are mixed, the first electrode 101 can be formed using any of a variety of metals, alloys, and electrically conductive compounds, a mixture thereof, and the like regardless of the work function. For example, aluminum (Al), silver (Ag), an alloy containing aluminum (e.g., Al—Si), or the like can be used.

The first electrode 101 can be formed by, for example, a sputtering method, an evaporation method (including a vacuum evaporation method), or the like.

The EL layer 102 formed over the first electrode 101 includes at least the light-emitting layer 113 and is formed by containing an organometallic complex which is one embodiment of the present invention. For a part of the EL layer 102, a known substance can be used, and either a low molecular compound or a high molecular compound can be used. Note that substances forming the EL layer 102 may consist of organic compounds or may include an inorganic compound as a part.

Further, as illustrated in FIG. 1A, the EL layer 102 includes the light-emitting layer 113 and also the following layers stacked in appropriate combination: a hole-injection layer 111 containing a substance having a high hole-injection property, a hole-transport layer 112 containing a substance having a high hole-transport property, an electron-transport layer 114 containing a substance having a high electron-transport property, an electron-injection layer 115 containing a substance having a high electron-injection property, and the like.

The hole-injection layer 111 is a layer containing a substance having a high hole-injection property. As the substance having a high hole-injection property, metal oxide such as molybdenum oxide, titanium oxide, vanadium oxide, rhenium oxide, ruthenium oxide, chromium oxide, zirconium oxide, hafnium oxide, tantalum oxide, silver oxide, tungsten oxide, or manganese oxide can be used. A phthalocyanine-based compound such as phthalocyanine (abbreviation: $H_2Pc$), or copper(II) phthalocyanine (abbreviation: CuPc) can also be used.

Alternatively, any of the following aromatic amine compounds which are low molecular organic compounds can be used: 4,4',4''-tris(N,N-diphenylamino)triphenylamine (abbreviation: TDATA), 4,4',4''-tris[N-(3-methylphenyl)-N-phenylamino]triphenylamine (abbreviation: MTDATA), 4,4'-bis[N-(4-diphenylaminophenyl)-N-phenylamino]biphenyl (abbreviation: DPAB), 4,4'-bis(N-{4-[N'-(3-methylphenyl)-N'-phenylamino]phenyl}-N-phenylamino)biphenyl (abbreviation: DNTPD), 1,3,5-tris[N-(4-diphenylaminophenyl)-N-phenylamino]benzene (abbreviation: DPA3B), 3-[N-(9-phenylcarbazol-3-yl)-N-phenylamino]-9-phenylcarbazole (abbreviation: PCzPCA1), 3,6-bis[N-(9-phenylcarbazol-3-yl)-N-phenylamino]-9-phenylcarbazole (abbreviation: PCzPCA2), 3-[N-(1-naphthyl)-N-(9-phenylcarbazol-3-yl)amino]-9-phenylcarbazole (abbreviation: PCzPCN1), or the like.

Further alternatively, any of high molecular compounds (e.g., oligomers, dendrimers, or polymers) can be used. Examples of the high molecular compounds include poly(N-vinylcarbazole) (abbreviation: PVK), poly(4-vinyltriphenylamine) (abbreviation: PVTPA), poly[N-(4-{N'-[4-(4-diphenylamino)phenyl]phenyl-N'-phenylamino}phenyl) methacrylamide] (abbreviation: PTPDMA), poly[N,N'-bis(4-butylphenyl)-N,N'-bis(phenyl)benzidine (abbreviation: Poly-TPD), and the like. Alternatively, a high molecular compound to which acid is added, such as poly(3,4-ethylenedioxythiophene)/poly(styrenesulfonic acid) (PEDOT/PSS) or polyaniline/poly(styrenesulfonic acid) (PAni/PSS), can be used.

A composite material in which an organic compound and an electron acceptor (acceptor) are mixed may be used for the hole-injection layer 111. Such a composite material is excellent in a hole-injection property and a hole-transport property because holes are generated in the organic compound by the electron acceptor. In this case, the organic compound is preferably a material excellent in transporting the generated holes (a substance having a high hole-transport property).

As the organic compound for the composite material, various compounds such as an aromatic amine compound, carbazole derivatives, aromatic hydrocarbon, and a high molecular compound (such as oligomer, dendrimer, or polymer) can be used. The organic compound used for the composite material is preferably an organic compound having a high hole-transport property. Specifically, a substance having a hole mobility of $10^{-6}$ $cm^2/V \cdot s$ or higher is preferably used. However, other substances than the above described materials may also be used as long as the substances have higher hole-transport properties than electron-transport properties. The organic compounds which can be used for the composite material are specifically shown below.

Examples of an organic compound that can be used for the composite material are aromatic amine compounds, such as TDATA, MTDATA, DPAB, DNTPD, DPA3B, PCzPCA1, PCzPCA2, PCzPCN1, 4,4'-bis[N-(1-naphthyl)-N-phenylamino]biphenyl (abbreviation: NPB or α-NPD), N,N'-bis(3-methylphenyl)-N,N'-diphenyl-[1,1'-biphenyl]-4,4'-diamine (abbreviation: TPD), and 4-phenyl-4'-(9-phenylfluoren-9-yl)triphenylamine (abbreviation: BPAFLP), and carbazole derivatives, such as 4,4'-di(N-carbazolyl)biphenyl (abbreviation: CBP), 1,3,5-tris[4-(N-carbazolyl)phenyl]benzene (abbreviation: TCPB), 9-[4-(N-carbazolyl)phenyl]-10-phenylanthracene (abbreviation: CzPA), 9-phenyl-3-[4-(10-phenyl-9-anthryflphenyl]-9H-carbazole (abbreviation: PCzPA), and 1,4-bis[4-(N-carbazolyl)phenyl-2,3,5,6-tetraphenylbenzene.

Alternatively, an aromatic hydrocarbon compounds such as 2-tert-butyl-9,10-di(2-naphthyl)anthracene (abbreviation: t-BuDNA), 2-tert-butyl-9,10-di(1-naphthyl)anthracene, 9,10-bis(3,5-diphenylphenyl)anthracene (abbreviation: DPPA), 2-tert-butyl-9,10-bis(4-phenylphenyflanthracene (abbreviation: t-BuDBA), 9,10-di(2-naphthyl)anthracene (abbreviation: DNA), 9,10-diphenylanthracene (abbreviation: DPAnth), 2-tert-butylanthracene (abbreviation: t-BuAnth), 9,10-bis(4-methyl-1-naphthyl)anthracene (abbreviation: DMNA), 9,10-bis[2-(1-naphthyl)phenyl)-2-tert-butylanthracene, 9,10-bis[2-(1-naphthyl)phenyl]anthracene, 2,3,6,7-tetramethyl-9,10-di(1-naphthyl)anthracene, or the like can be used.

Further alternatively, an aromatic hydrocarbon compound such as 2,3,6,7-tetramethyl-9,10-di(2-naphthyl)anthracene, 9,9'-bianthryl, 10,10'-diphenyl-9,9'-bianthryl, 10,10'-bis(2-phenylphenyl)-9,9'-bianthryl, 10,10'-bis[(2,3,4,5,6-pentaphenyl)phenyl]-9,9'-bianthryl, anthracene, tetracene, rubrene, perylene, 2,5,8,11-tetra(tert-butyl)perylene, pentacene, coronene, 4,4'-bis(2,2-diphenylvinyl)biphenyl (abbreviation: DPVBi), or 9,10-bis[4-(2,2-diphenylvinyl)phenyl]anthracene (abbreviation: DPVPA) can be used.

Further, as the electron acceptor, organic compounds such as 7,7,8,8-tetracyano-2,3,5,6-tetrafluoroquinodimethane (abbreviation: $F_4$-TCNQ) and chloranil; and transition metal oxides can be given. In addition, oxides of metals belonging to Groups 4 to 8 in the periodic table can also be given. Specifically, vanadium oxide, niobium oxide, tantalum oxide, chromium oxide, molybdenum oxide, tungsten oxide, manganese oxide, and rhenium oxide are preferable since their electron-accepting property is high. Among them, molybdenum oxide is especially preferable since it is stable in the air and its hygroscopic property is low and is easily treated.

Note that the hole-injection layer 111 may be formed using a composite material of the above-described high molecular compound, such as PVK, PVTPA, PTPDMA, or Poly-TPD, and the above-described electron acceptor.

The hole-transport layer 112 is a layer that contains a substance having a high hole-transport property. Examples of the substance having a high hole-transport property are aromatic amine compounds such as NPB, TPD, BPAFLP, 4,4'-bis[N-(9,9-dimethylfluoren-2-yl)-N-phenylamino]biphenyl (abbreviation: DFLDPBi), and 4,4'-bis[N-(spiro-9,9'-bifluoren-2-yl)-N-phenylamino]biphenyl (abbreviation: BSPB). The substances mentioned here are mainly ones that have a hole mobility of $10^{-6}$ $cm^2/V \cdot s$ or higher. However, other substances than the above described materials may also be used as long as the substances have higher hole-transport properties than electron-transport properties. The layer containing a substance having a high hole-transport property is not limited to a single layer, and two or more layers containing the aforementioned substances may be stacked.

For the hole-transport layer 112, a carbazole derivative such as CBP, CzPA, or PCzPA or an anthracene derivative such as t-BuDNA, DNA, or DPAnth may also be used.

Alternatively, for the hole-transport layer 112, a high molecular compound such as PVK, PVTPA, PTPDMA, or Poly-TPD can be used.

The light-emitting layer 113 is a layer that contains an organometallic complex which is one embodiment of the present invention described in Embodiment 1. The light-emitting layer 113 may be formed with a thin film containing an organometallic complex which is one embodiment of the present invention. The light-emitting layer 113 may be a thin film in which the organometallic complex which is one embodiment of the present invention is dispersed as a guest in a substance as a host which has higher triplet excitation energy than the organometallic complex which is one embodiment of the present invention. Thus, quenching of light emitted from the organometallic complex caused depending on the concentration can be prevented. Note that the triplet excited energy indicates an energy gap between a ground state and a triplet excited state.

The electron-transport layer 114 is a layer that contains a substance having a high electron-transport property. As the substance having a high electron-transport property, the following metal complexes can be given: $Alq_3$; tris(4-methyl-8-quinolinolato)aluminum (abbreviation: $Almq_3$); bis(10-hydroxybenzo[h]-quinolinato)beryllium (abbreviation: $BeBq_2$); BAlq; $Zn(BOX)_2$; bis[2-(2-hydroxyphenyl)benzothiazolato]zinc (abbreviation: $Zn(BTZ)_2$); and the like. Further, a heteroaromatic compound such as 2-(4-biphenylyl)-5-(4-tert-butylphenyl)-1,3,4-oxadiazole (abbreviation: PBD), 1,3-bis[5-(p-tert-butylphenyl)-1,3,4-oxadiazol-2-yl]benzene (abbreviation: OXD-7), 3-(4-tert-butylphenyl)-4-phenyl-5-(4-biphenylyl)-1,2,4-triazole (abbreviation: TAZ), 3-(4-tert-butylphenyl)-4-(4-ethylphenyl)-5-(4-biphenylyl)-1,2,4-triazole (abbreviation: p-EtTAZ), bathophenanthroline (abbreviation: BPhen), bathocuproine (abbreviation: BCP), or 4,4'-bis(5-methylbenzoxazol-2-yl)stilbene (abbreviation: BzOs) can also be used. Further alternatively, a high molecular compound such as poly(2,5-pyridinediyl) (abbreviation: PPy), poly[(9,9-dihexylfluorene-2,7-diyl)-co-(pyridine-3,5-diyl)] (abbreviation: PF-Py) or poly[(9,9-dioctylfluorene-2,7-diyl)-co-(2,2'-bipyridine-6,6'-diyl)] (abbreviation: PF-BPy) can be used. The substances mentioned here are mainly ones that have an electron mobility of $10^{-6}$ $cm^2/V \cdot s$ or higher. However, other substances than the above described materials may also be used as long as the substances have higher electron-transport properties than hole-transport properties.

Furthermore, the electron-transport layer is not limited to a single layer, and two or more layers formed using the aforementioned substances may be stacked.

The electron-injection layer 115 is a layer that contains a substance having a high electron-injection property. For the electron-injection layer 115, an alkali metal, an alkaline earth metal, or a compound thereof, such as lithium, cesium, calcium, lithium fluoride, cesium fluoride, calcium fluoride, or lithium oxide, can be used. In addition, a rare earth metal compound such as erbium fluoride can also be used. Alternatively, the above-mentioned substances for forming the electron-transport layer 114 can also be used.

Alternatively, a composite material in which an organic compound and an electron donor (donor) are mixed may be used for the electron-injection layer 115. Such a composite material is excellent in an electron-injection property and an electron-transport property because electrons are generated in the organic compound by the electron donor. In this case, the organic compound is preferably a material excellent in transporting the generated electrons. Specifically, for example, the substances for forming the electron-transport layer 114 (e.g., a metal complex or a heteroaromatic compound), which are described above, can be used. As the electron donor, a substance exhibiting an electron-donating property to the organic compound is used. Specifically, an alkali metal, an alkaline-earth metal, and a rare-earth metal are preferable, and lithium, cesium, magnesium, calcium, erbium, ytterbium, and the like can be given. Further, an alkali metal oxide or an alkaline-earth metal oxide is preferable, and there are, for example, lithium oxide, calcium oxide, barium oxide, and the like. Alternatively, Lewis base such as magnesium oxide can also be used. Further alternatively, an organic compound such as tetrathiafulvalene (abbreviation: TTF) can be used.

Note that each of the above-described hole-injection layer 111, hole-transport layer 112, light-emitting layer 113, electron-transport layer 114, and electron-injection layer 115 can be formed by a method such as an evaporation method (e.g., a vacuum evaporation method), an ink-jet method, or a coating method.

For the second electrode 103 functioning as a cathode, any of metals, alloys, electrically conductive compounds, mixtures thereof, and the like which has a low work function (specifically, a work function of 3.8 eV or less) is preferably used. Specifically, any of the following can be used: aluminum or silver; an element belonging to Group 1 or Group 2 of the periodic table, that is, an alkali metal such as lithium or cesium or an alkaline earth metal such as magnesium, calcium, or strontium; an alloy of the above metals (e.g., Mg—Ag or Al—Li); a rare earth metal such as europium or ytterbium; an alloy of the above metals; or the like.

Note that in the case where in the EL layer 102, a layer formed in contact with the second electrode 103 is formed using a composite material in which the organic compound and the electron donor (donor), which are described above, are mixed, a variety of conductive materials such as Al, Ag, ITO, and indium oxide-tin oxide containing silicon or silicon oxide can be used regardless of the work function.

Note that the second electrode 103 can be formed by a vacuum evaporation method or a sputtering method. Alternatively, in the case of using a silver paste or the like, a coating method, an inkjet method, or the like can be used In the above-described light-emitting element, current flows due to a potential difference generated between the first electrode 101 and the second electrode 103 and holes and electrons recombine in the EL layer 102, whereby light is emitted. Then, this emitted light is extracted out through one or both of the first electrode 101 and the second electrode 103. Therefore, one of or both the first electrode 101 and the second electrode 103 is/are an electrode having a property of transmitting visible light.

With the use of the light-emitting element described in this embodiment, a passive matrix light-emitting device or an active matrix light-emitting device in which a transistor controls driving of the light-emitting element can be manufactured.

Note that there is no particular limitation on the structure of a transistor in the case of manufacturing an active matrix light-emitting device. For example, a staggered transistor or an inverted staggered transistor can be used as appropriate. Furthermore, a driver circuit formed over a substrate may be formed with both n-channel transistors and p-channel transistors or may be formed with either n-channel transistors or p-channel transistors. Furthermore, there is no particular limitation on crystallinity of a semiconductor film used for the transistor. For example, an amorphous semiconductor film, a crystalline semiconductor film, or the like can be used. As a material of the semiconductor film, an oxide semiconductor can be used as well as an element such as silicon.

Note that in Embodiment 2, an organometallic complex which is one embodiment of the present invention, which is used for the light-emitting layer 113, has a broader emission spectrum in the wavelength range of red to green. Thus, a light-emitting element having a high color rendering property can be realized.

Further, the light-emitting element in this embodiment includes the organometallic complex which is one embodiment of the present invention, a light-emitting element with high emission efficiency can be realized. In addition, a light-emitting device with low power consumption can be realized. Thus, a light-emitting element having a high reliability can be realized.

In Embodiment 2, any of the structures described in another embodiment can be used in appropriate combination.
(Embodiment 3)

The light-emitting element which is one embodiment of the present invention may include a plurality of light-emitting layers. For example, by providing a plurality of light-emitting layers, light which is a combination of the light emitted from the plurality of layers can be obtained. Thus, white light emission can be obtained, for example. In Embodiment 3, a mode of a light-emitting element including a plurality of light-emitting layers is described with reference to FIG. 1B.

Figure 1B:
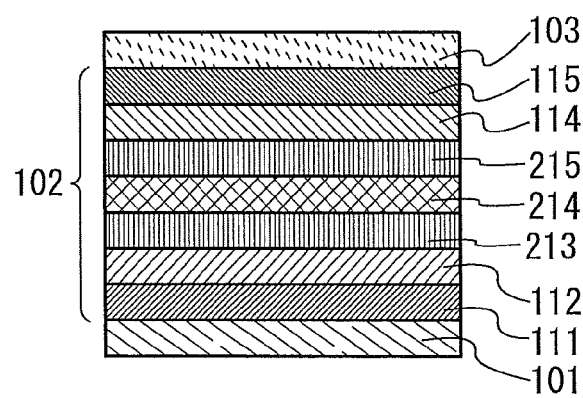

FIG. 1B illustrates a light-emitting element having the EL layer 102 between the first electrode 101 and the second electrode 103. The EL layer 102 includes a first light-emitting layer 213 and a second light-emitting layer 215, so that light emission that is a mixture of light emission from the first light-emitting layer 213 and light emission from the second light-emitting layer 215 can be obtained in the light-emitting element illustrated in FIG. 1B. A separation layer 214 is preferably formed between the first light-emitting layer 213 and the second light-emitting layer 215.

In Embodiment 3, a light-emitting element in which the first light-emitting layer 213 contains an organometallic compound that emits blue light and the second light-emitting layer 215 contains an organometallic complex which is one embodiment of the present invention is described; however, the present invention is not limited thereto.

The organometallic complex which is one embodiment of the present invention may be used in the first light-emitting layer 213, and another light-emitting substance may be applied to the second light-emitting layer 215.

The EL layer 102 may have three or more light-emitting layers.

When a voltage is applied so that the potential of the first electrode 101 is higher than the potential of the second electrode 103, a current flows between the first electrode 101 and the second electrode 103, and holes and electrons recombine in the first light-emitting layer 213, the second light-emitting layer 215, or the separation layer 214. Generated excitation energy is distributed to both the first light-emitting layer 213 and the second light-emitting layer 215 to excite a first light-emitting substance contained in the first light-emitting layer 213 and a second light-emitting substance contained in the second light-emitting layer 215. The excited first and second light-emitting substances emit light while returning to the ground state.

The first light-emitting layer 213 contains the first light-emitting substance typified by a fluorescent compound such as perylene, 2,5,8,11-tetra(tert-butyl)perylene (abbreviation: TBP), DPVBi, 4,4'-bis[2-(N-ethylcarbazol-3-yl)vinyl]biphenyl (abbreviation: BCzVBi), BAlq, or bis(2-methyl-8-quinolinolato)galliumchloride (abbreviation: Gamq$_2$Cl), or a phosphorescent compound such as bis{2-[3,5-bis(trifluoromethyl)phenyl]pyridinato-N,C$^{2'}$}iridium(III) picolinate (abbreviation: [Ir(CF$_3$ppy)$_2$(pic)]), bis[2-(4,6-difluorophenyl)pyridinato-N,C$^{2'}$]iridium(III)acetylacetonate (abbreviation: [FIr(acac)]), bis[2-(4,6-difluorophenyl)pyridinato-N, C$^{2'}$]iridium(III)picolinate (abbreviation: FIrpic), or bis[2-(4,6-difuluorophenyl)pyridinato-N,C$^{2'}$]iridium (III) tetra(1-pyrazolyl)borate (abbreviation: FIr6), from which light emission with a peak at 450 to 510 nm in an emission spectrum (i.e., blue light to blue green light) can be obtained.

In addition, when the first light-emitting substance is a fluorescent compound, the first light-emitting layer 213 preferably has a structure in which a substance that has larger singlet excitation energy than the first light-emitting substance is used as a first host and the first light-emitting substance is dispersed as a guest. Further, when the first light-emitting substance is a phosphorescent compound, the first light-emitting layer 213 preferably has a structure in which a substance that has larger triplet excitation energy than the first light-emitting substance is used as a first host and the first light-emitting substance is dispersed as a guest. As the first host, DNA, t-BuDNA, or the like can be used in addition to the above-described NPB, CBP, TCTA, and the like. Note that the singlet excitation energy is an energy difference between a ground state and a singlet excited state.

The second light-emitting layer 215 contains the organometallic complex which is one embodiment of the present invention and can emit red to green light. The second light-emitting layer 215 may have a structure similar to the light-emitting layer 113 described in Embodiment 2.

Specifically, the separation layer 214 can be formed using TPAQn, NPB, CBP, TCTA, $Znpp_2$, ZnBOX or the like described above. By thus providing the separation layer 214, a defect that emission intensity of one of the first light-emitting layer 213 and the second light-emitting layer 215 is stronger than that of the other can be prevented. Note that the separation layer 214 is not necessarily provided, and it may be provided as appropriate so that the ratio in emission intensity of the first light-emitting layer 213 and the second light-emitting layer 215 can be adjusted.

Other than the light-emitting layers, the hole-injection layer 111, the hole-transport layer 112, the electron-transport layer 114, and the electron-injection layer 115 are provided in the EL layer 102; as for structures of these layers, the structures of the respective layers described in Embodiment 2 can be applied. However, these layers are not necessarily provided and may be provided as appropriate according to element characteristics.

Note that a structure described in Embodiment 3 can be used in appropriate combination with any of the structures described in another embodiment.

(Embodiment 4)

In Embodiment 4, as one embodiment of the present invention, a structure of a light-emitting element which includes a plurality of EL layers (hereinafter, referred to as a stacked-type element) is described with reference to FIG. 1C. This light-emitting element is a stacked-type light-emitting element including a plurality of EL layers (a first EL layer 700 and a second EL layer 701 in FIG. 1C) between a first electrode 101 and a second electrode 103. Note that, although the structure in which two EL layers are formed is described in this embodiment, a structure in which three or more EL layers are formed may be employed.

In Embodiment 4, the structures described in Embodiment 2 can be applied to the first electrode 101 and the second electrode 103.

In Embodiment 4, all or any of the plurality of EL layers may have the same structure as the EL layer described in Embodiment 2. In other words, the structures of the first EL layer 700 and the second EL layer 701 may be the same as or different from each other and can be the same as in Embodiment 2.

Figure 1C:
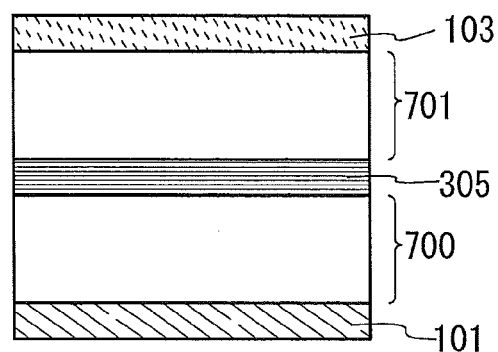

Further, in FIG. 1C, a charge generation layer 305 is provided between the first EL layer 700 and the second EL layer 701. The charge generation layer 305 has a function of injecting electrons into one of the EL layers and injecting holes into the other of the EL layers when a voltage is applied between the first electrode 101 and the second electrode 103. In the case of this embodiment, when a voltage is applied so that the potential of the first electrode 101 is higher than that of the second electrode 103, the charge generation layer 305 injects electrons into the first EL layer 700 and injects holes into the second EL layer 701.

Note that the charge generation layer 305 preferably has a property of transmitting visible light in terms of light extraction efficiency. Further, the charge generation layer 305 functions even if it has lower conductivity than the first electrode 101 or the second electrode 103.

The charge generation layer 305 may have either a structure including an organic compound having a high hole-transport property and an electron acceptor (acceptor) or a structure including an organic compound having a high electron-transport property and an electron donor (donor). Alternatively, both of these structures may be stacked.

In the case of the structure in which an electron acceptor is added to an organic compound having a high hole-transport property, as the organic compound having a high hole-transport property, for example, an aromatic amine compound such as NPB, TPD, TDATA, MTDATA, or 4,4'-bis[N-(spiro-9,9'-bifluoren-2-yl)-N-phenylamino]biphenyl (abbreviation: BSPB), or the like can be used. The substances mentioned here are mainly ones that have a hole mobility of $10^{-6}$ $cm^2/V \cdot s$ or higher. However, substances other than the above substances may be used as long as they are organic compounds having a hole-transport property higher than an electron-transport property.

Further, as the electron acceptor, 7,7,8,8-tetracyano-2,3,5,6-tetrafluoroquinodimethane (abbreviation: $F_4$-TCNQ), chloranil, and the like can be given. In addition, a transition metal oxide can be given. In addition, an oxide of metals that belong to Group 4 to Group 8 of the periodic table can be given. Specifically, vanadium oxide, niobium oxide, tantalum oxide, chromium oxide, molybdenum oxide, tungsten oxide, manganese oxide, and rhenium oxide are preferable since their electron-accepting property is high. Among these, molybdenum oxide is especially preferable since it is stable in the air and its hygroscopic property is low and is easily treated.

In contrast, in the case of the structure in which an electron donor is added to an organic compound having a high electron-transport property, as the organic compound having a high electron-transport property, a metal complex having a quinoline skeleton or a benzoquinoline skeleton, such as Alq, $Almq_3$, $BeBq_2$, or BAlq, or the like can be used, for example. Alternatively, a metal complex having an oxazole-based ligand or a thiazole-based ligand, such as $Zn(BOX)_2$ or $Zn(BTZ)_2$ can be used. Alternatively, in addition to such a metal complex, PBD, OXD-7, TAZ, BPhen, BCP, or the like can be used. The substances mentioned here are mainly ones that have an electron mobility of $10^{-6}$ $cm^2/V \cdot s$ or higher. Note that substances other than the above substances may be used as long as they are organic compounds having an electron-transport property higher than a hole-transport property.

Further, as the electron donor, an alkali metal, an alkaline earth metal, a rare earth metal, a metal belonging to Group 13 of the periodic table, or an oxide or carbonate thereof can be used. Specifically, lithium, cesium, magnesium, calcium, ytterbium, indium, lithium oxide, cesium carbonate, or the like is preferably used. Alternatively, an organic compound such as tetrathianaphthacene may be used as the electron donor.

Note that forming the charge generation layer 305 by using the above materials can suppress an increase in drive voltage caused by the stack of the EL layers.

Although the light-emitting element having two EL layers is described in this embodiment, the present invention can be similarly applied to a light-emitting element in which three or more EL layers are stacked. As in the case of the light-emitting element described in this embodiment, by arranging a plurality of EL layers to be partitioned from each other with charge-generation layers between a pair of electrodes, light emission in a high luminance region can be achieved with current density kept low. Since current density can be kept low, the element can have a long lifetime. When the light-emitting element is applied for illumination, voltage drop due to resistance of an electrode material can be reduced, thereby achieving homogeneous light emission in a large area. Moreover, a light-emitting device of low power consumption, which can be driven at a low voltage, can be achieved.

Further, by forming EL layers to emit light of different colors from each other, a light-emitting element as a whole can provide light emission of a desired color. For example, by forming a light-emitting element having two EL layers such that the emission color of the first EL layer and the emission color of the second EL layer are complementary colors, the light-emitting element can provide white light emission as a whole. Note that the word "complementary" means color relationship in which an achromatic color is obtained when colors are mixed. In other words, when light of complementary colors is mixed, white light emission can be obtained.

Further, the same can be applied to a light-emitting element having three EL layers. For example, the light-emitting element as a whole can provide white light emission when the emission color of the first EL layer is red, the emission color of the second EL layer is green, and the emission color of the third EL layer is blue.

Note that a structure described in Embodiment 4 can be used in appropriate combination with any of the structures described in another embodiment.

(Embodiment 5)

In Embodiment 5, a passive matrix light-emitting device and an active matrix light-emitting device in each of which a light-emitting element which is one embodiment of the present invention is used are described.

FIGS. 2A to 2D and FIG. 3 illustrate an example of the passive matrix light-emitting device.

In a passive matrix (also called simple matrix) light-emitting device, a plurality of anodes arranged in stripes (in stripe form) are provided to be perpendicular to a plurality of cathodes arranged in stripes. A light-emitting layer is interposed at each intersection. Therefore, a pixel at an intersection of an anode selected (to which a voltage is applied) and a cathode selected emits light.

Figure 2A:
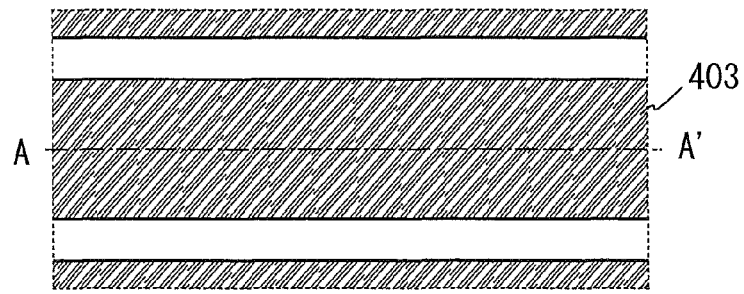
FIGS. 2A to 2D illustrate a passive matrix light-emitting device.
Figure 2B:
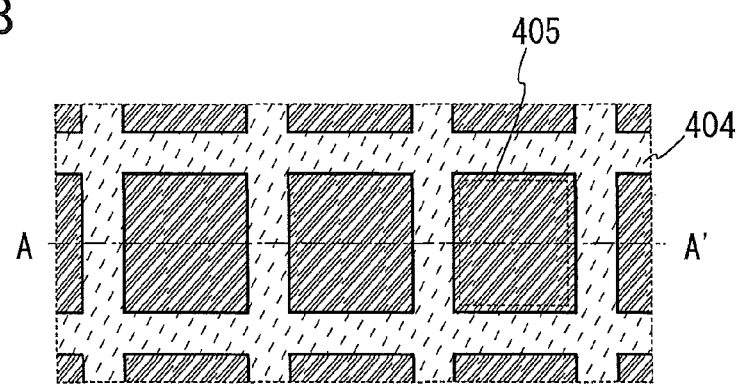
Figure 2C:
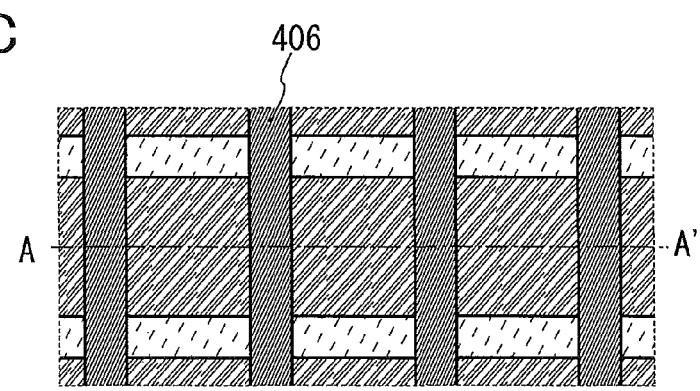
Figure 2D:
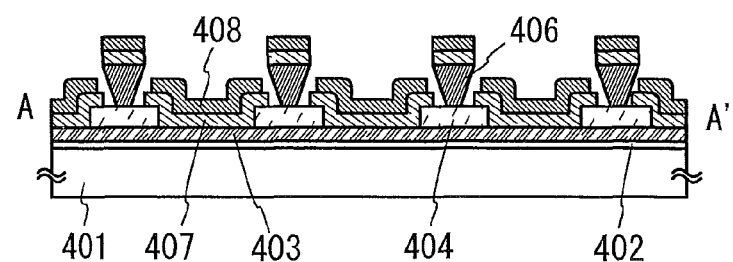

FIGS. 2A to 2C are top views of a pixel portion before sealing. FIG. 2D is a cross-sectional view taken along chain line A-A' in FIGS. 2A to 2C.

An insulating layer 402 is formed as a base insulating layer over a substrate 401. Note that the insulating layer 402 is not necessarily formed if the base insulating layer is not needed. A plurality of first electrodes 403 are arranged in stripes at regular intervals over the insulating layer 402 (see FIG. 2A).

In addition, partition 404 having openings corresponding to the pixels is provided over the first electrodes 403. The partition 404 having the openings is formed using an insulating material, such as a photosensitive or nonphotosensitive organic material (polyimide, acrylic, polyamide, polyimide amide, resist, or benzocyclobutene) or a SOG film (e.g., a $SiO_x$ film containing an alkyl group). Note that openings 405 corresponding to the pixels serve as light-emitting regions (FIG. 2B).

Over the partition 404 having, the openings, a plurality of reversely tapered partitions 406 which are parallel to each other are provided to intersect with the first electrodes 403 (FIG. 2C). The reversely tapered partitions 406 are formed in the following manner: according to a photolithography method, a positive photosensitive resin, an unexposed portion of which serves as a pattern, is used and the amount of exposed light or the length of development time is adjusted so that a lower portion of the pattern is etched more.

After the reversely tapered partitions 406 are formed as illustrated in FIG. 2C, an EL layer 407 and a second electrode 408 are sequentially formed as illustrated in FIG. 2D. The total thickness of the partition 404 having the openings and the reversely tapered partition 406 is set to be larger than the total thickness of the EL layer 407 and the second electrode 408; thus, as illustrated in FIG. 2D, EL layers 407 and second electrodes 408 which are separated for plural regions are formed. Note that the plurality of separated regions are electrically isolated from one another.

The second electrodes 408 are electrodes in stripe form that are parallel to each other and extend along a direction intersecting with the first electrodes 403. Note that parts of a layer for forming the EL layers 407 and parts of a conductive layer for forming the second electrodes 408 are also formed over the reversely tapered partitions 406; however, these parts are separated from the EL layers 407 and the second electrodes 408.

Note that there is no particular limitation on the first electrode 403 and the second electrode 408 in this embodiment as long as one of them is an anode and the other is a cathode. Note that a stacked structure in which the EL layer 407 is included may be adjusted as appropriate in accordance with the polarity of the electrode.

Further, if necessary, a sealing material such as a sealing can or a glass substrate may be attached to the substrate 401 for sealing with an adhesive such as a sealing material, so that the light-emitting element is placed in the sealed space. Thereby, deterioration of the light-emitting element can be prevented. The sealed space may be filled with filler or a dry inert gas. Furthermore, a desiccant or the like may be put between the substrate and the sealing material in order to prevent deterioration of the light-emitting element due to moisture or the like. The desiccant removes a minute amount of moisture, thereby achieving sufficient desiccation. The desiccant may be a substance which absorbs moisture by chemical adsorption such as an oxide of an alkaline earth metal such as calcium oxide or barium oxide. Additionally, a substance which adsorbs moisture by physical adsorption such as zeolite or silica gel may be used as well, as a desiccant.

Figure 3:
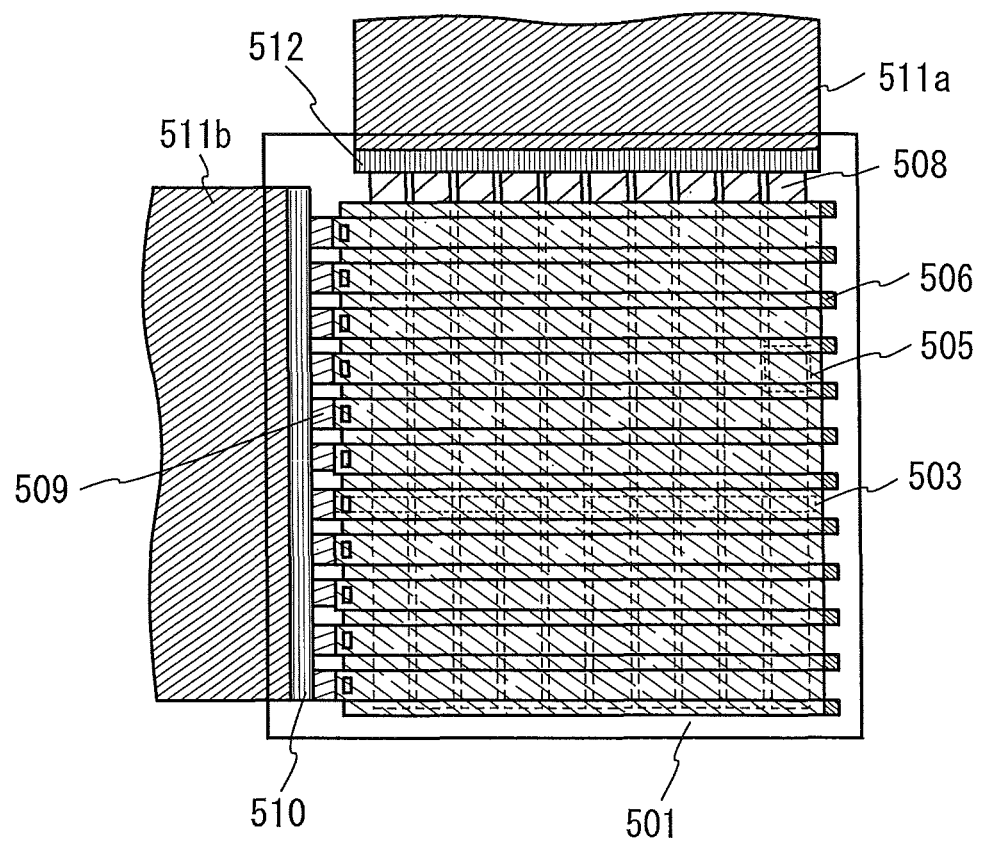
FIG. 3 illustrates a passive matrix light-emitting device.

FIG. 3 is a top view of the passive-matrix light-emitting device illustrated in FIGS. 2A to 2D that is provided with a flexible printed circuit (an FPC) and the like.

In FIG. 3, in a pixel portion forming an image display, scanning lines and data lines are arranged to intersect with each other so that the scanning lines and the data lines are perpendicular to each other.

The first electrodes 403 in FIGS. 2A to 2D correspond to scanning lines 503 in FIG. 3; the second electrodes 408 in FIGS. 2A to 2D correspond to data lines 508 in FIG. 3; and the reversely tapered partitions 406 correspond to partitions 506. The EL layer 407 in FIGS. 2A to 2D is interposed between the data lines 508 and the scan lines 503, and an intersection indicated as a region 505 corresponds to one pixel.

Note that the scan lines 503 are electrically connected at their ends to connection wirings 509, and the connection wirings 509 are connected to an FPC 511b through an input terminal 510. In addition, the data lines are connected to an FPC 511a through an input terminal 512.

If necessary, an optical film such a polarizing plate, a circularly polarizing plate (including an elliptically polarizing plate), a retardation plate (a quarter-wave plate or a half-wave plate), and a color filter may be provided as appropriate on a surface through which light is emitted. Further, the polarizing plate or the circularly polarizing plate may be provided with an anti-reflection film. For example, anti-glare treatment by which reflected light can be diffused by projections and depressions on the surface so as to reduce the glare can be performed.

Although FIG. 3 illustrates the example in which a driver circuit is not provided over a substrate 501, an IC chip including a driver circuit may be mounted on the substrate 501.

When the IC chip is mounted, a data line side IC and a scan line side IC, in each of which a driver circuit for transmitting a signal to a pixel portion is formed, are mounted on the periphery of the pixel portion (outside the pixel portion) by a COG method. The mounting may be performed using a TCP or a wire bonding method other than the COG method. The TCP is a TAB tape mounted with the IC, and the TAB tape is connected to a wiring over an element formation substrate to mount the IC. The ICs on the data line side and the scan line side may be formed using a silicon substrate, or may be obtained by formation of a driver circuit with a TFT over a glass substrate, a quartz substrate, or a plastic substrate.

Figure 4A:
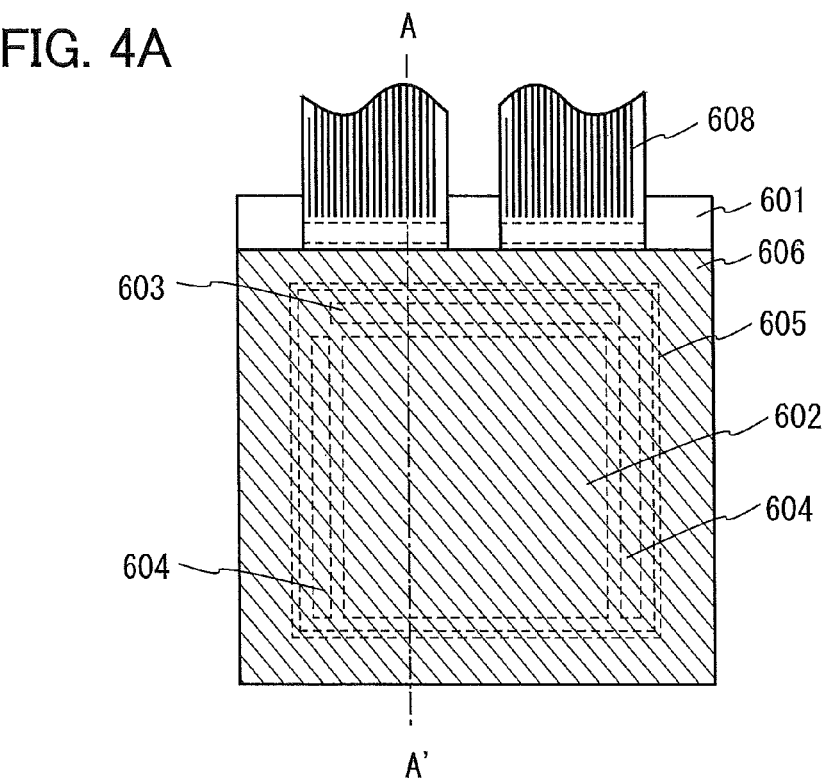
FIGS. 4A and 4B illustrate an active matrix light-emitting device.
Figure 4B:
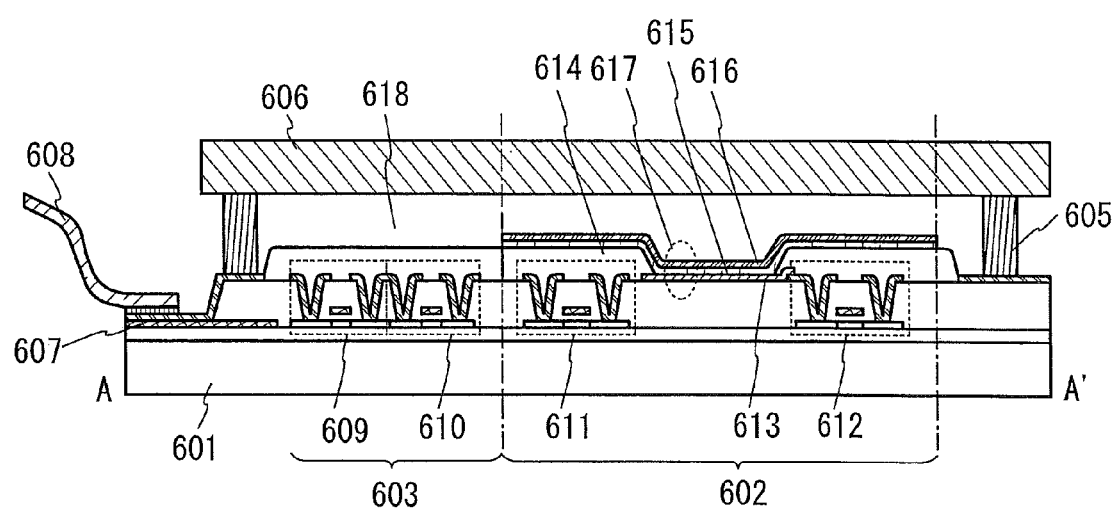

Next, an example of the active matrix light-emitting device is described with reference to FIGS. 4A and 4B. FIG. 4A is a top view illustrating a light-emitting device and FIG. 4B is a cross-sectional view taken along chain line A-A' in FIG. 4A. The active matrix light-emitting device according to this embodiment includes a pixel portion 602 provided over an element substrate 601, a driver circuit portion (a source side driver circuit) 603, and a driver circuit portion (a gate side driver circuit) 604. The pixel portion 602, the driver circuit portion 603, and the driver circuit portion 604 are sealed with a sealing material 605, between the element substrate 601 and a sealing substrate 606.

In addition, over the element substrate 601, a lead wiring 607 for connecting an external input terminal, through which a signal (e.g., a video signal, a clock signal, a start signal, a reset signal, or the like) or an electric potential is transmitted to the driver circuit portion 603 and the driver circuit portion 604, is provided. Here, an example is described in which a flexible printed circuit (FPC) 608 is provided as the external input terminal. Although only the FPC is illustrated here, a printed wiring board (PWB) may be attached to the FPC. The light-emitting device in the present specification includes, in its category, not only the light-emitting device itself but also the light-emitting device provided with the FPC or the PWB.

Next, a cross-sectional structure is described with reference to FIG. 4B. The driver circuit portion and the pixel portion are formed over the element substrate 601, and in FIG. 4B, the driver circuit portion 603 that is a source side driver circuit and the pixel portion 602 are illustrated.

An example is illustrated in which a CMOS circuit which is a combination of an n-channel TFT 609 and a p-channel TFT 610 is formed as the driver circuit portion 603. Note that a circuit included in the driver circuit portion may be formed using various CMOS circuits, PMOS circuits, or NMOS circuits. Although a driver integrated type in which the driver circuit is formed over the substrate is described in this embodiment, the driver circuit may not necessarily be formed over the substrate, and the driver circuit can be formed outside, not over the substrate.

The pixel portion 602 is formed of a plurality of pixels each of which includes a switching TFT 611, a current control TFT 612, and an anode 613 which is electrically connected to a wiring (a source electrode or a drain electrode) of the current control TFT 612. Note that an insulator 614 is formed to cover end portions of the anode 613. In this embodiment, the insulator 614 is formed using a positive photosensitive acrylic resin.

The insulator 614 is preferably formed so as to have a curved surface with curvature at an upper end portion or a lower end portion thereof in order to obtain favorable coverage by a film which is to be stacked over the insulator 614. For example, in the case of using a positive photosensitive acrylic resin as a material for the insulator 614, the insulator 614 is preferably formed so as to have a curved surface with a curvature radius (0.2 µm to 3 µm) at the upper end portion. Note that either a negative photosensitive material that becomes insoluble in an etchant by light irradiation or a positive photosensitive material that becomes soluble in an etchant by light irradiation can be used for the insulator 614. As the insulator 614, without limitation to an organic compound, either an organic compound or an inorganic compound such as silicon oxide or silicon oxynitride can be used.

An EL layer 615 and a cathode 616 are stacked over the anode 613. Note that when an ITO film is used as the anode 613, and a stacked film of a titanium nitride film and a film containing aluminum as its main component or a stacked film of a titanium nitride film, a film containing aluminum as its main component, and a titanium nitride film is used as the wiring of the current controlling TFT 612 which is connected to the anode 613, resistance of the wiring is low and favorable ohmic contact with the ITO film can be obtained. Note that, although not illustrated in FIGS. 4A and 4B, the cathode 616 is electrically connected to the FPC 608 which is an external input terminal.

Note that in the EL layer 615, at least a light-emitting layer is provided, and in addition to the light-emitting layer, a hole-injection layer, a hole-transport layer, an electron-transport layer, or an electron-injection layer is provided as appropriate. A light-emitting element 617 is formed of a stacked structure of the anode 613, the EL layer 615, and the cathode 616.

Although the cross-sectional view of FIG. 4B illustrates only one light-emitting element 617, a plurality of light-emitting elements are arranged in matrix in the pixel portion 602. Light-emitting elements which provide three kinds of emissions (R, G, and B) are selectively formed in the pixel portion 602, whereby a light-emitting device capable of full color display can be formed. Alternatively, a light-emitting device which is capable of full color display may be manufactured by a combination with color filters.

Further, the sealing substrate 606 is attached to the element substrate 601 with the sealing material 605, so that the light-emitting element 617 is provided in a space 618 enclosed by the element substrate 601, the sealing substrate 606, and the sealing material 605. The space 618 may be filled with an inert gas (such as nitrogen or argon), or the sealing material 605.

An epoxy based resin is preferably used for the sealing material 605. A material used for them is desirably a material which does not transmit moisture or oxygen as much as possible. As a material used for the sealing substrate 606, a plastic substrate formed of FRP (fiberglass-reinforced plastics), PVF (polyvinyl fluoride), polyester, acrylic, or the like can be used other than a glass substrate or a quartz substrate.

As described above, an active matrix light-emitting device can be obtained.

Note that a structure described in Embodiment 5 can be used in appropriate combination with any of the structures described in another embodiment.

(Embodiment 6)

In Embodiment 6, with reference to FIGS. 5A to 5E, FIGS. 6A and 6B, and FIG. 7, examples of a variety of electronic devices and lighting devices that are completed by using a light-emitting device which is one embodiment of the present invention are described.

Examples of the electronic devices to which the light-emitting device is applied are television devices (also referred to as TV or television receivers), monitors for computers and the like, cameras such as digital cameras and digital video cameras, digital photo frames, mobile phones (also referred to as portable telephone devices), portable game machines, portable information terminals, audio playback devices, large game machines such as pin-ball machines, and the like.

By fabricating a light-emitting element over a flexible substrate, in which any of the organometallic complexes each of which is one embodiment of the present invention is used, an electronic device or a lighting device that includes a light-emitting portion having a curved surface can be realized.

In addition, by using a material having a property of transmitting visible light to form a pair of electrodes that are included in a light-emitting element, in which the organometallic complex which is one embodiment of the present invention is used, an electronic device or a lighting device that includes a see-through light-emitting portion can be realized.

Further, a light-emitting device to which one embodiment of the present invention is applied can also be applied to lighting in a car; for example, lighting can be provided for a dashboard, on a windshield, ceiling, or the like.

Specific examples of these electronic devices and lighting devices are illustrated in FIGS. 5A to 5E, FIGS. 6A and 6B, and FIG. 7.

Figure 5A:
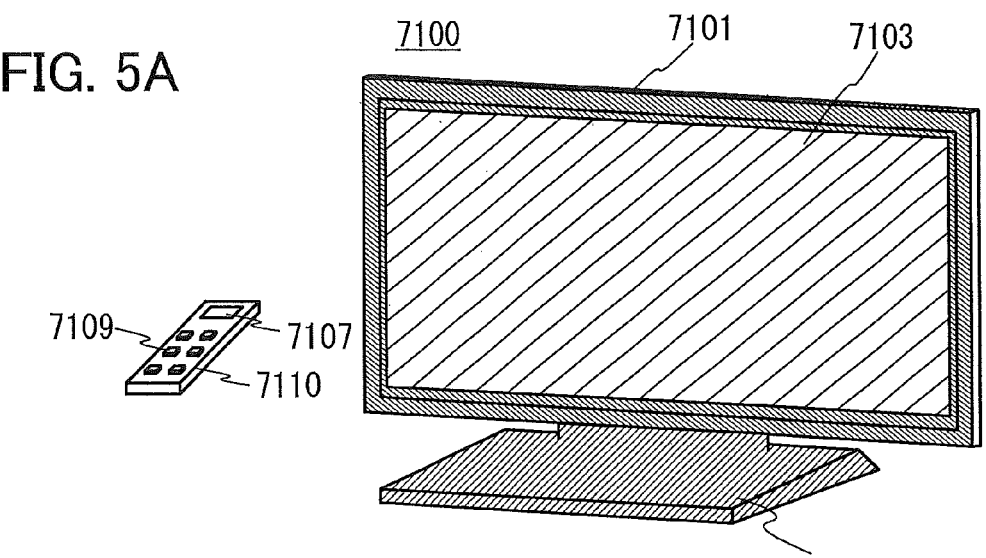
FIGS. 5A to 5E illustrate electronic devices.

FIG. 5A illustrates an example of a television device. In the television device 7100, a display portion 7103 is incorporated in a housing 7101. Images can be displayed by the display portion 7103, and the light-emitting device can be used for the display portion 7103. In addition, here, the housing 7101 is supported by a stand 7105.

The television device 7100 can be operated by an operation switch of the housing 7101 or a separate remote controller 7110. With operation keys 7109 of the remote controller 7110, channels and volume can be controlled and images displayed on the display portion 7103 can be controlled. Furthermore, the remote controller 7110 may be provided with a display portion 7107 for displaying data output from the remote controller 7110.

Note that the television device 7100 is provided with a receiver, a modem, and the like. With the receiver, a general television broadcast can be received. Furthermore, when the television 7100 is connected to a communication network by wired or wireless connection via the modem, one-way (from a transmitter to a receiver) or two-way (between a transmitter and a receiver, between receivers, or the like) data communication can be performed.

Figure 5B:
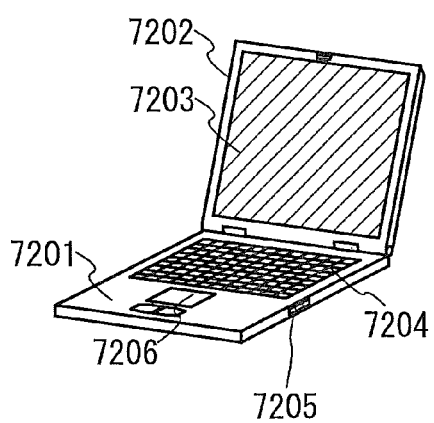

FIG. 5B illustrates a computer having a main body 7201, a housing 7202, a display portion 7203, a keyboard 7204, an external connection port 7205, a pointing device 7206, and the like. This computer is manufactured by using a light-emitting device for the display portion 7203.

Figure 5C:
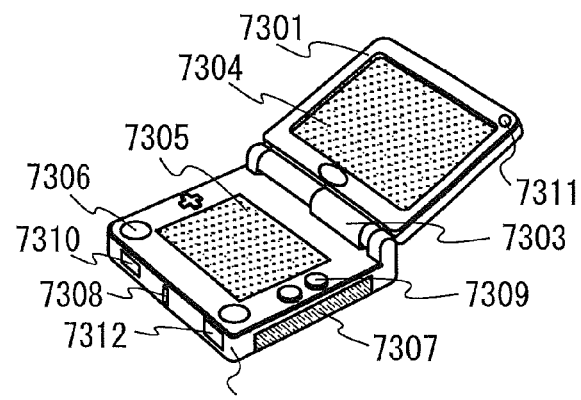

FIG. 5C illustrates a portable game machine having two housings, a housing 7301 and a housing 7302, which are connected with a joint portion 7303 so that the portable game machine can be opened or folded. A display portion 7304 is incorporated in the housing 7301 and a display portion 7305 is incorporated in the housing 7302. In addition, the portable game machine illustrated in FIG. 5C includes a speaker portion 7306, a recording medium insertion portion 7307, an LED lamp 7308, an input means (an operation key 7309, a connection terminal 7310, a sensor 7311 (a sensor having a function of measuring force, displacement, position, speed, acceleration, angular velocity, rotational frequency, distance, light, liquid, magnetism, temperature, chemical substance, sound, time, hardness, electric field, current, voltage, electric power, radiation, flow rate, humidity, gradient, oscillation, odor, or infrared rays), or a microphone 7312), and the like. It is needless to say that the structure of the portable games machine is not limited to the above as far as a light-emitting device is used for at least either the display portion 7304 or the display portion 7305, or both, and can include other accessories as appropriate. The portable game machine illustrated in FIG. 5C has a function of reading out a program or data stored in a storage medium to display it on the display portion, and a function of sharing information with another portable game machine by wireless communication. The portable game machine illustrated in FIG. 5C can have a variety of functions without limitation to the above.

Figure 5D:
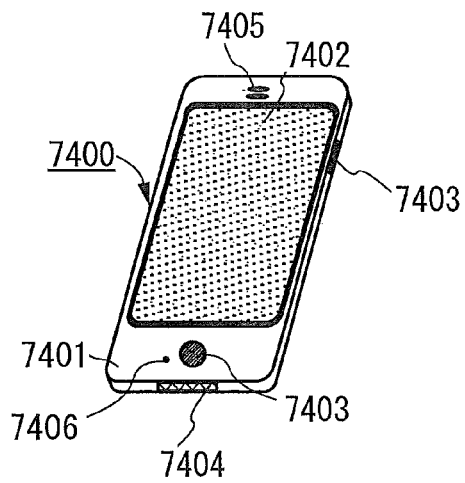

FIG. 5D illustrates an example of a mobile phone. The mobile phone 7400 is provided with a display portion 7402 incorporated in a housing 7401, operation buttons 7403, an external connection port 7404, a speaker 7405, a microphone 7406, and the like. Note that the mobile phone 7400 is manufactured using a light-emitting device for the display portion 7402.

When the display portion 7402 of the mobile phone 7400 illustrated in FIG. 5D is touched with a finger or the like, data can be input into the mobile phone 7400. Further, operations such as making a call and creating e-mail can be performed by touch on the display portion 7402 with a finger or the like.

There are mainly three screen modes of the display portion 7402. The first mode is a display mode mainly for displaying images. The second mode is an input mode mainly for inputting data such as text. The third mode is a display-and-input mode in which two modes of the display mode and the input mode are combined.

For example, in the case of making a call or creating e-mail, a text input mode mainly for inputting text is selected for the display portion 7402 so that text displayed on a screen can be input. In this case, it is preferable to display a keyboard or number buttons on almost the entire screen of the display portion 7402.

When a detection device including a sensor for detecting inclination, such as a gyroscope or an acceleration sensor, is provided inside the mobile phone 7400, display on the screen of the display portion 7402 can be automatically changed by determining the orientation of the mobile phone 7400 (whether the mobile phone is placed horizontally or vertically for a landscape mode or a portrait mode).

The screen modes are switched by touching the display portion 7402 or operating the operation buttons 7403 of the housing 7401. Alternatively, the screen modes can be switched depending on kinds of images displayed on the display portion 7402. For example, when a signal of an image displayed on the display portion is a signal of moving image data, the screen mode is switched to the display mode. When the signal is a signal of text data, the screen mode is switched to the input mode.

Moreover, in the input mode, when input by touching the display portion 7402 is not performed within a specified period while a signal detected by an optical sensor in the display portion 7402 is detected, the screen mode may be controlled so as to be switched from the input mode to the display mode.

The display portion 7402 may function as an image sensor. For example, an image of a palm print, a fingerprint, or the like is taken by touch on the display portion 7402 with the palm or the finger, whereby personal authentication can be performed. Further, by providing a backlight or a sensing light source which emits a near-infrared light in the display portion, an image of a finger vein, a palm vein, or the like can be taken.

As described above, by applying the light-emitting device which is one embodiment of the present invention, a display portion of an electronic device can realize high emission efficiency. By applying one embodiment of the present invention, an electronic device with high reliability can be provided. By applying one embodiment of the present invention, an electronic device with low power consumption can be provided.

Figure 5E:
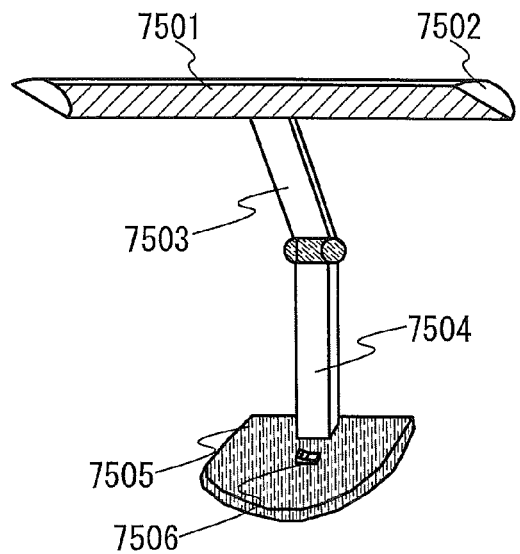

FIG. 5E illustrates a desk lamp including a lighting portion 7501, a shade 7502, an adjustable arm 7503, a support 7504, a base 7505, and a power supply switch 7506. The desk lamp is manufactured using a light-emitting device for the lighting portion 7501. Note that a lamp includes a ceiling light, a wall light, and the like in its category.

Figure 6A:
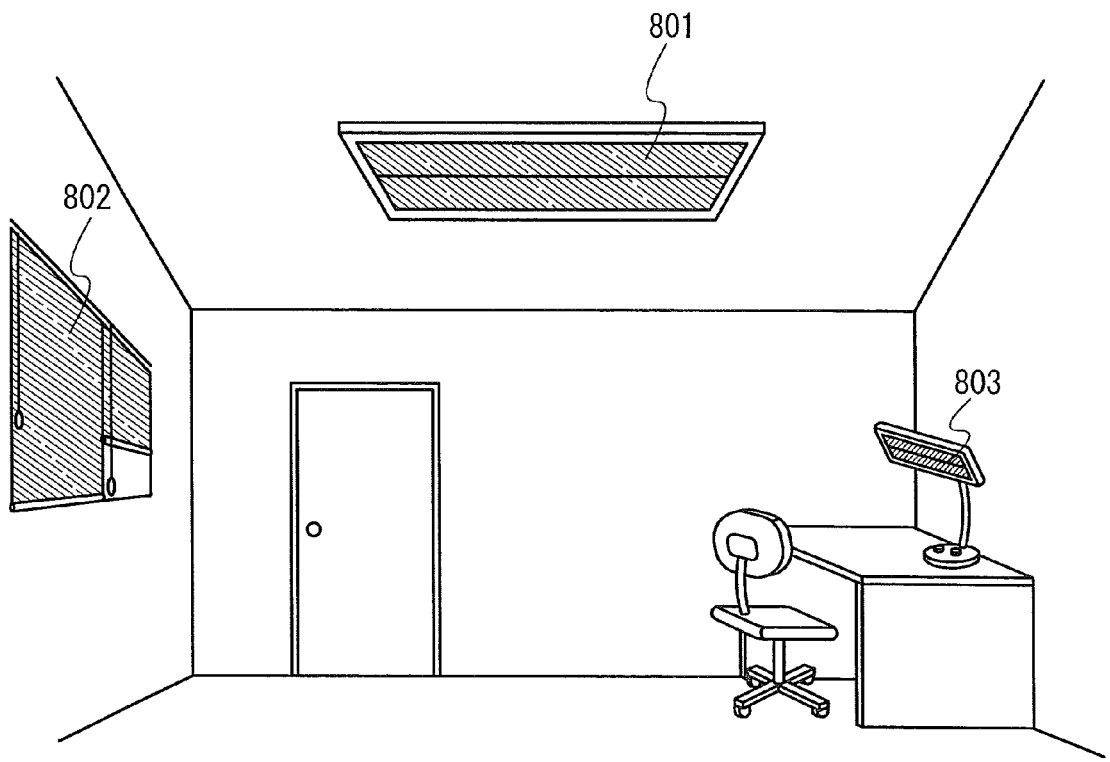
FIGS. 6A and 6B illustrate lighting devices.

FIG. 6A illustrates an example in which a light-emitting device is used for an interior lighting device 801. Since the light-emitting device can be enlarged, the light-emitting device can be used as a large-area lighting device. Alternatively, the light-emitting device can be used as a roll-type lighting device 802. As illustrated in FIG. 6A, a desk lamp 803 described with reference to FIG. 5E may be used together in a room provided with the interior lighting device 801.

Figure 6B:
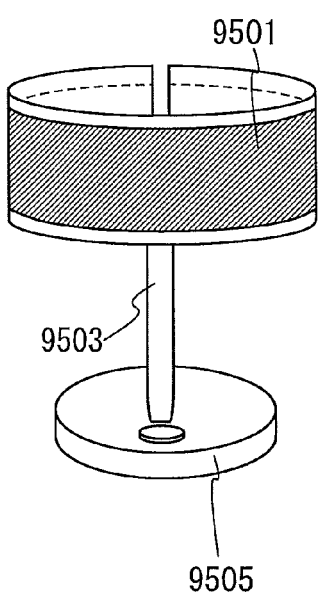

FIG. 6B illustrates an example of another lighting device. A desk lamp illustrated in FIG. 6B includes a lighting portion 9501, a support 9503, a support base 9505, and the like. The lighting portion 9501 contains any of the organometallic complexes each of which is one embodiment of the present invention. By thus fabricating a light-emitting device which is one embodiment of the present invention over a flexible substrate, a lighting device having a curved surface or having a flexible lighting portion can be provided. The use of a flexible light-emitting device for a lighting device as described above not only improves the degree of freedom in design of the lighting device but also enables the lighting device to be mounted onto a portion having a curved surface, such as the ceiling or a dashboard of a car.

Figure 7:
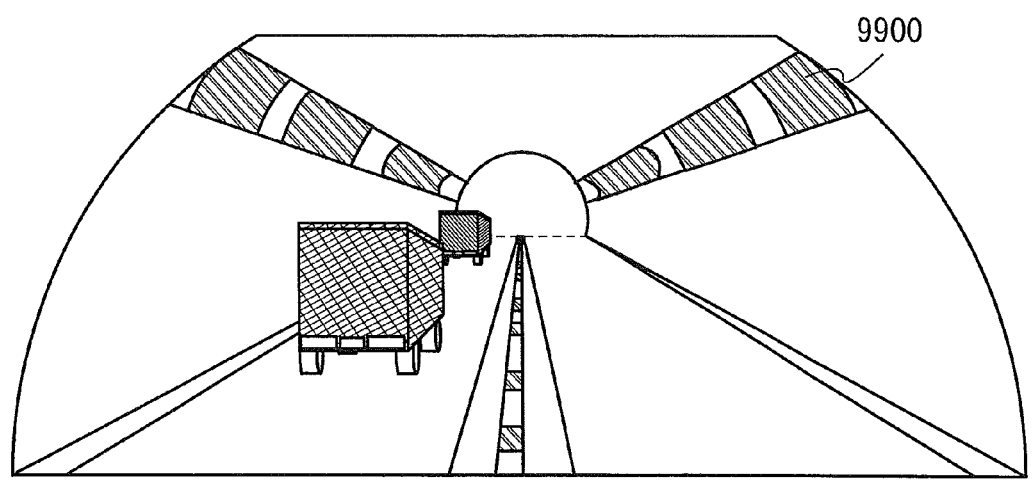
FIG. 7 illustrates a lighting device.

FIG. 7 illustrates an example of another lighting device. As described above, a lighting device having a curved surface can be fabricated by applying one embodiment of the present invention. In addition, since the organometallic complex which is one embodiment of the present invention emits yellow to orange light, a yellow lighting device or an orange lighting device can be provided. For example, one embodiment of the present invention can be applied to a lighting device 9900 in a tunnel illustrated in FIG. 7. By applying one embodiment of the present invention, a lighting device with high emission efficiency and high energy efficiency can be realized. In addition, since yellow to orange light emission has a high luminosity factor, accidents can be reduced. Further, since the lighting device to which one embodiment of the present invention is applied is a plane light source, the directivity can be prevented from being too strong, so that causes of accidents can be reduced.

Alternatively, the above-described yellow lighting device can be applied to a yellow room or the like. By using a lighting device to which one embodiment of the present invention is applied for lighting in a yellow room, a shade is unlikely to be generated and favorable environment for working can be provided.

As described above, by applying the light-emitting device which is one embodiment of the present invention, a lighting device can realize high emission efficiency. By applying one embodiment of the present invention, a lighting device with high reliability can be provided. By applying one embodiment of the present invention, a lighting device with low power consumption can be provided.

As described above, electronic devices or lighting devices can be obtained by application of the light-emitting device. Application range of the light-emitting device is so wide that the light-emitting device can be applied to electronic devices in a variety of fields.

Note that a structure described in Embodiment 6 can be used in appropriate combination with any of the structures described in another embodiment.

EXAMPLE 1

Synthetic Example 1

In Example 1, a synthetic example of an organometallic complex (acetylacetonato)bis(4,6-diphenylpyrimidinato)iridium(III) (another name: bis[2-(6-phenyl-4-pyrimidinyl-κN3)phenyl-κC](2,4-pentanedionato-κ$^2$O, O')iridium(III)) (abbreviation: [Ir(dppm)$_2$(acac)]), which is one embodiment of the present invention represented by the structural formula (100) in Embodiment 1, is specifically described. A structure of [Ir(dppm)$_2$(acac)] is shown below.

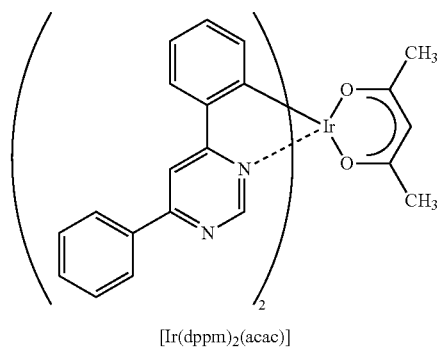

[Ir(dppm)$_2$(acac)]

Step 1: Synthesis of 4,6-diphenylpyrimidine
(abbreviation: Hdppm)

First, into a recovery flask equipped with a reflux pipe were put 5.02 g of 4,6-dichloropyrimidine, 8.29 g of phenylboronic acid, 7.19 g of sodium carbonate, 0.29 g of bis(triphenylphosphine)palladium(II)dichloride (abbreviation: Pd(PPh$_3$)$_2$Cl$_2$), 20 mL of water, and 20 mL of acetonitrile, and the air in the flask was replaced with argon. This reaction container was heated by irradiation with microwaves (2.45 GHz, 100 W) for 60 minutes. Here, into the flask were further put 2.08 g of phenylboronic acid, 1.79 g of sodium carbonate, 0.070 g of Pd(PPh$_3$)$_2$Cl$_2$, 5 mL of water, and 5 mL of acetonitrile, and the mixture was heated again by irradiation with microwaves (2.45 GHz, 100 W) for 60 minutes. After that, water was added to this solution and an organic layer was extracted with dichloromethane. The obtained solution of the extract was washed with water and dried with magnesium sulfate. The solution after drying was filtered. The solvent of this solution was distilled off, and then the obtained residue was purified by silica gel column chromatography using dichloromethane as a developing solvent, so that a pyrimidine derivative Hdppm was obtained (yellow white powder, yield of 38%). Note that for the irradiation with microwaves, a microwave synthesis system (Discover, manufactured by CEM Corporation) was used. A synthesis scheme (a-1) of Step 1 is shown below.

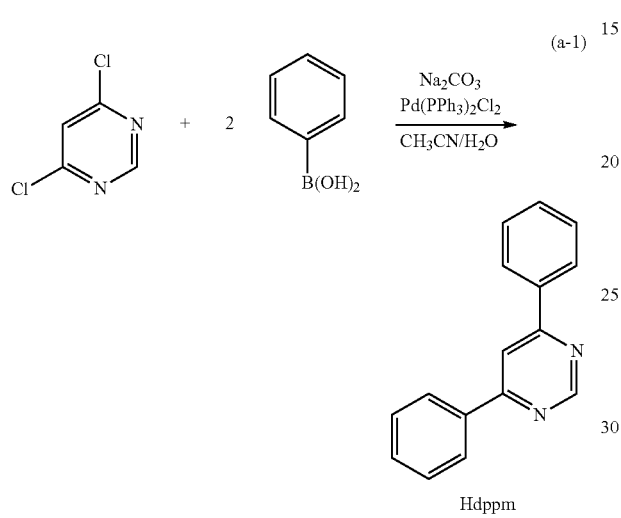

(a-1)

Step 2: Synthesis of di-μ-chloro-bis[bis(4,6-diphenylpyrimidinato)iridium(III)](abbreviation: [Ir(dppm)₂Cl]₂)

Next, into a recovery flask equipped with a reflux pipe were put 15 mL of 2-ethoxyethanol, 5 mL of water, 1.10 g of Hdppm obtained in Step 1, and 0.69 g of iridium chloride hydrate (IrCl₃.H₂O), and the air in the recovery flask was replaced with argon. After that, irradiation with microwaves (2.45 GHz, 100 W) was performed for 1 hour to cause a reaction. The solvent was distilled off, and then the obtained residue was filtered and washed with ethanol to give a dinuclear complex [Ir(dppm)₂Cl]₂ (reddish brown powder, yield of 88%). A synthesis scheme (a-2) of Step 2 is shown below.

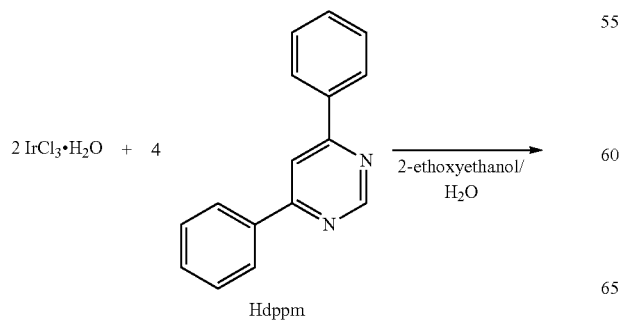

(a-2)

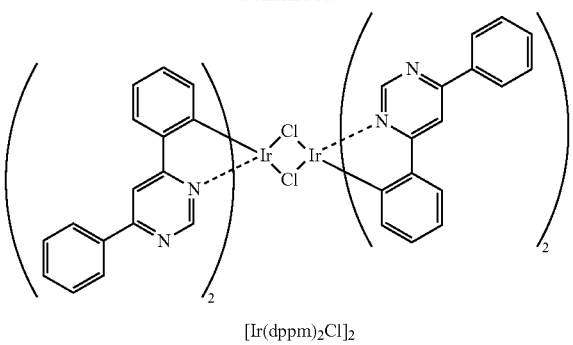

[Ir(dppm)₂Cl]₂

Step 3: Synthesis of (acetylacetonato)bis(4,6-diphenylpyrimidinato)iridium(III) (abbreviation: [Ir(dppm)₂(acac)])

Furthermore, into a recovery flask equipped with a reflux pipe were put 40 mL of 2-ethoxyethanol, 1.44 g of [Ir(dppm)₂Cl]₂ obtained in Step 2, 0.30 g of acetylacetone, and 1.07 g of sodium carbonate, and the air in the recovery flask was replaced with argon. After that, irradiation with microwaves (2.45 GHz, 120 W) was performed for 60 minutes to cause a reaction. The solvent was distilled off, the obtained residue was dissolved in dichloromethane, and filtration was performed to remove insoluble matter. The obtained filtrate was washed with water and then with saturated saline, and was dried with magnesium sulfate. The solution after drying was filtered. The solvent of this solution was distilled off, and then the obtained residue was purified by silica gel column chromatography using dichloromethane and ethyl acetate as a developing solvent in a volume ratio of 50:1. After that, recrystallization was carried out with a mixed solvent of dichloromethane and hexane to give orange powder that was the objective substance (yield of 32%). A synthesis scheme (a-3) of Step 3 is shown below.

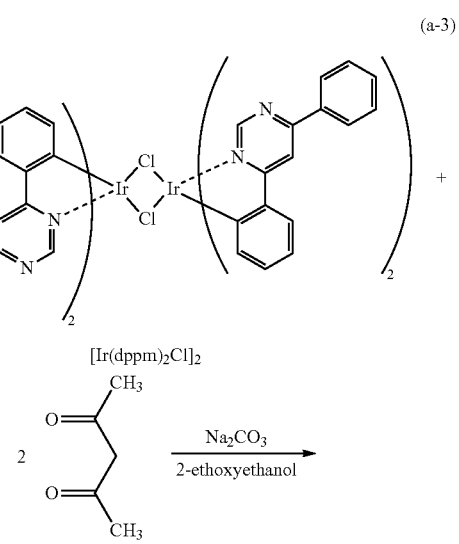

(a-3)

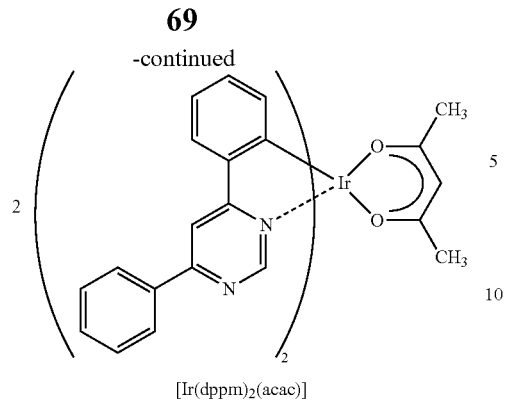

[Ir(dppm)₂(acac)]

Figure 8:
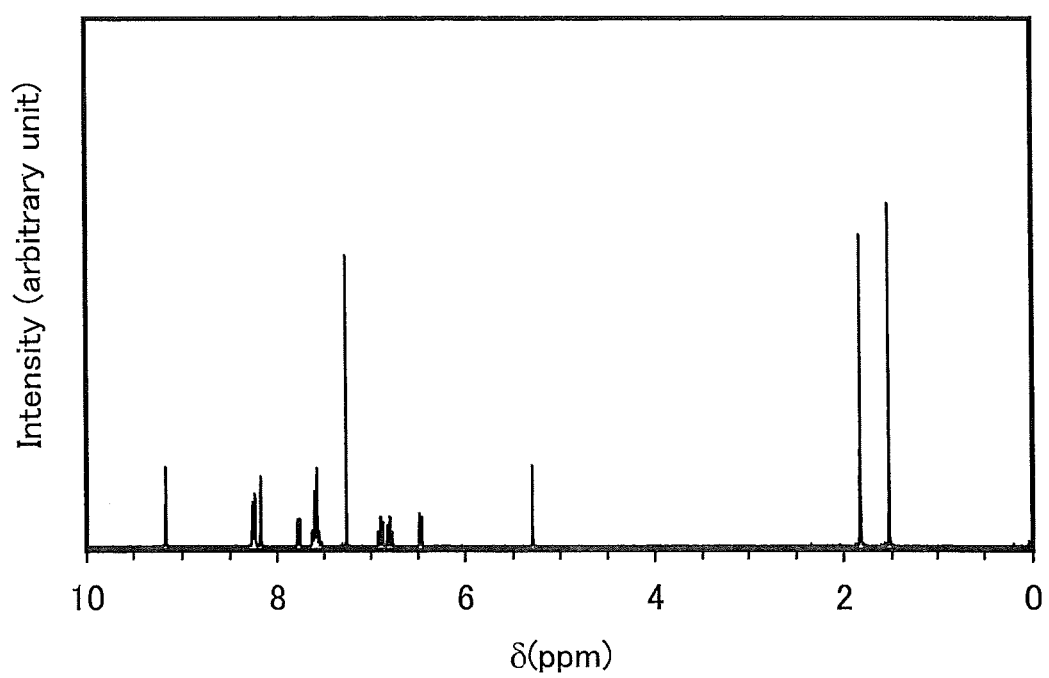
FIG. 8 shows a $^1$H NMR chart of an organometallic complex represented by a structural formula (100).

An analysis result by nuclear magnetic resonance spectrometry (¹H NMR) of the orange powder obtained in Step 3 is described below. The ¹H NMR chart is illustrated in FIG. 8. These results revealed that the organometallic complex [Ir(dppm)₂(acac)], which is one embodiment of the present invention represented by the structural formula (100), was obtained in Synthetic Example 1.

¹H NMR. δ (CDCl₃): 1.83 (s, 6H), 5.29 (s, 1H), 6.48 (d, 2H), 6.80 (t, 2H), 6.90 (t, 2H), 7.55-7.63 (m, 6H), 7.77 (d, 2H), 8.17 (s, 2H), 8.24 (d, 4H), 9.17 (s, 2H).

Figure 9:
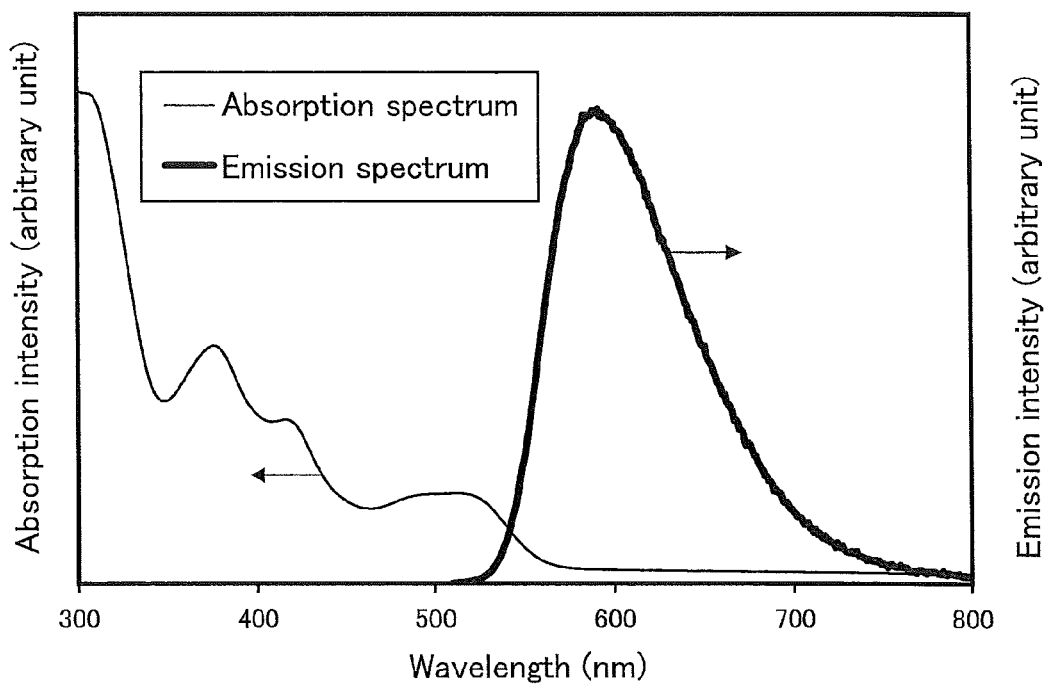
FIG. 9 shows an ultraviolet-visible absorption spectrum and an emission spectrum of the organometallic complex represented by the structural formula (100).

Next, an ultraviolet-visible absorption spectrum (hereinafter, simply referred to as an absorption spectrum) and an emission spectrum of [Ir(dppm)₂(acac)] in a dichloromethane solution were measured. The absorption spectrum was measured with the use of an ultraviolet-visible light spectrophotometer (V-550, manufactured by JASCO Corporation) in the state where the dichloromethane solution (0.093 mmol/L) was put in a quartz cell at room temperature. The emission spectrum was measured with the use of a fluorescence spectrophotometer (FS920, manufactured by Hamamatsu Photonics Corporation) in the state where the degassed dichloromethane solution (0.093 mmol/L) was put in a quartz cell at room temperature. FIG. 9 shows results of the measured absorption spectrum and emission spectrum. The horizontal axis represents wavelength (nm), and the vertical axis represents absorption intensity (arbitrary unit) and emission intensity (arbitrary unit). In FIG. 9, two solid lines are shown; a thin line represents the absorption spectrum, and a thick line represents the emission spectrum. Note that the absorption spectrum in FIG. 9 is a result obtained by subtraction of the absorption spectrum of only dichloromethane that was put in a quartz cell from the measured absorption spectrum of the dichloromethane solution (0.093 mmol/L) in a quartz cell.

As shown in FIG. 9, the organometallic complex [Ir(dppm)₂(acac)], which is one embodiment of the present invention, has an emission peak at 592 nm, and orange light was observed from the dichloromethane solution.

Note that in fabrication of a light-emitting element, [Ir(dppm)₂(acac)] was not burnt in a boat when being evaporated and the use efficiency of the material was high.

EXAMPLE 2

Synthetic Example 2

In Example 2, a synthetic example of an organometallic complex (acetylacetonato)bis(6-methyl-4-phenylpyrimidinato)iridium(III) (another name: bis[2-(6-methyl-4-pyrimidinyl-κN3)phenyl-κC](2,4-pentanedionato-κ²O,O')iridium(III)) (abbreviation: [Ir(mppm)₂(acac)]), which is one embodiment of the present invention represented by the structural formula (140) in Embodiment 1, is specifically described. A structure of [Ir(mppm)₂(acac)] is shown below.

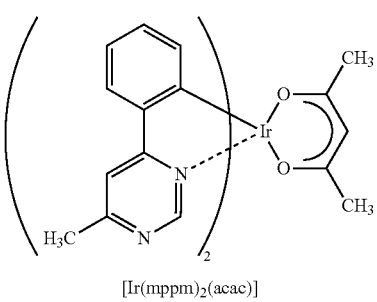

[Ir(mppm)₂(acac)]

Step 1: Synthesis of 4-methyl-6-phenylpyrimidine (abbreviation: Hmppm)

First, into a recovery flask equipped with a reflux pipe were put 4.90 g of 4-chloro-6-methylpyrimidine, 4.80 g of phenylboronic acid, 4.03 g of sodium carbonate, 0.16 g of bis(triphenylphosphine)palladium(II)dichloride (abbreviation: Pd(PPh₃)₂Cl₂), 20 mL of water, and 10 mL of acetonitrile, and the air in the flask was replaced with argon. This reaction container was heated by irradiation with microwaves (2.45 GHz, 100 W) for 60 minutes. Here, in the flask were further put 2.28 g of phenylboronic acid, 2.02 g of sodium carbonate, 0.082 g of Pd(PPh₃)₂Cl₂, 5 mL of water, and 10 mL of acetonitrile, and the mixture was heated again by irradiation with microwaves (2.45 GHz, 100 W) for 60 minutes. After that, water was added to this solution and extraction with dichloromethane was carried out. The obtained solution of the extract was washed with a saturated sodium carbonate aqueous solution, water, and then with saturated saline, and dried with magnesium sulfate. The solution after drying was filtered. The solvent of this solution was distilled off, and then the obtained residue was purified by silica gel column chromatography using dichloromethane and ethyl acetate as a developing solvent in a volume ratio of 9:1, so that a pyrimidine derivative Hmppm, which was the objective substance, was obtained (orange oily substance, yield of 46%). Note that the irradiation with microwaves was performed using a microwave synthesis system (Discover, manufactured by CEM Corporation). A synthesis scheme (b-1) of Step 1 is shown below.

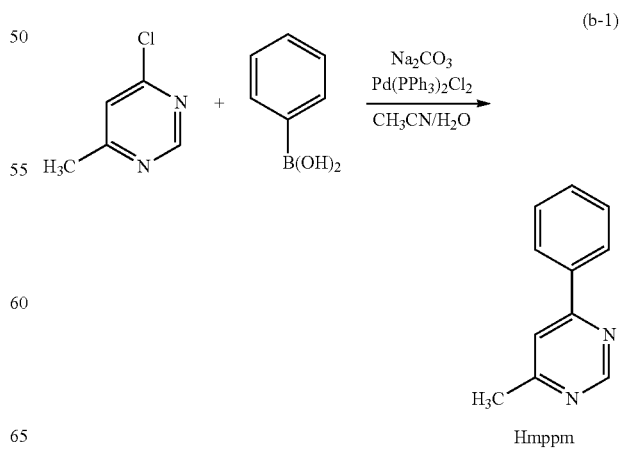

Step 2: Synthesis of di-μ-chloro-bis[bis(6-methyl-4-phenylpyrimidinato)iridium(III)] (abbreviation: [Ir(mppm)$_2$Cl]$_2$)

Next, into a recovery flask equipped with a reflux pipe were put 15 mL of 2-ethoxyethanol, 5 mL of water, 1.51 g of Hmppm obtained in Step 1, and 1.26 g of iridium chloride hydrate (IrCl$_3$·H$_2$O), and the air in the recovery flask was replaced with argon. After that, irradiation with microwaves (2.45 GHz, 100 W) was performed for 1 hour to cause a reaction. The solvent was distilled off, and then the obtained residue was washed with ethanol and filtered to give a dinuclear complex. [Ir(mppm)$_2$Cl]$_2$ (dark green powder, yield of 77%). A synthesis scheme (b-2) of Step 2 is shown below.

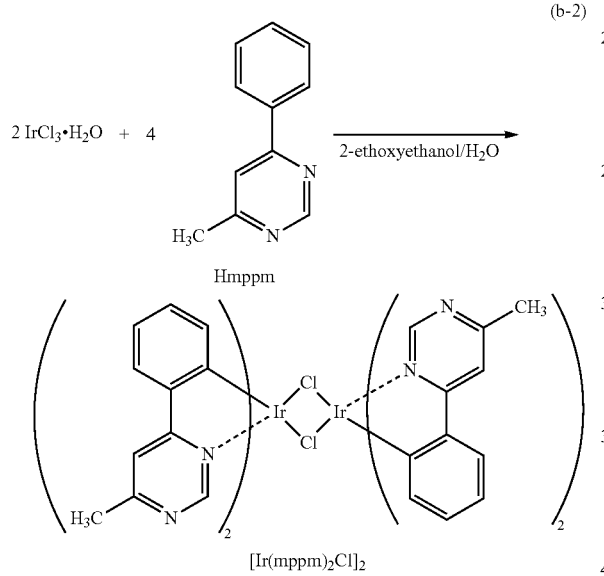

Step 3: Synthesis of (acetylacetonato)bis(6-methyl-4-phenylpyrimidinato)iridium(III) (abbreviation: [Ir(mppm)$_2$(acac)])

Furthermore, into a recovery flask equipped with a reflux pipe were put 40 mL of 2-ethoxyethanol, 1.84 g of the dinuclear complex [Ir(mppm)$_2$Cl]$_2$ obtained in Step 2, 0.48 g of acetylacetone, and 1.73 g of sodium carbonate, and the air in the recovery flask was replaced with argon. After that, irradiation with microwaves (2.45 GHz, 120 W) was performed for 60 minutes to cause a reaction. The solvent was distilled off, the obtained residue was dissolved in dichloromethane, and filtration was performed to remove insoluble matter. The obtained filtrate was washed with water and then with saturated saline, and was dried with magnesium sulfate. The solution after drying was filtered. The solvent of this solution was distilled off, and then the obtained residue was purified by silica gel column chromatography using dichloromethane and ethyl acetate as a developing solvent in a volume ratio of 4:1. After that, recrystallization was carried out with a mixed solvent of dichloromethane and hexane to give yellow powder that was the objective substance (yield of 22%). A synthesis scheme (b-3) of Step 3 is shown below.

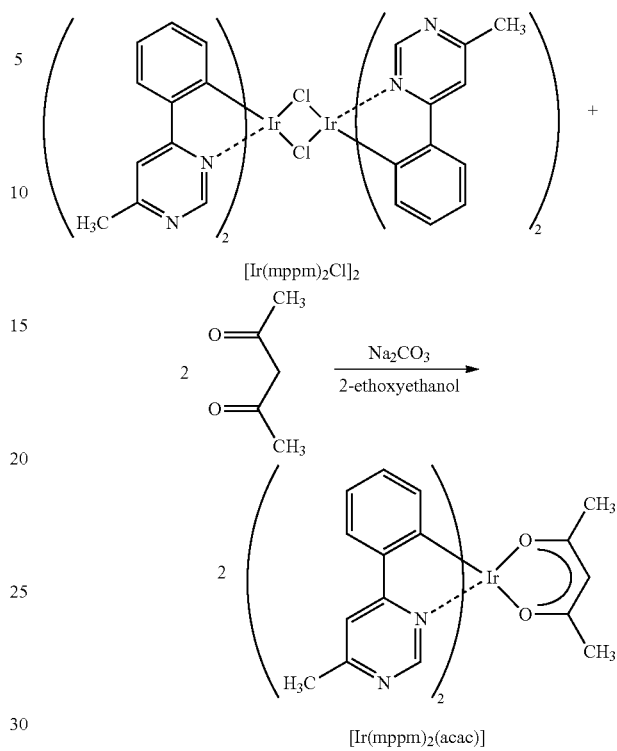

Figure 10:
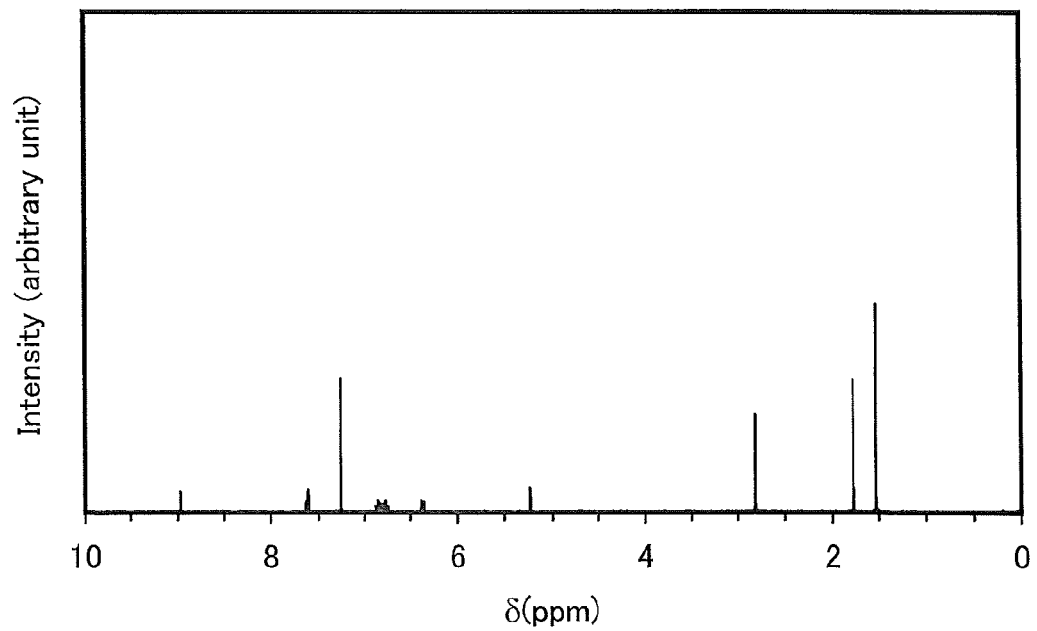
FIG. 10 shows a $^1$H NMR chart of an organometallic complex represented by a structural formula (140).

An analysis result by nuclear magnetic resonance spectrometry ($^1$H NMR) of the yellow powder obtained in Step 3 is described below. The $^1$H NMR. chart is illustrated in FIG. 10. These results revealed that the organometallic complex [Ir(mppm)$_2$(acac)], which is one embodiment of the present invention represented by the structural formula (140), was obtained in Synthetic Example 2.

$^1$H NMR. δ (CDCl$_3$): 1.78 (s, 6H), 2.81 (s, 6H), 5.24 (s, 1H), 6.37 (d, 2H), 6.77 (t, 2H), 6.85 (t, 2H), 7.61-7.63 (m, 4H), 8.97 (s, 2H).

Figure 11:
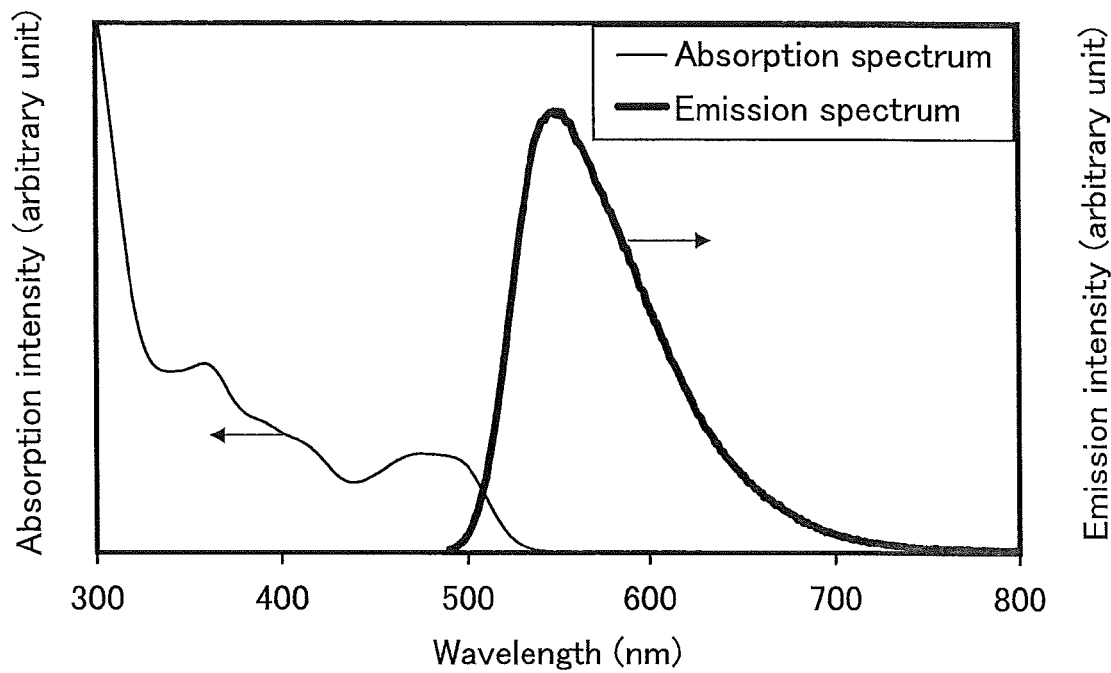
FIG. 11 shows an ultraviolet-visible absorption spectrum and an emission spectrum of the organometallic complex represented by the structural formula (140).

Next, an ultraviolet-visible absorption spectrum (hereinafter, simply referred to as an absorption spectrum) and an emission spectrum of [Ir(mppm)$_2$(acac)] in a dichloromethane solution were measured. The absorption spectrum was measured with the use of an ultraviolet-visible light spectrophotometer (V-550, manufactured by JASCO Corporation) in the state where the dichloromethane solution (0.10 mmol/L) was put in a quartz cell at room temperature. The emission spectrum was measured with the use of a fluorescence spectrophotometer (FS920, manufactured by Hamamatsu Photonics Corporation) in the state where the degassed dichloromethane solution (0.018 mmol/L) was put in a quartz cell at room temperature. FIG. 11 shows results of the measured absorption spectrum and emission spectrum. The horizontal axis represents wavelength (nm), and the vertical axis represents absorption intensity (arbitrary unit) and emission intensity (arbitrary unit). In FIG. 11, two solid lines are shown; a thin line represents the absorption spectrum, and a thick line represents the emission spectrum. Note that the absorption spectrum in FIG. 11 is a result obtained by subtraction of the absorption spectrum of only dichloromethane that was put in a quartz cell from the measured absorption spectrum of the dichloromethane solution (0.10 mmol/L) in a quartz cell.

As shown in FIG. 11, the organometallic complex [Ir(mppm)$_2$(acac)], which is one embodiment of the present invention, has an emission peak at 548 nm, and yellow green light was observed from the dichloromethane solution.

EXAMPLE 3

Synthetic Example 3

In Example 3, a synthetic example of an organometallic complex tris(4,6-diphenylpyrimidinato)iridium(III) (another name. tris[2-(6-phenyl-4-pyrimidinyl-κN3)phenyl-κC]iridium(III)) (abbreviation: [Ir(dppm)$_3$]), which is one embodiment of the present invention represented by the structural formula (152) in Embodiment 1, is specifically described. A structure of [Ir(dppm)$_3$] is shown below.

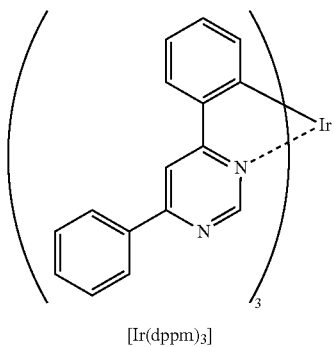

[Ir(dppm)$_3$]

Into a reaction container provided with a three-way cock were put 1.17 g of the ligand Hppm obtained in Step 1 in Synthetic Example 1 and 0.49 g of tris(acetylacetonato)iridium(III), and the air in the reaction container was replaced with argon. After that, the mixture was heated at 250° C. for 45.5 hours to be reacted. The reactant was dissolved in dichloromethane, and this solution was filtered. The solvent of the obtained filtrate was distilled of and purification was conducted by silica gel column chromatography. As developing solvents, first, dichloromethane was used, and then ethyl acetate was used. The solvent of the resulting fraction was distilled off, so that a red solid was obtained (yield of 41%). The obtained solid was recrystallized with a mixed solvent of dichloromethane and hexane to give red powder that was the objective substance (yield of 11%). A synthetic scheme (c-1) of Synthetic Example 3 is shown below.

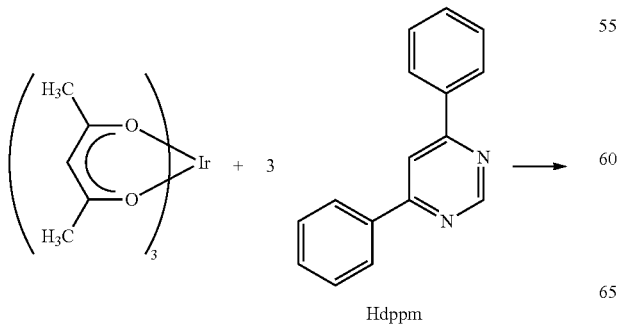

(c-1)

Hdppm

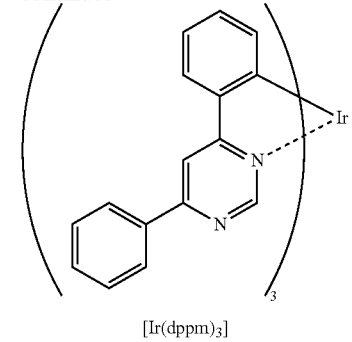

[Ir(dppm)$_3$]

Figure 12:
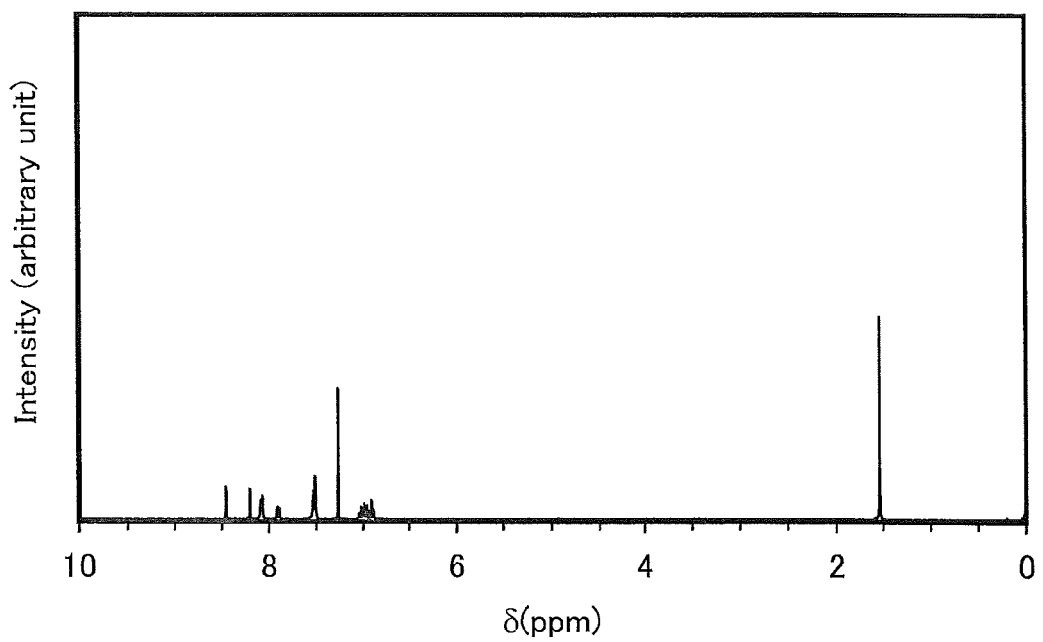
FIG. 12 shows a $^1$H NMR chart of an organometallic complex represented by a structural formula (152).

An analysis result by nuclear magnetic resonance spectrometry ($^1$H NMR) of the red powder obtained is described below. The $^1$H NMR chart is illustrated in FIG. 12. These results revealed that the organometallic complex [Ir(dppm)$_3$], which is one embodiment of the present invention represented by the structural formula (104), was obtained in Synthetic Example 3.

$^1$H NMR. δ (CDCl$_3$): 6.88-7.04 (m, 9H), 7.51-7.54 (m, 9H), 7.90 (d, 3H), 8.07 (d, 3H), 8.09 (d, 3H), 8.21 (s, 3H), 8.46 (s, 3H).

Figure 13:
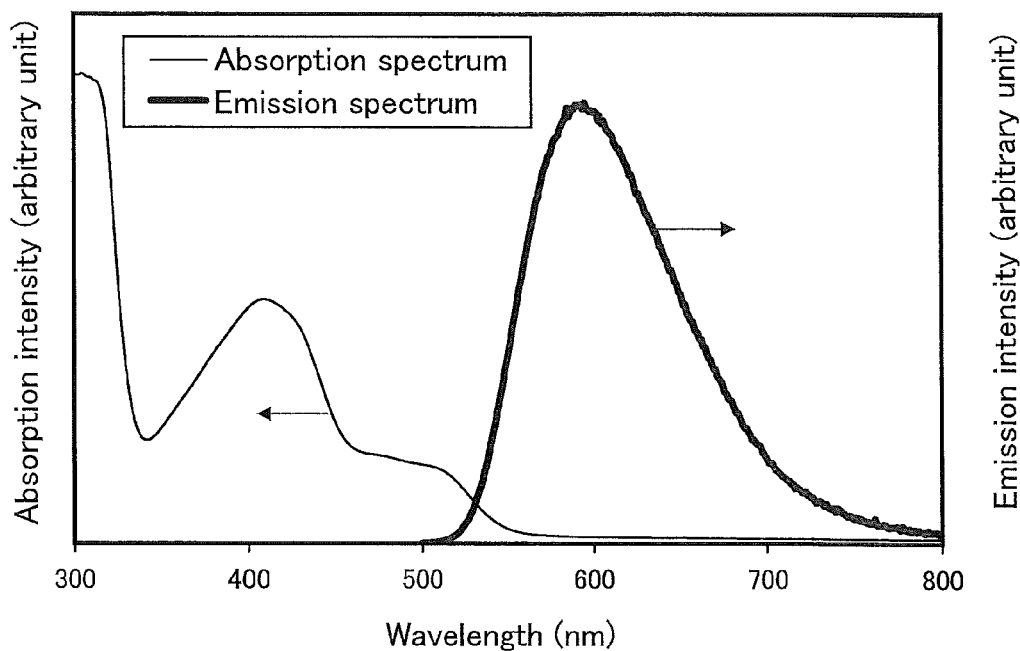
FIG. 13 shows an ultraviolet-visible absorption spectrum and an emission spectrum of the organometallic complex represented by the structural formula (152).

Next, an ultraviolet-visible absorption spectrum (hereinafter, simply referred to as an absorption spectrum) and an emission spectrum of [Ir(dppm)$_3$] in a dichloromethane solution were measured. The absorption spectrum was measured with the use of an ultraviolet-visible light spectrophotometer (V-550, manufactured by JASCO Corporation) in the state where the dichloromethane solution (0.075 mmol/L) was put in a quartz cell at room temperature. The emission spectrum was measured with the use of a fluorescence spectrophotometer (FS920, manufactured by Hamamatsu Photonics Corporation) in the state where the degassed dichloromethane solution (0.075 mmol/L) was put in a quartz cell at room temperature. FIG. 13 shows results of the measured absorption spectrum and emission spectrum. The horizontal axis represents wavelength (nm), and the vertical axis represents absorption intensity (arbitrary unit) and emission intensity (arbitrary unit). In FIG. 13, two solid lines are shown; a thin line represents the absorption spectrum, and a thick line represents the emission spectrum. Note that the absorption spectrum in FIG. 13 is a result obtained by subtraction of the absorption spectrum of only dichloromethane that was put in a quartz cell from the measured absorption spectrum of the dichloromethane solution (0.075 mmol/L) in a quartz cell.

As shown in FIG. 13, the organometallic complex [Ir(dppm)$_3$], which is one embodiment of the present invention, has an emission peak at 596 nm, and orange light was observed from the dichloromethane solution.

EXAMPLE 4

Comparative Example 1

In Example 4, a method of synthesizing an organometallic complex (acetylacetonato)bis(4-phenylpyrimidinato)iridium(III) (abbreviation: [Ir(ppm)$_2$(acac)]) is described. A structure of [Ir(ppm)$_2$(acac)] is shown below.

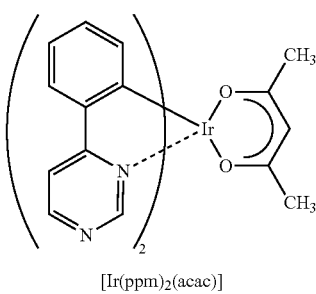

[Ir(ppm)₂(acac)]

Step 1: Synthesis of di-μ-chloro-bis[bis(4-phenylpyrimidine)iridium(III)](abbreviation: [Ir(ppm)₂Cl]₂)

First, into a three-neck flask equipped with a reflux pipe were put 30 mL of 2-ethoxyethanol, 10 mL of water, 0.67 g of a ligand 4-phenylpyrimidine (abbreviation: Hppm), 0.50 g of iridium chloride (IrCl₃.HCl.H₂O), and the air in the three-neck flask was replaced with nitrogen. After that, the mixture was heated and refluxed for 13 hours to be reacted. The reacted solution was cooled naturally to room temperature and filtered. The substance obtained by the filtration was washed with ethanol to give a dinuclear complex [Ir(ppm)₂Cl]₂ (red powder, yield of 42%). A synthesis scheme (d-1) of Step 1 is shown below.

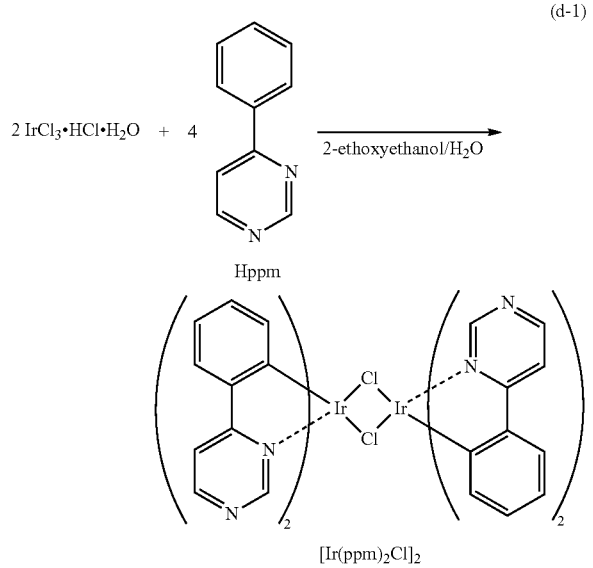

(d-1)

Step 2: Synthesis of (acetylacetonato)bis(4-phenylpyrimidinato)iridium(III) (abbreviation: [Ir(ppm)₂(acac)])

Further, into a three-neck flask equipped with a reflux pipe were put 20 mL of 2-ethoxyethanol, 0.37 g of the dinuclear complex [Ir(ppm)₂Cl]₂ obtained in Step 1, 0.11 mL of acetylacetone, and 0.37 g of sodium carbonate, and the air in the three-neck flask was replaced with nitrogen. After that, the mixture was heated and refluxed for 17.5 hours to be reacted. The reacted solution was cooled naturally to room temperature and filtered. The solvent of the filtrate was distilled off, and then the obtained residue was purified by silica gel column chromatography using dichloromethane as a developing solvent. However, fraction of an iridium complex that was the objective substance was not able to be collected. It is considered that the obtained fraction was obtained by decomposition of the dinuclear complex [Ir(ppm)₂Cl]₂. A synthesis scheme (d-2) of Step 2 is shown below.

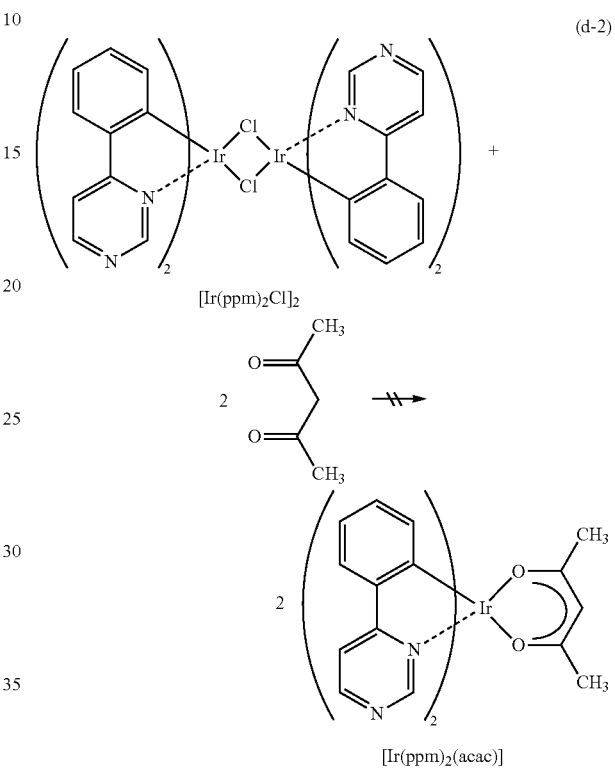

(d-2)

As described in Comparative Example 1, the synthesis of [Ir(ppm)₂(acac)] was difficult. Thus, it is found that as compared with the organometallic complexes which are described in Examples 1 to 3 and each of which is one embodiment of the present invention (a phenyl group is bonded to the 6-position of a pyrimidine ring), a substance where hydrogen is bonded to the 6-position of a pyrimidine ring has an extremely low yield or cannot be synthesized. This is considered to be because the dinuclear complex [Ir(ppm)₂Cl]₂ is decomposed as described above. That is, the decomposition reaction can be suppressed in the synthesis reaction of the organometallic complex which is one embodiment of the present invention; therefore, the yield of the synthesis is drastically improved as compared with [Ir(ppm)₂(acac)].

EXAMPLE 5

Comparative Example 2

In Example 5, a method of synthesizing an organometallic complex tris(4-phenylpyrimidinato)iridium(III) (abbreviation: [Ir(ppm)₃]) is described. A structure of [Ir(ppm)₃] is shown below.

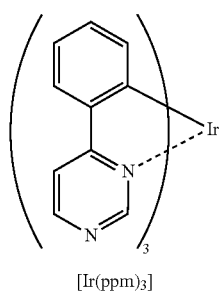

[Ir(ppm)₃]

First, into a reaction container provided with a three-way cock were put 1.95 g of a ligand 4-phenylpyrimidine (abbreviation: Hppm) and 1.20 g of tris(acetylacetonato)iridium (III), and the air in the reaction container was replaced with argon. After that, the mixture was heated at 250° C. for 41.5 hours to be reacted. The reactant was dissolved in dichloromethane, and this solution was filtered. The solvent of the obtained filtrate was distilled off, and a residue was obtained. This residue was purified by silica gel column chromatography. As developing solvents, first, dichloromethane was used, and then ethyl acetate was used. The solvent of the resulting fraction was distilled off, so that a brown solid was obtained. This solid was recrystallized with a mixed solvent of dichloromethane and hexane, so that a mixture containing the organometallic complex [Ir(ppm)₃] was obtained (brown powder, yield of 4%). From thin layer chromatography (TLC) of this mixture, a spot of the objective organometallic complex [Ir(ppm)₃] was extremely thin compared with a spot of brown impurities, so that the objective organometallic complex was not able to be isolated. A synthesis scheme (e-1) of Comparative Example 2 is shown below.

(e-1)

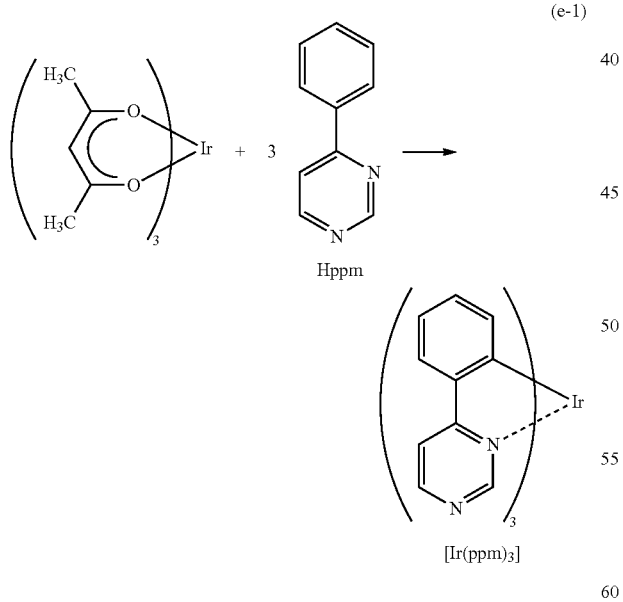

As described in Comparative Example 2, the synthesis of [Ir(ppm)₃] was difficult. Thus, it is found that as compared with the organometallic complexes which are described in Examples 1 to 3 and each of which is one embodiment of the present invention, a substance where a substituent bonded to the 6-position of a pyrimidine ring is hydrogen has an extremely low yield or cannot be synthesized. That is, in the case of an organometallic complex which is one embodiment of the present invention, it is possible to suppress decomposition reaction in the synthesis reaction of the complex; therefore, the yield of the synthesis is drastically improved as compared with [Ir(ppm)₃].

EXAMPLE 6

Figure 14:
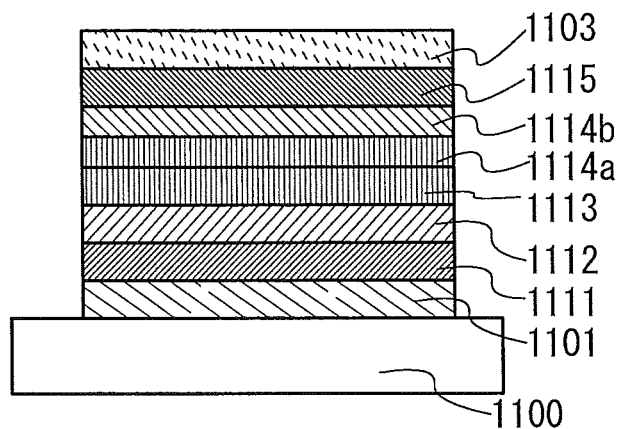
FIG. 14 illustrates a light-emitting element of Examples.

In Example 6, a light-emitting element which is one embodiment of the present invention is described with reference to FIG. 14. Chemical formulas of materials used in this example are shown below.

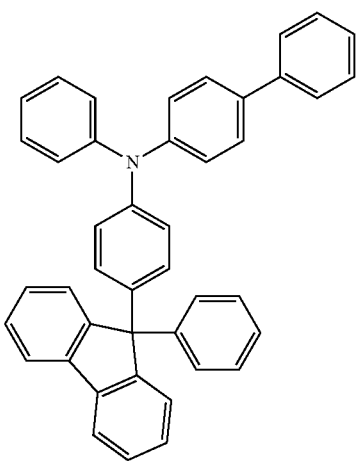

BPAFLP

PCBA1BP

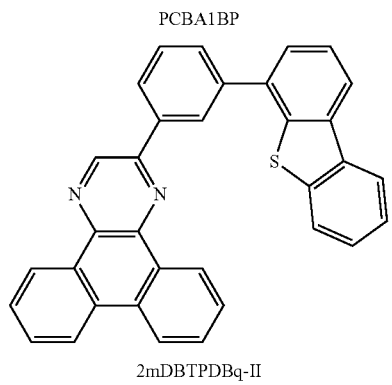

2mDBTPDBq-II

-continued

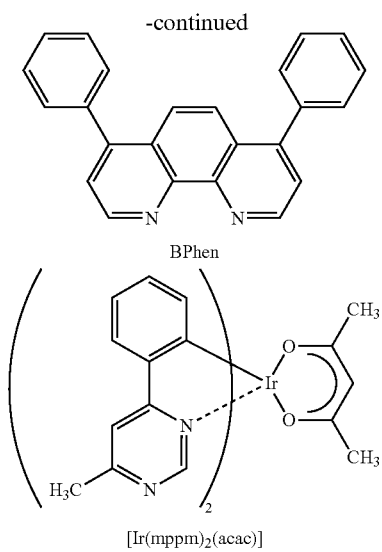

BPhen

[Ir(mppm)₂(acac)]

A method of fabricating a light-emitting element 1 of this example is described below.

(Light-Emitting Element 1)

First, a film of indium tin oxide containing silicon oxide (ITSO) was formed over a glass substrate 1100 by a sputtering method, so that a first electrode 1101 functioning as an anode was formed. The thickness was 110 nm and the electrode area was 2 mm×2 mm.

In pretreatment for forming the light-emitting element on the substrate 1100, UV ozone treatment was performed for 370 seconds after washing of a surface of the substrate with water and baking that was performed at 200° C. for 1 hour.

After that, the substrate 1100 was transferred into a vacuum evaporation apparatus where the pressure was reduced to approximately $10^{-4}$ Pa, and subjected to vacuum baking at 170° C. for 30 minutes in a heating chamber of the vacuum evaporation apparatus, and then the substrate 1100 was cooled down for about 30 minutes.

Next, the substrate 1100 provided with the first electrode 1101 was fixed to a substrate holder in a vacuum evaporation apparatus so that a surface on which the first electrode 1101 was provided faced downward. The pressure in the vacuum evaporation apparatus was reduced to about $10^{-4}$ Pa, and then 4-phenyl-4'-(9-phenylfluoren-9-yl)triphenylamine (abbreviation: BPAFLP) and molybdenum(VI) oxide were co-evaporated to form a hole-injection layer 1111 on the first electrode 1101. The thickness of the hole-injection layer 1111 was set to 40 nm, and the weight ratio of BPAFLP to molybdenum oxide was adjusted to 4:2 (=BPAFLP:molybdenum oxide). Note that the co-evaporation method means an evaporation method in which evaporation is carried out from a plurality of evaporation sources at the same time in one treatment chamber.

Next, a BPAFLP film was found to a thickness of 20 nm on the hole-injection layer 1111, whereby a hole-transport layer 1112 was formed.

Further, 2-[3-(dibenzothiophen-4-yl)phenyl]dibenzo[f,h]quinoxaline (abbreviation: 2mDBTPDBq-II), 4-phenyl-4'-(9-phenyl-9H-carbazol-3-yl)triphenylamine (abbreviation: PCBA1BP), and (acetylacetonato)bis(6-methyl-4-phenylpyrimidinato)iridium(III) (abbreviation: [Ir(mppm)₂(acac)]) synthesized in Example 2 were co-evaporated to form a light-emitting layer 1113 on the hole-transport layer 1112. The weight ratio of 2mDBTPDBq-II to PCBA1BP and [Ir(mppm)₂(acac)] was adjusted to 0.8:0.2:0.05 (=2mDBTPDBq-II:PCBA1BP:[Ir(mppm)₂(acac)]). The thickness of the light-emitting layer 1113 was set to 40 nm.

Next, a 2mDBTPDBq-II film was formed to a thickness of 10 nm on the light-emitting layer 1113, whereby a first electron-transport layer 1114a was formed.

Next, a bathophenanthroline (abbreviation: BPhen) film was formed to a thickness of 20 nm on the first electron-transport layer 1114a, whereby a second electron-transport layer 1114b was formed.

Further, a lithium fluoride (LiF) film was formed to a thickness of 1 nm on the second electron-transport layer 1114b by evaporation, whereby an electron-injection layer 1115 was formed.

Lastly, an aluminum film was formed to a thickness of 200 nm by evaporation to form a second electrode 1103 functioning as a cathode. Thus, the light-emitting element 1 of this example was fabricated.

Note that in the above evaporation process, evaporation was all performed by a resistance heating method.

Table 1 shows an element structure of the light-emitting element 1 obtained as described above.

TABLE 1

| | First Electrode | Hole-injection Layer | Hole-transport Layer | Light-emitting Layer | First electron-Transport Layer | Second electron-Transport Layer | Electron-injection Layer | Second Electrode |
|---|---|---|---|---|---|---|---|---|
| Light-emitting Element 1 | ITSO 110 nm | BPAFLP: MoOx (=4:2) 40 nm | BPAFLP 20 nm | 2mDBTPDBq-II: PCBA1BP: [Ir(mppm)₂(acac)] (=0.8:0.2:0.05) 40 nm | 2mDBTPDBq-II 10 nm | BPhen 20 nm | LiF 1 nm | Al 200 nm |

In a glove box containing a nitrogen atmosphere, the light-emitting element 1 was sealed so as not to be exposed to the air. After that, operation characteristics of the light-emitting element 1 were measured. Note that the measurements were carried out at room temperature (in an atmosphere kept at 25° C.).

Figure 15:
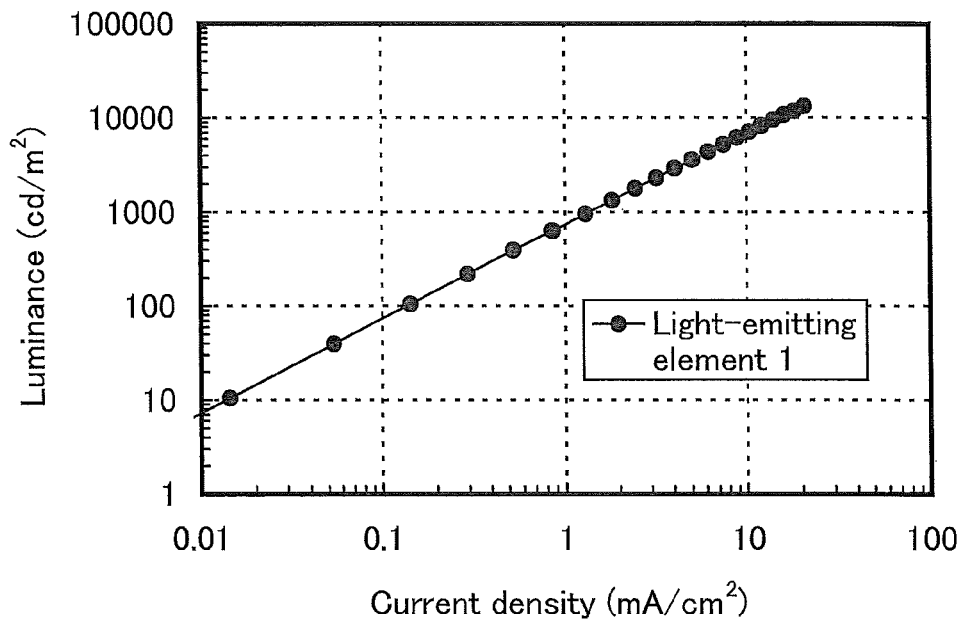
FIG. 15 shows current density vs. luminance characteristics of a light-emitting element 1.
Figure 16:
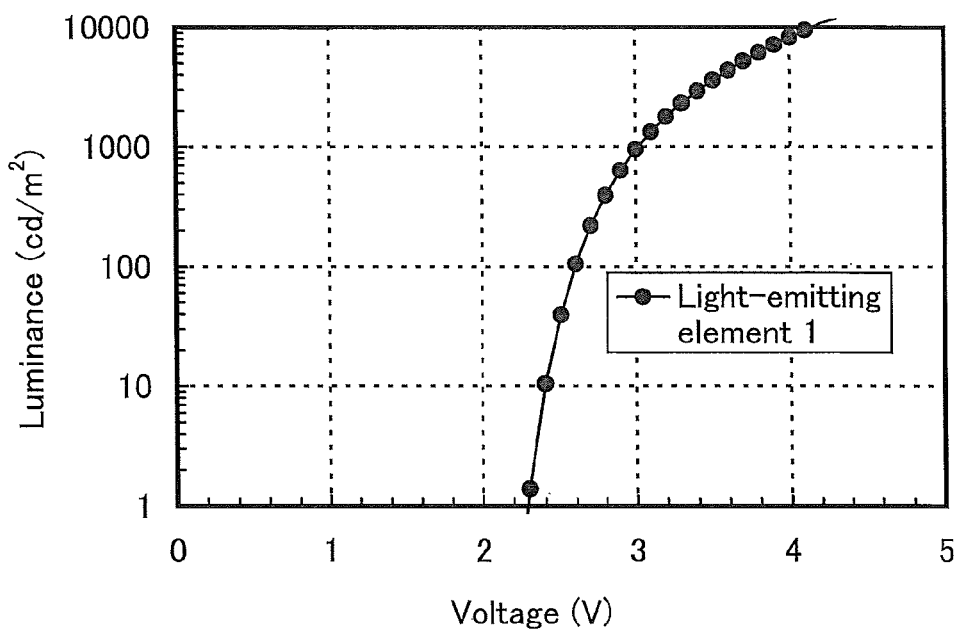
FIG. 16 shows voltage vs. luminance characteristics of the light-emitting element 1.
Figure 17:
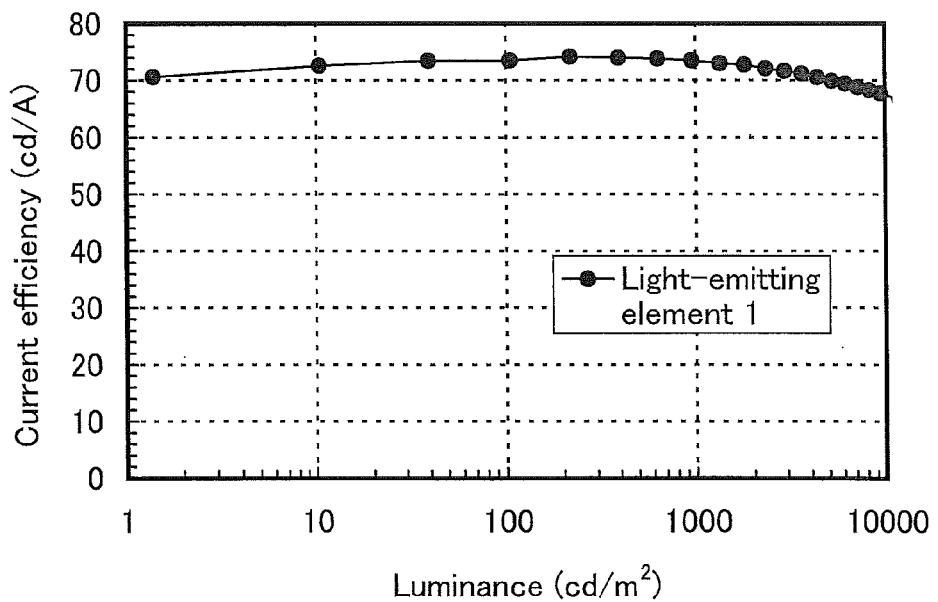
FIG. 17 shows luminance vs. current efficiency characteristics of the light-emitting element 1.

FIG. 15 shows current density vs. luminance characteristics of the light-emitting element 1. In FIG. 15, the horizontal axis represents current density (mA/cm²) and the vertical axis represents luminance (cd/m²). FIG. 16 shows voltage vs. luminance characteristics thereof. In FIG. 16, the horizontal axis represents voltage (V) and the vertical axis represents luminance (cd/m²). FIG. 17 shows luminance vs. current efficiency characteristics thereof. In FIG. 17, the horizontal axis represents luminance (cd/m²) and the vertical axis represents current efficiency (cd/A). Further, Table 2 shows voltage (V), current density (mA/cm²), CIE chromaticity coordinates (x, y), current efficiency (cd/A), power efficiency (lm/W), and external quantum efficiency (%) of the light-emitting element 1 at a luminance of 950 cd/m².

TABLE 2

| | Voltage (V) | Current Density (mA/cm$^2$) | Chromaticity (x, y) | Current Efficiency (cd/A) | Power Efficiency (lm/W) | External Quantum Efficiency (%) |
|---|---|---|---|---|---|---|
| Light-emitting Element 1 | 3.0 | 1.3 | (0.43, 0.56) | 73 | 77 | 22 |

Figure 18:
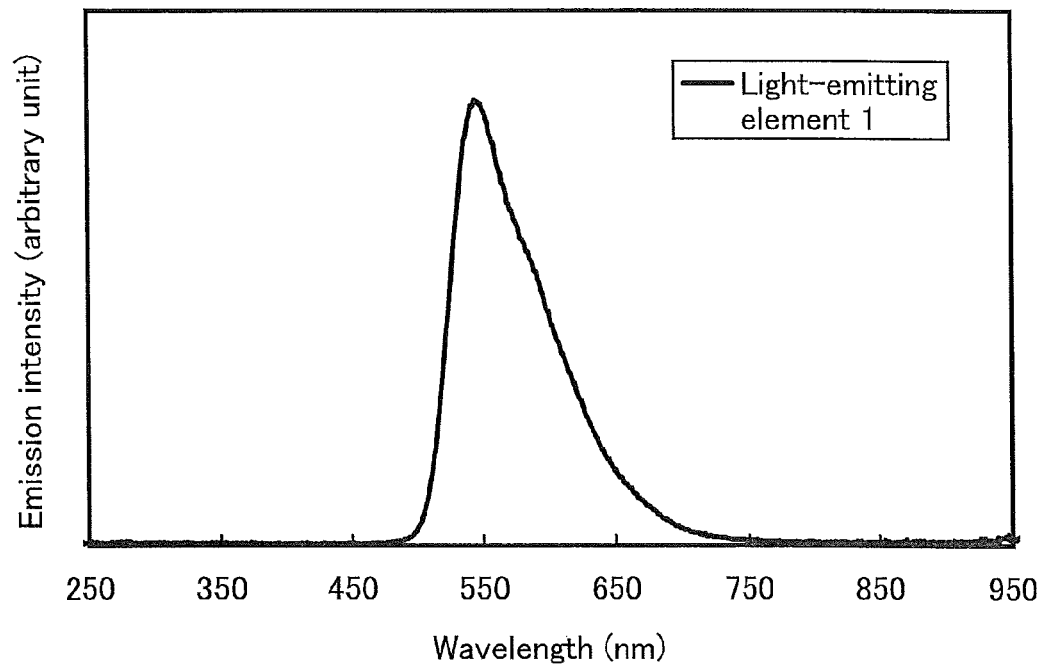
FIG. 18 shows an emission spectrum of the light-emitting element 1.

FIG. 18 shows an emission spectrum of the light-emitting element 1 which was obtained by applying a current of 0.1 mA. In FIG. 18, the horizontal axis represents wavelength (nm) and the vertical axis represents light emission intensity (arbitrary unit). As shown in FIG. 18, the emission spectrum of the light-emitting element 1 has a peak at 544 nm. In addition, as shown in Table 2, the CIE chromaticity coordinates of the light-emitting element 1 were (x, y)=(0.43, 0.56) at a luminance of 950 cd/m$^2$. The results show that yellow light emission originating from [Ir(mppm)$_2$(acac)] was obtained from the light-emitting element 1.

Table 2, FIG. 15, FIG. 16, and FIG. 17 indicate that the light-emitting element 1 has high emission efficiency.

The above results suggest that an element with high emission efficiency can be realized by using the organometallic complex which is one embodiment of the present invention as a light-emitting material.

Figure 19:
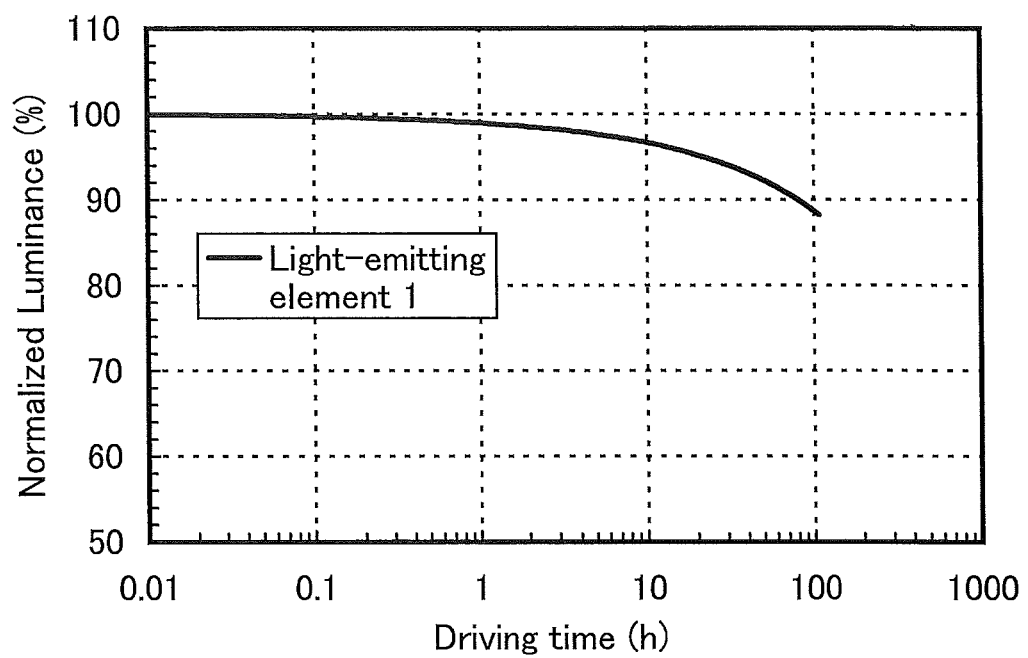
FIG. 19 shows results obtained by reliability testing of the light-emitting element 1.

Next, reliability testing of the light-emitting element 1 was carried out. Results of the reliability testing are shown in FIG. 19. In FIG. 19, the vertical axis represents normalized luminance (%) on the assumption that an initial luminance is 100%, and the horizontal axis represents driving time (h) of the element.

In the reliability testing, the light-emitting element 1 was driven under the conditions where the initial luminance was set to 5000 cd/m$^2$ and the current density was constant.

The light-emitting element 1 kept 88% of the initial luminance after the driving for 110 hours.

The above results suggest that an element having high reliability can be realized by using an organometallic complex which is one embodiment of the present invention as a light-emitting material.

EXAMPLE 7

In Example 7, a light-emitting element which is one embodiment of the present invention is described with reference to FIG. 14. Chemical formulas of materials used in this example are shown below. Note that the chemical formulas of the materials described above are omitted.

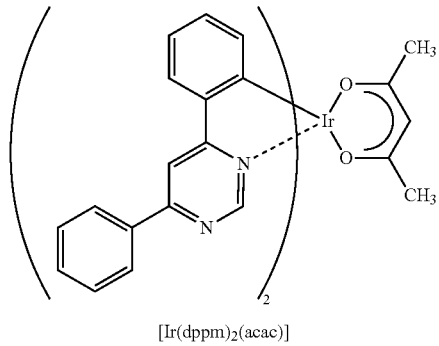

[Ir(dppm)$_2$(acac)]

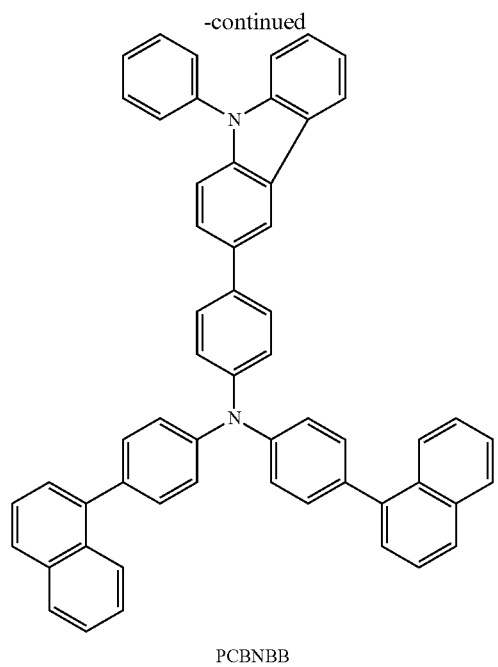

PCBNBB

A method of fabricating a light-emitting element 2 of this example is described below.

(Light-Emitting Element 2)

First, an ITSO film was formed over a glass substrate 1100 by a sputtering method, so that a first electrode 1101 functioning as an anode was formed. The thickness was 110 nm and the electrode area was 2 mm×2 mm.

In pretreatment for forming the light-emitting element on the substrate 1100, UV ozone treatment was performed for 370 seconds after washing of a surface of the substrate with water and baking that was performed at 200° C. for 1 hour.

After that, the substrate 1100 was transferred into a vacuum evaporation apparatus where the pressure was reduced to approximately 10$^{-4}$ Pa, and subjected to vacuum baking at 170° C. for 30 minutes in a heating chamber of the vacuum evaporation apparatus, and then the substrate 1100 was cooled down for about 30 minutes.

Next, the substrate 1100 provided with the first electrode 1101 was fixed to a substrate holder in a vacuum evaporation apparatus so that a surface on which the first electrode 1101 was provided faced downward. The pressure in the vacuum evaporation apparatus was reduced to about 10$^{-4}$ Pa, and then BPAFLP and molybdenum(VI) oxide were co-evaporated to form a hole-injection layer 1111 on the first electrode 1101. The thickness of the hole-injection layer 1111 was set to 40 nm, and the weight ratio of BPAFLP to molybdenum oxide was adjusted to 4:2 (=BPAFLP:molybdenum oxide).

Next, a BPAFLP film was formed to a thickness of 20 nm on the hole-injection layer 1111, whereby a hole-transport layer 1112 was formed.

Figure 22:
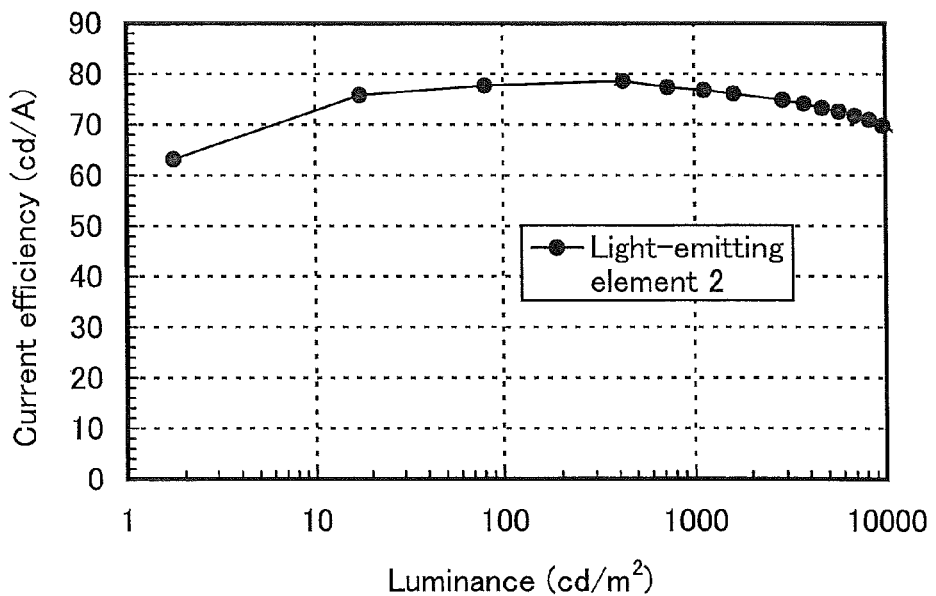
FIG. 22 shows luminance vs. current efficiency characteristics of the light-emitting element 2.
Figure 25:
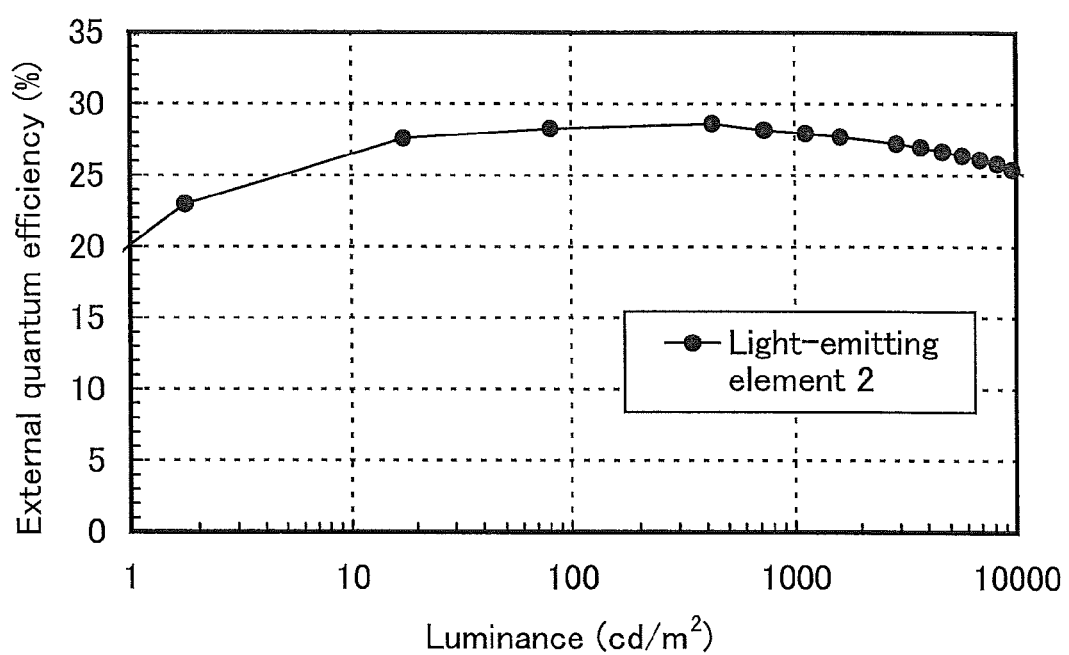
FIG. 25 shows luminance vs. external quantum efficiency characteristics of the light-emitting element 2.

Further, 2mDBTPDBq-II, 4,4'-di(1-naphthyl)-4"-(9-phenyl-9H-carbazol-3-yl)-triphenylamine (abbreviation: PCBNBB), and (acetylacetonato)bis(4,6-diphenylpyrimidinato)iridium(III) (abbreviation: [Ir(dppm)$_2$(acac)]) synthesized in Example 1 were co-evaporated to form a light-emitting layer 1113 on the hole-transport layer 1112. The weight ratio of 2mDBTPDBq-II to PCBNBB and [Ir(dppm)$_2$(acac)] was adjusted to 0.8:0.2:0.05 (=2mDBTPDBq-II:PCBNBB:[Ir(dppm)$_2$(acac)]). The thickness of the light-emitting layer 1113 was set to 40 nm efficiency characteristics thereof. In FIG. 22, the horizontal axis represents luminance (cd/m$^2$) and the vertical axis represents current efficiency (cd/A). In addition, FIG. 25 shows luminance vs. external quantum efficiency characteristics thereof. In FIG. 25, the horizontal axis represents luminance (cd/m$^2$) and the vertical axis represents external quantum efficiency (%).

Further, Table 4 shows voltage (V), current density (mA/cm$^2$), CIE chromaticity coordinates (x, y), current efficiency (cd/A), power efficiency (lm/W), and external quantum efficiency (%) of the light-emitting element 2 at a luminance of 1100 cd/m$^2$.

TABLE 4

|  | Voltage (V) | Current Density (mA/cm$^2$) | Chromaticity (x, y) | Current Efficiency (cd/A) | Power Efficiency (lm/W) | External Quantum Efficiency (%) |
|---|---|---|---|---|---|---|
| Light-emitting Element 2 | 2.9 | 1.5 | (0.54, 0.46) | 77 | 83 | 28 |

Next, a 2mDBTPDBq-II film was formed to a thickness of 10 nm on the light-emitting layer 1113, whereby a first electron-transport layer 1114a was formed.

Next, a BPhen film was fainted to a thickness of 20 nm on the first electron-transport layer 1114a, whereby a second electron-transport layer 1114b was formed.

Further, a LiF film was formed to a thickness of 1 nm on the second electron-transport layer 1114b by evaporation, whereby an electron-injection layer 1115 was formed.

Lastly, an aluminum film was formed to a thickness of 200 nm by evaporation to form a second electrode 1103 functioning as a cathode. Thus, the light-emitting element 2 of this example was fabricated.

Note that in the above evaporation process, evaporation was all performed by a resistance heating method.

Table 3 shows an element structure of the light-emitting element 2 obtained as described above.

Figure 23:
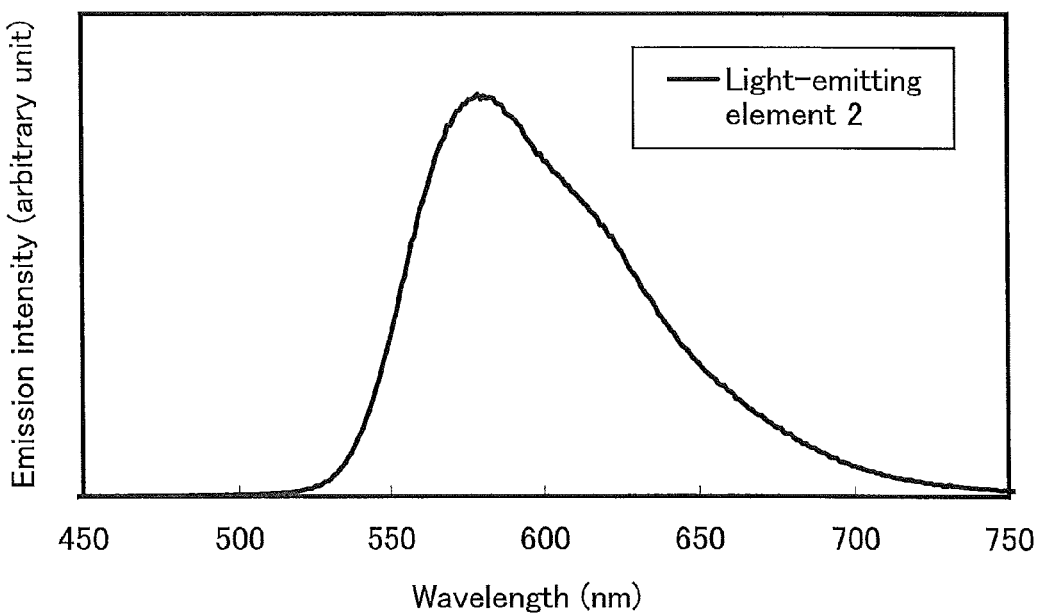
FIG. 23 shows an emission spectrum of the light-emitting element 2.

FIG. 23 shows an emission spectrum of the light-emitting element 2 which was obtained by applying a current of 0.1 mA. In FIG. 23, the horizontal axis represents wavelength (nm) and the vertical axis represents light emission intensity (arbitrary unit). As shown in FIG. 23, the emission spectrum of the light-emitting element 2 has a peak at 579 nm. In addition, as shown in Table 4, the CIE chromaticity coordinates of the light-emitting element 2 were (x, y)=(0.54, 0.46) at a luminance of 1100 cd/m$^2$. The results show that orange light emission originating from [Ir(dppm)$_2$(acac)] was obtained from the light-emitting element 2.

FIG. 20, FIG. 21, FIG. 22, FIG. 25, and Table 4 indicate that the light-emitting element 2 has high emission efficiency. In particular, the light-emitting element 2 has an extremely high external quantum efficiency at a luminance of 1100 cd/m$^2$, which is 28%. Note that it is said that the light extrac-

TABLE 3

|  | First Electrode | Hole-injection Layer | Hole-transport Layer | Light-emitting Layer | First electron-Transport Layer | Second electron-Transport Layer | Electron-injection Layer | Second Electrode |
|---|---|---|---|---|---|---|---|---|
| Light-emitting Element 2 | ITSO 110 nm | BPAFLP: MoOx (=4:2) 40 nm | BPAFLP 20 nm | 2mDBTPDBq-II: PCBNBB: [Ir(dppm)$_2$(acac)] (=0.8:0.2:0.05) 40 nm | 2mDBTPDBq-II 10 nm | BPhen 20 nm | LiF 1 nm | Al 200 nm |

In a glove box containing a nitrogen atmosphere, the light-emitting element 2 was sealed so as not to be exposed to the air. After that, operation characteristics of the light-emitting element 2 were measured. Note that the measurements were carried out at room temperature (in an atmosphere kept at 25° C.).

Figure 20:
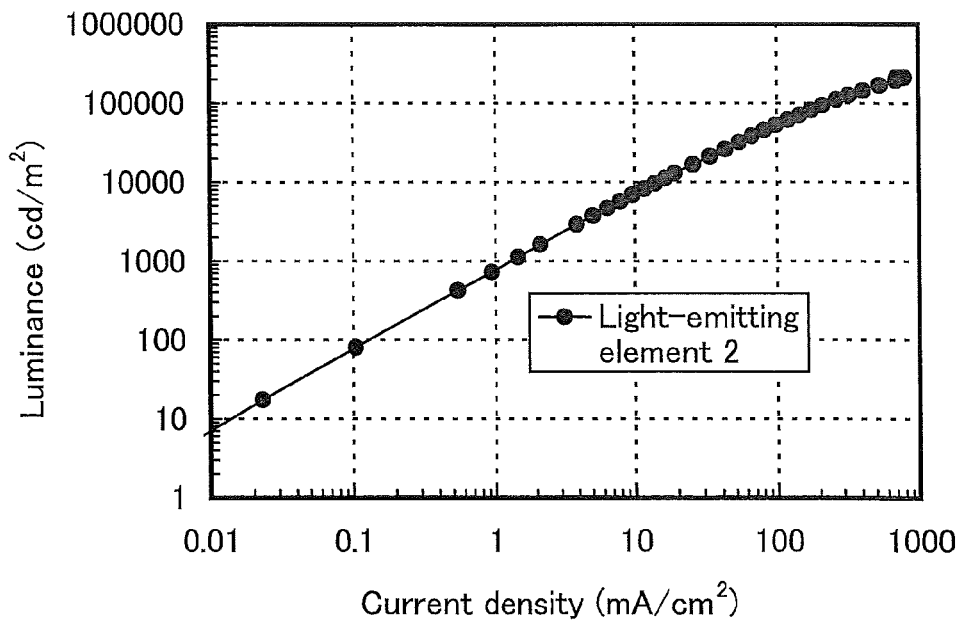
FIG. 20 shows current density vs. luminance characteristics of a light-emitting element 2.
Figure 21:
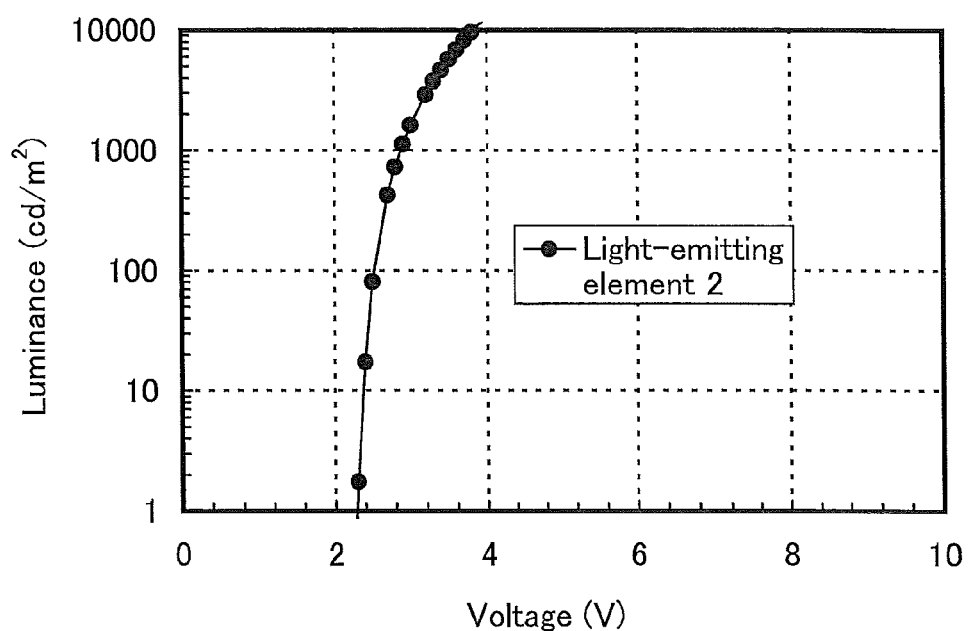
FIG. 21 shows voltage vs. luminance characteristics of the light-emitting element 2.

FIG. 20 shows current density vs. luminance characteristics of the light-emitting element 2. In FIG. 20, the horizontal axis represents current density (mA/cm$^2$) and the vertical axis represents luminance (cd/m$^2$). FIG. 21 shows voltage vs. luminance characteristics thereof. In FIG. 21, the horizontal axis represents voltage (V) and the vertical axis represents luminance (cd/m$^2$). FIG. 22 shows luminance vs. current tion efficiency of an organic EL element is approximately 20% to 30%, considering light absorption by upper and lower electrodes (the light extraction efficiency is considered to be reduced by approximately 10%) or the like, the limit of the external quantum efficiency can be approximately 25% at most. However, the results of the external quantum efficiency this time is over the limit, indicating that the conventional theoretical value of the light extraction efficiency was wrong. That is, by using the organometallic complex which is one embodiment of the present invention, a novel light-emitting element with such a high efficiency can be realized, so that it is possible to indicate the theoretical value of the light extraction efficiency is wrong.

The above results suggest that an element with high emission efficiency can be realized by using the organometallic complex which is one embodiment of the present invention as a light-emitting material.

Figure 24:
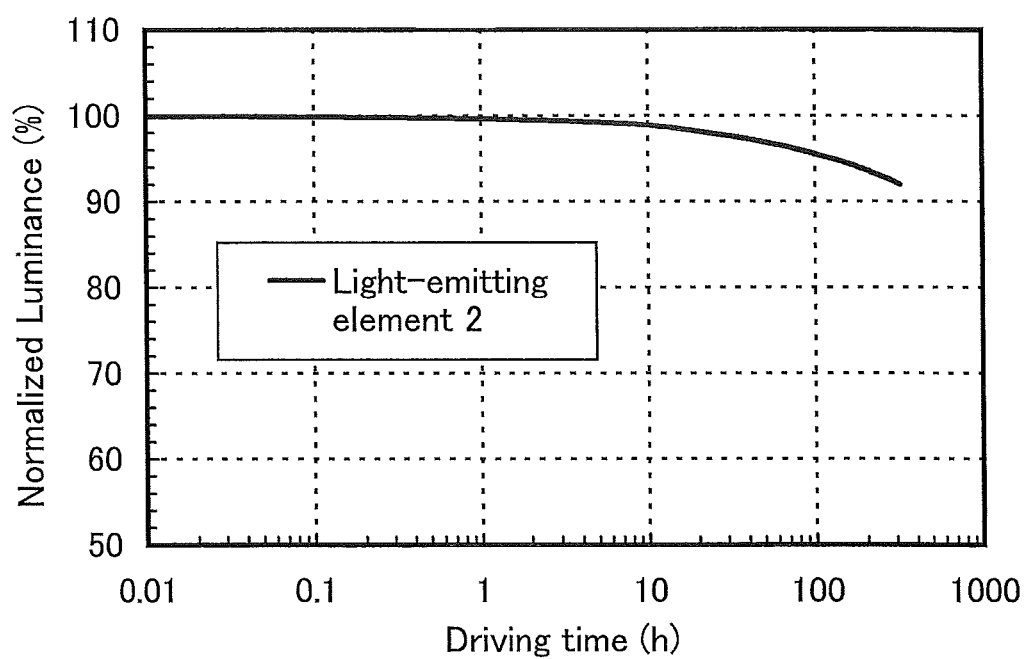
FIG. 24 shows results obtained by reliability testing of the light-emitting element 2.

Next, reliability testing of the light-emitting element 2 was carried out. Results of the reliability testing are shown in FIG. 24. In FIG. 24, the vertical axis represents normalized luminance (%) on the assumption that an initial luminance is 100%, and the horizontal axis represents driving time (h) of the element.

In the reliability testing, the light-emitting element 2 was driven under the conditions where the initial luminance was set to 5000 cd/m$^2$ and the current density was constant.

The light-emitting element 2 kept 92% of the initial luminance after the driving for 320 hours.

The above results suggest that an element having high reliability can be realized by using an organometallic complex which is one embodiment of the present invention as a light-emitting material.

EXAMPLE 8

In Example 8, a light-emitting element which is one embodiment of the present invention is described with reference to FIG. 14. Materials used in this example are the same as those used in Example 6 or 7, and their chemical formulas are omitted here.

A method of fabricating a light-emitting element 3 of this example is described below.
(Light-Emitting Element 3)

First, an ITSO film was formed over a glass substrate 1100 by a sputtering method, so that a first electrode 1101 functioning as an anode was formed. The thickness was 110 nm and the electrode area was 2 mm×2 mm.

In pretreatment for forming the light-emitting element on the substrate 1100, UV ozone treatment was performed for 370 seconds after washing of a surface of the substrate with water and baking that was performed at 200° C. for 1 hour.

After that, the substrate 1100 was transferred into a vacuum evaporation apparatus where the pressure was reduced to approximately 10$^{-4}$ Pa, and subjected to vacuum baking at 170° C. for 30 minutes in a heating chamber of the vacuum evaporation apparatus, and then the substrate 1100 was cooled down for about 30 minutes.

Next, the substrate 1100 provided with the first electrode 1101 was fixed to a substrate holder in a vacuum evaporation apparatus so that a surface on which the first electrode 1101 was provided faced downward. The pressure in the vacuum evaporation apparatus was reduced to about 10$^{-4}$ Pa, and then BPAFLP and molybdenum(VI) oxide were co-evaporated to form a hole-injection layer 1111 on the first electrode 1101. The thickness of the hole-injection layer 1111 was set to 40 nm, and the weight ratio of BPAFLP to molybdenum oxide was adjusted to 4:2 (=BPAFLP:molybdenum oxide).

Next, a BPAFLP film was formed to a thickness of 20 nm on the hole-injection layer 1111, whereby a hole-transport layer 1112 was formed.

Further, 2mDBTPDBq-II, PCBA1BP, and [Ir(dppm)$_2$(acac)] synthesized in Example 1 were co-evaporated to form a light-emitting layer 1113 on the hole-transport layer 1112. The weight ratio of 2mDBTPDBq-II to PCBA1BP and [Ir(dppm)$_2$(acac)] was adjusted to 0.8:0.2:0.1 (=2mDBTPDBq-II:PCBA1BP:[Ir(dppm)$_2$(acac)]). The thickness of the light-emitting layer 1113 was set to 40 nm.

Next, a 2mDBTPDBq-II film was formed to a thickness of 15 nm on the light-emitting layer 1113, whereby a first electron-transport layer 1114a was formed.

Next, a BPhen film was foamed to a thickness of 15 nm on the first electron-transport layer 1114a, whereby a second electron-transport layer 1114b was formed.

Further, a LiF film was formed to a thickness of 1 nm on the second electron-transport layer 1114b by evaporation, whereby an electron-injection layer 1115 was formed.

Lastly, an aluminum film was formed to a thickness of 200 nm by evaporation to form a second electrode 1103 functioning as a cathode. Thus, the light-emitting element 3 of this example was fabricated.

Note that in the above evaporation process, evaporation was all performed by a resistance heating method.

Table 5 shows an element structure of the light-emitting element 3 obtained as described above.

TABLE 5

| | First Electrode | Hole-injection Layer | Hole-transport Layer | Light-emitting Layer | First electron-Transport Layer | Second electron-Transport Layer | Electron-injection Layer | Second Electrode |
|---|---|---|---|---|---|---|---|---|
| Light-emitting Element 3 | ITSO 110 nm | BPAFLP:MoOx (=4:2) 40 nm | BPAFLP 20 nm | 2mDBTPDBq-II:PCBA1BP:[Ir(dppm)$_2$(acac)] (=0.8:0.2:0.1) 40 nm | 2mDBTPDBq-II 15 nm | BPhen 15 nm | LiF 1 nm | Al 200 nm |

In a glove box containing a nitrogen atmosphere, the light-emitting element 3 was sealed so as not to be exposed to the air. After that, operation characteristics of the light-emitting element 3 were measured. Note that the measurements were carried out at room temperature (in an atmosphere kept at 25° C.).

Figure 26:
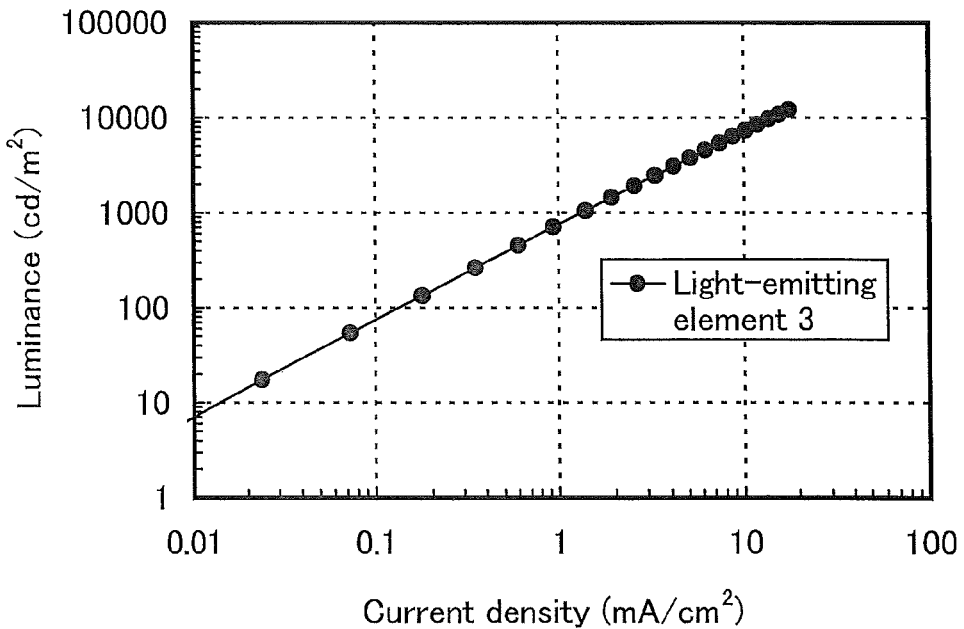
FIG. 26 shows current density vs. luminance characteristics of a light-emitting element 3.
Figure 27:
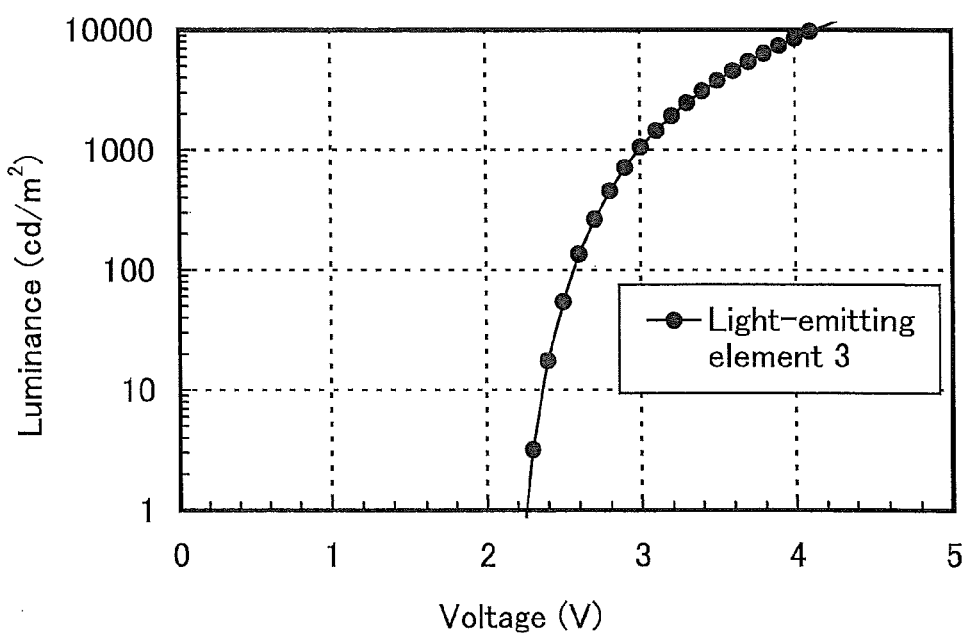
FIG. 27 shows voltage vs. luminance characteristics of the light-emitting element 3.
Figure 28:
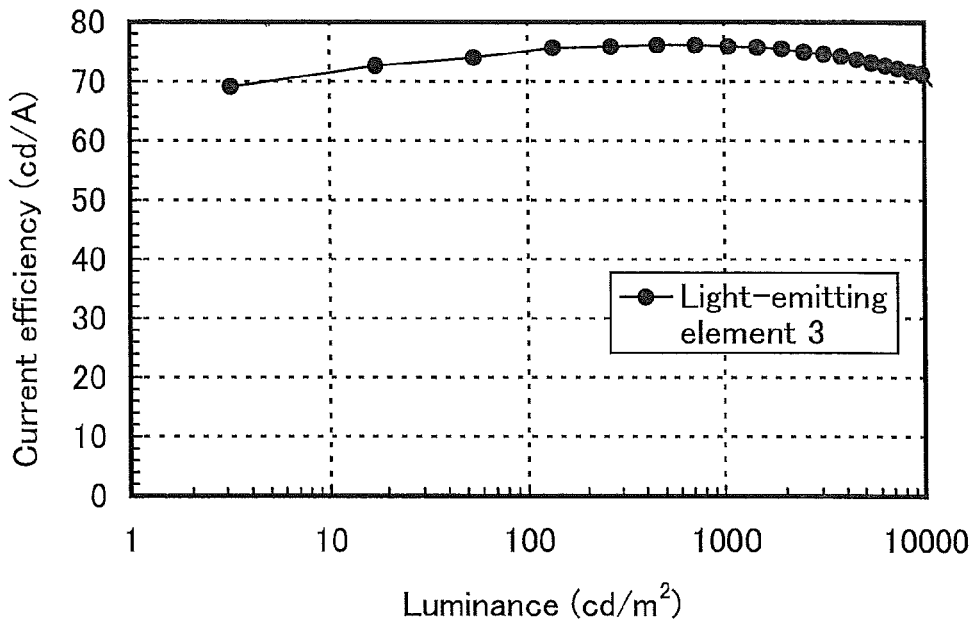
FIG. 28 shows luminance vs. current efficiency characteristics of the light-emitting element 3.
Figure 31:
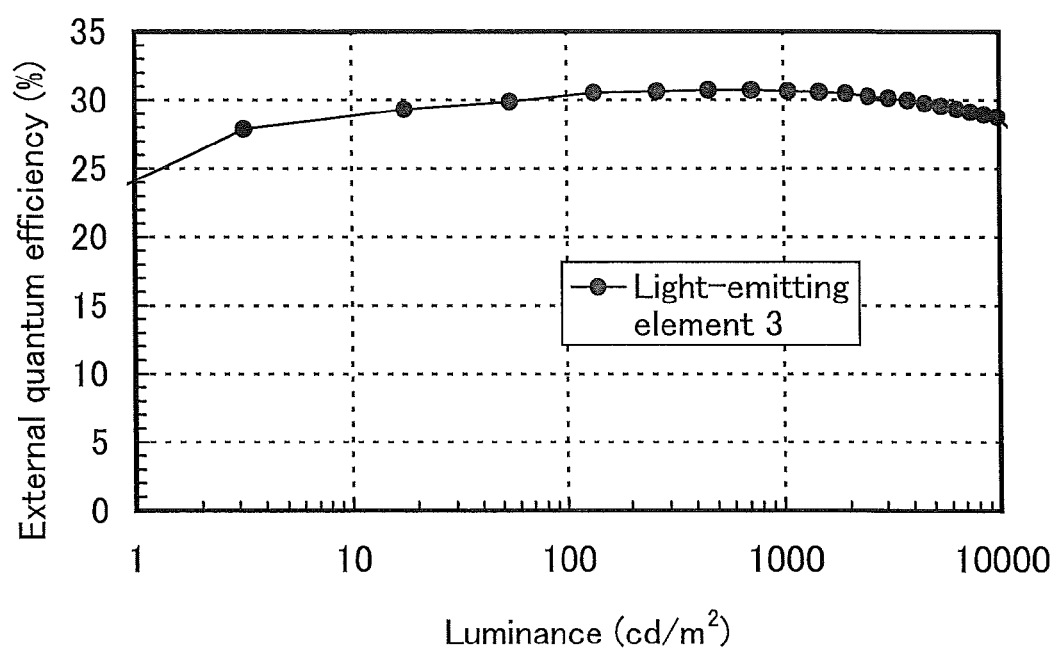
FIG. 31 shows luminance vs. external quantum efficiency characteristics of the light-emitting element 3.

FIG. 26 shows current density vs. luminance characteristics of the light-emitting element 3. In FIG. 26, the horizontal axis represents current density (mA/cm$^2$) and the vertical axis represents luminance (cd/m$^2$). FIG. 27 shows voltage vs. luminance characteristics thereof. In FIG. 27, the horizontal axis represents voltage (V) and the vertical axis represents luminance (cd/m$^2$). FIG. 28 shows luminance vs. current efficiency characteristics thereof. In FIG. 28, the horizontal axis represents luminance (cd/m$^2$) and the vertical axis represents current efficiency (cd/A). In addition, FIG. 31 shows luminance vs. external quantum efficiency characteristics thereof. In FIG. 31, the horizontal axis represents luminance (cd/m$^2$) and the vertical axis represents external quantum efficiency (%).

Further, Table 6 shows voltage (V), current density (mA/cm$^2$), CIE chromaticity coordinates (x, y), current efficiency (cd/A), power efficiency (lm/W), and external quantum efficiency (%) of the light-emitting element 3 at a luminance of 1100 cd/m$^2$.

TABLE 6

|  | Voltage (V) | Current Density (mA/cm$^2$) | Chromaticity (x, y) | Current Efficiency (cd/A) | Power Efficiency (lm/W) | External Quantum Efficiency (%) |
|---|---|---|---|---|---|---|
| Light-emitting Element 3 | 3.0 | 1.4 | (0.57, 0.43) | 76 | 70 | 31 |

Figure 29:
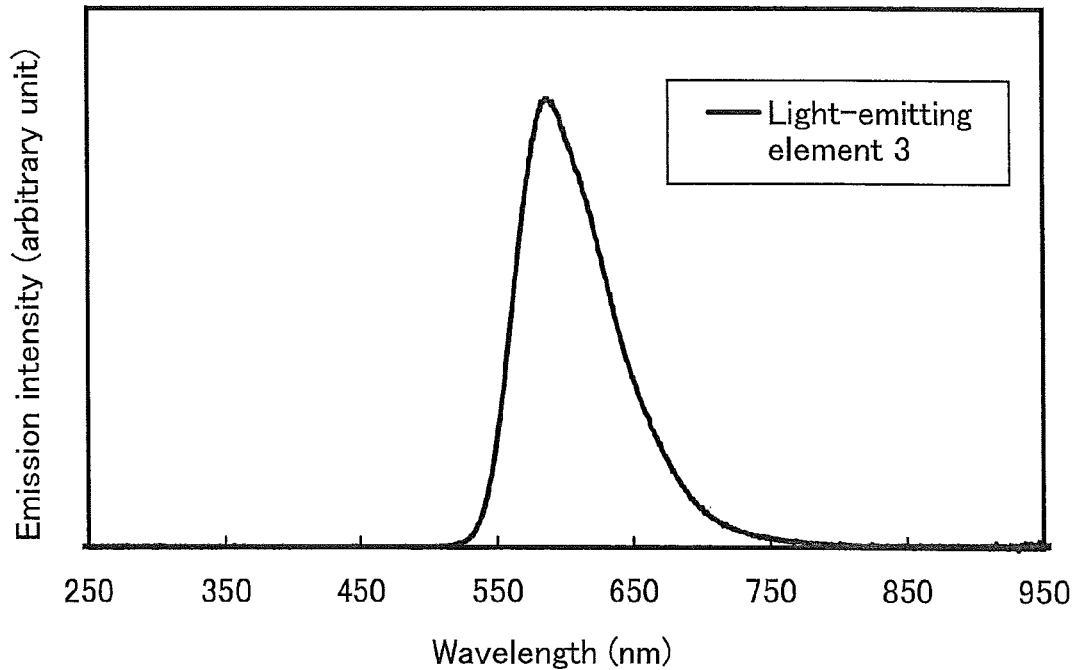
FIG. 29 shows an emission spectrum of the light-emitting element 3.

FIG. 29 shows an emission spectrum of the light-emitting element 3 which was obtained by applying a current of 0.1 mA. In FIG. 29, the horizontal axis represents wavelength (nm) and the vertical axis represents light emission intensity (arbitrary unit). As shown in FIG. 29, the emission spectrum of the light-emitting element 3 has a peak at 586 nm. In addition, as shown in Table 6, the CIE chromaticity coordinates of the light-emitting element 3 were (x, y)=(0.57, 0.43) at a luminance of 1100 cd/m$^2$. The results show that orange light emission originating from [Ir(dppm)$_2$(acac)] was obtained from the light-emitting element 3.

FIG. 26, FIG. 27, FIG. 28, FIG. 31, and Table 6 indicate that the light-emitting element 3 has high emission efficiency. In particular, the light-emitting element 3 has an extremely high external quantum efficiency at a luminance of 1100 cd/m$^2$, which is 31%. Note that it is said that the light extraction efficiency of an organic EL element is approximately 20% to 30%, considering light absorption by upper and lower electrodes (the light extraction efficiency is considered to be reduced by approximately 10%) or the like, the limit of the external quantum efficiency can be approximately 25% at most. However, the results of the external quantum efficiency this time is over the limit, indicating that the conventional theoretical value of the light extraction efficiency was wrong. That is, by using the organometallic complex which is one embodiment of the present invention, a novel light-emitting element with such a high efficiency can be realized, so that it is possible to indicate the theoretical value of the light extraction efficiency is wrong.

The above results suggest that an element with high emission efficiency can be realized by using the organometallic complex which is one embodiment of the present invention as a light-emitting material.

Figure 30:
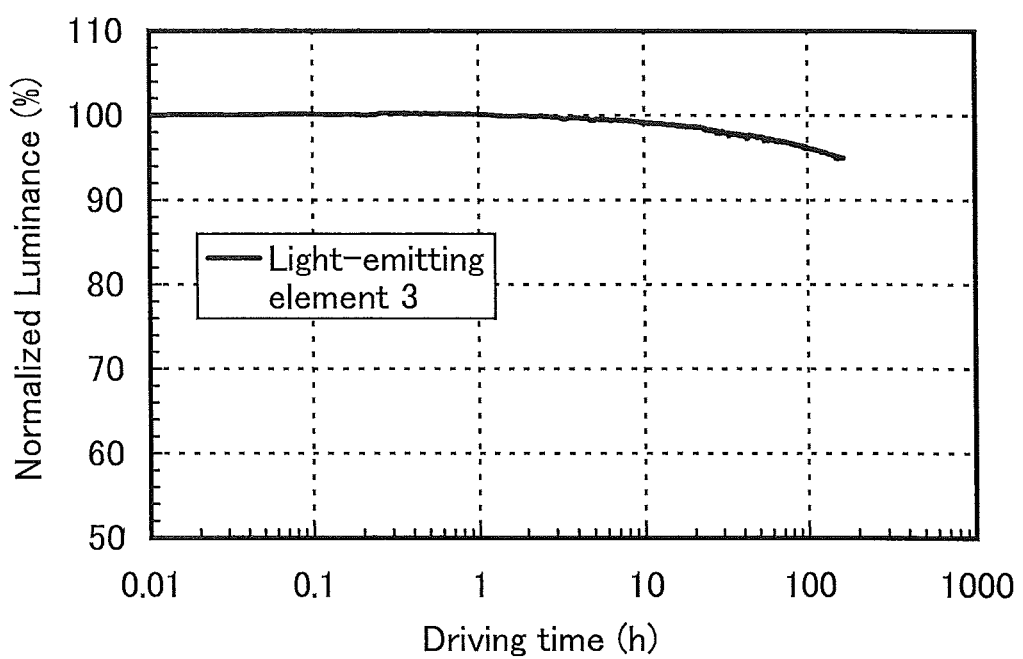
FIG. 30 shows results obtained by reliability testing of the light-emitting element 3.

Next, reliability testing of the light-emitting element 3 was carried out. Results of the reliability testing are shown in FIG. 30. In FIG. 30, the vertical axis represents normalized luminance (%) on the assumption that an initial luminance is 100%, and the horizontal axis represents driving time (h) of the element.

In the reliability testing, the light-emitting element 3 was driven under the conditions where the initial luminance was set to 5000 cd/m$^2$ and the current density was constant.

The light-emitting element 3 kept 95% of the initial luminance after the driving for 170 hours.

The above results suggest that an element having high reliability can be realized by using an organometallic complex which is one embodiment of the present invention as a light-emitting material.

Note that the concentration of the organometallic complex which is one embodiment of the present invention added to the light-emitting layer in Example 8 is higher than that in Example 7. Therefore, the element in Example 8 has a more redshifted emission spectrum (emission color) than the element in Example 7. However, the values of the external quantum efficiency of both elements are high and the reliability of them is also high. Thus, it is one of features of one embodiment of the present invention that hues of light emission can be changed by changing the concentration of the organometallic complex which is one embodiment of the present invention added to a light-emitting layer, without a decrease in emission efficiency and reliability of an element.

EXAMPLE 9

Synthetic Example 4

In Example 9, a synthetic example of an organometallic complex (acetylacetonato)bis(6-tert-butyl-4-phenylpyrimidinato)iridium(III) (another name: bis[2-(6-tert-butyl-4-pyrimidinyl-κN3)phenyl-κC] [2,4-pentanedionato-κ$^2$O,O')iridium(I II)) (abbreviation: [Ir(tBuppm)$_2$(acac)]), which is one embodiment of the present invention represented by the structural formula (190) in Embodiment 1, is specifically described. A structure of [Ir(tBuppm)$_2$(acac)] is shown below.

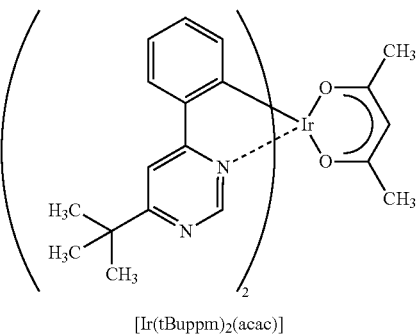

[Ir(tBuppm)$_2$(acac)]

Step 1: Synthesis of 4-tert-butyl-6-phenylpyrimidine (abbreviation: HtBuppm)

First, into a recovery flask equipped with a reflux pipe were put 22.5 g of 4,4-dimethyl-1-phenylpentane-1,3-dione and 50 g of formamide, and the air in the flask was replaced with nitrogen. This reaction container was heated, so that the reacted solution was refluxed for 5 hours. After that, this solution was poured into an aqueous sodium hydroxide solution, and an organic layer was extracted with dichloromethane. The obtained organic layer was washed with water and saturated saline, and dried with magnesium sulfate. The solution after drying was filtered. The solvent of this solution was distilled off, and then the obtained residue was purified by silica gel column chromatography using hexane and ethyl acetate as a developing solvent in a volume ratio of 10:1, so that a pyrimidine derivative HtBuppm (colorless oily substance, yield of 14%) was obtained. A synthetic scheme (f-1) of Step 1 is shown below.

(f-1)

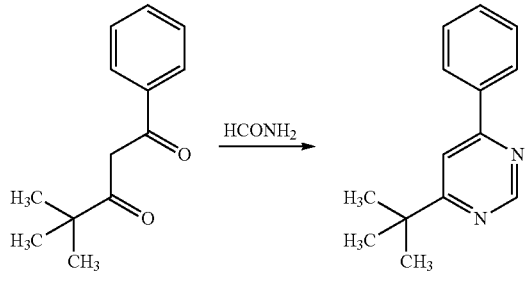

HtBuppm

Step 2: Synthesis of di-μ-chloro-bis[bis(6-tert-butyl-4-phenylpyrimidinato)iridium(III)] (abbreviation: [Ir(tBuppm)₂Cl]₂))

Next, into a recovery flask equipped with a reflux pipe were put 15 mL of 2-ethoxyethanol, 5 mL of water, 1.49 g of HtBuppm obtained in Step 1, and 1.04 g of iridium chloride hydrate (IrCl₃·H₂O), and the air in the flask was replaced with argon. After that, irradiation with microwaves (2.45 GHz, 100 W) was performed for 1 hour to cause a reaction. The solvent was distilled off, and then the obtained residue was suction-filtered and washed with ethanol to give a dinuclear complex [h(tBuppm)₂Cl]₂ (yellow green powder, yield of 73%). A synthesis scheme (f-2) of Step 2 is shown below.

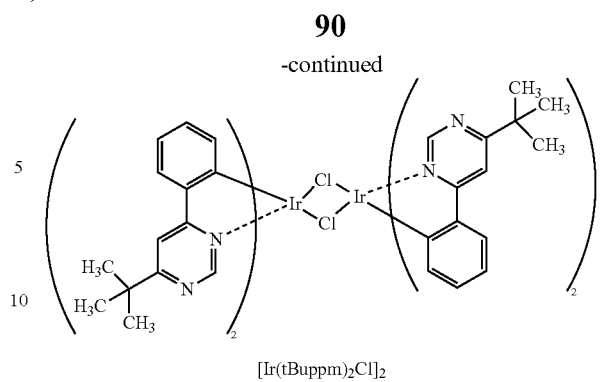

[Ir(tBuppm)₂Cl]₂

Step 3: Synthesis of (acetylacetonato)bis(6-tert-butyl-4-phenylpyrimidinato)iridium(III) (abbreviation: [Ir(tBuppm)₂(acac)])

Further, into a recovery flask equipped with a reflux pipe were put 40 mL of 2-ethoxyethanol, 1.61 g of the dinuclear complex [Ir(tBuppm)₂Cl]₂ obtained in Step 2, 0.36 g of acetylacetone, and 1.27 g of sodium carbonate, and the air in the flask was replaced with argon. After that, irradiation with microwaves (2.45 GHz, 120 W) was performed for 60 minutes to cause a reaction. The solvent was distilled off, and the obtained residue was suction-filtered with ethanol and washed with water and ethanol. This solid was dissolved in dichloromethane, and the mixture was filtered through a filter aid in which Celite (produced by Wako Pure Chemical Industries, Ltd., Catalog No. 531-16855), alumina, and Celite were stacked in this order. The solvent was distilled off, and the obtained solid was recrystallized with a mixed solvent of dichloromethane and hexane, so that the objective substance was obtained as yellow powder (yield of 68%). A synthesis scheme (f-3) of Step 3 is shown below.

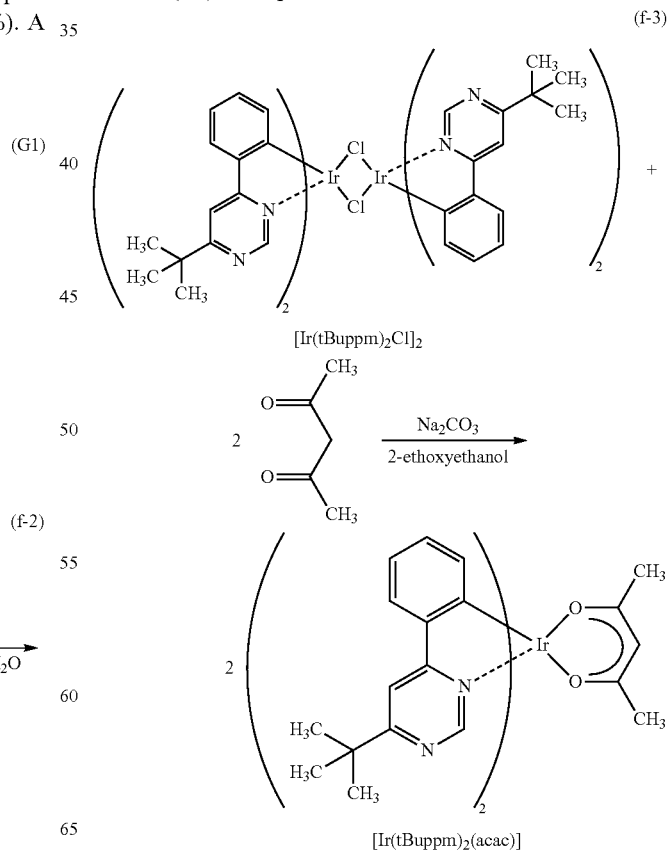

Figure 32:
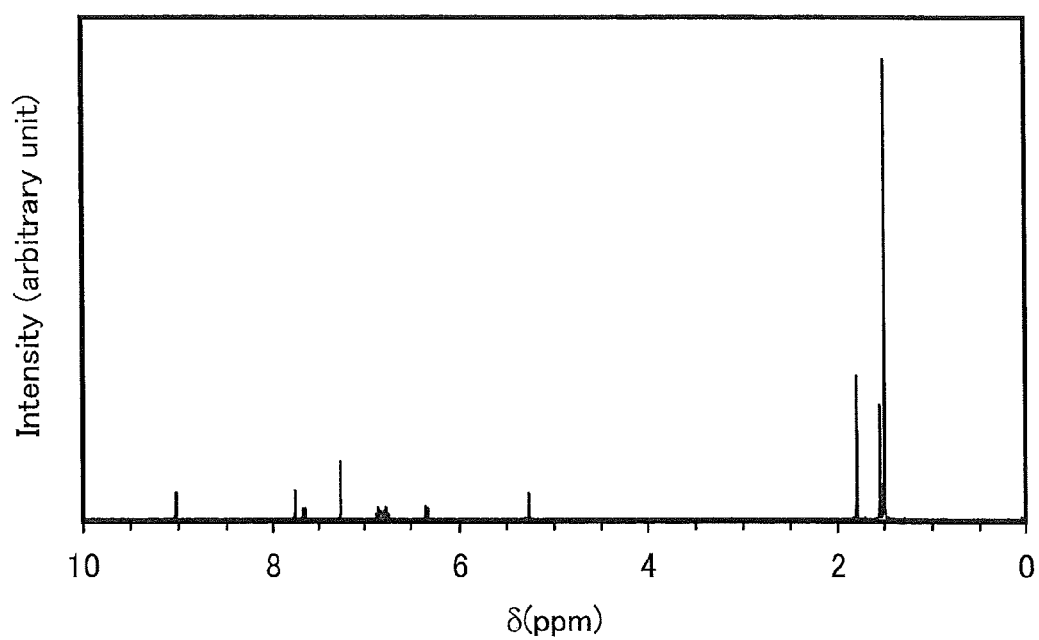
FIG. 32 shows a $^1$H NMR chart of an organometallic complex represented by a structural formula (190).

An analysis result by nuclear magnetic resonance spectrometry ($^1$H NMR) of the yellow powder obtained in Step 3 is described below. The $^1$H NMR chart is illustrated in FIG. 32. These results revealed that the organometallic complex [Ir(tBuppm)$_2$(acac)], which is one embodiment of the present invention represented by the structural formula (190), was obtained in Synthetic Example 4.

$^1$H NMR. δ (CDCl$_3$): 1.50 (s, 18H), 1.79 (s, 6H), 5.26 (s, 1H), 6.33 (d, 2H), 6.77 (t, 2H), 6.85 (t, 2H), 7.70 (d, 2H), 7.76 (s, 2H), 9.02 (s, 2H).

Figure 33:
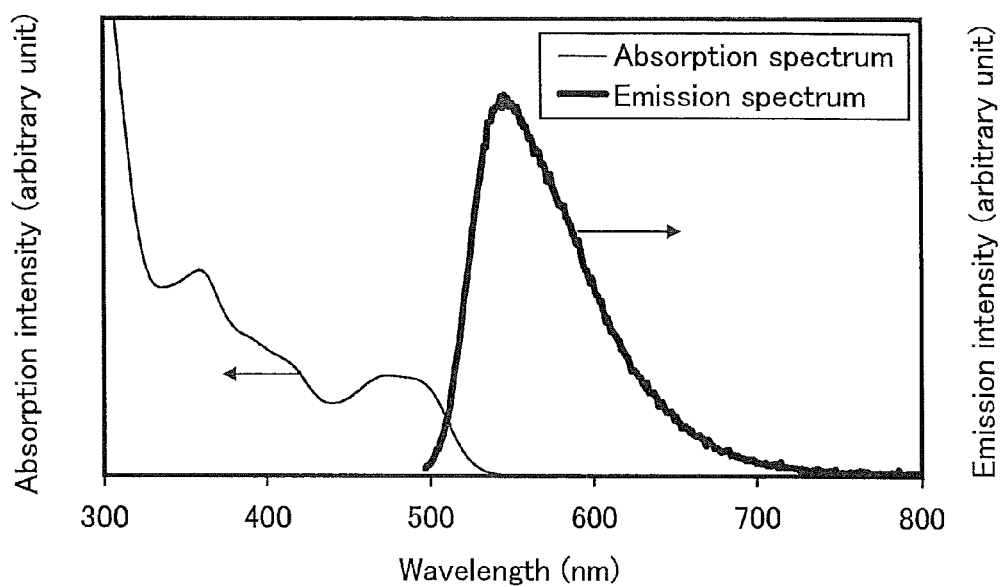
FIG. 33 shows an ultraviolet-visible absorption spectrum and an emission spectrum of the organometallic complex represented by the structural formula (190).

Next, an ultraviolet-visible absorption spectrum (hereinafter, simply referred to as an absorption spectrum) and an emission spectrum of [ft(tBuppm)$_2$(acac)] in a dichloromethane solution were measured. The absorption spectrum was measured with the use of an ultraviolet-visible light spectrophotometer (V-550, manufactured by JASCO Corporation) in the state where the dichloromethane solution (0.093 mmol/L) was put in a quartz cell at room temperature. The emission spectrum was measured with the use of a fluorescence spectrophotometer (FS920, manufactured by Hamamatsu Photonics Corporation) in the state where the degassed dichloromethane solution (0.093 mmol/L) was put in a quartz cell at room temperature. FIG. 33 shows results of the measured absorption spectrum and emission spectrum. The horizontal axis represents wavelength (nm), and the vertical axis represents absorption intensity (arbitrary unit) and emission intensity (arbitrary unit). In FIG. 33, two solid lines are shown; a thin line represents the absorption spectrum, and a thick line represents the emission spectrum. Note that the absorption spectrum in FIG. 33 is a result obtained by subtraction of the absorption spectrum of only dichloromethane that was put in a quartz cell from the measured absorption spectrum of the dichloromethane solution (0.093 mmol/L) in a quartz cell.

As shown in FIG. 33, the organometallic complex [Ir(tBuppm)$_2$(acac)], which is one embodiment of the present invention, has an emission peak at 547 nm, and yellow green light was observed from the dichloromethane solution.

EXAMPLE 10

In Example 10, a light-emitting element which is one embodiment of the present invention is described with reference to FIG. 14. Chemical formulas of materials used in this example are shown below. Note that the chemical formulas of the materials described above are omitted.

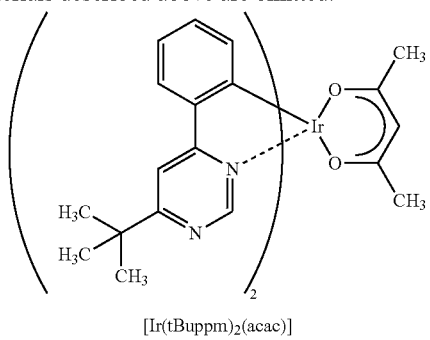

[Ir(tBuppm)2(acac)]

A method of fabricating a light-emitting element 4 of this example is described below.

(Light-Emitting Element 4)

First, an ITSO film was formed over a glass substrate 1100 by a sputtering method, so that a first electrode 1101 functioning as an anode was formed. The thickness was 110 nm and the electrode area was 2 mm×2 mm.

In pretreatment for forming the light-emitting element on the substrate 1100, UV ozone treatment was performed for 370 seconds after washing of a surface of the substrate with water and baking that was performed at 200° C. for 1 hour.

After that, the substrate 1100 was transferred into a vacuum evaporation apparatus where the pressure was reduced to approximately 10$^{-4}$ Pa, and subjected to vacuum baking at 170° C. for 30 minutes in a heating chamber of the vacuum evaporation apparatus, and then the substrate 1100 was cooled down for about 30 minutes.

Next, the substrate 1100 provided with the first electrode 1101 was fixed to a substrate holder in a vacuum evaporation apparatus so that a surface on which the first electrode 1101 was provided faced downward. The pressure in the vacuum evaporation apparatus was reduced to about 10$^{-4}$ Pa, and then BPAFLP and molybdenum(VI) oxide were co-evaporated to form a hole-injection layer 1111 on the first electrode 1101. The thickness of the hole-injection layer 1111 was set to 40 nm, and the weight ratio of BPAFLP to molybdenum oxide was adjusted to 4:2 (=BPAFLP:molybdenum oxide).

Next, a BPAFLP film was formed to a thickness of 20 nm on the hole-injection layer 1111, whereby a hole-transport layer 1112 was formed.

Further, 2mDBTPDBq-II, PCBA1BP, and (acetylacetonato)bis(6-tert-butyl-4-phenylpyrimidinato)iridium(III) (abbreviation: [Ir(tBuppm)$_2$(acac)]) synthesized in Example 9 were co-evaporated to form a light-emitting layer 1113 on the hole-transport layer 1112. The weight ratio of 2mDBTPDBq-II to PCBA1BP and [Ir(tBuppm)$_2$(acac)] was adjusted to 0.8:0.2:0.075 (=2mDBTPDBq-II:PCBA1BP:[Ir(tBuppm)$_2$(acac)]). The thickness of the light-emitting layer 1113 was set to 40 nm.

Next, a 2mDBTPDBq-II film was formed to a thickness of 10 nm on the light-emitting layer 1113, whereby a first electron-transport layer 1114a was formed.

Next, a BPhen film was formed to a thickness of 20 nm on the first electron-transport layer 1114a, whereby a second electron-transport layer 1114b was formed.

Further, a LiF film was formed to a thickness of 1 nm on the second electron-transport layer 1114b by evaporation, whereby an electron-injection layer 1115 was formed.

Lastly, an aluminum film was Ruined to a thickness of 200 nm by evaporation to form a second electrode 1103 functioning as a cathode. Thus, the light-emitting element 4 of this example was fabricated.

Note that in the above evaporation process, evaporation was all performed by a resistance heating method.

Table 7 shows an element structure of the light-emitting element 4 obtained as described above.

TABLE 7

| | First Electrode | Hole-injection Layer | Hole-transport Layer | Light-emitting Layer | First electron-Transport Layer | Second electron-Transport Layer | Electron-injection Layer | Second Electrode |
|---|---|---|---|---|---|---|---|---|
| Light-emitting Element 4 | ITSO 110 nm | BPAFLP:MoOx (=4:2) 40 nm | BPAFLP 20 nm | 2mDBTPDBq-II:PCBA1BP:[Ir(tBuppm)$_2$(acac)] (=0.8:0.2:0.075) 40 nm | 2mDBTPDBq-II 10 nm | BPhen 20 nm | LiF 1 nm | Al 200 nm |

In a glove box containing a nitrogen atmosphere, the light-emitting element 4 was sealed so as not to be exposed to the air. After that, operation characteristics of the light-emitting element 4 were measured. Note that the measurements were carried out at room temperature (in an atmosphere kept at 25° C.).

Figure 34:
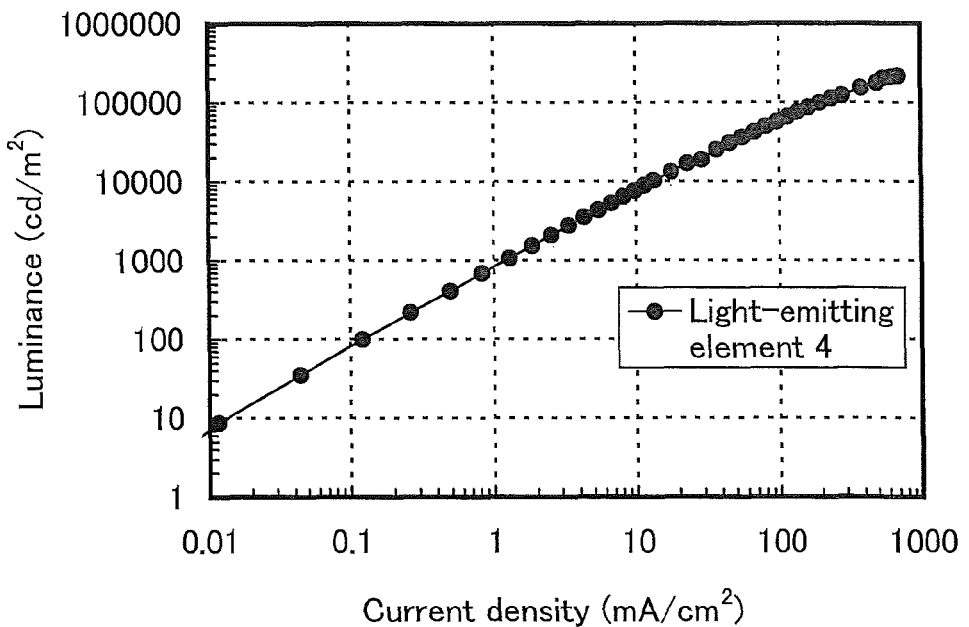
FIG. 34 shows current density vs. luminance characteristics of a light-emitting element 4.
Figure 35:
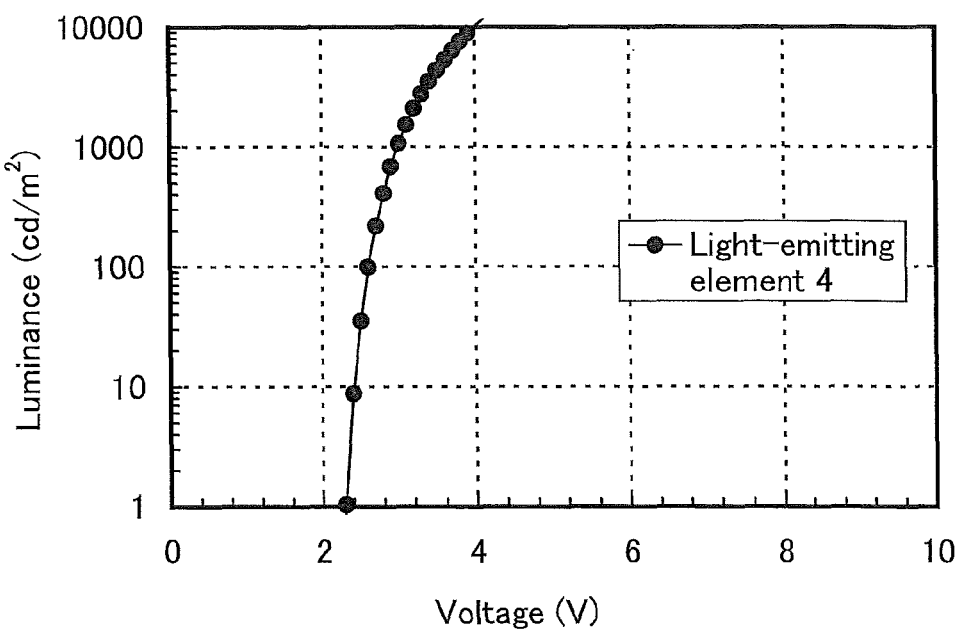
FIG. 35 shows voltage vs. luminance characteristics of the light-emitting element 4.
Figure 36:
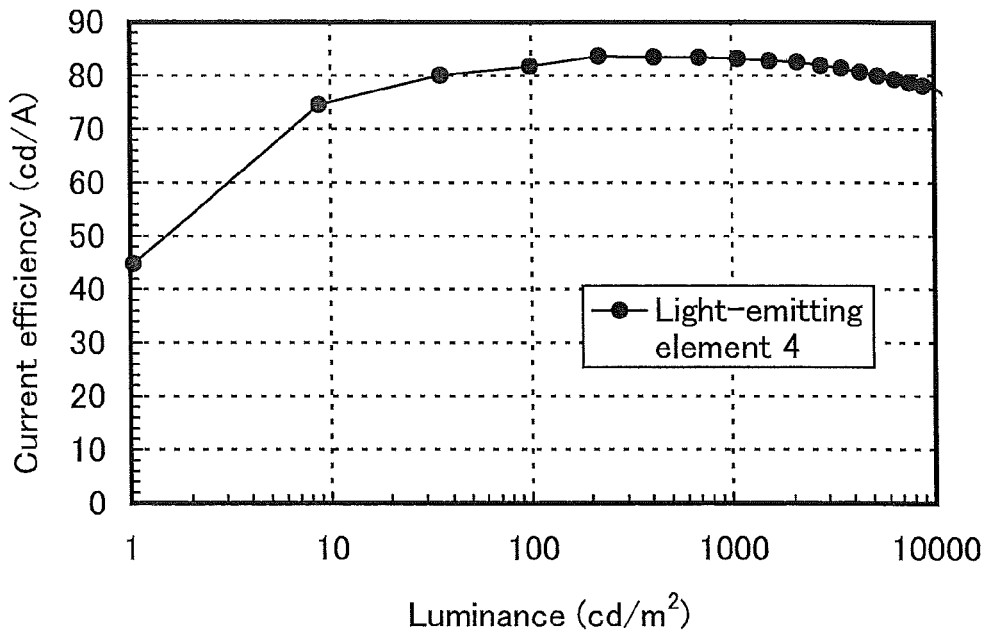
FIG. 36 shows luminance vs. current efficiency characteristics of the light-emitting element 4.

FIG. 34 shows current density vs. luminance characteristics of the light-emitting element 4. In FIG. 34, the horizontal axis represents current density (mA/cm$^2$) and the vertical axis represents luminance (cd/m$^2$). FIG. 35 shows voltage vs. luminance characteristics thereof. In FIG. 35, the horizontal axis represents voltage (V) and the vertical axis represents luminance (cd/m$^2$). FIG. 36 shows luminance vs. current efficiency characteristics thereof. In FIG. 36, the horizontal axis represents luminance (cd/m$^2$) and the vertical axis represents current efficiency (cd/A).

Further, Table 8 shows voltage (V), current density (mA/cm$^2$), CIE chromaticity coordinates (x, y), current efficiency (cd/A), power efficiency (lm/W), and external quantum efficiency (%) of the light-emitting element 4 at a luminance of 1100 cd/m$^2$.

Figure 37:
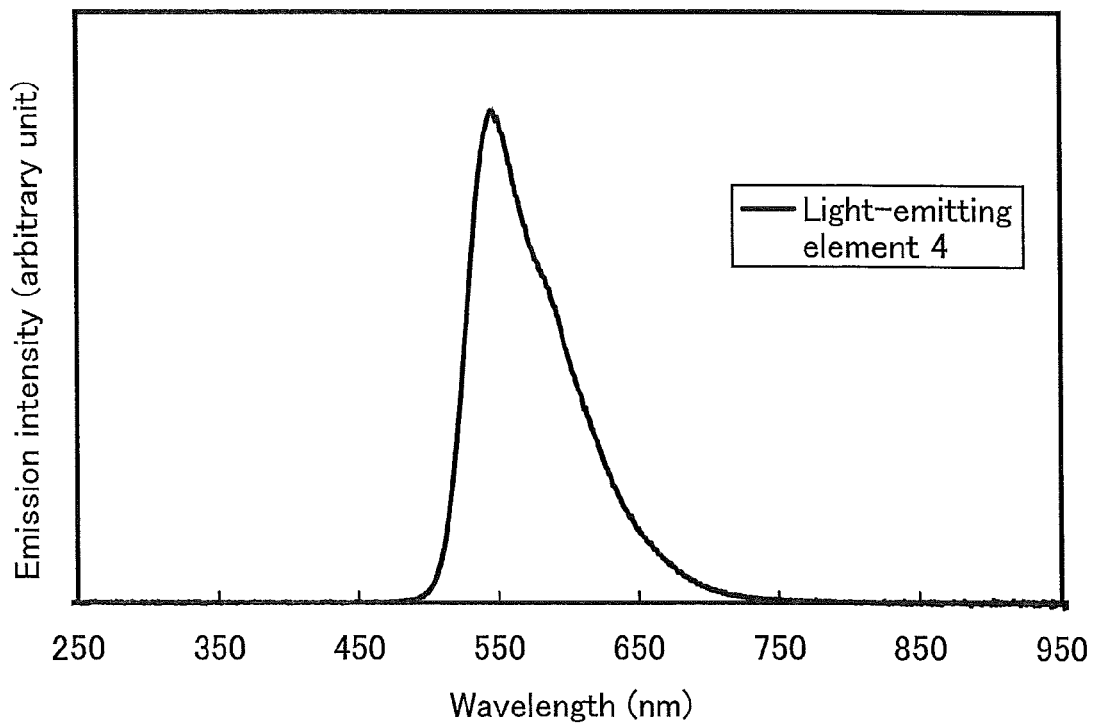
FIG. 37 shows an emission spectrum of the light-emitting element 4.

FIG. 37 shows an emission spectrum of the light-emitting element 4 which was obtained by applying a current of 0.1 mA. In FIG. 37, the horizontal axis represents wavelength (nm) and the vertical axis represents light emission intensity (arbitrary unit). As shown in FIG. 37, the emission spectrum of the light-emitting element 4 has a peak at 546 nm. In addition, as shown in Table 8, the CIE chromaticity coordinates of the light-emitting element 4 were (x, y)=(0.44, 0.55) at a luminance of 1100 cd/m$^2$. The results show that orange light emission originating from [Ir(tBuppm)$_2$(acac)] was obtained from the light-emitting element 4.

Table 8, FIG. 34, FIG. 35, and FIG. 36 indicate that the light-emitting element 4 has high emission efficiency.

The above results suggest that an element with high emission efficiency can be realized by using the organometallic complex which is one embodiment of the present invention as a light-emitting material.

EXAMPLE 11

Figure 38:
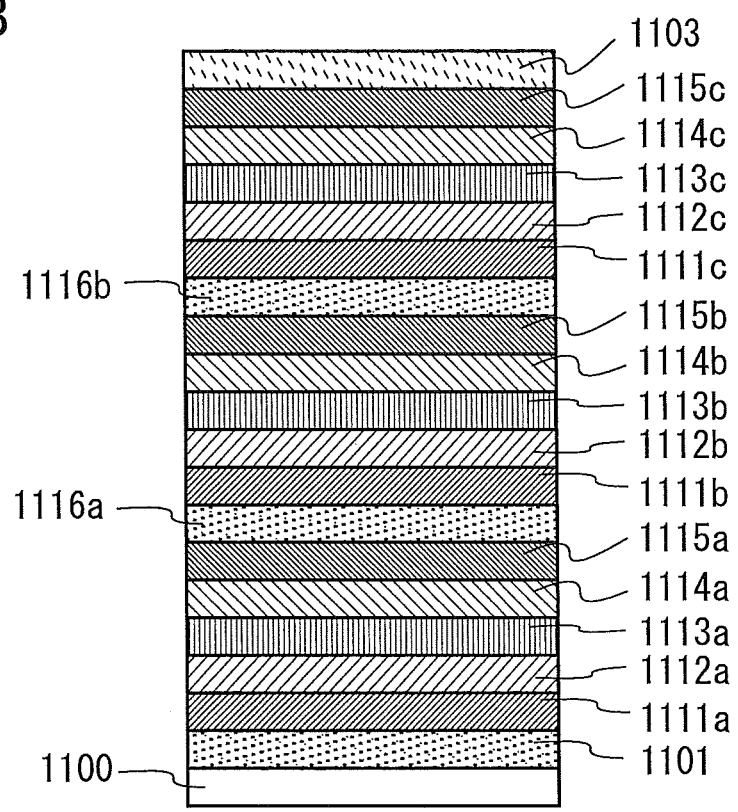
FIG. 38 illustrates a light-emitting element of Example.

In Example 11, a light-emitting element which is one embodiment of the present invention is described with reference to FIG. 38. Chemical formulas of materials used in this example are shown below. Note that the chemical formulas of the materials described above are omitted.

TABLE 8

| | Voltage (V) | Current Density (mA/cm$^2$) | Chromaticity (x, y) | Current Efficiency (cd/A) | Power Efficiency (lm/W) | External Quantum Efficiency (%) |
|---|---|---|---|---|---|---|
| Light-emitting Element 4 | 3.0 | 1.3 | (0.44, 0.55) | 83 | 87 | 23 |

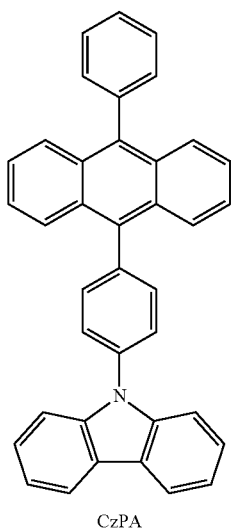

CzPA

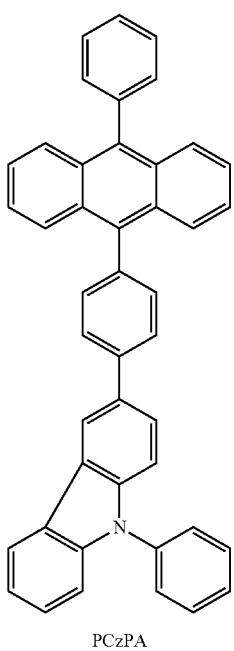

PCzPA

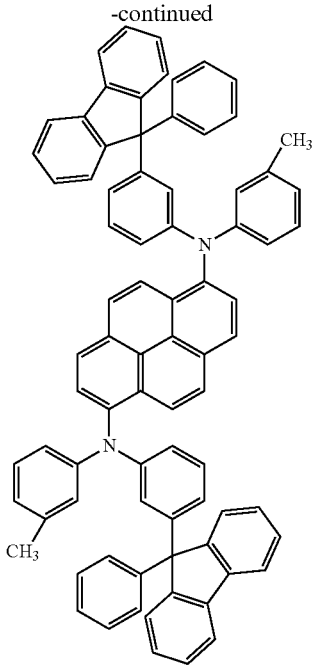

1,6mMemFLPAPrn

A method of fabricating a light-emitting element 5 of this example is described below.

(Light-Emitting Element 5)

First, an ITSO film was formed over a glass substrate 1100 by a sputtering method, so that a first electrode 1101 functioning as an anode was formed. The thickness was 110 nm and the electrode area was 2 mm×2 mm In pretreatment for forming the light-emitting element on the substrate 1100, UV ozone treatment was performed for 370 seconds after washing of a surface of the substrate with water and baking that was performed at 200° C. for 1 hour.

After that, the substrate 1100 was transferred into a vacuum evaporation apparatus where the pressure was reduced to approximately 1e Pa, and subjected to vacuum baking at 170° C. for 30 minutes in a heating chamber of the vacuum evaporation apparatus, and then the substrate 1100 was cooled down for about 30 minutes.

Next, the substrate 1100 provided with the first electrode 1101 was fixed to a substrate holder in a vacuum evaporation apparatus so that a surface on which the first electrode 1101 was provided faced downward. The pressure in the vacuum evaporation apparatus was reduced to about $10^{-4}$ Pa, and then 9-phenyl-3-[4-(10-phenyl-9-anthryl)phenyl]-9H-carbazol (abbreviation: PCzPA)] and molybdenum(VI) oxide were co-evaporated to form a first hole-injection layer 1111a on the first electrode 1101. The thickness of the first hole-injection layer 1111a was set to 60 nm, and the weight ratio of PCzPA to molybdenum oxide was adjusted to 1:0.5 (=PCzPA:molybdenum oxide).

Next, a PCzPA film was formed to a thickness of 30 nm on the first hole-injection layer 1111a, whereby a first hole-transport layer 1112a was formed.

Furthermore, 9-[4-(N-carbazolyl)]phenyl-10-phenylanthracene (abbreviation: CzPA) and N,N'-bis(3-methylphenyl)-N,N'-bis[3-(9-phenyl-9H-fluoren-9-yl)phenyl]pyrene-1,6-dia mine (abbreviation: 1,6mMemFLPAPrn) were co-evaporated on the first hole-transport layer 1112a, so that a first light-emitting layer 1113a was formed. The thickness of the first light-emitting layer 1113a was 30 nm. The weight ratio of CzPA to 1,6mMemFLPAPrn was adjusted to 1:0.05 (=CzPA:1,6mMemFLPAPrn).

Next, on the first light-emitting layer 1113a, CzPA was deposited to a thickness of 5 nm and BPhen was deposited to a thickness of 15 nm, so that a first electron-transport layer 1114a was formed.

Further, on the first electron-transport layer 1114a, lithium oxide ($Li_2O$) was evaporated to a thickness of 0.1 nm, whereby a first electron-injection layer 1115a was formed.

After that, on the first electron-injection layer 1115a, copper phthalocyanine (abbreviation: CuPc) was evaporated to a thickness of 2 nm, whereby a first intermediate layer 1116a was formed.

Next, on the first intermediate layer 1116a, PCzPA and molybdenum(VI) oxide were co-evaporated, whereby a second hole-injection layer 1111b was formed. The thickness thereof was 20 nm and the weight ratio of PCzPA to molybdenum oxide was adjusted to 1:0.5 (=PCzPA:molybdenum oxide).

Next, BPAFLP was deposited to a thickness of 20 nm on the second hole-injection layer 1111b, whereby a second hole-transport layer 1112b was formed.

Further, 2mDBTPDBq-II, PCBA1BP, and [ft(dpppm)$_2$(acac)]) synthesized in Example 1 were co-evaporated to form a second light-emitting layer 1113b on the second hole-transport layer 1112b. The thickness of the second light-emitting layer 1113b was set to 40 nm and the weight ratio of 2mDBTPDBq-II to PCBA1BP and [Ir(dppm)$_2$(acac)] was adjusted to 0.8:0.2:0.06 (=2mDBTPDBq-II:PCBA1BP:[Ir(dppm)$_2$(acac)]).

Next, on the second light-emitting layer 1113b, 2mDBTPDBq-II and BPhen were each deposited to a thickness of 15 nm, whereby a second electron-transport layer 1114b was formed.

Further, a $Li_2O$ film was formed to a thickness of 0.1 nm on the second electron-transport layer 1114b by evaporation, whereby a second electron-injection layer 1115b was formed.

After that, on the second electron-injection layer 1115b, CuPc was evaporated to a thickness of 2 nm, whereby a second intermediate layer 1116b was formed.

Next, on the second intermediate layer 1116b, PCzPA and molybdenum(VI) oxide were co-evaporated, whereby a third hole-injection layer 1111c was formed. The thickness thereof was 67 nm and the weight ratio of PCzPA to molybdenum oxide was adjusted to 1:0.5 (=PCzPA:molybdenum oxide).

Next, on the third hole-injection layer 1111c, BPAFLP was deposited to a thickness of 20 nm, whereby a third hole-transport layer 1112c was formed.

Then, on the third hole-transport layer 1112c, a third light-emitting layer 1113c and a third electron-transport layer 1114c were formed in this order. The third light-emitting layer 1113c and the third electron-transport layer 1114c were formed with the use of the same structure as the second light-emitting layer 1113b and the second electron-transport layer 1114b, respectively.

Next, on the third electron-transport layer 1114c, LiF was evaporated to a thickness of 1 nm, whereby a third electron-injection layer 1115c was formed.

Lastly, on the third electron-injection layer 1115c, an aluminum film was formed to a thickness of 200 nm by evaporation to form a second electrode 1103 functioning as a cathode. Thus, the light-emitting element 5 of this example was fabricated.

Note that in the above evaporation process, evaporation was all performed by a resistance heating method.

Table 9 shows an element structure of the light-emitting element 5 obtained as described above.

TABLE 9

| First Electrode ITSO 110 nm | | | | | | |
|---|---|---|---|---|---|---|
| First Hole-injection Layer | First Hole-transport Layer | First Light-emitting Layer | First Electron-transport Layer | | First Electron-injection Layer | First Intermediate Layer |
| PCzPA: MoOx (=1:0.5) 60 nm | PCzPA 30 nm | CzPA: 1,6mMemFLPAPrn (=1:0.05) 30 nm | CzPA 5 nm | BPhen 15 nm | $Li_2O$ 0.1 nm | CuPc 2 nm |
| Second Hole-injection Layer | Second Hole-transport Layer | Second Light-emitting Layer | Second Electron-transport Layer | | Second Electron-injection Layer | Second Intermediate Layer |
| PCzPA: MoOx (=1:0.5) 20 nm | BPAFLP 20 nm | 2mDBTPDBq-II: PCBA1BP: [Ir(dppm)$_2$(acac)] (=0.8:0.2:0.06) 40 nm | 2mDBTPDBq-II 15 nm | BPhen 15 nm | $Li_2O$ 0.1 nm | CuPc 2 nm |
| Third Hole-injection Layer | Third Hole-transport Layer | Third Light-emitting Layer | Third Electron-transport Layer | | Third Electron-injection Layer | Second Electrode |
| PCzPA: MoOx (=1:0.5) 67 nm | BPAFLP 20 nm | 2mDBTPDBq-II: PCBA1BP: [Ir(dppm)$_2$(acac)] (=0.8:0.2:0.06) 40 nm | 2mDBTPDBq-II 15 nm | BPhen 15 nm | LiF 1 nm | Al 200 nm |

In a glove box containing a nitrogen atmosphere, the light-emitting element 5 was sealed so as not to be exposed to the air. After that, operation characteristics of the light-emitting element 5 were measured. Note that the measurements were carried out at room temperature (in an atmosphere kept at 25° C.).

Figure 39:
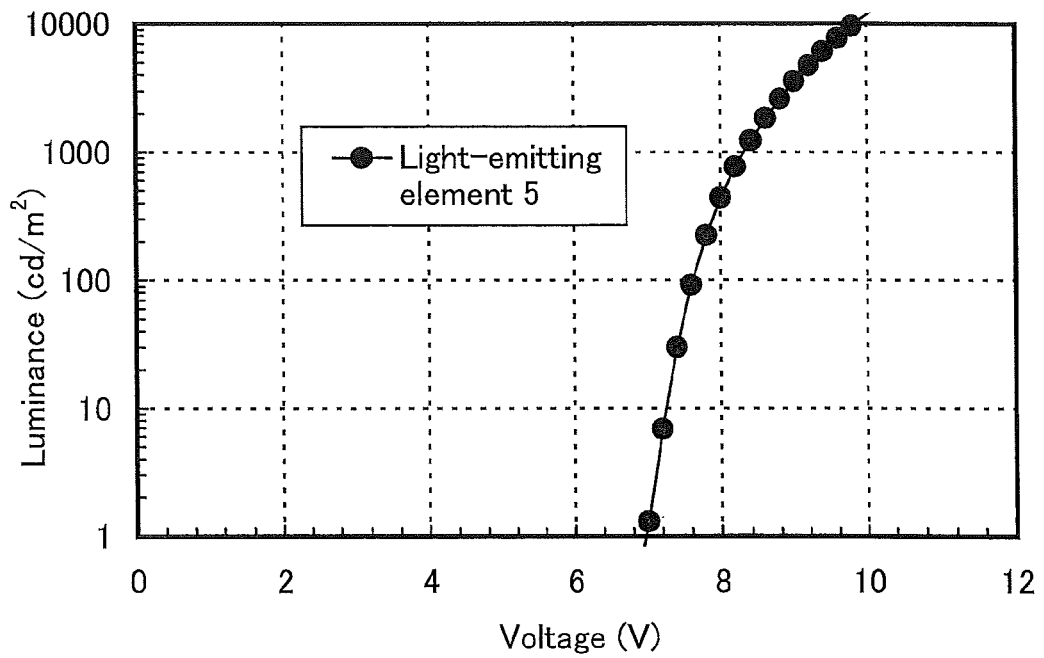
FIG. 39 shows voltage vs. luminance characteristics of the light-emitting element 5.
Figure 40:
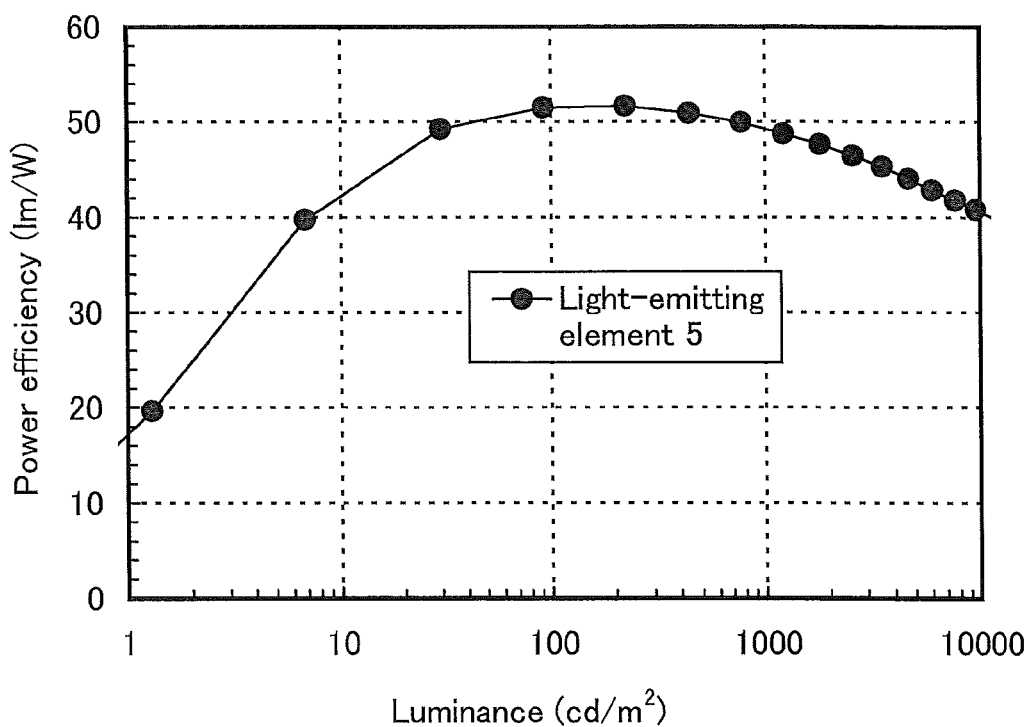
FIG. 40 shows luminance vs. power efficiency characteristics of the light-emitting element 5.
Figure 41:
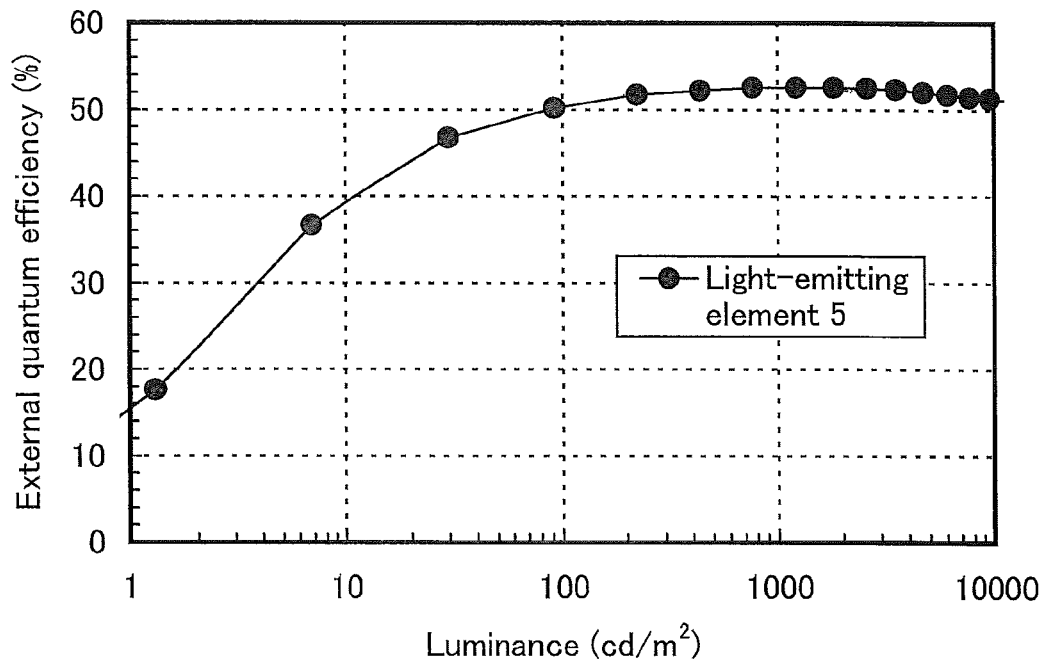
FIG. 41 shows luminance vs. external quantum efficiency characteristics of the light-emitting element 5.

FIG. 39 shows voltage vs. luminance characteristics of the light-emitting element 5. In FIG. 39, the horizontal axis represents voltage (V) and the vertical axis represents luminance ($cd/m^2$). FIG. 40 shows luminance vs. power efficiency characteristics thereof. In FIG. 40, the horizontal axis represents luminance ($cd/m^2$) and the vertical axis represents power efficiency (lm/W). In addition, FIG. 41 shows luminance vs. external quantum efficiency characteristics thereof. In FIG. 41, the horizontal axis represents luminance ($cd/m^2$) and the vertical axis represents external quantum efficiency (%).

Further, Table 10 shows voltage (V), current density ($mA/cm^2$), CIE chromaticity coordinates (x, y), current efficiency (cd/A), power efficiency (lm/W), and external quantum efficiency (%) of the light-emitting element 5 at a luminance of 4700 $cd/m^2$.

TABLE 10

| | Voltage (V) | Current Density ($mA/cm^2$) | Chromaticity (x, y) | Current Efficiency (cd/A) | Power Efficiency (lm/W) | External Quantum Efficiency (%) |
|---|---|---|---|---|---|---|
| Light-emitting Element 5 | 9.2 | 3.28 | (0.49, 0.42) | 143 | 44 | 52 |

Figure 42:
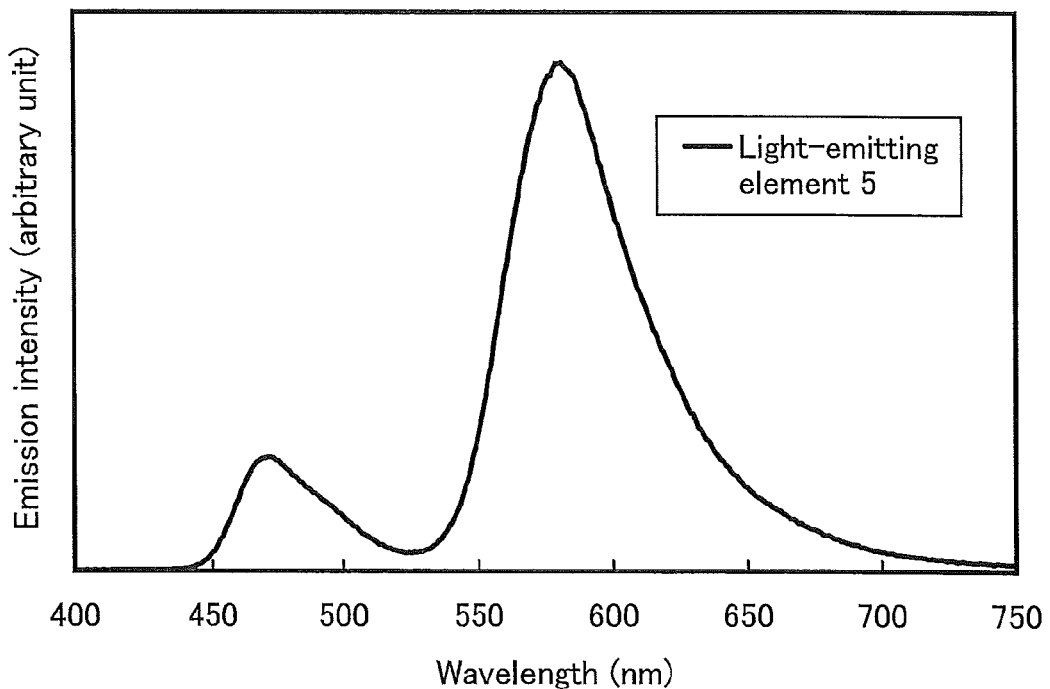
FIG. 42 shows an emission spectrum of the light-emitting element 5.
Figure 43:
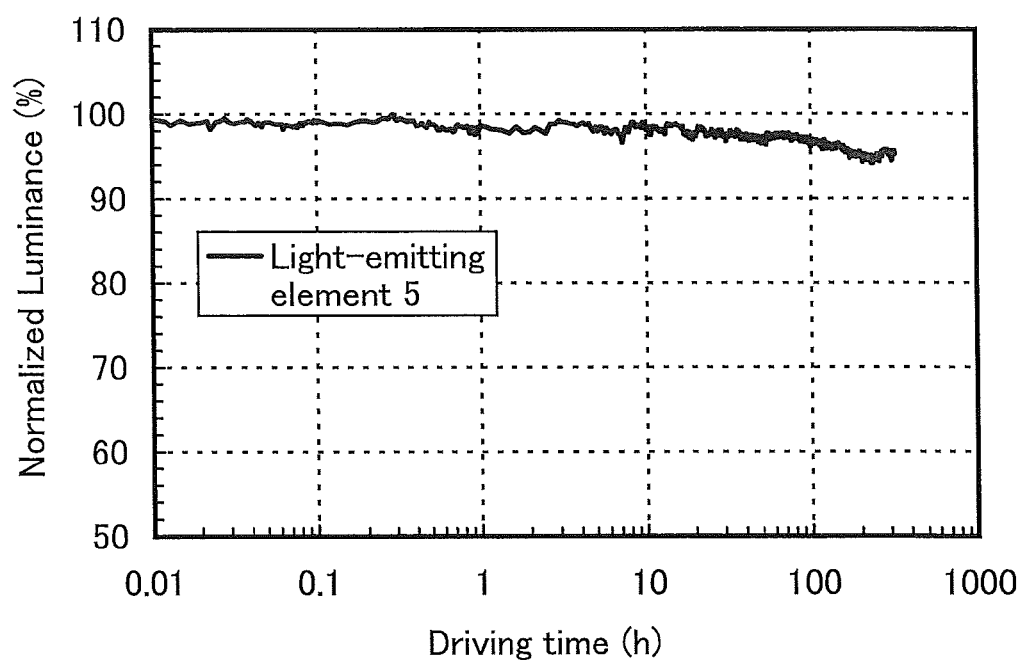
FIG. 43 shows results obtained by reliability testing of the light-emitting element 5.

FIG. 42 shows an emission spectrum of the light-emitting element 5 which was obtained by applying a current of 0.1 mA. In FIG. 43, the horizontal axis represents wavelength (nm) and the vertical axis represents light emission intensity (arbitrary unit). As shown in FIG. 42, the emission spectrum of the light-emitting element 5 has a peak at 581 nm. In addition, as shown in Table 10, the CIE chromaticity coordinates of the light-emitting element 5 were (x, y)=(0.49, 0.42) at a luminance of 4700 $cd/m^2$.

Table 10, FIG. 39, FIG. 40, and FIG. 41 indicate that the light-emitting element 5 has high emission efficiency. As seen in FIG. 40, in particular, the light-emitting element 5 has a power efficiency of higher than 50 lm/W.

The above results suggest that an element with high emission efficiency can be realized by using the organometallic complex which is one embodiment of the present invention as a light-emitting material.

Next, reliability testing of the light-emitting element 5 was carried out. Results of the reliability testing are shown in FIG. 43. In FIG. 43, the vertical axis represents normalized luminance (%) on the assumption that an initial luminance is 100%, and the horizontal axis represents driving time (h) of the element.

In the reliability testing, the light-emitting element 5 was driven under the conditions where the initial luminance was set to 5000 $cd/m^2$ and the current density was constant.

The light-emitting element 5 kept 95% of the initial luminance after the driving for 320 hours.

Further, accelerated testing for the luminance of the light-emitting element 5 was carried out. In the accelerated testing for the luminance, elements having the same structure as the light-emitting element 5 were driven at a constant current by setting the initial luminance to 20000 $cd/m^2$, 30000 $cd/m^2$, 40000 $cd/m^2$, 50000 $cd/m^2$, 70000 $cd/m^2$, and 100000 $cd/m^2$.

From the correlation plot between initial luminance and lifetime, the lifetime at an initial luminance of 5000 $cd/m^2$ was estimated. In this example, lifetime means the time by which the luminance of a light-emitting element is decreased to lower than 70% of the initial luminance.

Figure 44:
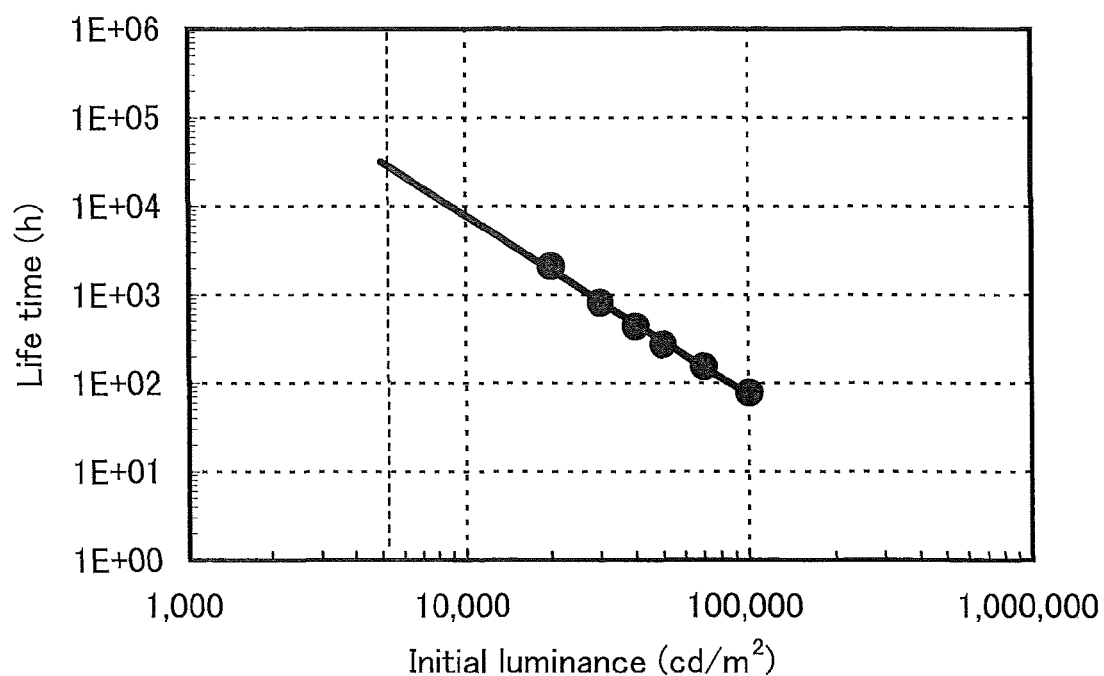
FIG. 44 shows results of accelerated testing for the luminance of the light-emitting element 5.

FIG. 44 shows the correlation plot between initial luminance and lifetime. In FIG. 44, the vertical axis represents lifetime (h), and the horizontal axis represents initial luminance ($cd/m^2$). At an initial luminance of each of 20000 $cd/m^2$ and 30000 $cd/m^2$, because the luminance was not reduced to lower than 70% of the initial luminance, a deterioration curve was extrapolated to estimate the lifetime. From these results, the lifetime of the light-emitting element 5 at an initial luminance of 5000 $cd/m^2$ is estimated as 30000 hours, and it is found that the light-emitting element 5 is an element having a very long lifetime.

The above results suggest that an element having high reliability can be realized by using an organometallic complex which is one embodiment of the present invention as a light-emitting material.

EXAMPLE 12

Synthetic Example 5

In Example 12, a synthetic example of an organometallic complex bis(4,6-diphenylpyrimidinato)(dipivaloylmethanato)iridium(III) (another name: (2,2,6,6-tetramethyl-3,5-heptanedionato-$\kappa^2 O,O'$)bis[2-(6-phenyl-4-pyrimidinyl-$\kappa N3$)phenyl-$\kappa C$]iridium(III)) (abbreviation: [Ir(dppm)$_2$(dpm)]), which is one embodiment of the present invention represented by the structural formula (101) in Embodiment 1, is specifically described. A structure of [Ir(dppm)$_2$(dpm)] is shown below.

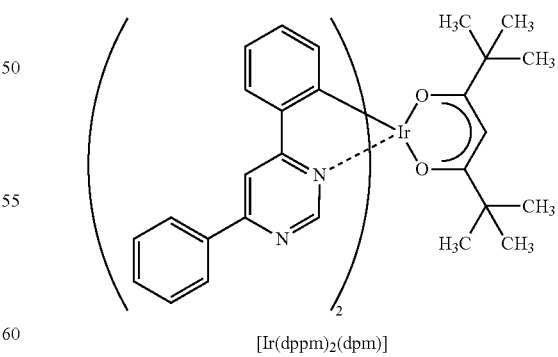

[Ir(dppm)$_2$(dpm)]

First, into a recovery flask equipped with a reflux pipe were put 30 mL of 2-ethoxyethanol, 1.93 g of the dinuclear complex [Ir(dppm)$_2$Cl]$_2$ obtained in Step 2 in Synthetic Example 1, 0.77 g of dipivaloylmethane, and 1.51 g of sodium carbonate, and the air in the flask was replaced with argon. After that, the mixture was heated by irradiation with microwaves (2.45 GHz, 100 W) for 60 minutes. Here, into the flask was further put 0.26 g of dipivaloylmethane, and the mixture was heated again by irradiation with microwaves (2.45 GHz, 100 W) for 60 minutes. The solvent was distilled off, the obtained residue was dissolved in dichloromethane, and filtration was performed to remove insoluble matter. The obtained filtrate was washed with water and saturated saline, and was dried with magnesium sulfate. The solution after drying was filtered. The solvent was distilled off, and then the obtained residue was washed with toluene. After that, recrystallization was carried out with a mixed solvent of dichloromethane and hexane to give a red solid (yield of 28%, purity of 95%). This solid was purified by silica gel column chromatography using dichloromethane as a developing solvent. After that, recrystallization was carried out with a mixed solvent of dichloromethane and hexane to give red powder (yield of 6%). A synthesis scheme (g-1) is shown below.

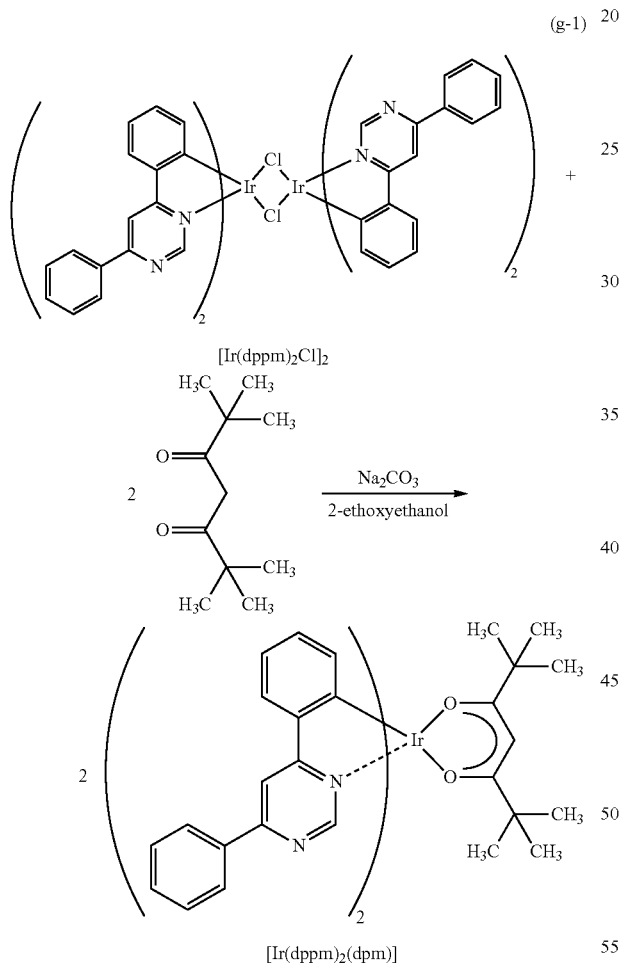

Figure 45:
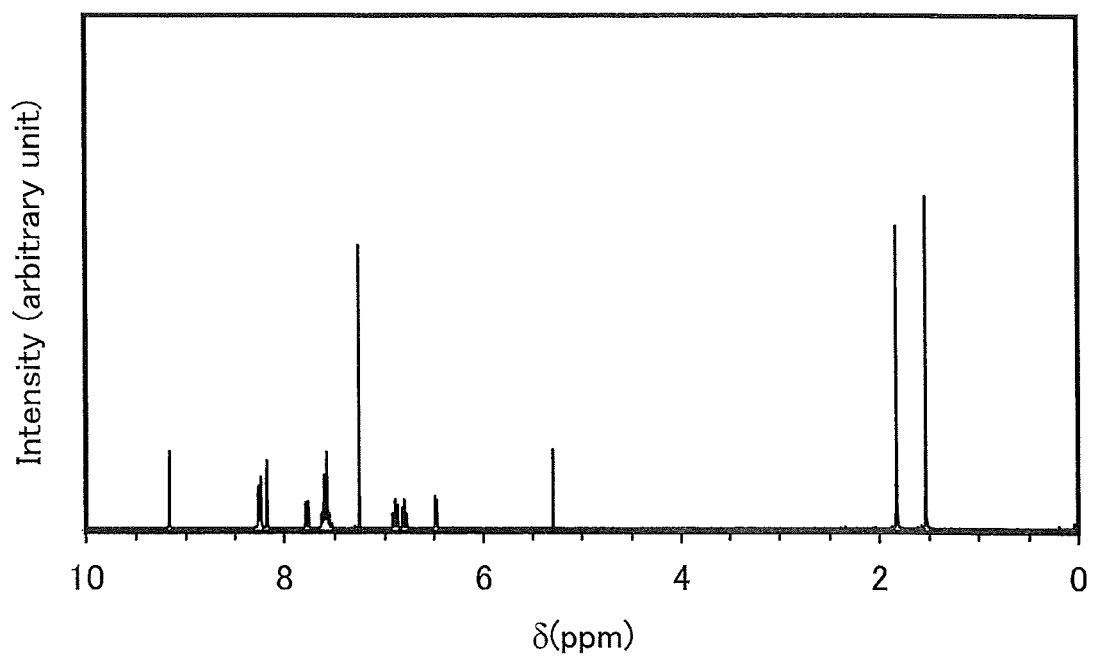
FIG. 45 shows a $^1$H NMR chart of an organometallic complex represented by a structural formula (101).

An analysis result by nuclear magnetic resonance spectrometry ($^1$H NMR) of the red powder obtained is described below. The $^1$H NMR chart is illustrated in FIG. 45. These results revealed that the organometallic complex [Ir(dppm)$_2$(dpm)], which is one embodiment of the present invention represented by the structural formula (101), was obtained in Synthetic Example 5.

$^1$H NMR. δ (CDCl$_3$): 1.83 (s, 18H), 5.29 (s, 1H), 6.55 (d, 2H), 6.80 (t, 2H), 6.91 (t, 2H), 7.55-7.63 (m, 6H), 7.78 (d, 2H), 8.16 (d, 2H), 8.25 (d, 4H), 9.04 (d, 2H).

Figure 46:
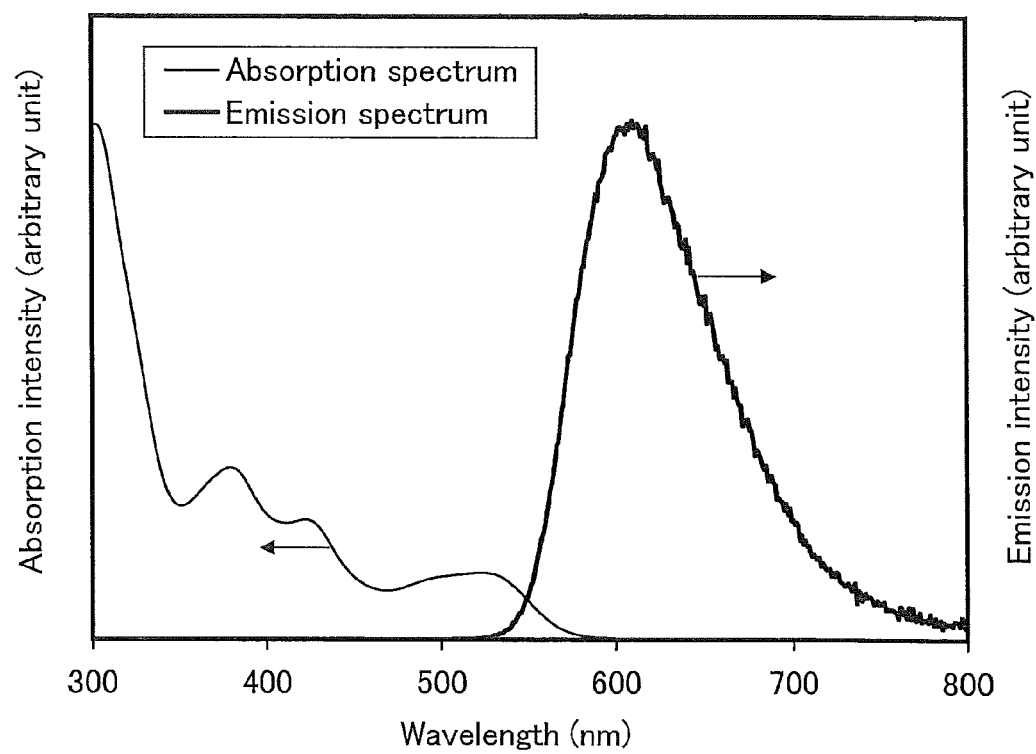
FIG. 46 shows an ultraviolet-visible absorption spectrum and an emission spectrum of the organometallic complex represented by the structural formula (101).

Next, an ultraviolet-visible absorption spectrum (hereinafter, simply referred to as an absorption spectrum) and an emission spectrum of [Ir(dppm)$_2$(dpm)] in a dichloromethane solution were measured. The absorption spectrum was measured with the use of an ultraviolet-visible light spectrophotometer (V-550, manufactured by JASCO Corporation) in the state where the dichloromethane solution (0.080 mmol/L) was put in a quartz cell at room temperature. The emission spectrum was measured with the use of a fluorescence spectrophotometer (FS920, manufactured by Hamamatsu Photonics Corporation) in the state where the degassed dichloromethane solution (0.080 mmol/L) was put in a quartz cell at room temperature. FIG. 46 shows results of the measured absorption spectrum and emission spectrum. The horizontal axis represents wavelength (nm), and the vertical axis represents absorption intensity (arbitrary unit) and emission intensity (arbitrary unit). In FIG. 46, two solid lines are shown; a thin line represents the absorption spectrum, and a thick line represents the emission spectrum. Note that the absorption spectrum in FIG. 46 is a result obtained by subtraction of the absorption spectrum of only dichloromethane that was put in a quartz cell from the measured absorption spectrum of the dichloromethane solution (0.080 mmol/L) in a quartz cell.

As shown in FIG. 46, the organometallic complex [Ir(dppm)$_2$(dpm)], which is one embodiment of the present invention, has an emission peak at 610 nm, and reddish orange light was observed from the dichloromethane solution.

EXAMPLE 13

Synthetic Example 6

In Example 13, a synthetic example of an organometallic complex (acetylacetonato)bis[4,6-di(naphthalen-2-yl)pyrimidinato]iridium(III) (another name: bis[3-(6-naphthalen-2-yl-4-pyrimidinyl-κN3)-2-naphthalenyl-κC](2,4-pentanedionato-κ$^2$O,O')iridium(III)) (abbreviation: [Ir(d2npm)$_2$(acac)]), which is one embodiment of the present invention represented by the structural formula (114) in Embodiment 1, is specifically described. A structure of [Ir(d2npm)$_2$(acac)] is shown below.

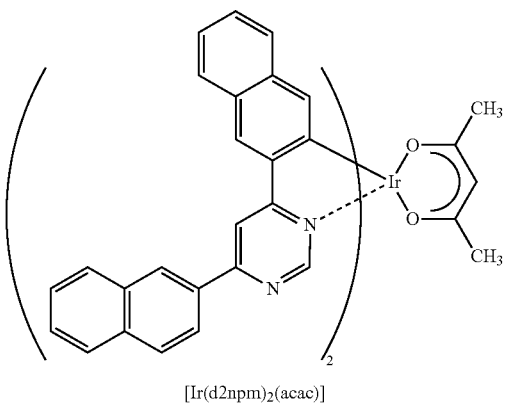

Step 1: Synthesis of 4-chloro-6-(naphthalen-2-yl)pyrimidine

First, into a recovery flask equipped with a reflux pipe were put 5.0 g of 4,6-dichloropyrimidine, 11.7 g of 2-naphthaleneboronic acid, 7.2 g of sodium carbonate, 0.29 g of bis(triphenylphosphine)palladium(II)dichloride (abbreviation: $Pd(PPh_3)_2Cl_2$), 20 mL of water, and 20 mL of acetonitrile, and the air in the flask was replaced with argon. This reaction container was heated by irradiation with microwaves (2.45 GHz, 100 W) for 60 minutes. Here, into the flask were further put 2.9 g of 2-naphthaleneboronic acid, 1.8 g of sodium carbonate, 0.070 g of $Pd(PPh_3)_2Cl_2$, 5 mL of water, and 5 mL of acetonitrile, and the mixture was heated again by irradiation with microwaves (2.45 GHz, 100 W) for 60 minutes. After that, water was added to this solution and an organic layer was extracted with dichloromethane. The obtained organic layer was washed with water and dried with magnesium sulfate. The solution after drying was filtered. The solvent of this solution was distilled off, and then the obtained residue was purified by silica gel column chromatography using hexane and ethyl acetate as a developing solvent in a ratio of 5:1, so that a pyrimidine derivative 4-chloro-6-(naphthalen-2-yl)pyrimidine, which was the objective substance, was obtained (yellow white powder, yield of 48%). Note that the irradiation with microwaves was performed using a microwave synthesis system (Discover, manufactured by CEM Corporation). A synthesis scheme (h-1) of Step 1 is shown below.

acid, 0.9 g of sodium carbonate, 0.070 g of $Pd(PPh_3)_2Cl_2$, 5 mL of water, and 5 mL of acetonitrile, and the mixture was heated again by irradiation with microwaves (2.45 GHz, 100 W) for 60 minutes. After that, water was added to this solution and an organic layer was extracted with dichloromethane. The obtained organic layer was washed with water and dried with magnesium sulfate. The solution after drying was filtered. The solvent of this solution was distilled off, and then the obtained residue was purified by flash column chromatography using hexane and ethyl acetate as a developing solvent in a ratio of 5:1, so that a pyrimidine derivative Hd2npm, which was the objective substance, was obtained (yellow white powder, yield of 19%). A synthesis scheme (h-2) of Step 2 is shown below.

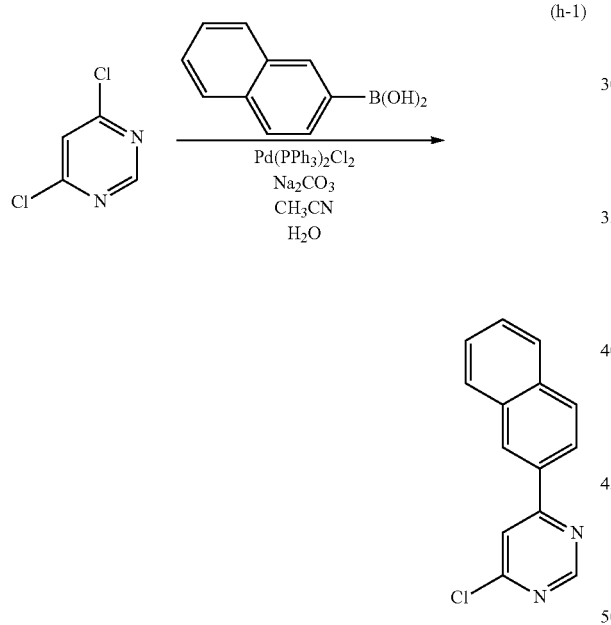

(h-1)

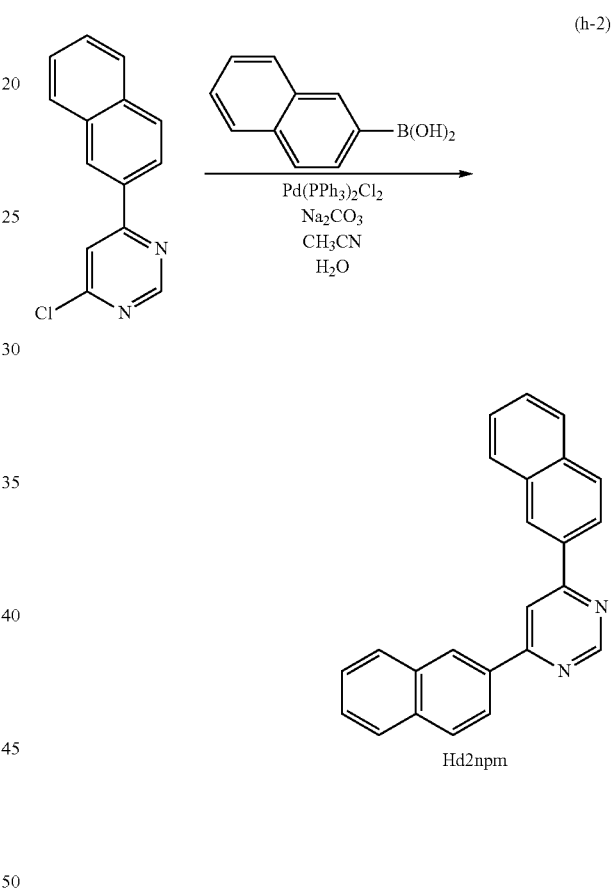

(h-2)

Hd2npm

Step 2: Synthesis of 4,6-di(naphthalen-2-yl)pyrimidine (abbreviation: Hd2npm)

Next, into a recovery flask equipped with a reflux pipe were put 3.9 g of 4-chloro-6-(naphthalen-2-yl)pyrimidine obtained in Step 1, 2.8 g of 2-naphthaleneboronic acid, 1.7 g of sodium carbonate, 0.14 g of bis(triphenylphosphine)palladium(II)dichloride (abbreviation: $Pd(PPh_3)_2Cl_2$), 20 mL of water, and 20 mL of acetonitrile, and the air in the flask was replaced with argon. This reaction container was heated by irradiation with microwaves (2.45 GHz, 100 W) for 60 minutes. Here, into the flask were further put 1.4 g of 2-naphthaleneboronic (Step 3: Synthesis of di-µ-chloro-bis{bis[4,6-di(naphthalen-2-yl)pyrimidinato]iridium(III)}(abbreviation: $[Ir(d2npm)_2Cl]_2$))

Next, into a recovery flask equipped with a reflux pipe were put 15 mL of 2-ethoxyethanol, 5 mL of water, 1.00 g of Hd2npm obtained in Step 2, and 0.44 g of iridium chloride hydrate ($ftCl_3·H_2O$) (produced by Sigma-Aldrich Corp.), and the air in the flask was replaced with argon. After that, irradiation with microwaves (2.45 GHz, 100 W) was performed for 1 hour to cause a reaction. The solvent was distilled off, and then the obtained residue was suction-filtered and washed with ethanol to give a dinuclear complex $[Ir(d2npm)_2Cl]_2$ (brown powder, yield of 98%). A synthesis scheme (h-3) of Step 3 is shown below.

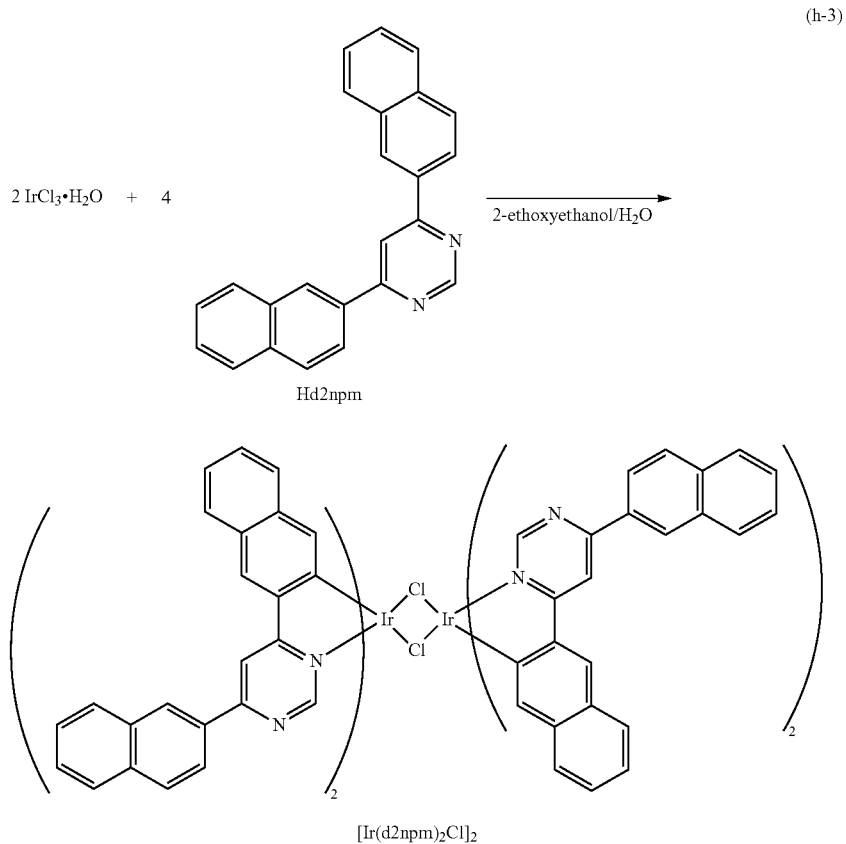

(h-3)

Step 4: Synthesis of (acetylacetonato)bis[4,6-di(naphthalen-2-yl)pyrimidinato]iridium(III) (abbreviation: [Ir(d2npm)₂(acac)])

Furthermore, into a recovery flask equipped with a reflux pipe were put 30 mL of 2-ethoxyethanol, 1.28 g of the dinuclear complex [Ir(d2npm)₂Cl]₂ obtained in Step 3, 0.22 g of acetylacetone, and 0.76 g of sodium carbonate, and the air in the flask was replaced with argon. After that, the mixture was heated by irradiation with microwaves (2.45 GHz, 120 W) for 60 minutes. Here, into the flask was further put 0.22 g of acetylacetone, and the mixture was heated again by irradiation with microwaves (2.45 GHz, 120 W) for 60 minutes. The solvent was distilled off, and the obtained residue was suction-filtered with ethanol. The obtained solid was washed with water, ethanol, and dichloromethane. This solid was dissolved in toluene, and the mixture was filtered through a filter aid in which Celite, alumina, and Celite were stacked in this order. After that, recrystallization was carried out with a mixed solvent of toluene and hexane to give red powder (yield of 11%). A synthesis scheme (h-4) of Step 4 is shown below.

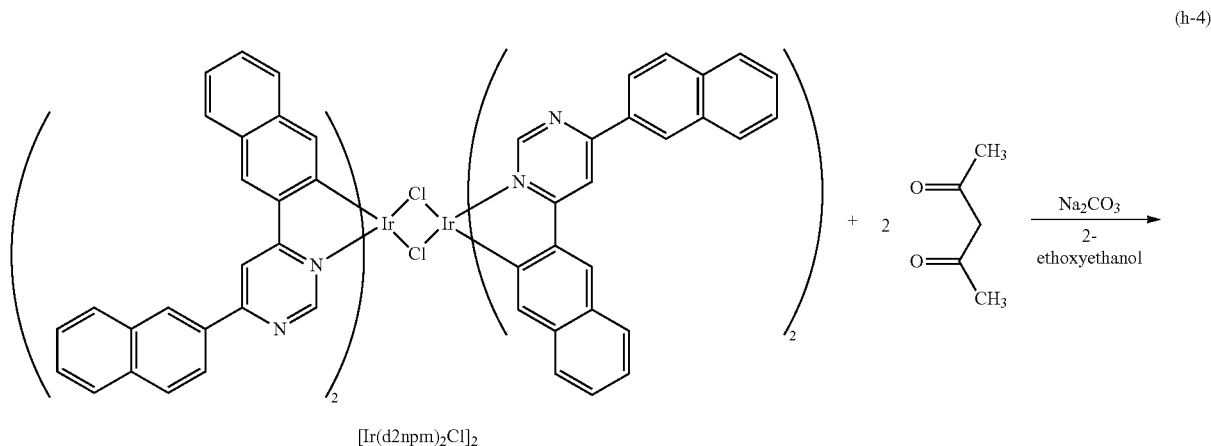

(h-4)

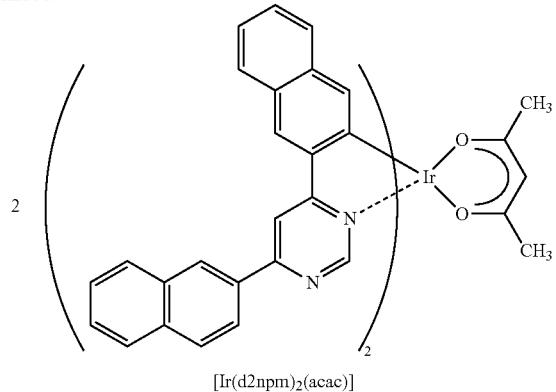

[Ir(d2npm)₂(acac)]

Figure 47:
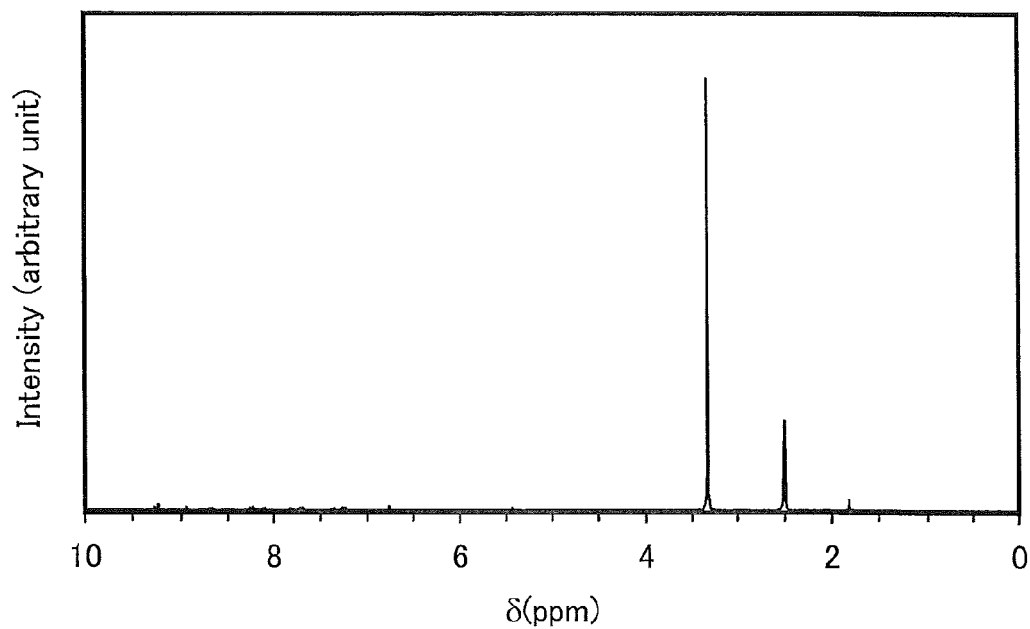
FIG. 47 shows a $^1$H NMR chart of an organometallic complex represented by a structural formula (114).

An analysis result by nuclear magnetic resonance spectrometry (¹H NMR) of the red powder obtained is described below. The ¹H NMR chart is illustrated in FIG. 47. These results revealed that the organometallic complex [Ir(d2npm)₂(acac)], which is one embodiment of the present invention represented by the structural formula (114), was obtained in Synthetic Example 6.

¹H NMR. δ (DMSO-d6): 1.82 (s, 6H), 5.43 (s, 1H), 6.77 (s, 2H), 7.23-7.26 (m, 4H), 7.35-7.38 (m, 2H), 7.69-7.72 (m, 4H), 7.79-7.82 (m, 2H), 8.09-8.12 (m, 2H), 8.21-8.26 (m, 4H), 8.68 (d, 2H), 8.95 (s, 2H), 9.24-9.27 (m, 6H).

Figure 48:
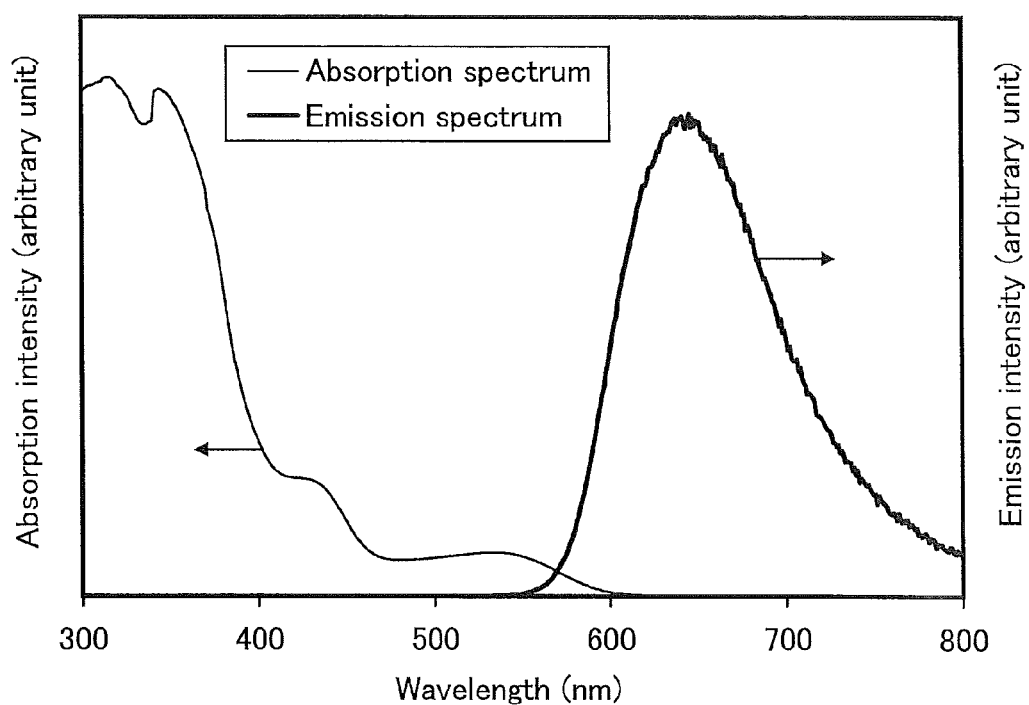
FIG. 48 shows an ultraviolet-visible absorption spectrum and an emission spectrum of the organometallic complex represented by the structural formula (114).

Next, an ultraviolet-visible absorption spectrum (hereinafter, simply referred to as an absorption spectrum) and an emission spectrum of [Ir(d2npm)₂(acac)] in a dichloromethane solution were measured. The absorption spectrum was measured with the use of an ultraviolet-visible light spectrophotometer (V-550, manufactured by JASCO Corporation) in the state where the dichloromethane solution (0.073 mmol/L) was put in a quartz cell at room temperature. The emission spectrum was measured with the use of a fluorescence spectrophotometer (FS920, manufactured by Hamamatsu Photonics Corporation) in the state where the degassed dichloromethane solution (0.073 mmol/L) was put in a quartz cell at room temperature. FIG. 48 shows results of the measured absorption spectrum and emission spectrum. The horizontal axis represents wavelength (nm), and the vertical axis represents absorption intensity (arbitrary unit) and emission intensity (arbitrary unit). In FIG. 48, two solid lines are shown; a thin line represents the absorption spectrum, and a thick line represents the emission spectrum. Note that the absorption spectrum in FIG. 48 is a result obtained by subtraction of the absorption spectrum of only dichloromethane that was put in a quartz cell from the measured absorption spectrum of the dichloromethane solution (0.073 mmol/L) in a quartz cell.

As shown in FIG. 48, the organometallic complex [Ir(d2npm)₂(acac)], which is one embodiment of the present invention, has an emission peak at 645 nm, and red light was observed from the dichloromethane solution.

EXAMPLE 14

Synthetic Example 7

In Example 14, a synthetic example of an organometallic complex (acetylacetonato)bis[4,6-di(naphthalen-1-yl)pyrimidinato]iridium(III) (another name: bis[1-(6-naphthalen-1-yl-4-pyrimidinyl-κC)-2-naphthalenyl-κC](2,4-pentanedionato-κ²O,O')iridium(III)) (abbreviation: [Ir(d1npm)₂(acac)]), which is one embodiment of the present invention represented by the structural formula (115) in Embodiment 1, is specifically described. A structure of [Ir(d1npm)₂(acac)] is shown below.

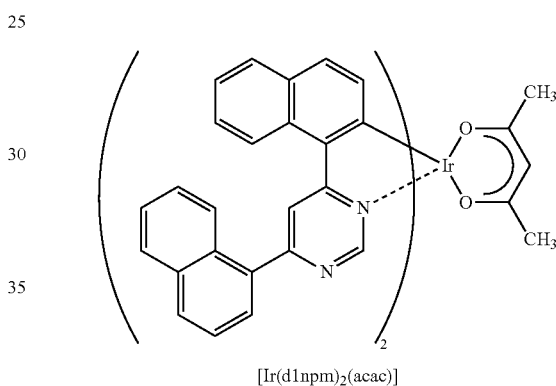

[Ir(d1npm)₂(acac)]

Step 1: Synthesis of
4,6-di(naphthalen-1-yl)pyrimidine (abbreviation: Hd1npm)

First, into a recovery flask equipped with a reflux pipe were put 5.00 g of 4,6-dichloropyrimidine, 11.56 g of 1-naphthaleneboronic acid, 7.12 g of sodium carbonate, 0.29 g of bis(triphenylphosphine)palladium(II)dichloride (abbreviation: Pd(PPh₃)₂Cl₂), 20 mL of water, and 20 mL of acetonitrile, and the air in the flask was replaced with argon. This reaction container was heated by irradiation with microwaves (2.45 GHz, 100 W) for 60 minutes. Here, into the flask were further put 2.91 g of 1-naphthaleneboronic acid, 1.82 g of sodium carbonate, 0.070 g of Pd(PPh₃)₂Cl₂, 5 mL of water, and 5 mL of acetonitrile, and the mixture was heated again by irradiation with microwaves (2.45 GHz, 100 W) for 60 minutes. After that, water was added to this solution and an organic layer was extracted with dichloromethane. The obtained organic layer was washed with saturated aqueous solution of sodium hydrogen carbonate, water, and saturated saline, and was dried with magnesium sulfate. The solution after drying was filtered. The solvent of this solution was distilled off, and then the obtained residue was purified by flash column chromatography using hexane and ethyl acetate as a developing solvent in a ratio of 2:1, so that a pyrimidine derivative Hd1npm, which was the objective substance, was obtained (yellow white powder, yield of 41%). Note that the irradiation with microwaves was performed using a microwave synthesis system (Discover, manufactured by CEM Corporation). A synthesis scheme (i-1) of Step 1 is shown below.

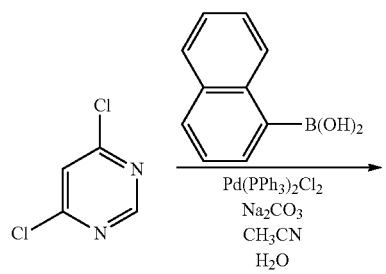

(i-1)

Step 2: Synthesis of di-μ-chloro-bis{bis[4,6-di(naphthalen-1-yl)pyrimidinato]iridium(III)} (abbreviation: [Ir(d1npm)$_2$Cl]$_2$)

Next, into a recovery flask equipped with a reflux pipe were put 30 mL of 2-ethoxyethanol, 10 mL of water, 2.29 g of Hd1npm obtained in Step 1, and 1.01 g of iridium chloride hydrate (IrCl$_3$·H$_2$O) (produced by Sigma-Aldrich Corp.), and the air in the flask was replaced with argon. After that, irradiation with microwaves (2.45 GHz, 100 W) was performed for 1 hour to cause a reaction. The solvent was distilled off, and then the obtained residue was suction-filtered and washed with ethanol to give a dinuclear complex [Ir(d1npm)$_2$Cl]$_2$ (reddish brown powder, yield of 82%). A synthesis scheme (i-2) of Step 2 is shown below.

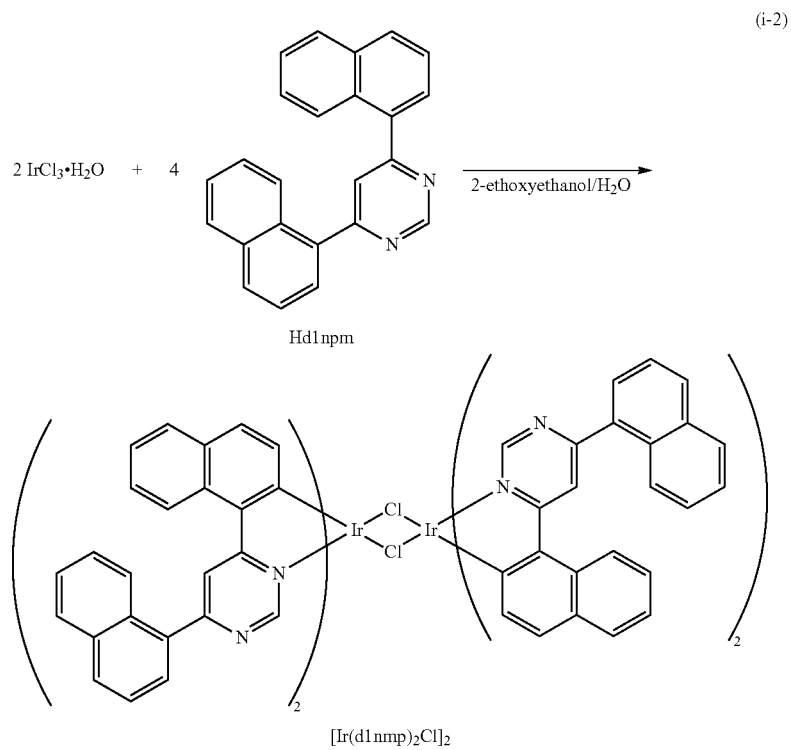

(i-2)

-continued

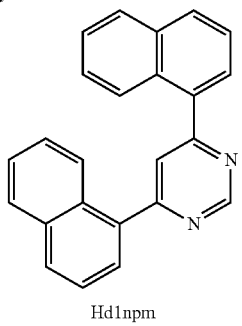

Hd1npm

Step 3: Synthesis of (acetylacetonato)bis[4,6-di(naphthalen-1-yl)pyrimidinato]iridium(III) (abbreviation: [Ir(d1npm)$_2$(acac)])

Figure 50:
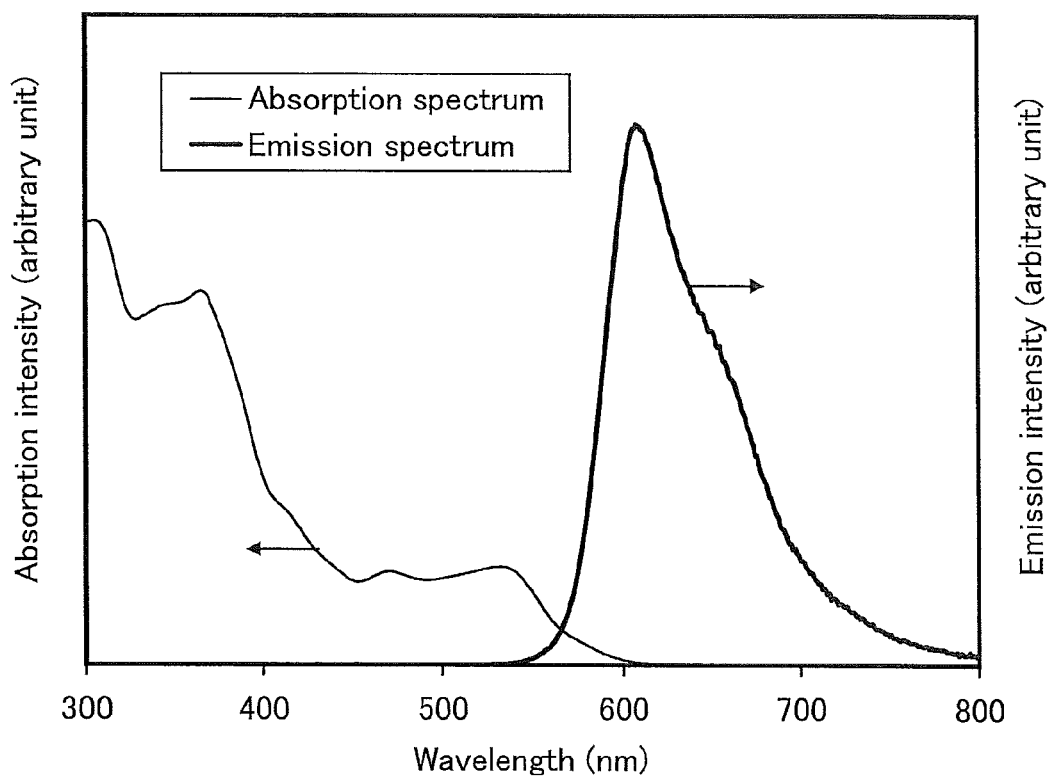
FIG. 50 shows an ultraviolet-visible absorption spectrum and an emission spectrum of the organometallic complex represented by the structural formula (115).

Further, into a recovery flask equipped with a reflux pipe were put 30 mL of 2-ethoxyethanol, 1.18 g of the dinuclear complex [Ir(d1npm)$_2$Cl]$_2$ obtained in Step 2, 0.20 g of acetylacetone, and 0.70 g of sodium carbonate, and the air in the flask was replaced with argon. After that, the mixture was heated by irradiation with microwaves (2.45 GHz, 120 W) for 60 minutes. Here, into the flask was further put 0.20 g of acetylacetone, and the mixture was heated again by irradiation with microwaves (2.45 GHz, 120 W) for 60 minutes. The solvent was distilled off, and the obtained residue was suction-filtered with ethanol. The obtained solid was washed with water and ethanol, and purified by flash column chromatography using dichloromethane as a developing solvent. After that, recrystallization was carried out with a mixed solvent of dichloromethane and hexane to give dark red powder (yield of 27%). A synthesis scheme (i-3) of Step 3 is shown below.

tical axis represents absorption intensity (arbitrary unit) and emission intensity (arbitrary unit). In FIG. 50, two solid lines are shown; a thin line represents the absorption spectrum, and a thick line represents the emission spectrum. Note that the absorption spectrum in FIG. 50 is a result obtained by sub-

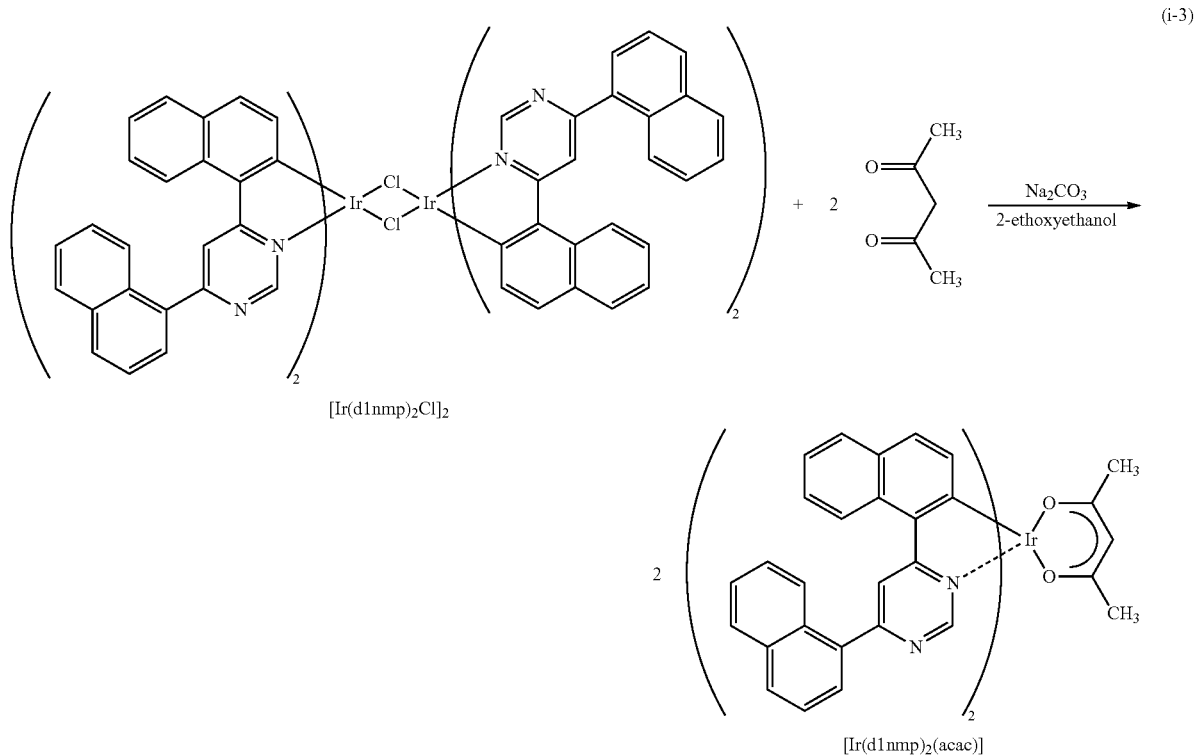

(i-3)

[Ir(d1nmp)₂Cl]₂

[Ir(d1nmp)₂(acac)]

Figure 49:
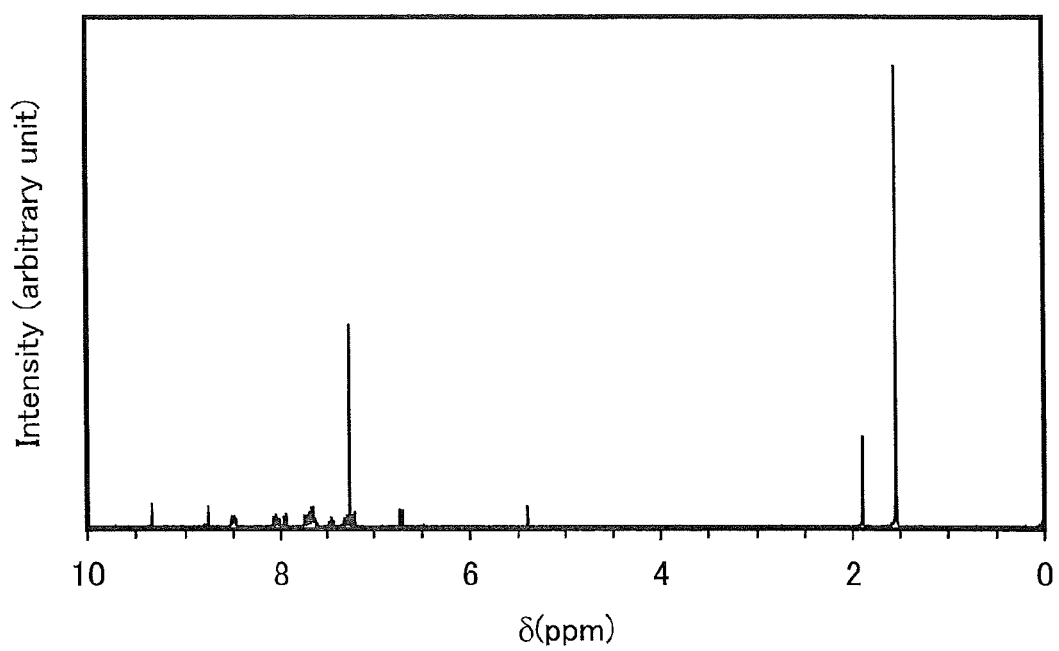
FIG. 49 shows a $^1$H NMR chart of an organometallic complex represented by a structural formula (115).

An analysis result by nuclear magnetic resonance spectrometry ($^1$H NMR) of the dark red powder obtained is described below. The $^1$H NMR chart is illustrated in FIG. 49. These results revealed that the organometallic complex [Ir(d1npm)₂(acac)], which is one embodiment of the present invention represented by the structural formula (115), was obtained in Synthetic Example 7.

$^1$H NMR. δ (CDCl₃): 1.90 (s, 6H), 5.40 (s, 1H), 6.72 (d, 2H), 7.22 (d, 2H), 7.31 (d, 2H), 7.45 (t, 2H), 7.62-7.74 (m, 8H), 7.95 (d, 2H), 8.01-8.08 (m, 4H), 8.48-8.52 (m, 4H), 8.77 (s, 2H), 9.34 (s, 2H).

Next, an ultraviolet-visible absorption spectrum (hereinafter, simply referred to as an absorption spectrum) and an emission spectrum of [Ir(d1npm)₂(acac)] in a dichloromethane solution were measured. The absorption spectrum was measured with the use of an ultraviolet-visible light spectrophotometer (V-550, manufactured by JASCO Corporation) in the state where the dichloromethane solution (0.070 mmol/L) was put in a quartz cell at room temperature. The emission spectrum was measured with the use of a fluorescence spectrophotometer (FS920, manufactured by Hamamatsu Photonics Corporation) in the state where the degassed dichloromethane solution (0.070 mmol/L) was put in a quartz cell at room temperature. FIG. 50 shows results of the measured absorption spectrum and emission spectrum. The horizontal axis represents wavelength (nm), and the vertraction of the absorption spectrum of only dichloromethane that was put in a quartz cell from the measured absorption spectrum of the dichloromethane solution (0.070 mmol/L) in a quartz cell.

As shown in FIG. 50, the organometallic complex [Ir(d1npm)₂(acac)], which is one embodiment of the present invention, has an emission peak at 608 nm, and orange light was observed from the dichloromethane solution.

EXAMPLE 15

Synthetic Example 8

In Example 15, a synthetic example of an organometallic complex (acetylacetonato)bis[4,6-di(3-biphenyl)pyrimidinato]iridium(III) (another name: bis{3-[6-(1,1'-biphenyl-3-yl)-4-pyrimidinyl-κN3]-1,1'-biphenyl-4-yl-KC} (2,4-pentanedionato-κ²O,O')iridium(III)) (abbreviation: [Ir(d5bpm)₂(acac)]), which is one embodiment of the present invention represented by the structural formula (119) in Embodiment 1, is specifically described. A structure of [Ir(d5bpm)₂(acac)] is shown below.

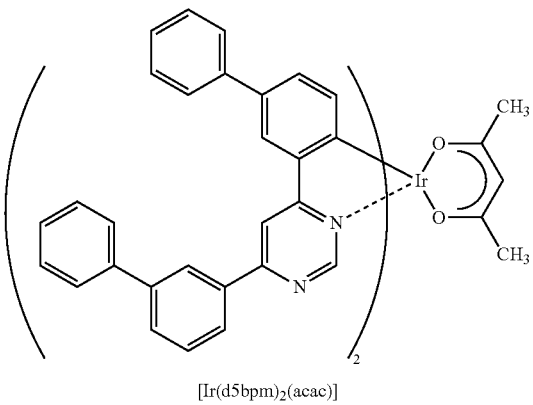

[Ir(d5bpm)₂(acac)]

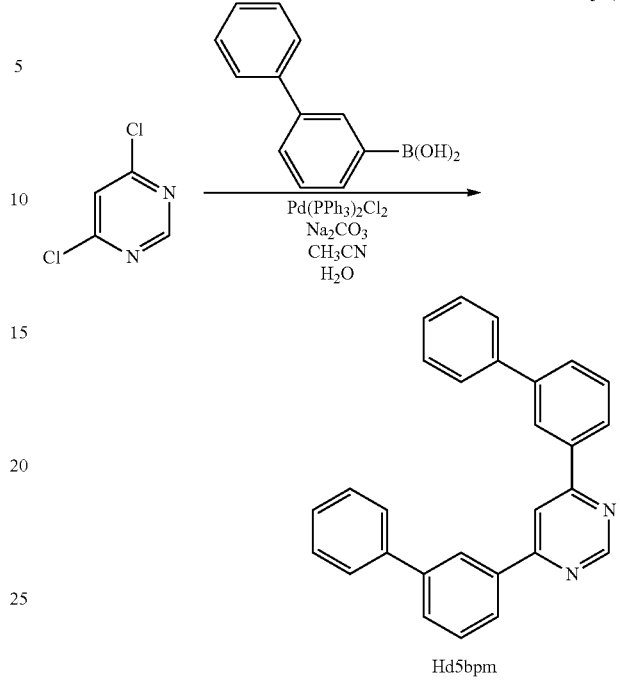

(j-1)

Hd5bpm

Step 1: Synthesis of 4,6-di(3-biphenyl)pyrimidine (abbreviation: Hd5bpm)

First, into a recovery flask equipped with a reflux pipe were put 5.03 g of 4,6-dichloropyrimidine, 13.51 g of 3-biphenylboronic acid, 7.17 g of sodium carbonate, 0.29 g of bis(triphenylphosphine)palladium(II)dichloride (abbreviation: Pd(PPh₃)₂Cl₂), 30 mL of water, and 30 mL of acetonitrile, and the air in the flask was replaced with argon. This reaction container was heated by irradiation with microwaves (2.45 GHz, 100 W) for 60 minutes. Here, into the flask were further put 3.40 g of 3-biphenylboronic acid, 1.77 g of sodium carbonate, and 0.070 g of Pd(PPh₃)₂Cl₂, and the mixture was heated again by irradiation with microwaves (2.45 GHz, 100 W) for 60 minutes. After that, water was added to this solution and an organic layer was extracted with dichloromethane. The obtained organic layer was washed with saturated aqueous solution of sodium hydrogen carbonate, water, and saturated saline, and was dried with magnesium sulfate. The solution after drying was filtered. The solvent of this solution was distilled off, and then the obtained residue was purified by silica gel column chromatography using toluene and ethyl acetate as a developing solvent in a ratio of 40:1, so that a pyrimidine derivative Hd5bpm, which was the objective substance, was obtained (white powder, yield of 10%). Note that the irradiation with microwaves was performed using a microwave synthesis system (Discover, manufactured by CEM Corporation). A synthesis scheme (j-1) of Step 1 is shown below.

Step 2: Synthesis of di-μ-chloro-bis {bis[4,6-di(3-biphenyl)pyrimidinato]iridium(III)} (abbreviation: [Ir(d5bpm)₂Cl]₂)

Next, into a recovery flask equipped with a reflux pipe were put 15 mL of 2-ethoxyethanol, 5 mL of water, 1.14 g of Hd5bpm obtained in Step 1, and 0.42 g of iridium chloride hydrate (IrCl₃·H₂O) (produced by Sigma-Aldrich Corp.), and the air in the flask was replaced with argon. After that, irradiation with microwaves (2.45 GHz, 100 W) was performed for 1 hour to cause a reaction. The solvent was distilled off, and then the obtained residue was suction-filtered and washed with ethanol to give a dinuclear complex [Ir(d5bpm)₂Cl]₂ (reddish brown powder, yield of 99%). A synthesis scheme (j-2) of Step 2 is shown below.

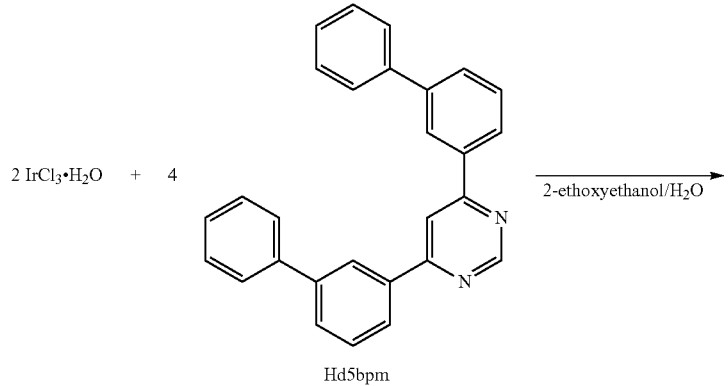

(j-2)

Hd5bpm

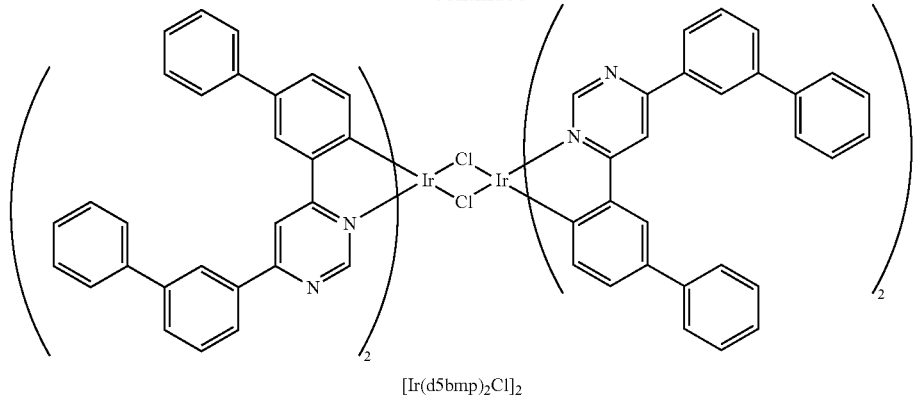

[Ir(d5bmp)₂Cl]₂

(Step 3: Synthesis of (acetylacetonato)bis[4,6-di(3-biphenyl)pyrimidinato]iridium(III) (abbreviation: [Ir(d5bpm)₂(acac)])

Further, into a recovery flask equipped with a reflux pipe were put 40 mL of 2-ethoxyethanol, 1.38 g of the dinuclear complex [Ir(d5bpm)₂Cl]₂ obtained in Step 2, 0.21 g of acetylacetone, and 0.74 g of sodium carbonate, and the air in the flask was replaced with argon. After that, the mixture was heated by irradiation with microwaves (2.45 GHz, 120 W) for 60 minutes. Here, into the flask was further put 0.070 g of acetylacetone, and the mixture was heated again by irradiation with microwaves (2.45 GHz, 120 W) for 60 minutes. The solvent was distilled off, and the obtained residue was suction-filtered with ethanol. The obtained solid was washed with water and ethanol, and purified by silica gel column chromatography using dichloromethane as a developing solvent. After that, recrystallization was carried out with a mixed solvent of dichloromethane and hexane to give a reddish orange solid. This solid was purified by silica gel column chromatography using dichloromethane as a developing solvent and recrystallized with a mixed solvent of dichloromethane and hexane to give reddish orange powder (yield of 17%). A synthesis scheme (j-3) of Step 3 is shown below.

(j-3)

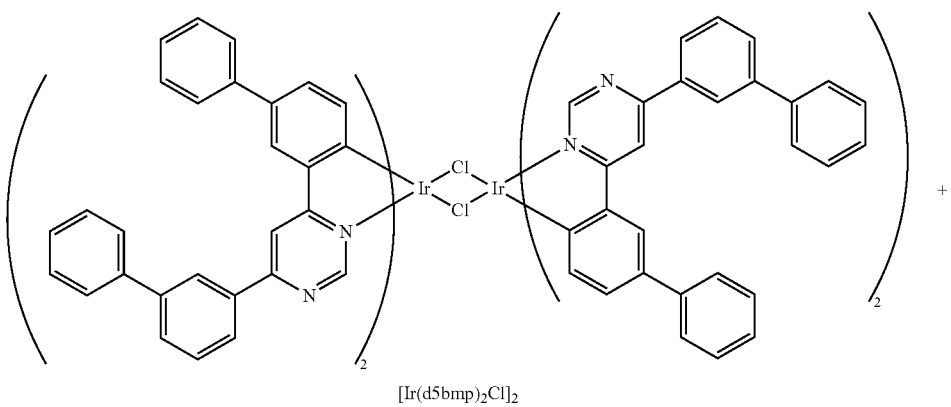

[Ir(d5bmp)₂Cl]₂

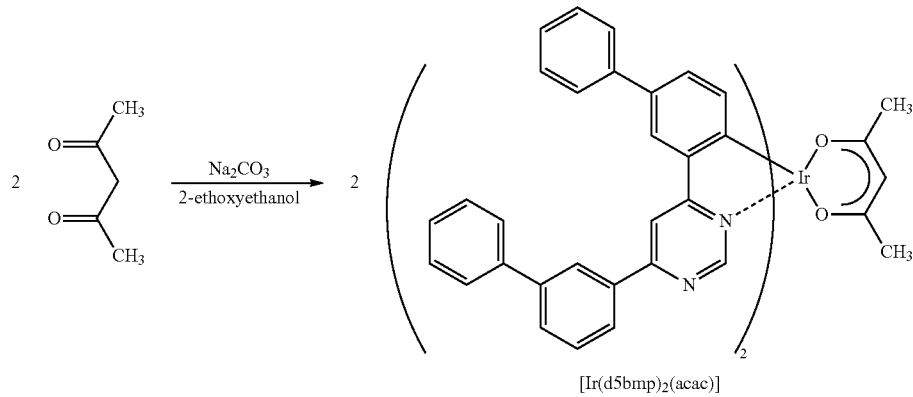

[Ir(d5bmp)₂(acac)]

Figure 51:
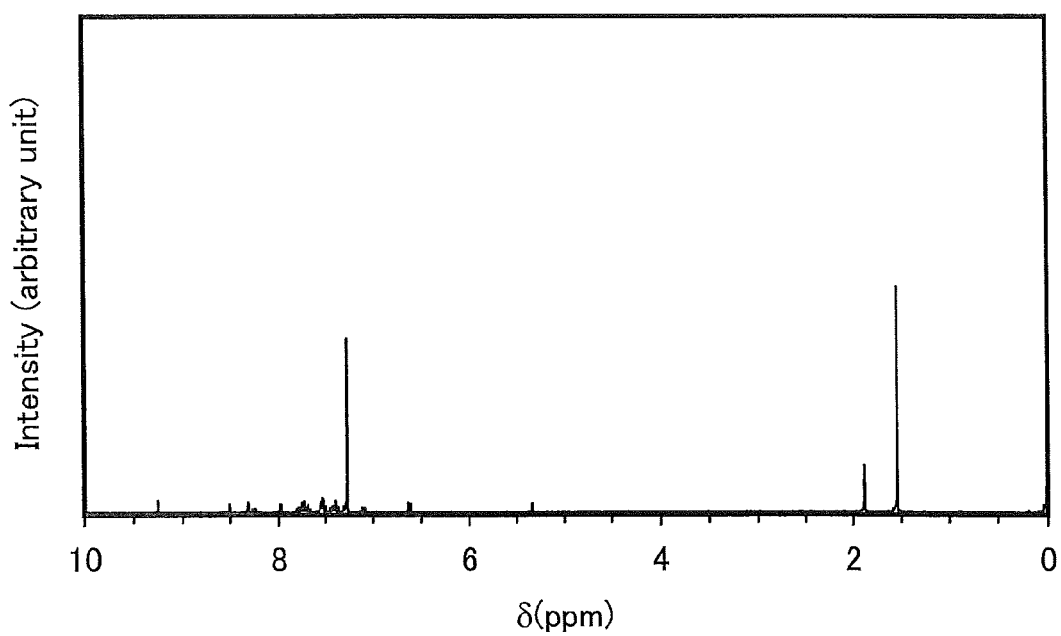
FIG. 51 shows a $^1$H NMR chart of an organometallic complex represented by a structural formula (119).

An analysis result by nuclear magnetic resonance spectrometry ($^1$H NMR) of the reddish orange powder obtained is described below. The $^1$H NMR chart is illustrated in FIG. 51. These results revealed that the organometallic complex [Ir(d5bpm)$_2$(acac)], which is one embodiment of the present invention represented by the structural formula (119), was obtained in Synthetic Example 8.

$^1$H NMR. δ (CDCl$_3$): 1.88 (s, 6H), 5.34 (s, 1H), 6.62 (d, 2H), 7.10 (d, 2H), 7.29 (d, 2H), 7.36-7.45 (m, 6H), 7.50-7.56 (m, 8H), 7.69 (t, 2H), 7.74 (d, 4H), 7.80 (d, 2H), 7.98 (s, 2H), 8.26 (d, 2H), 8.32 (s, 2H), 8.51 (s, 2H), 9.25 (s, 2H).

Figure 52:
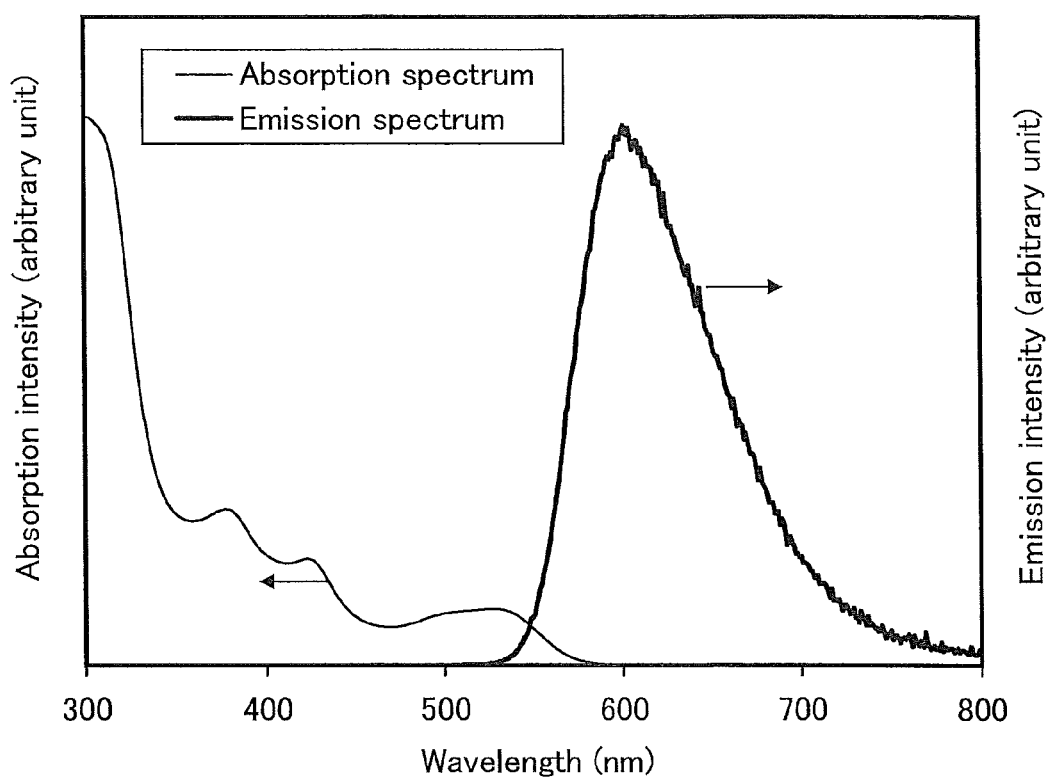
FIG. 52 shows an ultraviolet-visible absorption spectrum and an emission spectrum of the organometallic complex represented by the structural formula (119).

Next, an ultraviolet-visible absorption spectrum (hereinafter, simply referred to as an absorption spectrum) and an emission spectrum of [Ir(d5bpm)$_2$(acac)] in a dichloromethane solution were measured. The absorption spectrum was measured with the use of an ultraviolet-visible light spectrophotometer (V-550, manufactured by JASCO Corporation) in the state where the dichloromethane solution (0.066 mmol/L) was put in a quartz cell at room temperature. The emission spectrum was measured with the use of a fluorescence spectrophotometer (FS920, manufactured by Hamamatsu Photonics Corporation) in the state where the degassed dichloromethane solution (0.066 mmol/L) was put in a quartz cell at room temperature. FIG. 52 shows results of the measured absorption spectrum and emission spectrum. The horizontal axis represents wavelength (nm), and the vertical axis represents absorption intensity (arbitrary unit) and emission intensity (arbitrary unit). In FIG. 52, two solid lines are shown; a thin line represents the absorption spectrum, and a thick line represents the emission spectrum. Note that the absorption spectrum in FIG. 52 is a result obtained by subtraction of the absorption spectrum of only dichloromethane that was put in a quartz cell from the measured absorption spectrum of the dichloromethane solution (0.066 mmol/L) in a quartz cell.

As shown in FIG. 52, the organometallic complex [Ir(d5bpm)$_2$(acac)], which is one embodiment of the present invention, has an emission peak at 601 nm, and orange light was observed from the dichloromethane solution.

EXAMPLE 16

Synthetic Example 9

In Example 16, a synthetic example of an organometallic complex (acetylacetonato)bis[4,6-bis(4-methoxyphenyl)pyrimidinato]iridium(III) (another name: bis{2-[6-(4-methoxyphenyl)-4-pyrimidinyl-κN3]-5-methoxyphenyl-κC}(2,4-pentanedio nato-κ$^2$O,O')iridium(III)) (abbreviation: [Ir(modppm)$_2$(acac)]), which is one embodiment of the present invention represented by the structural formula (123) in Embodiment 1, is specifically described. A structure of [Ir(modppm)$_2$(acac)] is shown below.

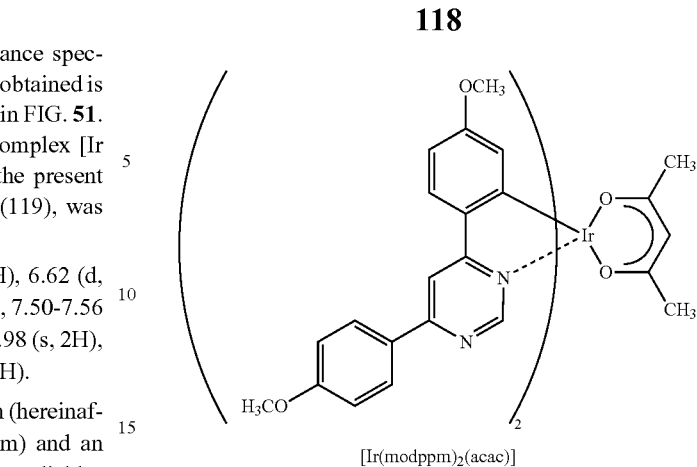

[Ir(modppm)$_2$(acac)]

Step 1: Synthesis of 4,6-bis(4-methoxyphenyl)pyrimidine (abbreviation: Hmodppm)

First, into a recovery flask equipped with a reflux pipe were put 5.01 g of 4,6-dichloropyrimidine, 10.32 g of 4-methoxyphenylboronic acid, 7.22 g of sodium carbonate, 0.29 g of bis(triphenylphosphine)palladium(II)dichloride (abbreviation: Pd(PPh$_3$)$_2$Cl$_2$), 20 mL of water, and 20 mL of acetonitrile, and the air in the flask was replaced with argon. This reaction container was heated by irradiation with microwaves (2.45 GHz, 100 W) for 60 minutes. Here, into the flask were further put 2.58 g of 4-methoxyphenylboronic acid, 1.81 g of sodium carbonate, 0.070 g of Pd(PPh$_3$)$_2$Cl$_2$, 5 mL of water, and 5 mL of acetonitrile, and the mixture was heated again by irradiation with microwaves (2.45 GHz, 100 W) for 60 minutes. After that, water was added to this solution and an organic layer was extracted with dichloromethane. The obtained organic layer was washed with saturated aqueous solution of sodium hydrogen carbonate, water, and saturated saline, and was dried with magnesium sulfate. The solution after drying was filtered. The solvent of this solution was distilled off, and then the obtained residue was purified by silica gel column chromatography using dichloromethane and ethyl acetate as a developing solvent in a ratio of 10:1, so that a pyrimidine derivative Hmodppm, which was the objective substance, was obtained (white powder, yield of 62%). Note that the irradiation with microwaves was performed using a microwave synthesis system (Discover, manufactured by CEM Corporation). A synthesis scheme (k-1) of Step 1 is shown below.

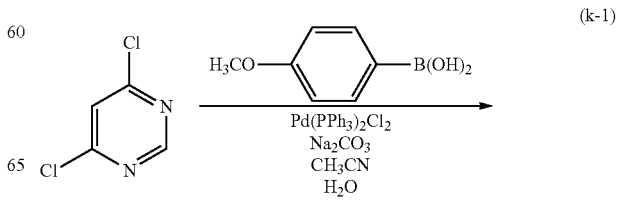

(k-1)

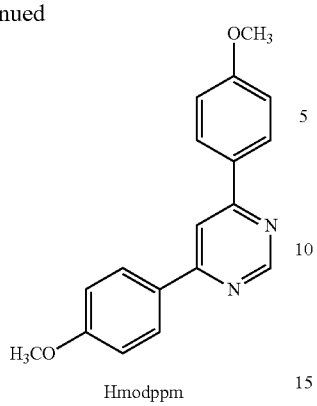

Hmodppm

Step 2: Synthesis of di-μ-chloro-bis{bis[4,6-bis(4-methoxyphenyl)pyrimidine]iridium(III)} (abbreviation: [Ir(modppm)₂Cl]₂)

Next, into a recovery flask equipped with a reflux pipe were put 15 mL of 2-ethoxyethanol, 5 mL of water, 1.97 g of Hmodppm obtained in Step 1, and 1.00 g of iridium chloride hydrate (IrCl₃·H₂O) (produced by Sigma-Aldrich Corp.), and the air in the flask was replaced with argon. After that, irradiation with microwaves (2.45 GHz, 100 W) was performed for 1 hour to cause a reaction. The solvent was distilled off, and then the obtained residue was suction-filtered and washed with ethanol to give a dinuclear complex [Ir(modppm)₂Cl]₂ (grayish green powder, yield of 100%). A synthesis scheme (k-2) of Step 2 is shown below.

Step 3: Synthesis of (acetylacetonato)bis[4,6-bis(4-methoxyphenyl)pyrimidinato]iridium(III) (abbreviation: [Ir(modppm)₂(acac)])

Further, into a recovery flask equipped with a reflux pipe were put 40 mL of 2-ethoxyethanol, 2.80 g of the dinuclear complex [Ir(modppm)₂Cl]₂ obtained in Step 2, 0.52 g of acetylacetone, and 1.83 g of sodium carbonate, and the air in the flask was replaced with argon. After that, the mixture was heated by irradiation with microwaves (2.45 GHz, 120 W) for 60 minutes. Here, into the flask was further put 0.17 g of acetylacetone, and the mixture was heated again by irradiation with microwaves (2.45 GHz, 120 W) for 60 minutes. The solvent was distilled off, and the obtained residue was suction-filtered with ethanol. The obtained solid was washed with water and ethanol, and purified by silica gel column chromatography using dichloromethane and ethyl acetate as a developing solvent in a ratio of 25:1. After that, recrystallization was carried out with a mixed solvent of dichloromethane and hexane to give yellow orange powder (yield of 13%). A synthesis scheme (k-3) of Step 3 is shown below.

(k-2)

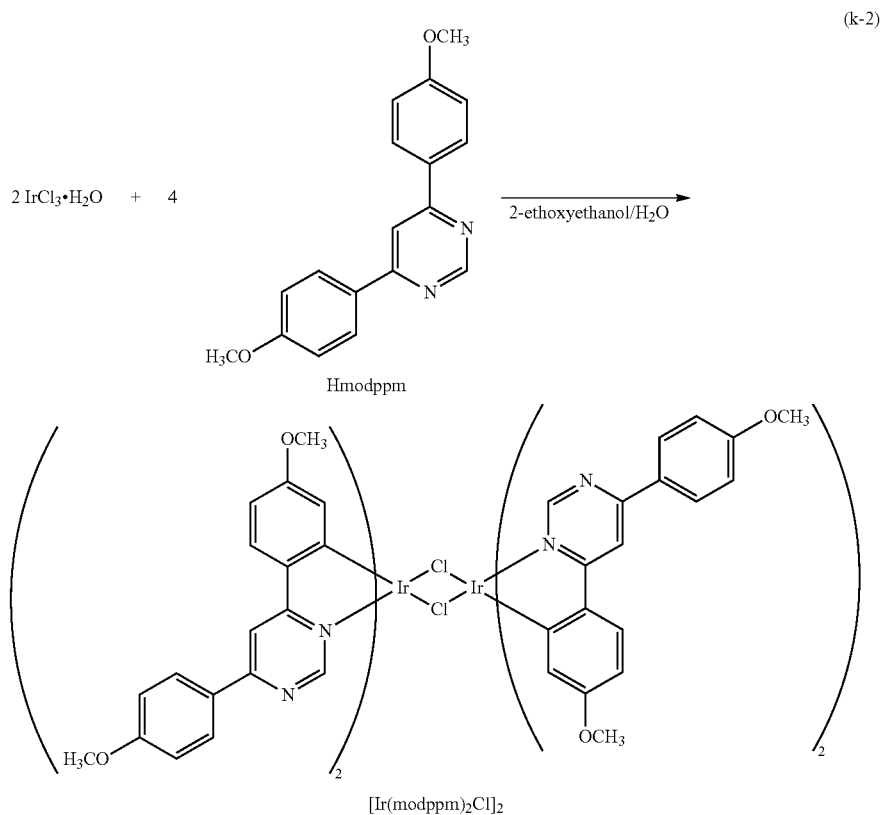

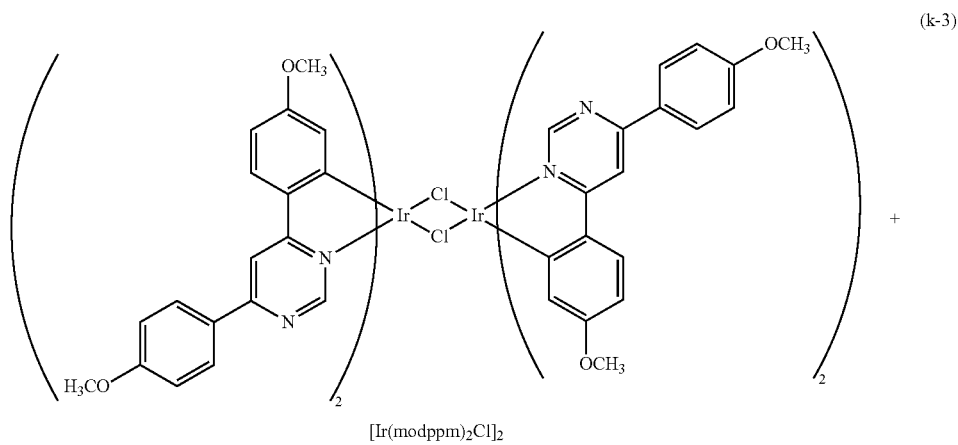

[Ir(modppm)₂Cl]₂ (k-3)

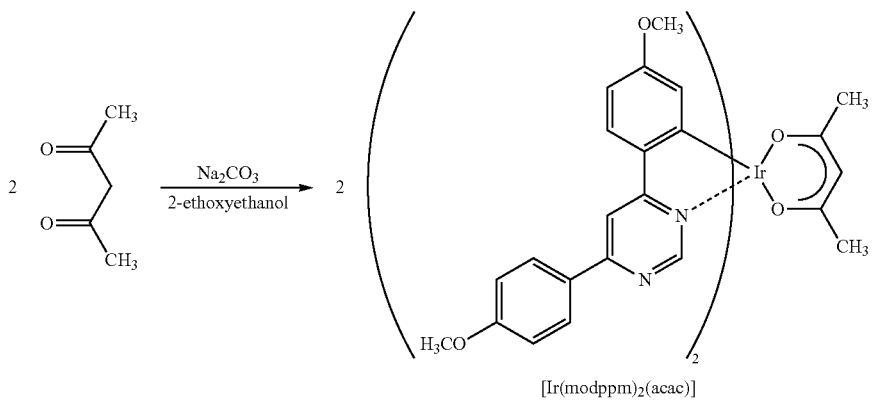

[Ir(modppm)₂(acac)]

Figure 53:
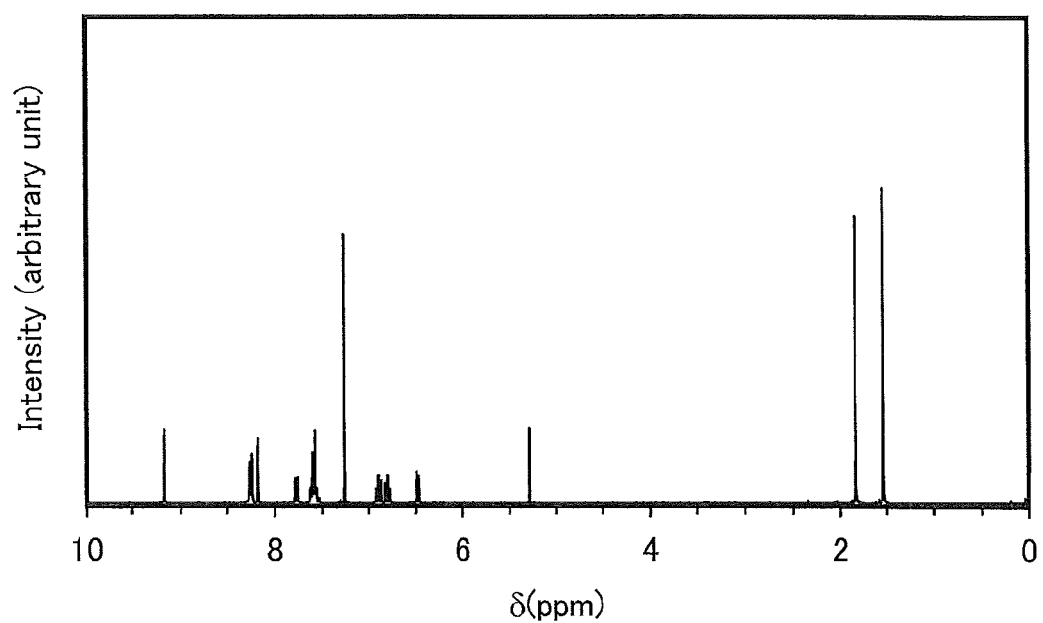
FIG. 53 shows a $^1$H NMR chart of an organometallic complex represented by a structural formula (123).

An analysis result by nuclear magnetic resonance spectrometry (¹H NMR) of the yellow orange powder obtained is described below. The ¹H NMR chart is illustrated in FIG. 53. These results revealed that the organometallic complex [Ir(modppm)₂(acac)], which is one embodiment of the present invention represented by the structural formula (123), was obtained in Synthetic Example 9.

¹H NMR. δ (CDCl₃): 1.82 (s, 6H), 3.58 (s, 6H), 3.93 (s, 6H), 5.27 (s, 1H), 5.97 (d, 2H), 6.48 (d, 2H), 7.08 (d, 4H), 7.69 (d, 2H), 7.95 (s, 2H), 8.19 (d, 4H), 9.01 (s, 2H).

Figure 54:
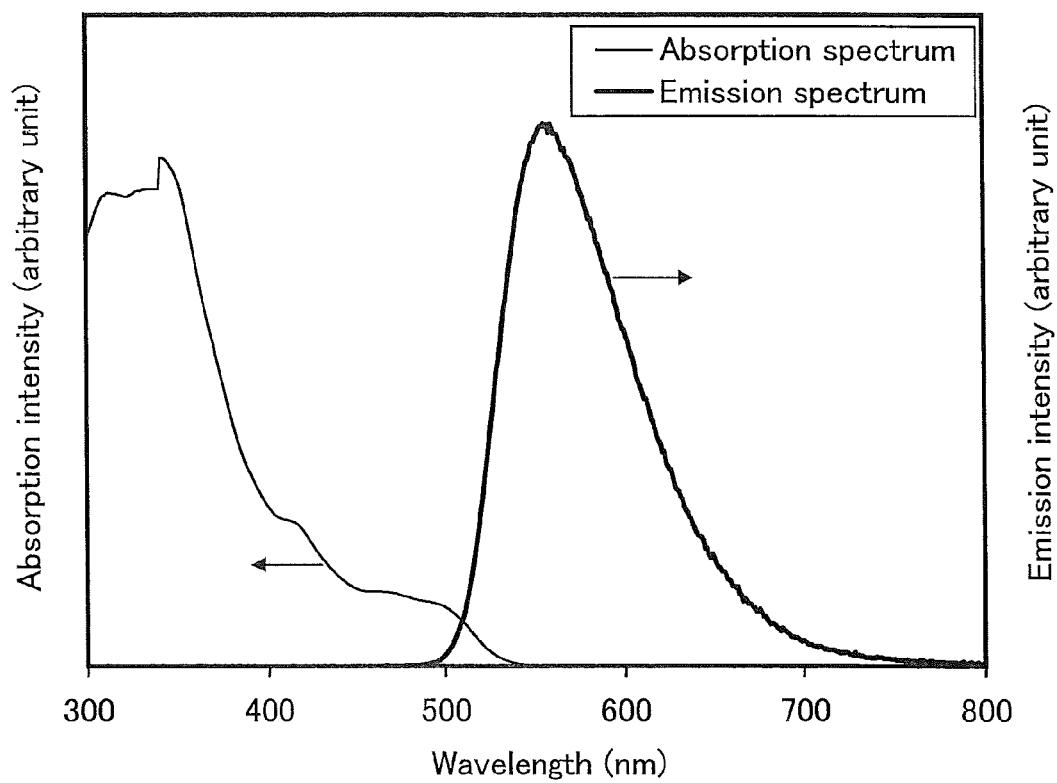
FIG. 54 shows an ultraviolet-visible absorption spectrum and an emission spectrum of the organometallic complex represented by the structural formula (123).

Next, an ultraviolet-visible absorption spectrum (hereinafter, simply referred to as an absorption spectrum) and an emission spectrum of [Ir(modppm)₂(acac)] in a dichloromethane solution were measured. The absorption spectrum was measured with the use of an ultraviolet-visible light spectrophotometer (V-550, manufactured by JASCO Corporation) in the state where the dichloromethane solution (0.072 mmol/L) was put in a quartz cell at room temperature. The emission spectrum was measured with the use of a fluorescence spectrophotometer (FS920, manufactured by Hamamatsu Photonics Corporation) in the state where the degassed dichloromethane solution (0.072 mmol/L) was put in a quartz cell at room temperature. FIG. 54 shows results of the measured absorption spectrum and emission spectrum. The horizontal axis represents wavelength (nm), and the vertical axis represents absorption intensity (arbitrary unit) and emission intensity (arbitrary unit). In FIG. 54, two solid lines are shown; a thin line represents the absorption spectrum, and a thick line represents the emission spectrum. Note that the absorption spectrum in FIG. 54 is a result obtained by subtraction of the absorption spectrum of only dichloromethane that was put in a quartz cell from the measured absorption spectrum of the dichloromethane solution (0.072 mmol/L) in a quartz cell.

As shown in FIG. 54, the organometallic complex [Ir(modppm)₂(acac)], which is one embodiment of the present invention, has an emission peak at 556 nm, and yellow light was observed from the dichloromethane solution.

EXAMPLE 17

Synthetic Example 10

In Example 17, a synthetic example of an organometallic complex (acetylacetonato)bis(4,5,6-triphenylpyrimidinato)iridium(III) (another name: bis[2-(5,6-diphenyl-4-pyrimidinyl-κN3])phenyl-κC)(2,4-pentanedionato-κ²O,O')iridium (III)) (abbreviation: [Ir(tppm)₂(acac)]), which is one embodiment of the present invention represented by the structural formula (134) in Embodiment 1, is specifically described. A structure of [Ir(tppm)₂(acac)] is shown below.

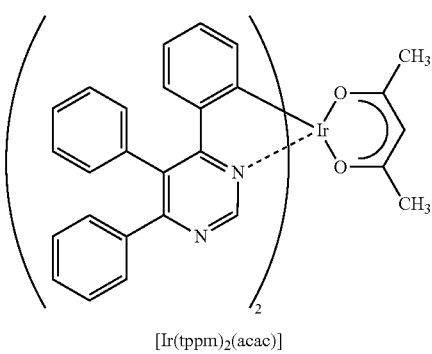

[Ir(tppm)₂(acac)]

Step 1: Synthesis of 4,5,6-triphenylpyrimidine (abbreviation: Htppm)

First, into a recovery flask equipped with a reflux pipe were put 4.25 g of 5-bromo-4,6-dichloropyrimidine, 6.84 g of phenylboronic acid, 5.95 g of sodium carbonate, 0.16 g of bis(triphenylphosphine)palladium(II)dichloride (abbreviation: Pd(PPh₃)₂Cl₂), 20 mL of water, and 20 mL of acetonitrile, and the air in the flask was replaced with argon. This reaction container was heated by irradiation with microwaves (2.45 GHz, 100 W) for 60 minutes. Here, into the flask were further put 2.28 g of phenylboronic acid, 1.98 g of sodium carbonate, 0.053 g of Pd(PPh₃)₂Cl₂, 5 mL of water, and 5 mL of acetonitrile, and the mixture was heated again by irradiation with microwaves (2.45 GHz, 100 W) for 60 minutes. After that, the precipitated solid was suction-filtered and washed with water. The obtained residue was purified by flash column chromatography using dichloromethane and ethyl acetate as a developing solvent in a ratio of 10:1, so that a pyrimidine derivative Htppm, which was the objective substance, was obtained (white powder, yield of 46%). Note that the irradiation with microwaves was performed using a microwave synthesis system (Discover, manufactured by CEM Corporation). A synthesis scheme (1-1) of Step 1 is shown below.

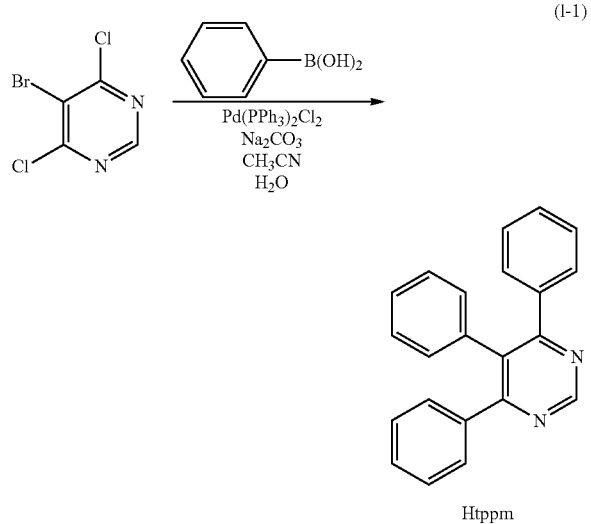

Step 2: Synthesis of di-μ-chloro-bis[bis(4,5,6-triphenylpyrimidinato)iridium(III)](abbreviation: [Ir(tppm)₂Cl]₂)

Next, into a recovery flask equipped with a reflux pipe were put 30 mL of 2-ethoxyethanol, 10 mL of water, 2.60 g of Htppm obtained in Step 1, and 1.25 g of iridium chloride hydrate (IrCl₃.H₂O) (produced by Sigma-Aldrich Corp.), and the air in the flask was replaced with argon. After that, irradiation with microwaves (2.45 GHz, 100 W) was performed for 1 hour to cause a reaction. The solvent was distilled off, and then the obtained residue was suction-filtered and washed with ethanol to give a dinuclear complex [Ir(tppm)₂Cl]₂ (brown powder, yield of 75%). A synthesis scheme (1-2) of Step 2 is shown below.

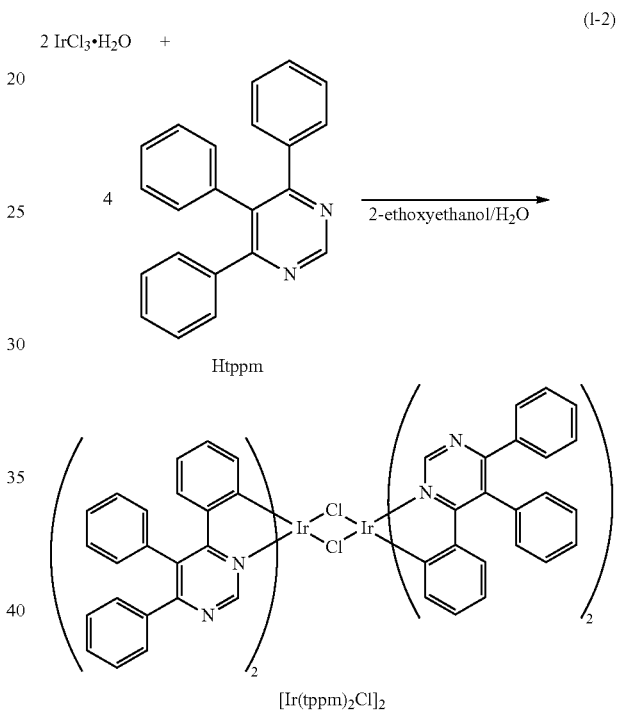

Step 3: Synthesis of (acetylacetonato)bis(4,5,6-triphenylpyrimidinato)iridium(III) (abbreviation: [Ir(tppm)₂(acac)])

Further, into a recovery flask equipped with a reflux pipe were put 30 mL of 2-ethoxyethanol, 1.30 g of the dinuclear complex [Ir(tppm)₂Cl]₂ obtained in Step 2, 0.23 g of acetylacetone, and 0.82 g of sodium carbonate, and the air in the flask was replaced with argon. After that, the mixture was heated by irradiation with microwaves (2.45 GHz, 120 W) for 60 minutes. Here, into the flask was further put 0.23 g of acetylacetone, and the mixture was heated again by irradiation with microwaves (2.45 GHz, 120 W) for 60 minutes. The solvent was distilled off, and the obtained residue was suction-filtered with ethanol. The obtained solid was washed with water and ethanol, and purified by flash column chromatography using hexane and ethyl acetate as a developing solvent in a ratio of 2:1. After that, recrystallization was carried out with a mixed solvent of dichloromethane and ethanol to give reddish orange powder (yield of 29%). A synthesis scheme (1-3) of Step 3 is shown below.

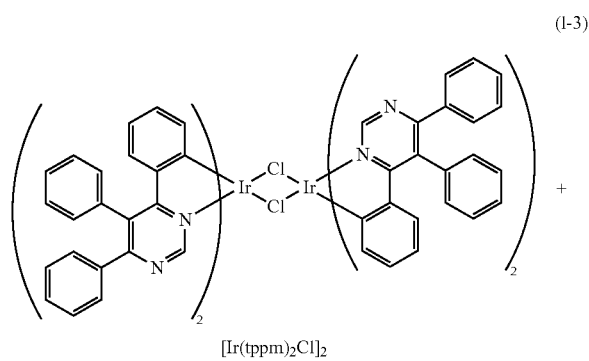

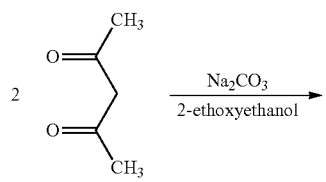

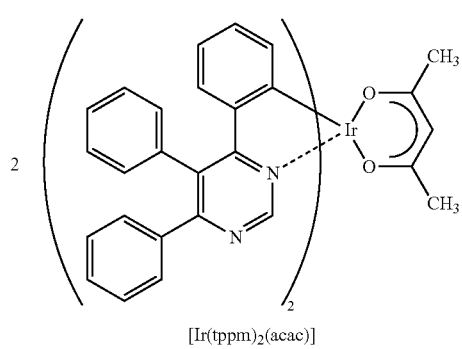

[Ir(tppm)₂(acac)]

Figure 55:
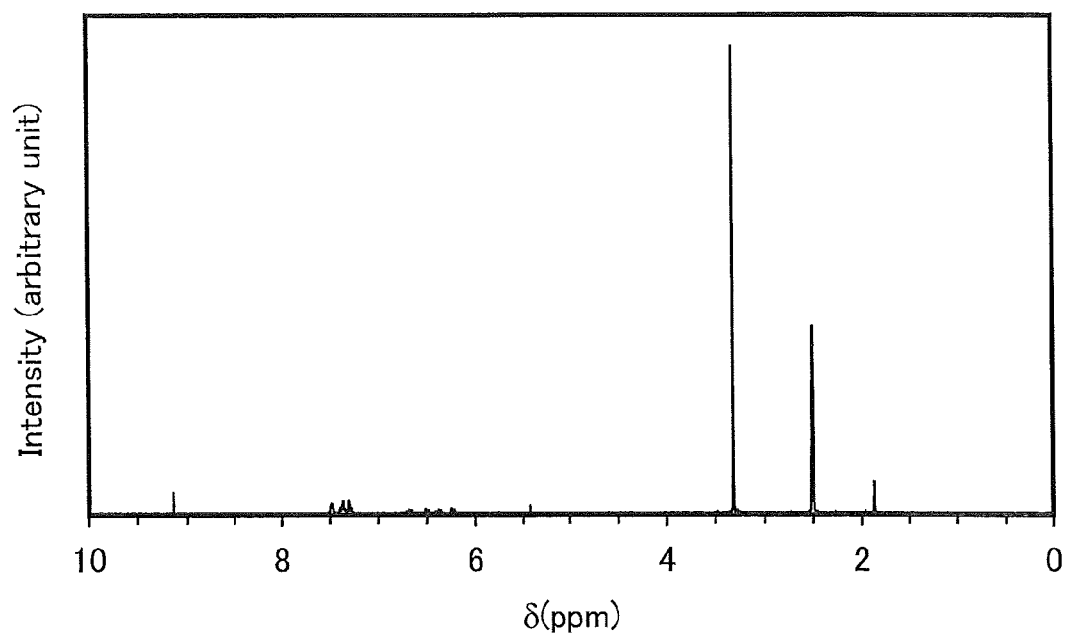
FIG. 55 shows a $^1$H NMR chart of an organometallic complex represented by a structural formula (134).

An analysis result by nuclear magnetic resonance spectrometry ($^1$H NMR) of the reddish orange powder obtained is described below. The $^1$H NMR chart is illustrated in FIG. 55. These results revealed that the organometallic complex [Ir(tppm)₂(acac)], which is one embodiment of the present invention represented by the structural formula (134), was obtained in Synthetic Example 10.

$^1$H NMR. δ (DMSO-d6): 1.87 (s, 6H), 5.43 (s, 1H), 6.23 (d, 2H), 6.38 (t, 2H), 6.50 (d, 2H), 6.68 (t, 2H), 7.28-7.32 (m, 6H), 7.34-7.40 (m, 8H), 7.48-7.49 (m, 6H), 9.14 (s, 2H).

Figure 56:
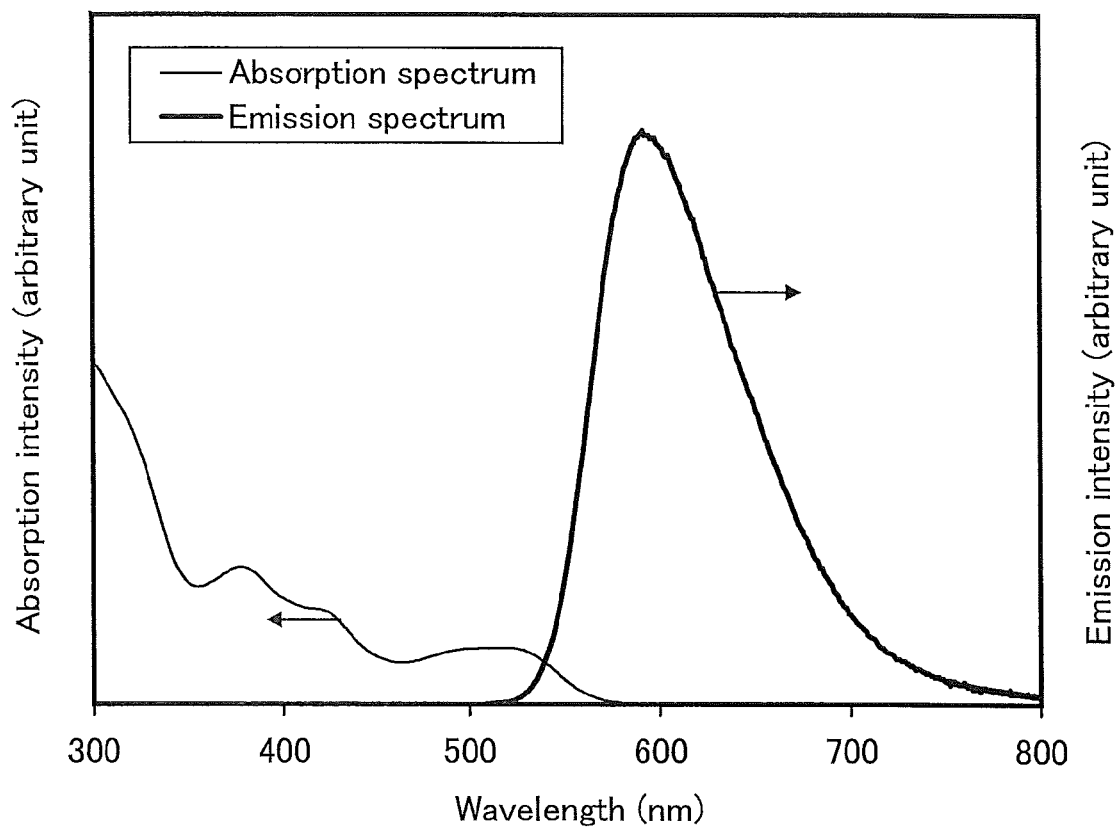
FIG. 56 shows an ultraviolet-visible absorption spectrum and an emission spectrum of the organometallic complex represented by the structural formula (134).

Next, an ultraviolet-visible absorption spectrum (hereinafter, simply referred to as an absorption spectrum) and an emission spectrum of [Ir(tppm)₂(acac)] in a dichloromethane solution were measured. The absorption spectrum was measured with the use of an ultraviolet-visible light spectrophotometer (V-550, manufactured by JASCO Corporation) in the state where the dichloromethane solution (0.074 mmol/L) was put in a quartz cell at room temperature. The emission spectrum was measured with the use of a fluorescence spectrophotometer (FS920, manufactured by Hamamatsu Photonics Corporation) in the state where the degassed dichloromethane solution (0.074 mmol/L) was put in a quartz cell at room temperature. FIG. 56 shows results of the measured absorption spectrum and emission spectrum. The horizontal axis represents wavelength (nm), and the vertical axis represents absorption intensity (arbitrary unit) and emission intensity (arbitrary unit). In FIG. 56, two solid lines are shown; a thin line represents the absorption spectrum, and a thick line represents the emission spectrum. Note that the absorption spectrum in FIG. 56 is a result obtained by subtraction of the absorption spectrum of only dichloromethane that was put in a quartz cell from the measured absorption spectrum of the dichloromethane solution (0.074 mmol/L) in a quartz cell.

As shown in FIG. 56, the organometallic complex [Ir(tppm)₂(acac)], which is one embodiment of the present invention, has an emission peak at 592 nm, and orange light was observed from the dichloromethane solution.

EXAMPLE 18

Synthetic Example 11

In Example 18, a synthetic example of an organometallic complex tris(4-methyl-6-phenylpyrimidinato)iridium(III) (another name: tris[2-(6-methyl-4-pyrimidinyl-κN3)phenyl-κC]iridium(III)) (abbreviation: [Ir(mppm)₃]), which is one embodiment of the present invention represented by the structural formula (178) in Embodiment 1, is specifically described. A structure of [Ir(mppm)₃] is shown below.

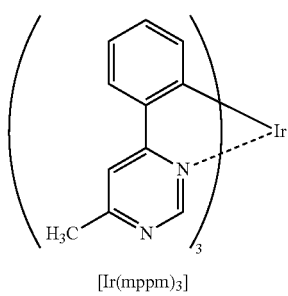

[Ir(mppm)₃]

First, into a reaction container provided with a three-way cock were put 1.35 g of the ligand Hmppm obtained in Example 2 and 0.78 g of tris(acetylacetonato)iridium(III), and the air in the reaction container was replaced with argon. After that, the mixture was heated at 250° C. for 52 hours to be reacted. The reactant was dissolved in dichloromethane, and the solution was filtered. The solvent of the obtained filtrate was distilled off, and purification was conducted by silica gel column chromatography. As developing solvents, dichloromethane was used, and then ethyl acetate was used. The solvent of the resulting fraction was distilled off, so that a yellow brown solid was obtained (crude yield: 26%). The obtained solid was purified by flash column chromatography using ethyl acetate and methanol as a developing solvent in a ratio of 5:1. The solvent of the fraction was distilled off, and the obtained solid was recrystallized with a mixed solvent of dichloromethane and hexane, so that brown powder was obtained (yield of 4%). A synthesis scheme (m-1) is shown below.

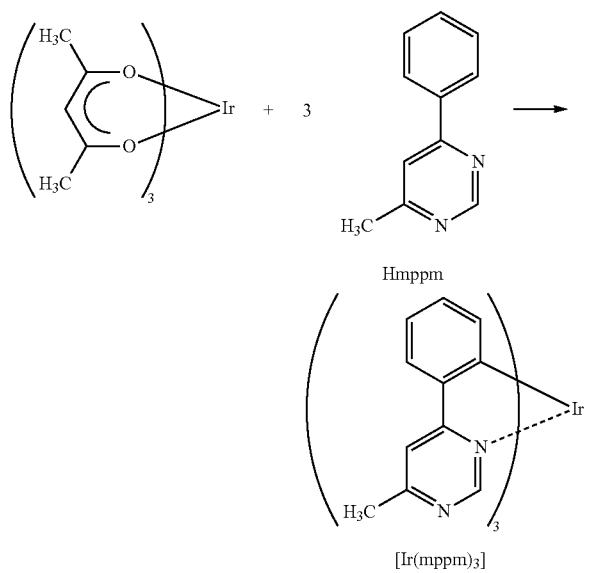

(m-1)

Hmppm

[Ir(mppm)₃]

Figure 57:
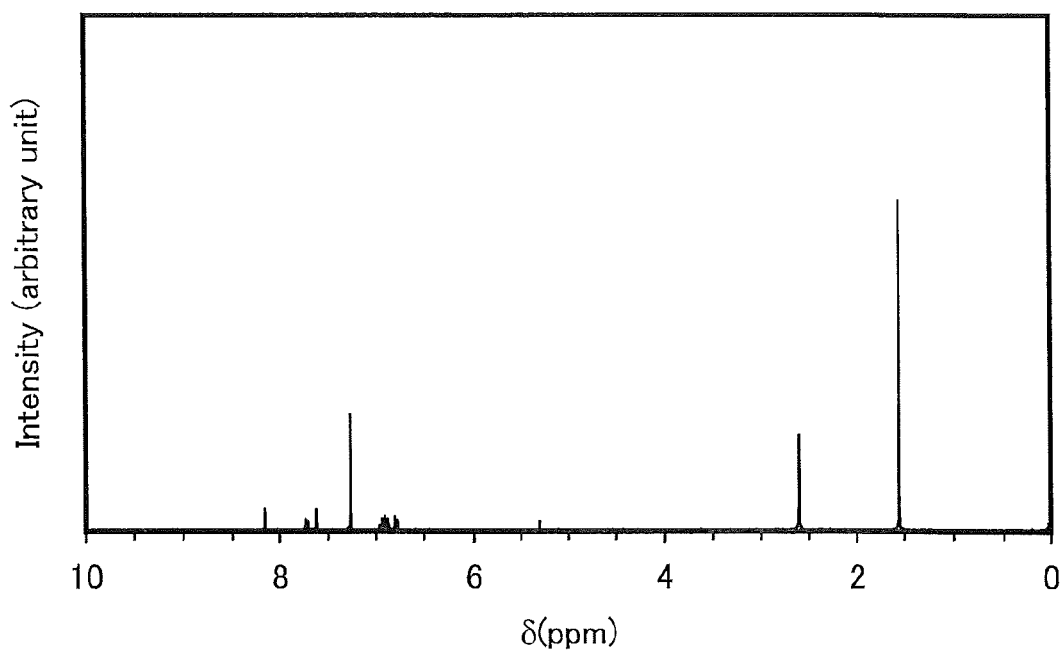
FIG. 57 shows a $^1$H NMR chart of an organometallic complex represented by a structural formula (178).

An analysis result by nuclear magnetic resonance spectrometry (¹H NMR) of the brown powder obtained is described below. The ¹H NMR chart is illustrated in FIG. 57. These results revealed that the organometallic complex [Ir(mppm)₂(acac)], which is one embodiment of the present invention represented by the structural formula (178), was obtained in Synthetic Example 11.

¹H NMR. δ (CDCl₃): 2.69 (s, 9H), 6.79 (d, 3H), 6.86-6.97 (m, 6H), 7.63 (s, 3H), 7.72 (d, 3H), 8.16 (s, 3H).

Figure 58:
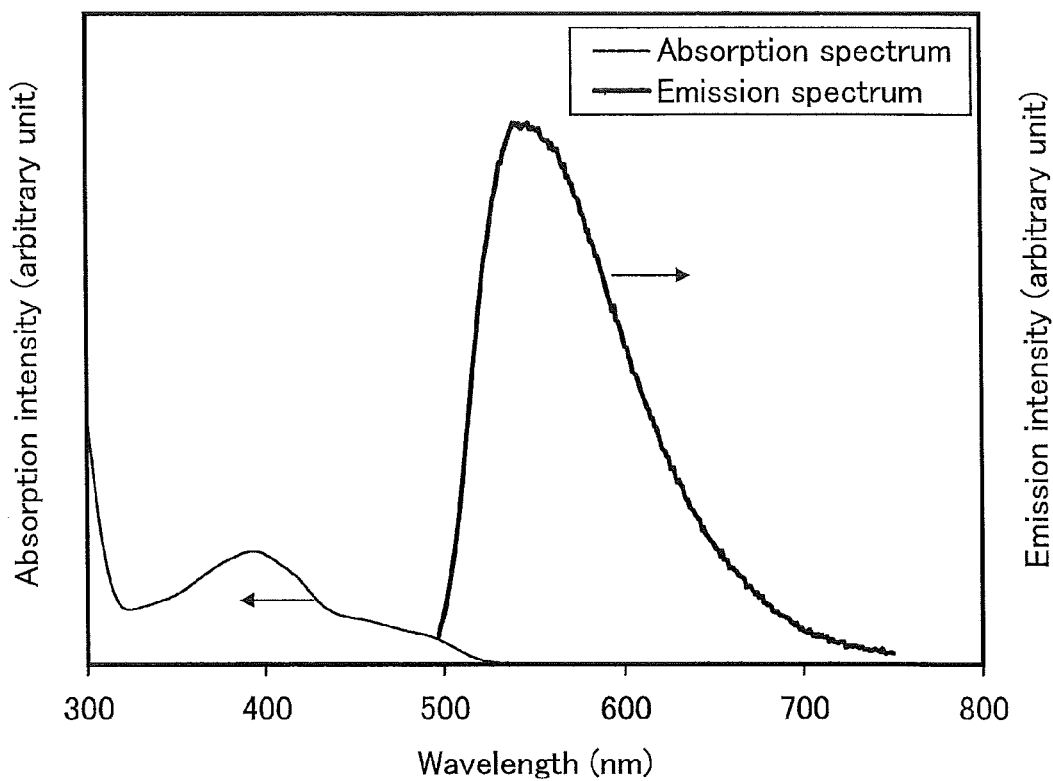
FIG. 58 shows an ultraviolet-visible absorption spectrum and an emission spectrum of the organometallic complex represented by the structural formula (178).

Next, an ultraviolet-visible absorption spectrum (hereinafter, simply referred to as an absorption spectrum) and an emission spectrum of [Ir(mppm)₃] in a dichloromethane solution were measured. The absorption spectrum was measured with the use of an ultraviolet-visible light spectrophotometer (V-550, manufactured by JASCO Corporation) in the state where the dichloromethane solution (0.095 mmol/L) was put in a quartz cell at room temperature. The emission spectrum was measured with the use of a fluorescence spectrophotometer (F5920, manufactured by Hamamatsu Photonics Corporation) in the state where the degassed dichloromethane solution (0.095 mmol/L) was put in a quartz cell at room temperature. FIG. 58 shows results of the measured absorption spectrum and emission spectrum. The horizontal axis represents wavelength (nm), and the vertical axis represents absorption intensity (arbitrary unit) and emission intensity (arbitrary unit). In FIG. 58, two solid lines are shown; a thin line represents the absorption spectrum, and a thick line represents the emission spectrum. Note that the absorption spectrum in FIG. 58 is a result obtained by subtraction of the absorption spectrum of only dichloromethane that was put in a quartz cell from the measured absorption spectrum of the dichloromethane solution (0.095 mmol/L) in a quartz cell.

As shown in FIG. 58, the organometallic complex [Ir(mppm)₃], which is one embodiment of the present invention, has an emission peak at 548 nm, and yellow green light was observed from the dichloromethane solution.

EXAMPLE 19

Synthetic Example 12

In Example 19, a synthetic example of an organometallic complex bis[4,6-bis(3-methylphenyl)pyrimidinato](dipivaloylmethanato)iridium(III) (another name: (2,2,6,6-tetramethyl-3,5-heptanedionato-κ²O,O')bis{4-methyl-2-[6-(3-methylphenyl)-4-pyrimidinyl-κN3])phenyl-κC} iridium(III)) (abbreviation: [Ir(5mdppm)₂(dpm)]), which is one embodiment of the present invention represented by the structural formula (194) in Embodiment 1, is specifically described. A structure of [Ir(5mdppm)₂(dpm)] is shown below.

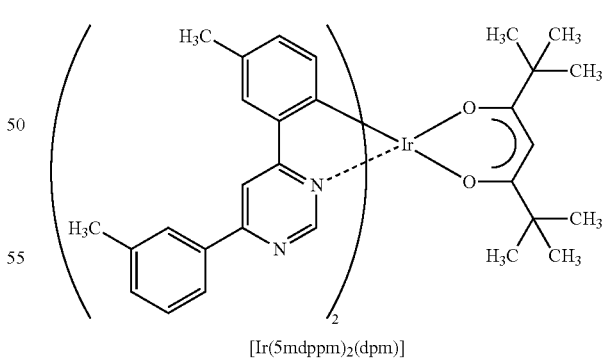

[Ir(5mdppm)₂(dpm)]

Step 1: Synthesis of
4,6-bis(3-methylphenyl)pyrimidine (abbreviation: H5mdppm)

First, into a recovery flask equipped with a reflux pipe were put 4.99 g of 4,6-dichloropyrimidine, 9.23 g of 3-methylphenylboronic acid, 7.18 g of sodium carbonate, 0.29 g of bis(triphenylphosphine)palladium(II)dichloride (abbreviation: Pd(PPh₃)₂Cl₂), 20 mL of water, and 20 mL of acetonitrile, and the air in the flask was replaced with argon. This reaction container was heated by irradiation with microwaves (2.45 GHz, 100 W) for 60 minutes. Here, into the flask were further put 2.31 g of 3-methylphenylboronic acid, 1.82 g of sodium carbonate, 0.070 g of Pd(PPh₃)₂Cl₂, 5 mL of water, and 5 mL of acetonitrile, and the mixture was heated again by irradiation with microwaves (2.45 GHz, 100 W) for 60 minutes. After that, water was added to this solution and an organic layer was extracted with dichloromethane. The obtained organic layer was washed with saturated aqueous solution of sodium hydrogen carbonate, water, and saturated saline, and was dried with magnesium sulfate. The solution after drying was filtered. The solvent of this solution was distilled off, and then the obtained residue was purified by silica gel column chromatography using dichloromethane and ethyl acetate as a developing solvent in a ratio of 20:1, so that a pyrimidine derivative H5mdppm, which was the objective substance, was obtained (pale yellow powder, yield of 15%). Note that the irradiation with microwaves was performed using a microwave synthesis system (Discover, manufactured by CEM Corporation). A synthesis scheme (n-1) of Step 1 is shown below.

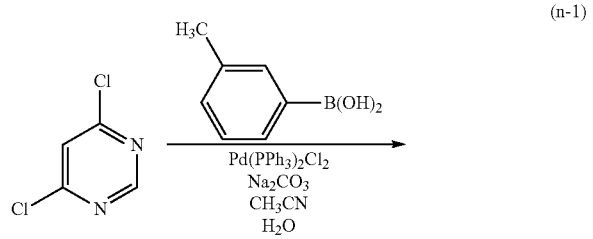

(n-1)

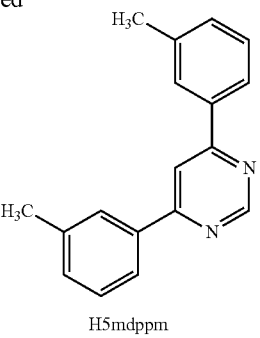

H5mdppm

Step 2: Synthesis of di-μ-chloro-bis{bis[4,6-bis(3-methylphenyl)pyrimidinato]iridium(III)} (abbreviation: [Ir(5mdppm)₂Cl]₂)

Next, into a recovery flask equipped with a reflux pipe were put 15 mL of 2-ethoxyethanol, 5 mL of water, 1.06 g of H5mdppm obtained in Step 1, and 0.60 g of iridium chloride hydrate (IrCl₃·H₂O) (produced by Sigma-Aldrich Corp.), and the air in the flask was replaced with argon. After that, irradiation with microwaves (2.45 GHz, 100 W) was performed for 1 hour to cause a reaction. The solvent was distilled off, and then the obtained residue was suction-filtered and washed with ethanol to give a dinuclear complex [Ir(5mdppm)₂Cl]₂ (reddish brown powder, yield of 86%). A synthesis scheme (n-2) of Step 2 is shown below.

(n-2)

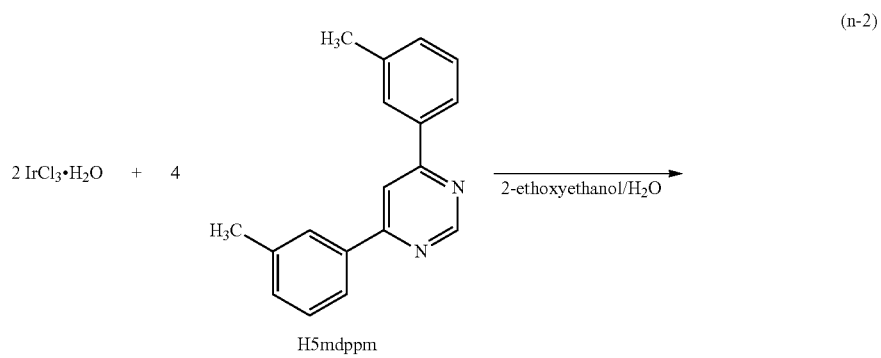

H5mdppm

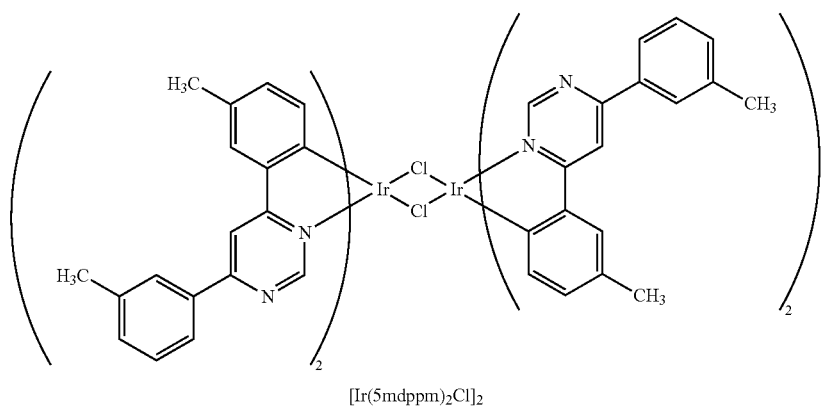

[Ir(5mdppm)₂Cl]₂

Step 3: Synthesis of bis[4,6-bis(3-methylphenyl)pyrimidinato](dipivaloylmethanato)iridium(III) (abbreviation: [Ir(5mdppm)$_2$(dpm)])

Further, into a recovery flask equipped with a reflux pipe were put 30 mL of 2-ethoxyethanol, 1.40 g of the dinuclear complex [Ir(5mdppm)$_2$Cl]$_2$ obtained in Step 2, 0.52 g of dipivaloylmethane, and 1.00 g of sodium carbonate, and the air in the flask was replaced with argon. After that, the mixture was heated by irradiation with microwaves (2.45 GHz, 120 W) for 60 minutes. Here, into the flask were further put 0.17 g of dipivaloylmethane and 10 mL of 2-ethoxyethanol, and the mixture was heated again by irradiation with microwaves (2.45 GHz, 120 W) for 60 minutes. The solvent was distilled off, and the obtained residue was suction-filtered with ethanol. The obtained solid was washed with water and ethanol, dissolved in dichloromethane, and filtered through Celite. After that, recrystallization was carried out with a mixed solvent of dichloromethane and ethanol to give a red solid (yield of 41%, purity of 96%). This solid was purified by silica gel column chromatography using toluene as a developing solvent and recrystallized with a mixed solvent of dichloromethane and ethanol to give vermilion powder (yield of 8%). A synthesis scheme (n-3) of Step 3 is shown below.

Figure 59:
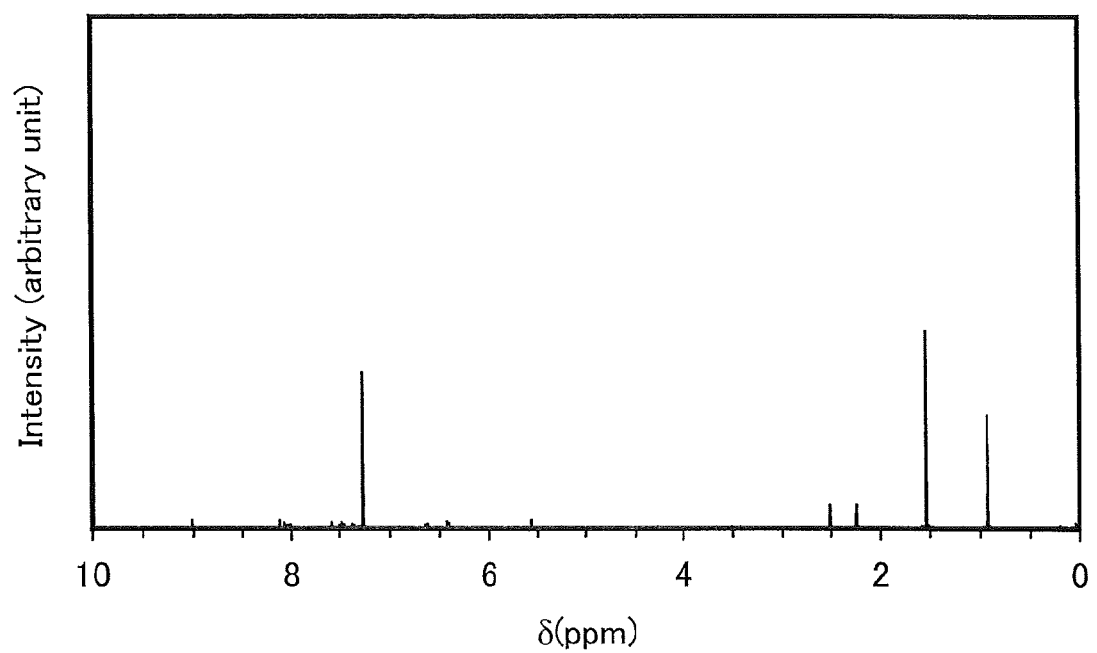
FIG. 59 shows a $^1$H NMR chart of an organometallic complex represented by a structural formula (194).

An analysis result by nuclear magnetic resonance spectrometry ($^1$H NMR) of the vermilion powder obtained is described below. The $^1$H NMR chart is illustrated in FIG. 59. These results revealed that the organometallic complex [Ir(5mdppm)$_2$(dpm)], which is one embodiment of the present invention represented by the structural formula (194), was obtained in Synthetic Example 12.

$^1$H NMR. δ (CDCl$_3$): 0.92 (s, 18H), 2.24 (s, 6H), 2.51 (s, 6H), 5.56 (s, 11-1), 6.41 (d, 2H), 6.62 (d, 2H), 7.36 (d, 2H), 7.48 (t, 2H), 7.58 (s, 2H), 8.01 (d, 2H), 8.08 (s, 2H), 8.12 (s, 2H), 9.02 (s, 2H).

Figure 60:
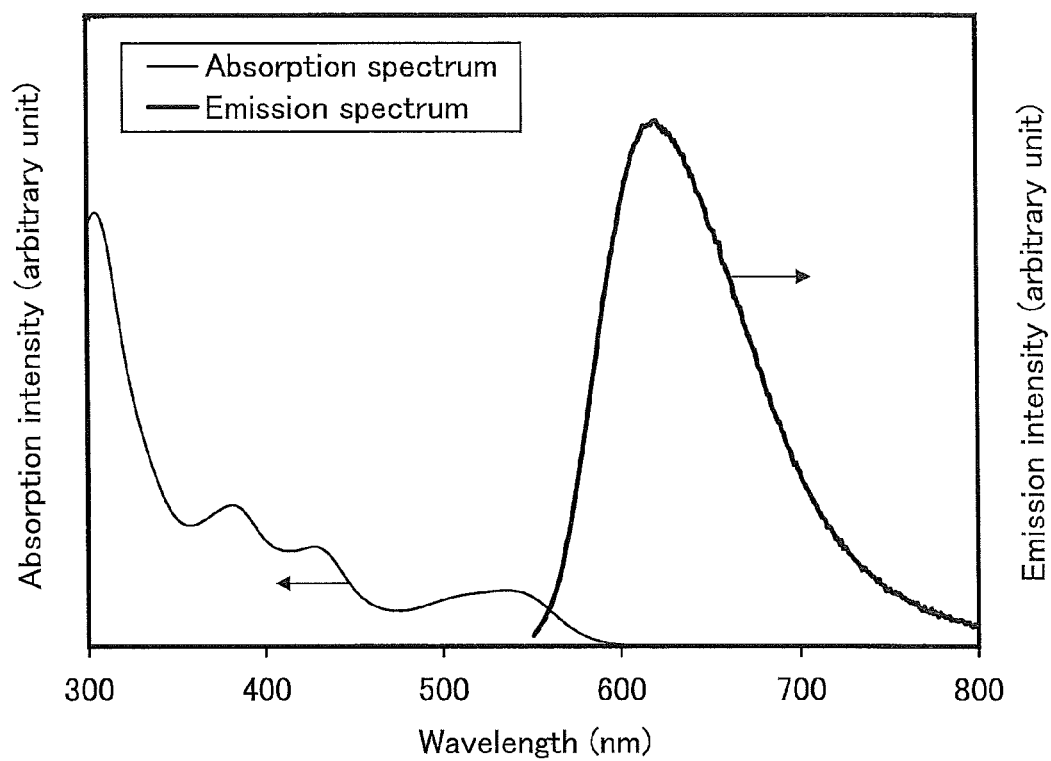
FIG. 60 shows an ultraviolet-visible absorption spectrum and an emission spectrum of the organometallic complex represented by the structural formula (194).

Next, an ultraviolet-visible absorption spectrum (hereinafter, simply referred to as an absorption spectrum) and an emission spectrum of [Ir(5mdppm)$_2$(dpm)] in a dichloromethane solution were measured. The absorption spectrum was measured with the use of an ultraviolet-visible light spectrophotometer (V-550, manufactured by JASCO Corporation) in the state where the dichloromethane solution (0.075 mmol/L) was put in a quartz cell at room temperature. The emission spectrum was measured with the use of a fluorescence spectrophotometer (FS920, manufactured by Hamamatsu Photonics Corporation) in the state where the degassed dichloromethane solution (0.075 mmol/L) was put in a quartz cell at room temperature. FIG. 60 shows results of

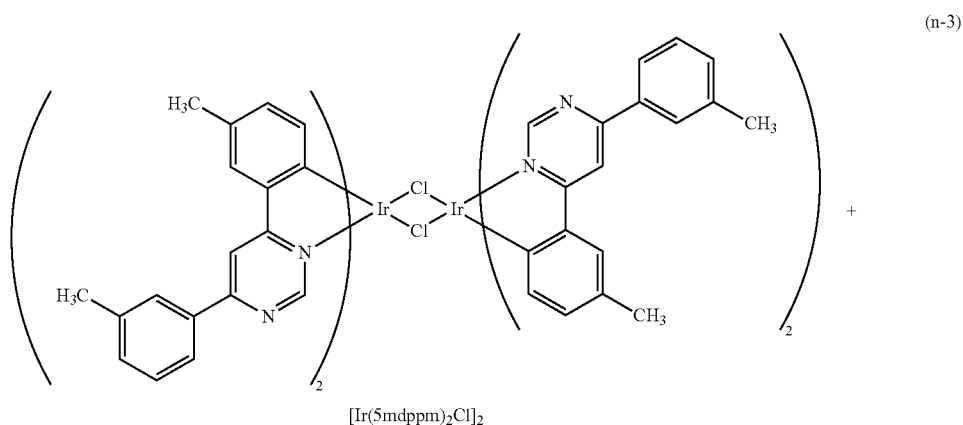

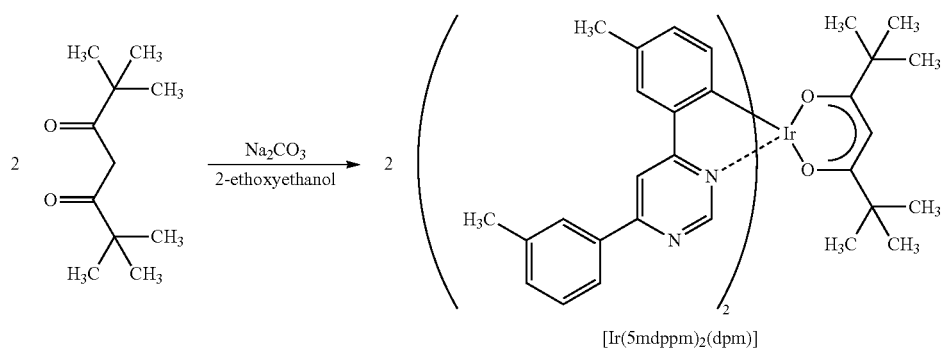

the measured absorption spectrum and emission spectrum. The horizontal axis represents wavelength (nm), and the vertical axis represents absorption intensity (arbitrary unit) and emission intensity (arbitrary unit). In FIG. 60, two solid lines are shown; a thin line represents the absorption spectrum, and a thick line represents the emission spectrum. Note that the absorption spectrum in FIG. 60 is a result obtained by subtraction of the absorption spectrum of only dichloromethane that was put in a quartz cell from the measured absorption spectrum of the dichloromethane solution (0.075 mmol/L) in a quartz cell.

As shown in FIG. 60, the organometallic complex [ft(5mdppm)$_2$(dpm)], which is one embodiment of the present invention, has an emission peak at 620 nm, and reddish orange light was observed from the dichloromethane solution.

EXAMPLE 20

Synthetic Example 13

In Example 20, a synthetic example of an organometallic complex (diisobutyrylmethanato)bis[4,6-bis(3-methylphenyl)pyrimidinato]iridium(III) (another name: (2,6-dimethyl-3,5-heptanedionato-κ$^2$O,O')bis[4-methyl-2-(3-methyl-4-pyrimidinyl-κN3) phenyl-κC]iridium(III)) (abbreviation: [Ir(5mdppm)$_2$(dibm)]), which is one embodiment of the present invention represented by the structural formula (195) in Embodiment 1, is specifically described. A structure of [Ir(5mdppm)$_2$(dibm)] is shown below.

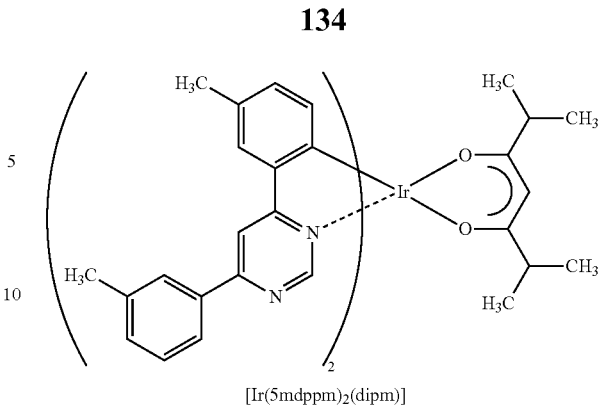

[Ir(5mdppm)$_2$(dipm)]

First, into a recovery flask equipped with a reflux pipe were put 30 mL of 2-ethoxyethanol, 1.27 g of the dinuclear complex [Ir(5mdppm)$_2$Cl]$_2$ obtained in Step 2 in Synthetic Example 12, 0.40 g of diisobutyrylmethane, and 0.90 g of sodium carbonate, and the air in the flask was replaced with argon. After that, the mixture was heated by irradiation with microwaves (2.45 GHz, 120 W) for 60 minutes. Here, into the flask was further put 0.13 g of diisobutyrylmethane, and the mixture was heated again by irradiation with microwaves (2.45 GHz, 200 W) for 60 minutes. The solvent was distilled off, and the obtained residue was suction-filtered with ethanol. The obtained solid was washed with water and ethanol, and purified by flash column chromatography using dichloromethane as a developing solvent. After that, recrystallization was carried out with a mixed solvent of dichloromethane and ethanol to give orange powder (yield of 15%). A synthesis scheme (o-1) is shown below.

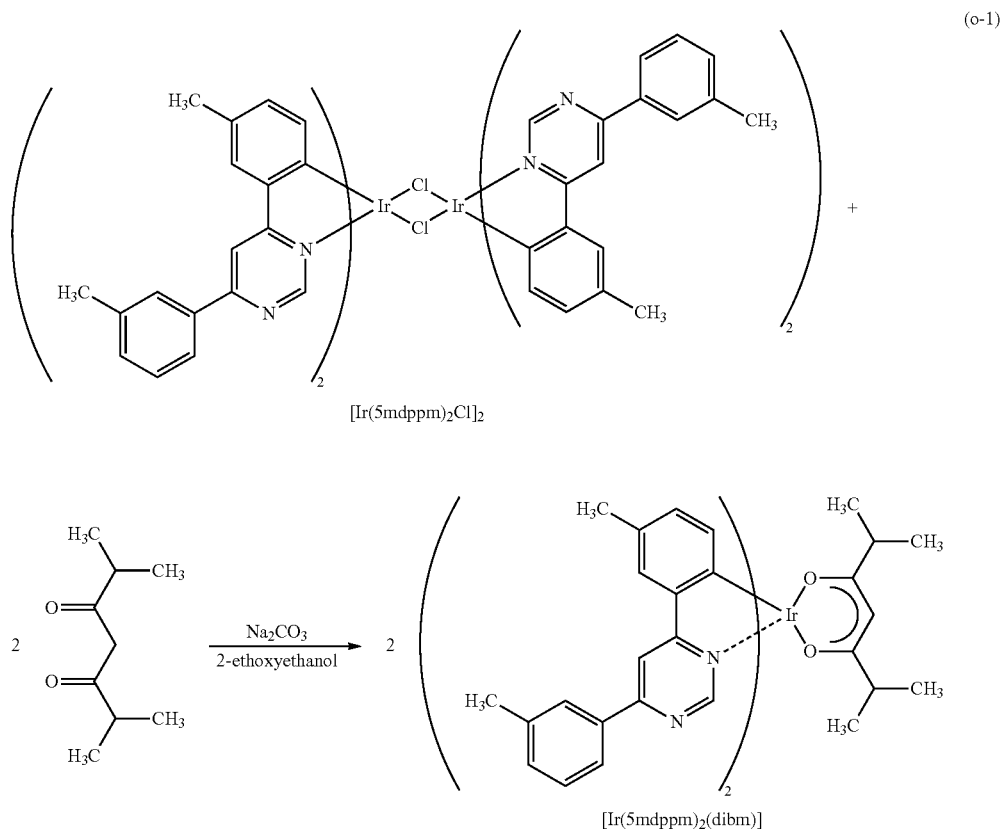

(o-1)

Figure 61:
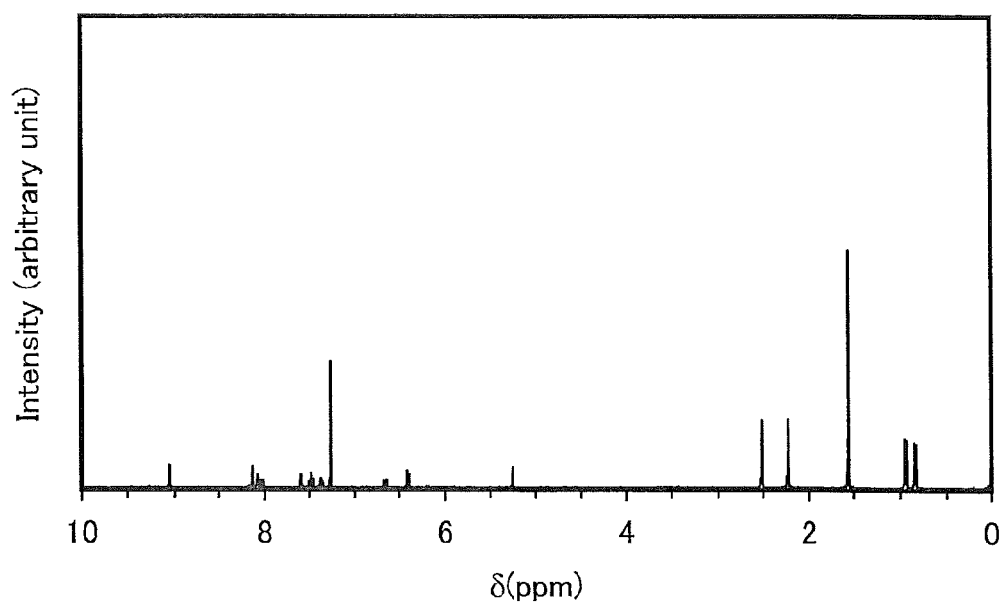
FIG. 61 shows a $^1$H NMR chart of an organometallic complex represented by a structural formula (195).

An analysis result by nuclear magnetic resonance spectrometry ($^1$H NMR) of the orange powder obtained is described below. The $^1$H NMR chart is illustrated in FIG. 61. These results revealed that the organometallic complex [Ir(5mdppm)$_2$(dibm)], which is one embodiment of the present invention represented by the structural formula (195), was obtained in Synthetic Example 13.

$^1$H NMR. δ (CDCl$_3$): 0.84 (d, 6H), 0.94 (d, 6H), 2.19-2.25 (m, 8H), 2.51 (d, 6H), 5.25 (s, 1H), 6.40 (d, 2H), 6.65 (d, 2H), 7.36 (d, 2H), 7.48 (t, 2H), 7.60 (s, 2H), 8.03 (d, 2H), 8.08 (s, 2H), 8.13 (s, 2H), 9.05 (s, 2H).

Figure 62:
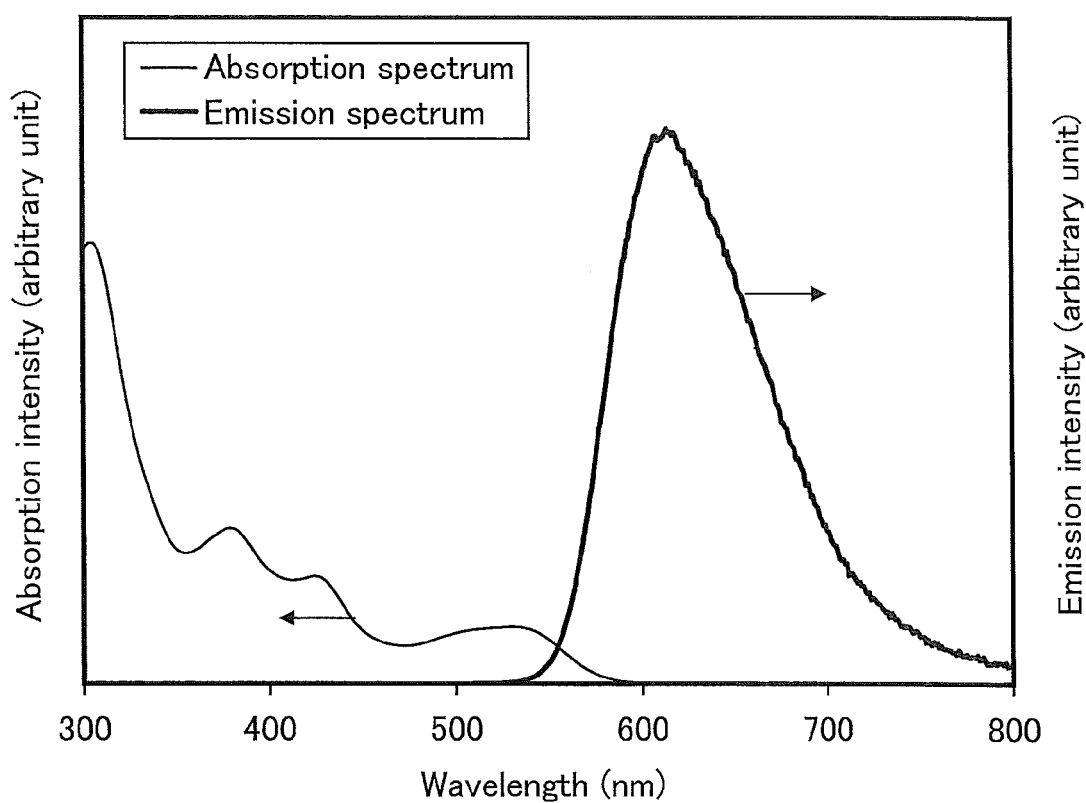
FIG. 62 shows an ultraviolet-visible absorption spectrum and an emission spectrum of the organometallic complex represented by the structural formula (195).

Next, an ultraviolet-visible absorption spectrum (hereinafter, simply referred to as an absorption spectrum) and an emission spectrum of [Ir(5mdppm)$_2$(dibm)] in a dichloromethane solution were measured. The absorption spectrum was measured with the use of an ultraviolet-visible light spectrophotometer (V-550, manufactured by JASCO Corporation) in the state where the dichloromethane solution (0.081 mmol/L) was put in a quartz cell at room temperature. The emission spectrum was measured with the use of a fluorescence spectrophotometer (FS920, manufactured by Hamamatsu Photonics Corporation) in the state where the degassed dichloromethane solution (6.081 mmol/L) was put in a quartz cell at room temperature. FIG. 62 shows results of the measured absorption spectrum and emission spectrum. The horizontal axis represents wavelength (nm), and the vertical axis represents absorption intensity (arbitrary unit) and emission intensity (arbitrary unit). In FIG. 62, two solid lines are shown; a thin line represents the absorption spectrum, and a thick line represents the emission spectrum. Note that the absorption spectrum in FIG. 62 is a result obtained by subtraction of the absorption spectrum of only dichloromethane that was put in a quartz cell from the measured absorption spectrum of the dichloromethane solution (0.081 mmol/L) in a quartz cell.

As shown in FIG. 62, the organometallic complex [Ir(5mdppm)$_2$(dibm)], which is one embodiment of the present invention, has an emission peak at 614 nm, and reddish orange light was observed from the dichloromethane solution.

EXAMPLE 21

Synthetic Example 14

In Example 21, a synthetic example of an organometallic complex bis[4,6-di(naphthalen-1-yl)pyrimidinato](dipivaloylmethanato)iridium(III) (another name: (2,2,6,6-tetramethyl-3,5-heptanedionato-κ$^2$O,O')bis[1-(6-naphthalen-1-yl-4-pyrimidinyl-κN3)-2-naphthalenyl-κC]iridium(III)) (abbreviation: [Ir(d1npm)$_2$(dpm)]), which is one embodiment of the present invention represented by the structural formula (196) in Embodiment 1, is specifically described. A structure of [Ir(d1npm)$_2$(dpm)] is shown below.

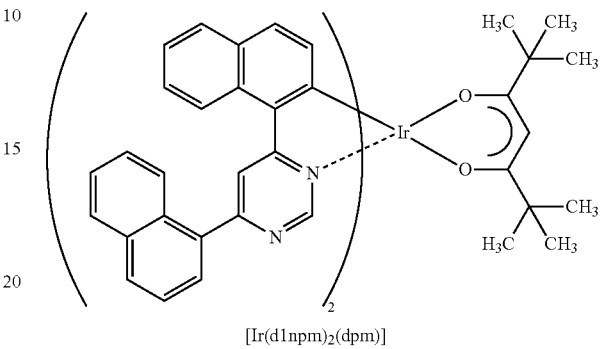

[Ir(d1npm)$_2$(dpm)]

First, into a recovery flask equipped with a reflux pipe were put 30 mL of 2-ethoxyethanol, 1.20 g of the dinuclear complex [Ir(d1npm)$_2$Cl]$_2$ obtained in Step 2 in Synthetic Example 7, 0.37 g of dipivaloylmethane, and 0.71 g of sodium carbonate, and the air in the flask was replaced with argon. After that, the mixture was heated by irradiation with microwaves (2.45 GHz, 120 W) for 60 minutes. Here, into the flask was further put 0.37 g of dipivaloylmethane, and the mixture was heated again by irradiation with microwaves (2.45 GHz, 120 W) for 60 minutes. The solvent was distilled off, and the obtained residue was suction-filtered with ethanol. The obtained solid was washed with water and ethanol, and purified by flash column chromatography using hexane and ethyl acetate as a developing solvent in a ratio of 5:1. After that, recrystallization was carried out with a mixed solvent of dichloromethane and ethanol to give dark red powder (yield of 24%). A synthesis scheme (p-1) is shown below.

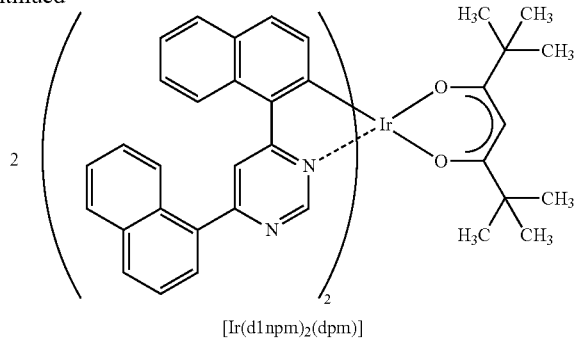

[Ir(d1npm)₂(dpm)]

Figure 63:
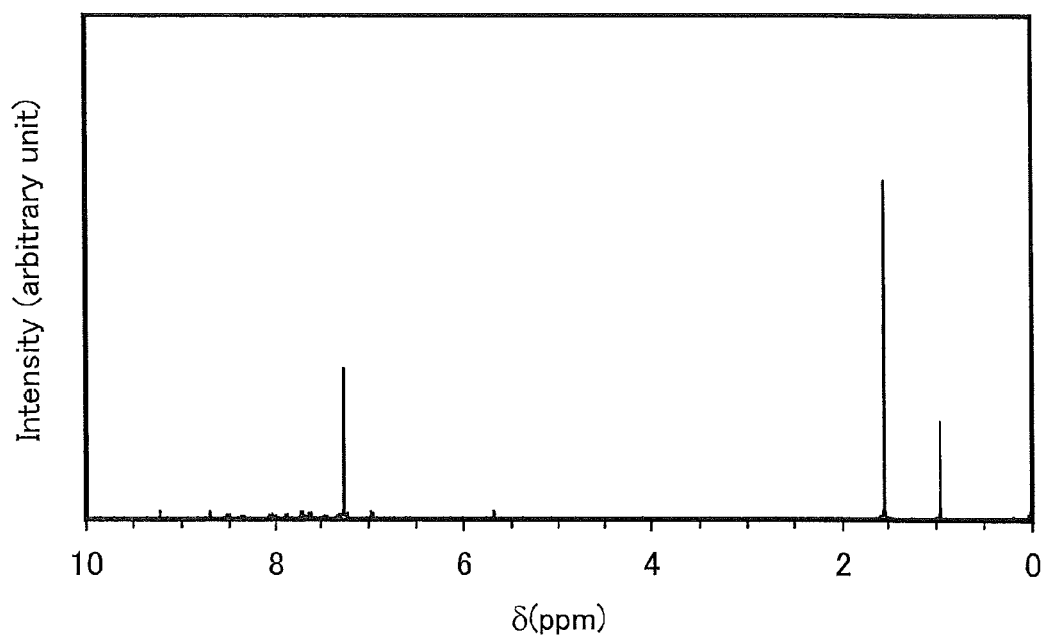
FIG. 63 shows a $^1$H NMR chart of an organometallic complex represented by a structural formula (196).

An analysis result by nuclear magnetic resonance spectrometry (¹H NMR) of the dark red powder obtained is described below. The ¹H NMR chart is illustrated in FIG. 63. These results revealed that the organometallic complex [Ir(d1npm)₂(dpm)], which is one embodiment of the present invention represented by the structural formula (196), was obtained in Synthetic Example 14.

¹H NMR. δ (CDCl₃): 0.95 (s, 18H), 5.68 (s, 1H), 6.96 (d, 2H), 7.23 (d, 2H), 7.35 (d, 2H), 7.45 (t, 2H), 7.60-7.63 (m, 4H), 7.67-7.72 (m, 4H), 7.88 (d, 2H), 8.00-8.07 (m, 4H), 8.33-8.37 (m, 2H), 8.51 (s, 2H), 8.70 (s, 2H), 9.22 (s, 2H).

Figure 64:
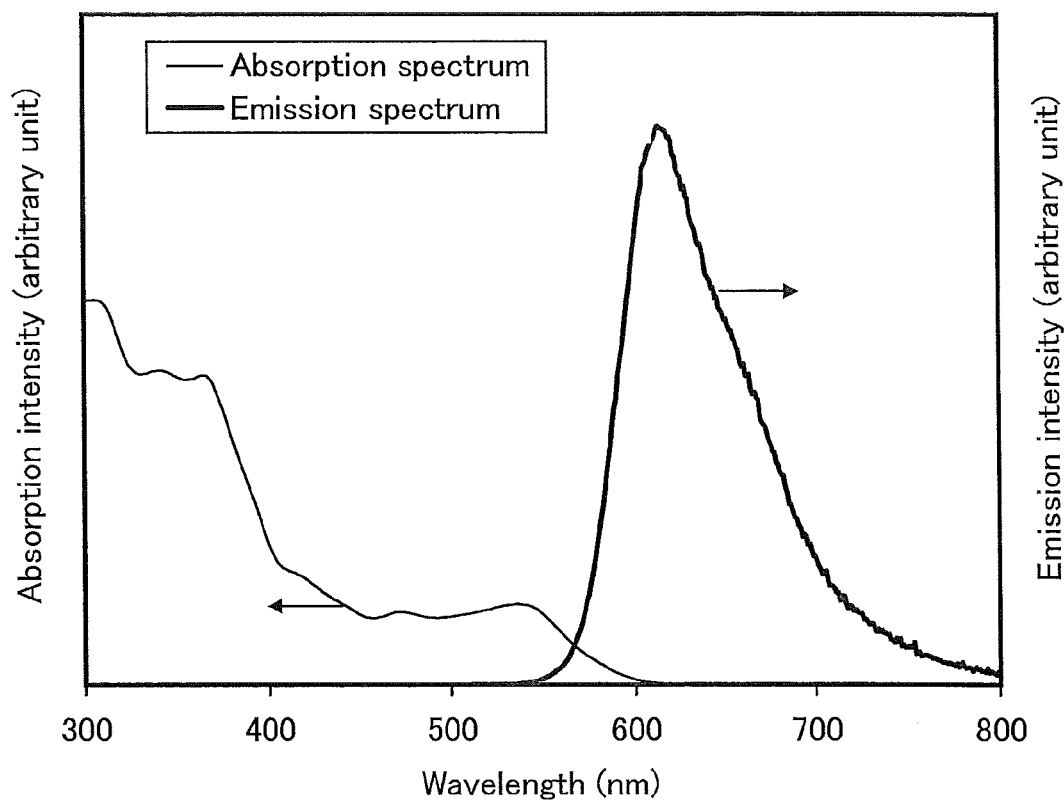
FIG. 64 shows an ultraviolet-visible absorption spectrum and an emission spectrum of the organometallic complex represented by the structural formula (196).

Next, an ultraviolet-visible absorption spectrum (hereinafter, simply referred to as an absorption spectrum) and an emission spectrum of [Ir(d1npm)₂(dpm)] in a dichloromethane solution were measured. The absorption spectrum was measured with the use of an ultraviolet-visible light spectrophotometer (V-550, manufactured by JASCO Corporation) in the state where the dichloromethane solution (0.064 mmol/L) was put in a quartz cell at room temperature. The emission spectrum was measured with the use of a fluorescence spectrophotometer (FS920, manufactured by Hamamatsu Photonics Corporation) in the state where the degassed dichloromethane solution (0.064 mmol/L) was put in a quartz cell at room temperature. FIG. 64 shows results of the measured absorption spectrum and emission spectrum. The horizontal axis represents wavelength (nm), and the vertical axis represents absorption intensity (arbitrary unit) and emission intensity (arbitrary unit). In FIG. 64, two solid lines are shown; a thin line represents the absorption spectrum, and a thick line represents the emission spectrum. Note that the absorption spectrum in FIG. 64 is a result obtained by subtraction of the absorption spectrum of only dichloromethane that was put in a quartz cell from the measured absorption spectrum of the dichloromethane solution (0.064 mmol/L) in a quartz cell.

As shown in FIG. 64, the organometallic complex [Ir(d1npm)₂(dpm)], which is one embodiment of the present invention, has an emission peak at 613 nm, and reddish orange light was observed from the dichloromethane solution.

EXAMPLE 22

Synthetic Example 15

In Example 22, a synthetic example of an organometallic complex (acetylacetonato)bis[5-methyl-6-(2-methylphenyl)-4-phenylpyrimidinato]iridium(III) (another name: bis{2-[5-methyl-6-(2-methylphenyl)-4-pyrimidinyl-κN3]phenyl-κC} (2,4-pentanedionat o-κ²O,O') iridium(III)) (abbreviation: [Ir(mpmppm)₂(acac)]), which is one embodiment of the present invention represented by the structural formula (199) in Embodiment 1, is specifically described. A structure of [Ir(mpmppm)₂(acac)] is shown below.

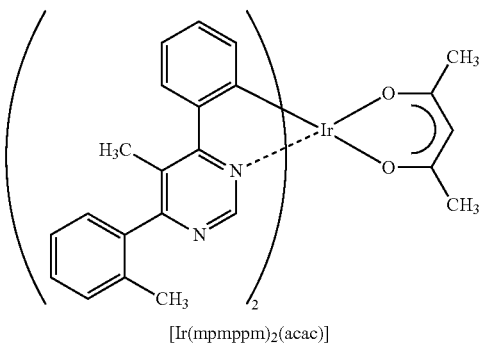

[Ir(mpmppm)₂(acac)]

Step 1: Synthesis of
4-chloro-5-methyl-6-(2-methylphenyl)pyrimidine

First, into a recovery flask equipped with a reflux pipe were put 5.0 g of 4,6-dichloro-5-methylpyrimidine, 4.6 g of 2-methylphenylboronic acid, 20 g of cesium carbonate, 2.5 mL of 15% toluene solution of tricyclohexylphosphine (abbreviation: Cy₃P), 0.47 g of tris(dibenzylideneacetone)dipalladium (0) (abbreviation: Pd₂(dba)₃), and 40 mL of dioxane, and the air in the flask was replaced with argon. This reaction container was heated by irradiation with microwaves (2.45 GHz, 150W) for 2 hours. After that, water was added to this solution and an organic layer was extracted with dichloromethane. The obtained organic layer was washed with saturated aqueous solution of sodium hydrogen carbonate, water, and saturated saline, and was dried with magnesium sulfate. The solution after drying was filtered. The solvent of this solution was distilled off, and then the obtained residue was purified by silica gel column chromatography using dichloromethane as a developing solvent and the obtained fraction was concentrated, so that 4-chloro-5-methyl-6-(2-methylphenyl)pyrimidine was obtained (a white solid, yield of 58%). Note that the irradiation with microwaves was performed using a microwave synthesis system (Discover, manufactured by CEM Corporation). A synthesis scheme (q-1) of Step 1 is shown below.

(q-1)

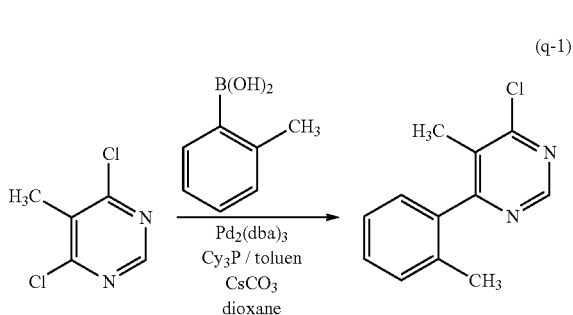

Step 2: Synthesis of 5-methyl-6-(2-methylphenyl)-4-phenylpyrimidine

Next, into a recovery flask equipped with a reflux pipe were put 1.9 g of 4-chloro-5-methyl-6-(2-methylphenyl)pyrimidine obtained in Step 1, 1.7 g of phenylboronic acid, 1.1 g of sodium carbonate, 0.105 g of bis(triphenylphosphine)palladium(II)dichloride (abbreviation: $Pd(PPh_3)_2Cl_2$), 20 mL of water, and 20 mL of acetonitrile, and the air in the flask was replaced with argon. This reaction container was heated by irradiation with microwaves (2.45 GHz, 100 W) for 1 hour. After that, water was added to this solution and an organic layer was extracted with dichloromethane. The obtained organic layer was washed with saturated aqueous solution of sodium hydrogen carbonate, water, and saturated saline, and was dried with magnesium sulfate. The solution after drying was filtered. The solvent of this solution was distilled off, and then the obtained residue was purified by silica gel column chromatography using hexane and ethyl acetate as a developing solvent in a ratio of 9:1 and the obtained fraction was concentrated, so that 5-methyl-6-(2-methylphenyl)-4-phenylpyrimidine was obtained (a white solid, yield of 87%). A synthesis scheme (q-2) of Step 2 is shown below.

(q-2)

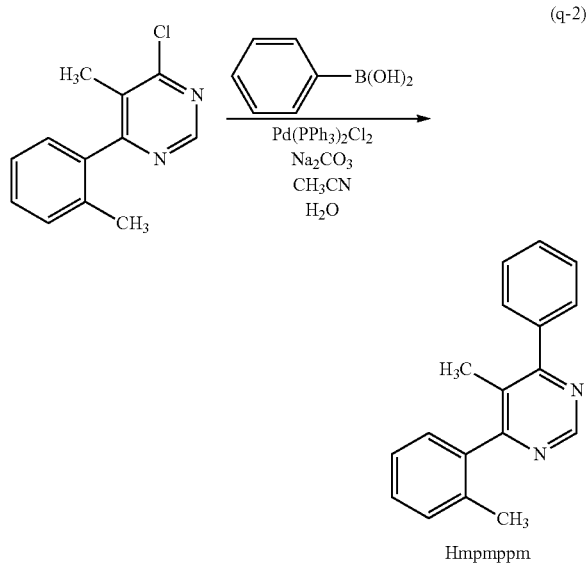

Step 3: Synthesis of di-µ-chloro-bis{bis[5-methyl-6-(2-methylphenyl)-4-phenylpyrimidinato]iridium (III)} (abbreviation: [Ir(mpmppm)$_2$Cl]$_2$)

Next, into a recovery flask equipped with a reflux pipe were put 30 mL of 2-ethoxyethanol, 10 mL of water, 2.0 g of 5-methyl-6-(2-methylphenyl)-4-phenylpyrimidine obtained in Step 2, and 0.955 g of iridium chloride hydrate ($IrCl_3 \cdot H_2O$) (produced by Sigma-Aldrich Corp.), and the air in the flask was replaced with argon. After that, irradiation with microwaves (2.45 GHz, 100 W) was performed for 1 hour to cause a reaction. The solvent was distilled off, and then the obtained residue was suction-filtered and washed with ethanol to give a dinuclear complex [Ir(mpmppm)$_2$Cl]$_2$ (a brown solid, yield of 75%). A synthesis scheme (q-3) of Step 3 is shown below.

(q-3)

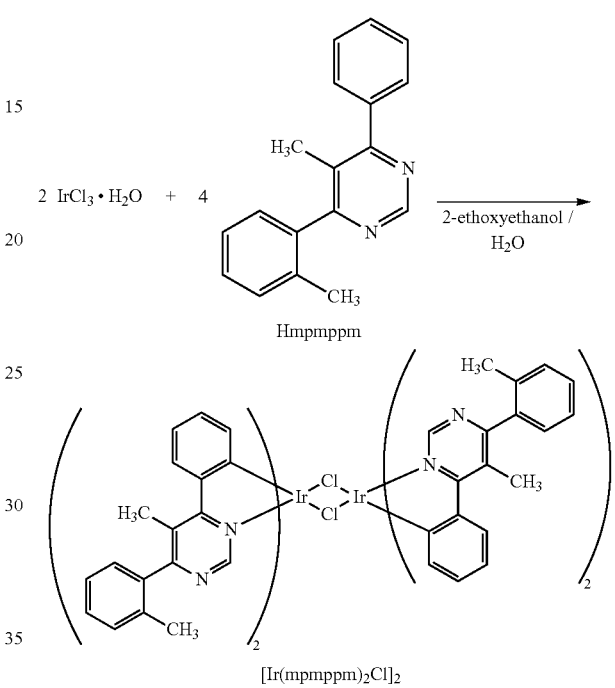

Step 4: Synthesis of (acetylacetonato)bis[5-methyl-6-(2-methylphenyl)-4-phenylpyrimidinato]iridium (III) (abbreviation: [Ir(mpmppm)$_2$(acac)])

Next, into a recovery flask equipped with a reflux pipe were put 20 mL of 2-ethoxyethanol, 1.8 g of the dinuclear complex [Ir(mpmppm)$_2$Cl]$_2$ obtained in Step 3, 0.360 g of acetylacetone, and 1.3 g of sodium carbonate, and the air in the flask was replaced with argon. After that, the mixture was heated by irradiation with microwaves (2.45 GHz, 120 W) for 1 hour. After reaction, water was added to the obtained reacted mixture, and an aqueous layer was extracted with dichloromethane. The obtained solution of the extract was washed with saturated saline, and anhydrate magnesium sulfate was added to the organic layer for drying. The obtained mixture was gravity-filtered, and a filtrate was obtained. This filtrate was concentrated to give a brown solid. After concentration, about 500 mL of dichloromethane was added to this mixture, and this mixture was filtered through a filter aid in which Florisil (produced by Wako Pure Chemical Industries, Ltd., Catalog No. 540-00135), alumina, and Celite were stacked in this order. The obtained filtrate was concentrated to give a red solid. This solid was recrystallized from a mixed solvent of ethyl acetate and hexane, so that orange powder was obtained (yield of 57%). A synthesis scheme (q-4) of Step 4 is shown below.

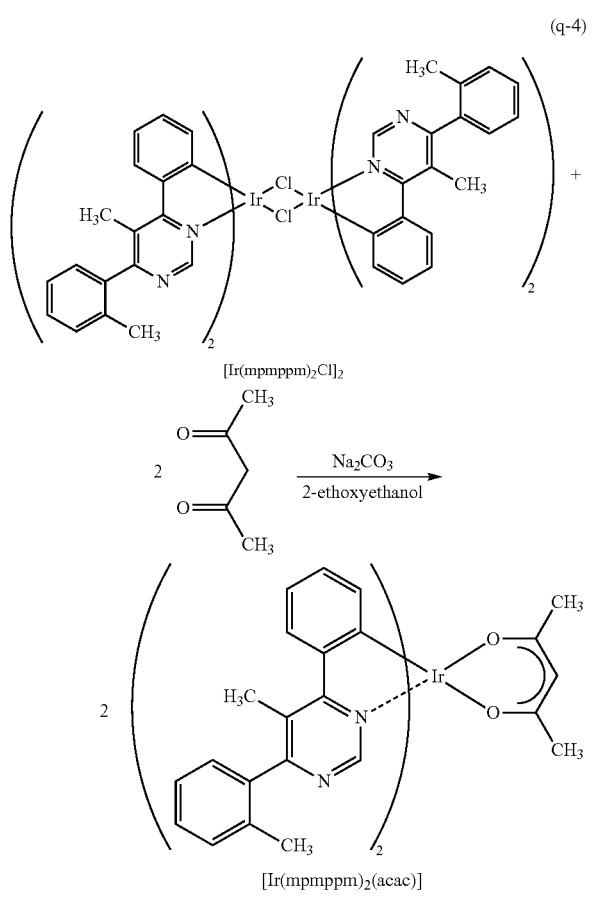

[Ir(mpmppm)₂Cl]₂

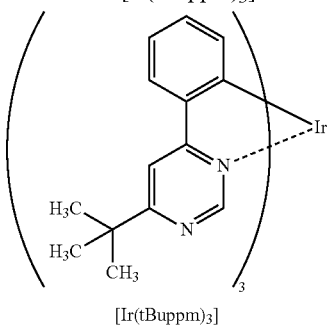

[Ir(mpmppm)₂(acac)]

Figure 65:
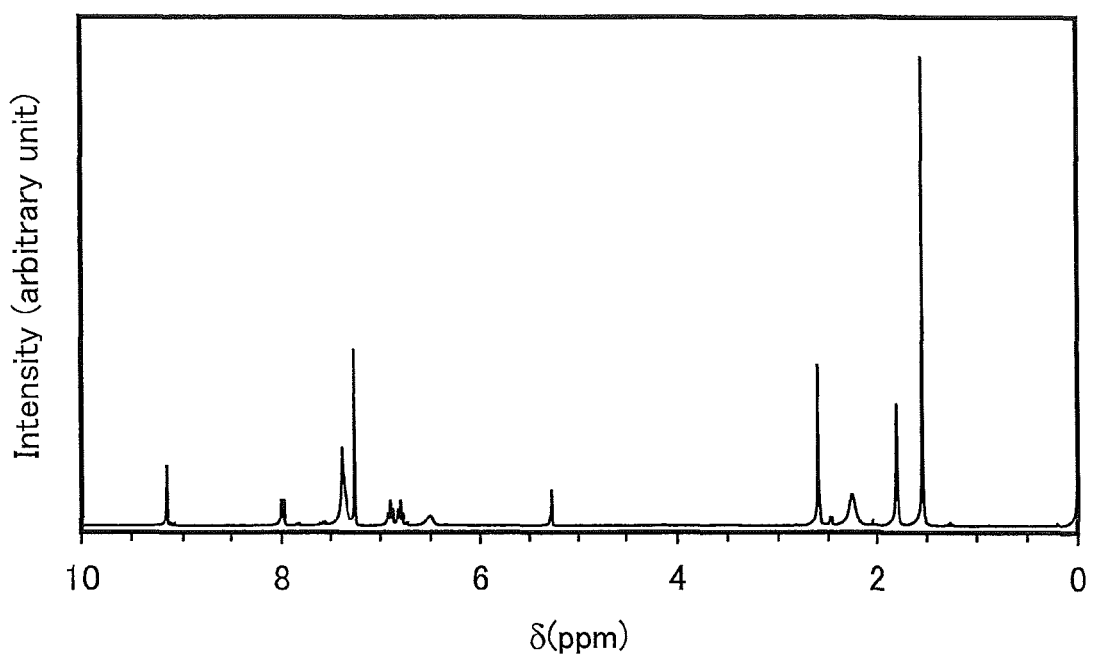
FIG. 65 shows a $^1$H NMR chart of an organometallic complex represented by a structural formula (199).

An analysis result by nuclear magnetic resonance spectrometry (¹H NMR) of the orange powder obtained is described below. The ¹H NMR chart is illustrated in FIG. 65. These results revealed that the organometallic complex [Ir(mpmppm)₂(acac)], which is one embodiment of the present invention represented by the structural formula (199), was obtained in Synthetic Example 15.

¹H NMR. δ (CDCl₃): 1.80 (s, 6H), 2.26 (br, 6H), 2.60 (s, 6H), 5.28 (s, 1H), 6.51 (br, 2H), 6.80 (t, 2H), 6.90 (t, 2H), 7.39 (m, 8H), 8.00 (d, 2H), 9.12 (s, 2H).

Figure 66:
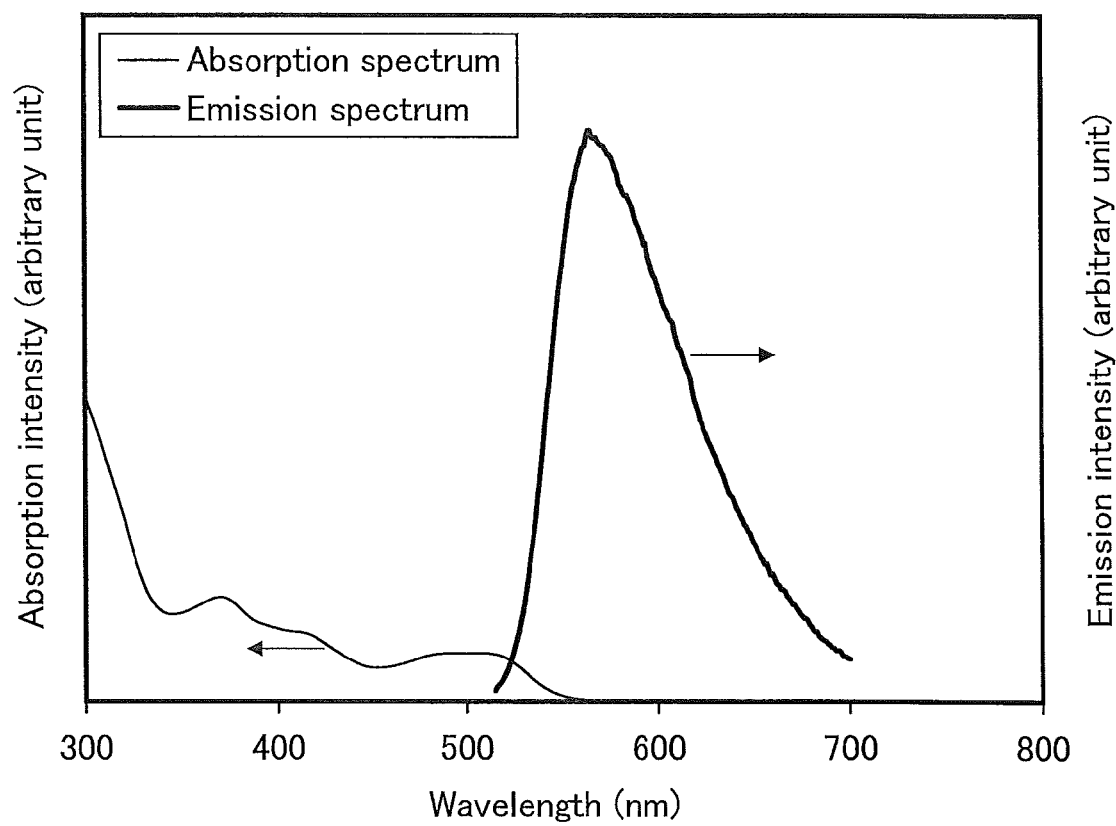
FIG. 66 shows an ultraviolet-visible absorption spectrum and an emission spectrum of the organometallic complex represented by the structural formula (199).

Next, an ultraviolet-visible absorption spectrum (hereinafter, simply referred to as an absorption spectrum) and an emission spectrum of [Ir(mpmppm)₂(acac)] in a dichloromethane solution were measured. The absorption spectrum was measured with the use of an ultraviolet-visible light spectrophotometer (V-550, manufactured by JASCO Corporation) in the state where the dichloromethane solution (0.080 mmol/L) was put in a quartz cell at room temperature. The emission spectrum was measured with the use of a fluorescence spectrophotometer (FS920, manufactured by Hamamatsu Photonics Corporation) in the state where the degassed dichloromethane solution (0.080 mmol/L) was put in a quartz cell at room temperature. FIG. 66 shows results of the measured absorption spectrum and emission spectrum. The horizontal axis represents wavelength (nm), and the vertical axis represents absorption intensity (arbitrary unit) and emission intensity (arbitrary unit). In FIG. 66, two solid lines are shown; a thin line represents the absorption spectrum, and a thick line represents the emission spectrum. Note that the absorption spectrum in FIG. 66 is a result obtained by subtraction of the absorption spectrum of only dichloromethane that was put in a quartz cell from the measured absorption spectrum of the dichloromethane solution (0.080 mmol/L) in a quartz cell.

As shown in FIG. 66, the organometallic complex [Ir(mpmppm)₂(acac)], which is one embodiment of the present invention, has an emission peak at 564 nm, and yellow light was observed from the dichloromethane solution.

EXAMPLE 23

Synthetic Example 16

In Example 23, a synthetic example of an organometallic complex tris(4-t-butyl-6-phenylpyrimidinato)iridium(III) (another name: tris[2-(6-tert-butyl-4-pyrimidinyl-κN3)phenyl-κC]iridium(III)) (abbreviation: [Ir(tBuppm)₃]), which is one embodiment of the present invention represented by the structural formula (200) in Embodiment 1, is specifically described. A structure of [Ir(tBuppm)₃] is shown below.

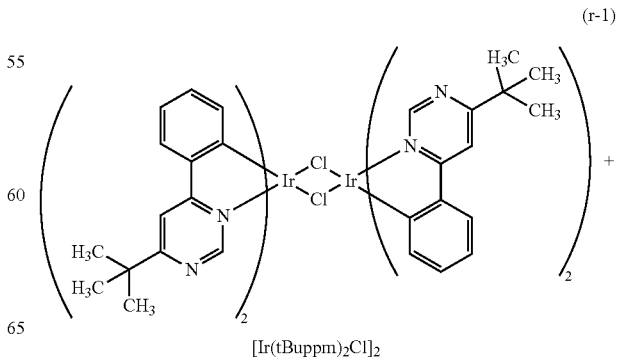

[Ir(tBuppm)₃]

First, into a 100-mL three-neck flask were put 10 g of phenol, 0.97 g of the dinuclear complex [Ir(tBuppm)₂Cl]₂ obtained in Step 2 in Synthetic Example 4, 0.62 g of HtBuppm obtained in Step 1 in Synthetic Example 4, and 1.03 g of potassium carbonate, and the air in the flask was replaced with argon. After that, the mixture was heated at 185° C. to be reacted. The obtained residue was irradiated with ultrasonic waves in methanol, suction-filtered, and washed with ethyl acetate. The obtained solid was dissolved in dichloromethane, and the mixture was filtered through a filter aid in which Celite, alumina, and Celite were stacked in this order. The solvent of this solution was distilled off, so that yellow powder was obtained (yield of 17%). A synthesis scheme (r-1) is shown below.

[Ir(tBuppm)₂Cl]₂

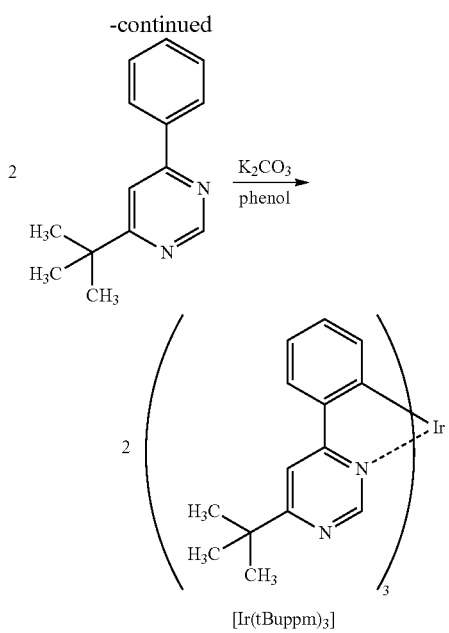

[Ir(tBuppm)₃]

Figure 67:
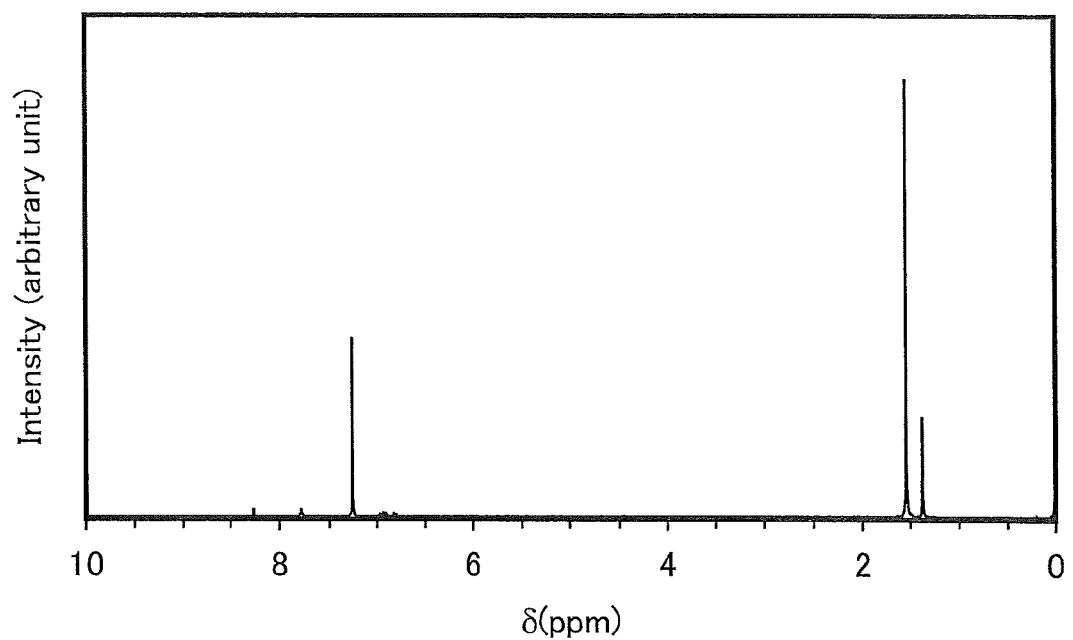
FIG. 67 shows a $^1$H NMR chart of an organometallic complex represented by a structural formula (200).

An analysis result by nuclear magnetic resonance spectrometry (¹H NMR) of the yellow powder obtained is described below. The ¹H NMR chart is illustrated in FIG. 67. These results revealed that the organometallic complex [Ir(tBuppm)₃], which is one embodiment of the present invention represented by the structural formula (200), was obtained in Synthetic Example 16.

¹H NMR. δ (CDCl₃): 1.37 (s, 27H), 6.81 (d, 3H), 6.91-6.97 (m, 6H), 7.77-7.78 (m, 6H), 8.26 (s, 3H).

Figure 68:
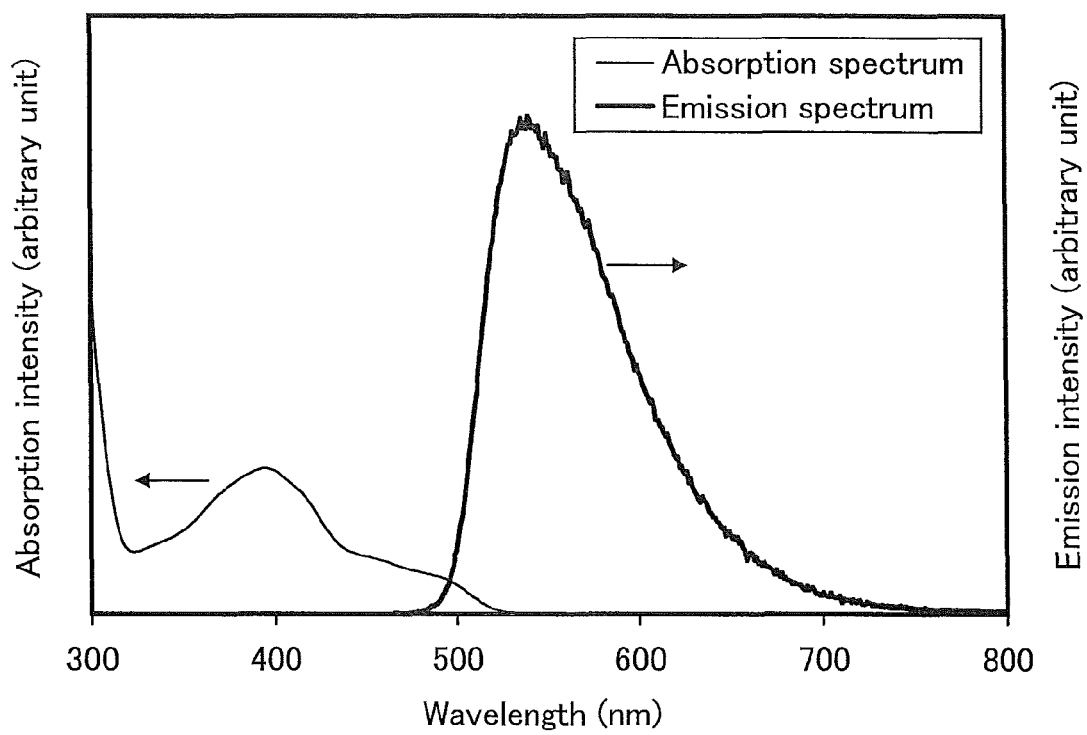
FIG. 68 shows an ultraviolet-visible absorption spectrum and an emission spectrum of the organometallic complex represented by the structural formula (200).

Next, an ultraviolet-visible absorption spectrum (hereinafter, simply referred to as an absorption spectrum) and an emission spectrum of [Ir(tBuppm)₃] in a dichloromethane solution were measured. The absorption spectrum was measured with the use of an ultraviolet-visible light spectrophotometer (V-550, manufactured by JASCO Corporation) in the state where the dichloromethane solution (0.036 mmol/L) was put in a quartz cell at room temperature. The emission spectrum was measured with the use of a fluorescence spectrophotometer (FS920, manufactured by Hamamatsu Photonics Corporation) in the state where the degassed dichloromethane solution (0.036 mmol/L) was put in a quartz cell at room temperature. FIG. 68 shows results of the measured absorption spectrum and emission spectrum. The horizontal axis represents wavelength (nm), and the vertical axis represents absorption intensity (arbitrary unit) and emission intensity (arbitrary unit). In FIG. 68, two solid lines are shown; a thin line represents the absorption spectrum, and a thick line represents the emission spectrum. Note that the absorption spectrum in FIG. 68 is a result obtained by subtraction of the absorption spectrum of only dichloromethane that was put in a quartz cell from the measured absorption spectrum of the dichloromethane solution (0.036 mmol/L) in a quartz cell.

As shown in FIG. 68, the organometallic complex [Ir(tBuppm)₃], which is one embodiment of the present invention, has an emission peak at 540 nm, and yellow green light was observed from the dichloromethane solution.

EXAMPLE 24

Synthetic Example 17

In Example 24, a synthetic example of an organometallic complex bis[4-(2,5-dimethylphenyl)-6-(naphthalen-2-yl)pyrimidinato](dipivaloylmethanato)iridium(III) (another name: (2,2,6,6-tetramethyl-3,5-heptanedionato-κ²O,O') bis{3-[6-(2,5-dimethylphenyl)-4-pyrimidinyl-κN3]-2-naphthalenyl-κC}iridium(III)) (abbreviation: [Ir(dmp2npm)₂(dpm)]), which is one embodiment of the present invention represented by the structural formula (201) in Embodiment 1, is specifically described. A structure of [Ir(dmp2npm)₂(dpm)] is shown below.

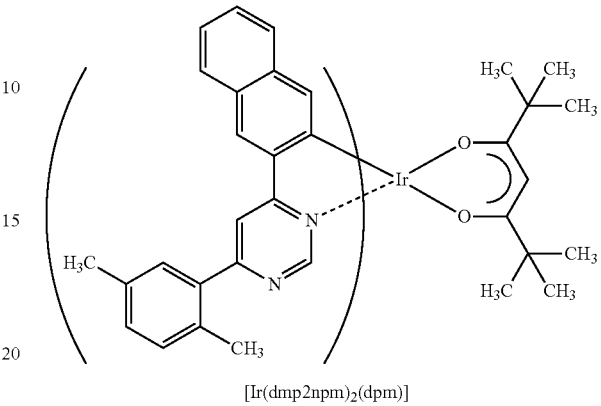

[Ir(dmp2npm)₂(dpm)]

Step 1: Synthesis of 4-chloro-6-(naphthalen-2-yl)pyrimidine

First, into a recovery flask equipped with a reflux pipe were put 5.0 g of 4,6-dichloropyrimidine, 11.7 g of 2-naphthaleneboronic acid, 7.2 g of sodium carbonate, 0.29 g of bis(triphenylphosphine)palladium(II)dichloride (abbreviation: Pd(PPh₃)₂Cl₂), 20 mL of water, and 20 mL of acetonitrile, and the air in the flask was replaced with argon. This reaction container was heated by irradiation with microwaves (2.45 GHz, 100 W) for 60 minutes. Here, into the flask were further put 2.9 g of 2-naphthaleneboronic acid, 1.8 g of sodium carbonate, 0.070 g of Pd(PPh₃)₂Cl₂, 5 mL of water, and 5 mL of acetonitrile, and the mixture was heated again by irradiation with microwaves (2.45 GHz, 100 W) for 60 minutes. After that, water was added to this solution and an organic layer was extracted with dichloromethane. The obtained organic layer was washed with water and dried with magnesium sulfate. The solution after drying was filtered. The solvent of this solution was distilled off, and then the obtained residue was purified by silica gel column chromatography using hexane and ethyl acetate as a developing solvent in a ratio of 5:1, so that a pyrimidine derivative 4-chloro-6-(naphthalen-2-yl)pyrimidine was obtained (yellow white powder, yield of 48%). Note that the irradiation with microwaves was performed using a microwave synthesis system (Discover, manufactured by CEM Corporation). A synthesis scheme (s-1) of Step 1 is shown below.

(s-1)

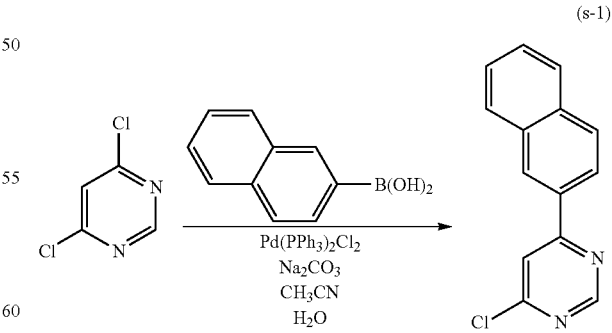

Step 2: Synthesis of 4-(2,5-dimethylphenyl)-6-(naphthalen-2-yl)pyrimidine (abbreviation: Hdmp2npm)

Next, into a recovery flask equipped with a reflux pipe were put 3.3 g of 4-chloro-(6-naphthalen-2-yl)pyrimidine, 2.1 g of 2,5-dimethylphenylboronic acid, 1.5 g of sodium carbonate, 0.11 g of bis(triphenylphosphine)palladium(II)dichloride (abbreviation: Pd(PPh₃)₂Cl₂), 20 mL of water, and 20 mL of acetonitrile, and the air in the flask was replaced with argon. This reaction container was heated by irradiation with microwaves (2.45 GHz, 100 W) for 60 minutes. Here, into the flask were further put 1.0 g of 2,5-dimethylphenylboronic acid, 0.73 g of sodium carbonate, 0.050 g of Pd(PPh₃)₂Cl₂, 5 mL of water, and 5 mL of acetonitrile, and the mixture was heated again by irradiation with microwaves (2.45 GHz, 100 W) for 60 minutes. After that, water was added to this solution and an organic layer was extracted with dichloromethane. The obtained organic layer was washed with water and dried with magnesium sulfate. The solution after drying was filtered. The solvent of this solution was distilled off, and then the obtained residue was purified by flash column chromatography using hexane and ethyl acetate as a developing solvent in a ratio of 2:1, so that a pyrimidine derivative Hdmp2npm was obtained (pale yellow oil, yield of 97%). A synthesis scheme (s-2) of Step 2 is shown below.

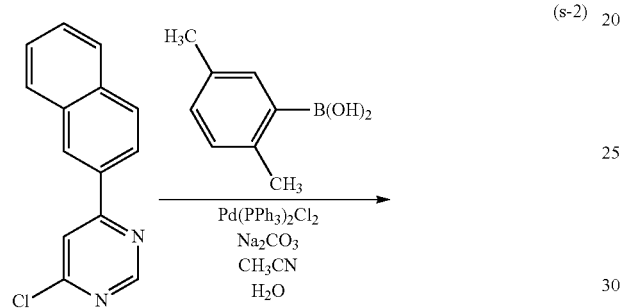

(s-2)

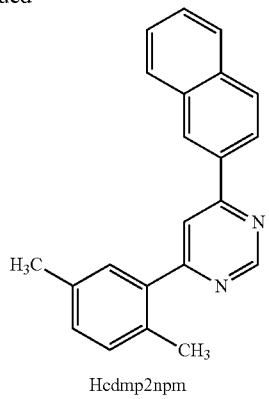

Hcdmp2npm (Step 3: Synthesis of di-μ-chloro-bis{bis[4-(2,5-dimethylphenyl)-6-(naphthalen-2-yl)pyrimidinato]iridium(III)} (abbreviation: [Ir(dmp2npm)₂Cl]₂)

Next, into a recovery flask equipped with a reflux pipe were put 30 mL of 2-ethoxyethanol, 10 mL of water, 4.11 g of Hdmp2npm obtained in Step 2, and 1.90 g of iridium chloride hydrate (IrCl₃.H₂O), and the air in the flask was replaced with argon. After that, irradiation with microwaves (2.45 GHz, 100 W) was performed for 1 hour to cause a reaction. The solvent was distilled off, and then the obtained residue was suction-filtered and washed with ethanol to give a dinuclear complex [Ir(dmp2npm)₂Cl]₂ (reddish brown powder, yield of 97%). A synthesis scheme (s-3) of Step 3 is shown below.

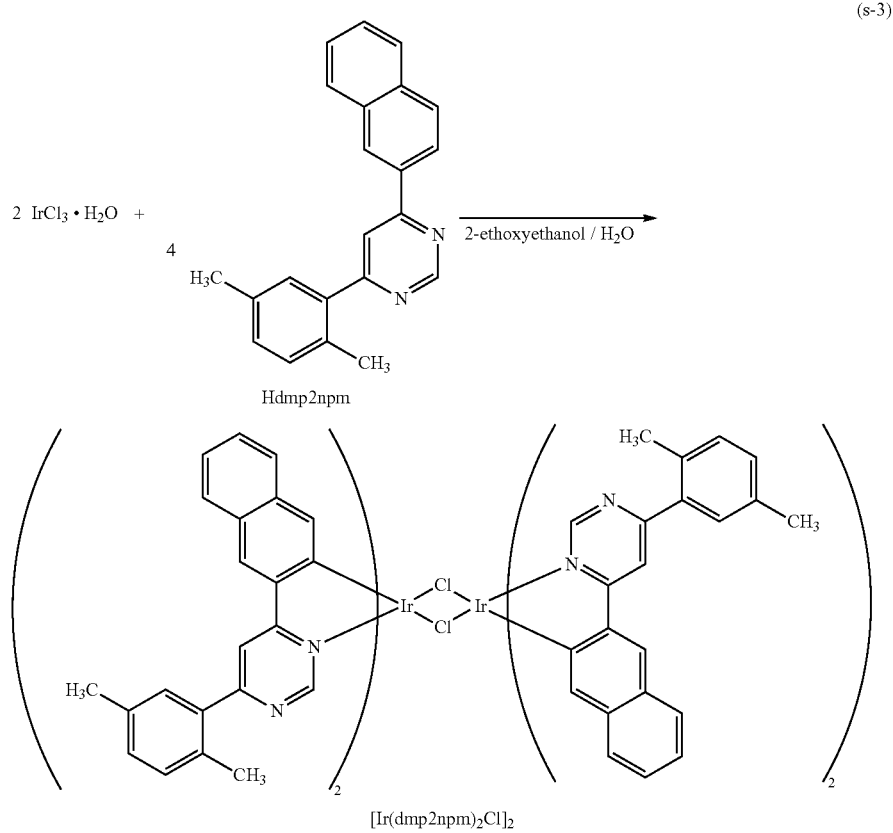

(s-3)

Step 4: Synthesis of bis[4-(2,5-dimethylphenyl)-6-(naphthalen-2-yl)pyrimidinato](dipivaloylmethanato)iridium(III) (abbreviation: [Ir(dmp2npm)₂(dpm)])

Further, into a recovery flask equipped with a reflux pipe were put 40 mL of 2-ethoxyethanol, 1.99 g of the dinuclear complex [Ir(dmp2npm)₂Cl]₂ obtained in Step 3, 0.65 g of dipivaloylmethane, and 1.25 g of sodium carbonate, and the air in the flask was replaced with argon. After that, the mixture was heated by irradiation with microwaves (2.45 GHz, 120 W) for 60 minutes. Here, into the flask was further put 0.32 g of dipivaloylmethane, and the mixture was heated again by irradiation with microwaves (2.45 GHz, 120 W) for 60 minutes. The solvent was distilled off, and the obtained residue was suction-filtered with ethanol. The obtained solid was washed with water and ethanol. This solid was purified by flash column chromatography using hexane and ethyl acetate as a developing solvent in a ratio of 5:1. After that, recrystallization was carried out with a mixed solvent of dichloromethane and hexane to give vermilion powder (yield of 12%). A synthesis scheme (s-4) of Step 4 is shown below.

¹H NMR. δ (CDCl₃): 0.93 (s, 18H), 2.47 (s, 6H), 2.56 (s, 6H), 5.63 (s, 1H), 6.90 (s, 2H), 7.14-7.36 (m, 10H), 7.54 (s, 2H), 7.69 (d, 2H), 8.10 (s, 2H), 8.25 (s, 2H), 9.20 (s, 2H).

Figure 70:
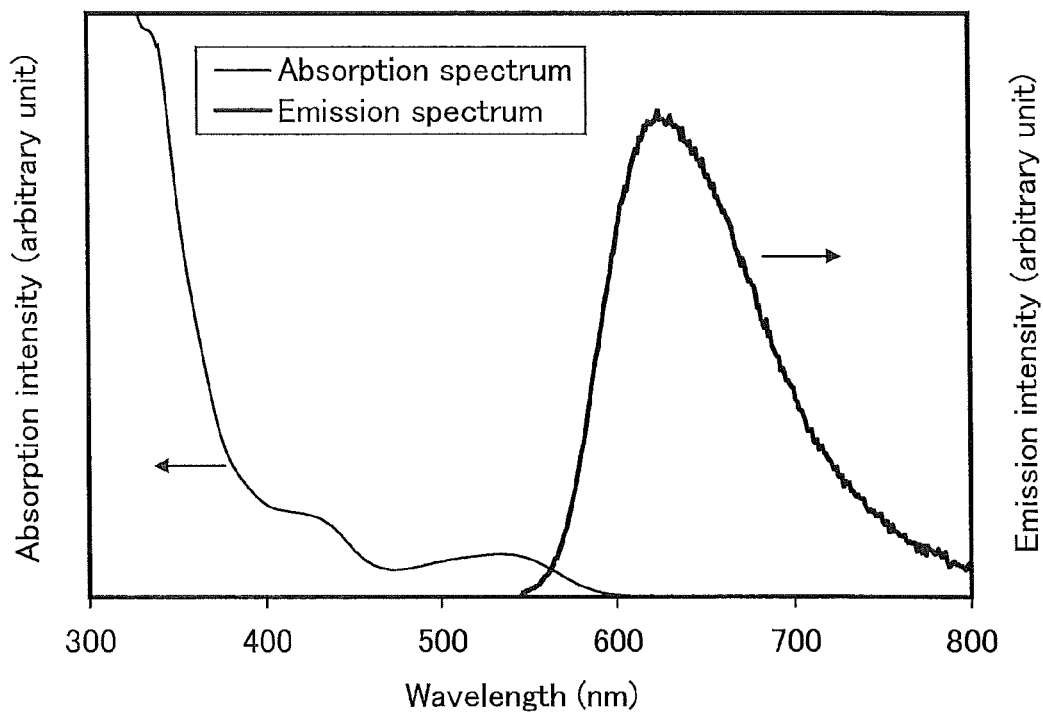
FIG. 70 shows an ultraviolet-visible absorption spectrum and an emission spectrum of the organometallic complex represented by the structural formula (201).

Next, an ultraviolet-visible absorption spectrum (hereinafter, simply referred to as an absorption spectrum) and an emission spectrum of [Ir(dpm2npm)₂(dpm)] in a dichloromethane solution were measured. The absorption spectrum was measured with the use of an ultraviolet-visible light spectrophotometer (V-550, manufactured by JASCO Corporation) in the state where the dichloromethane solution (0.067 mmol/L) was put in a quartz cell at room temperature. The emission spectrum was measured with the use of a fluorescence spectrophotometer (FS920, manufactured by Hamamatsu Photonics Corporation) in the state where the degassed dichloromethane solution (0.067 mmol/L) was put in a quartz cell at room temperature. FIG. 70 shows results of the measured absorption spectrum and emission spectrum. The horizontal axis represents wavelength (nm), and the vertical axis represents absorption intensity (arbitrary unit) and emission intensity (arbitrary unit). In FIG. 70, two solid lines are shown; a thin line represents the absorption spectrum, and

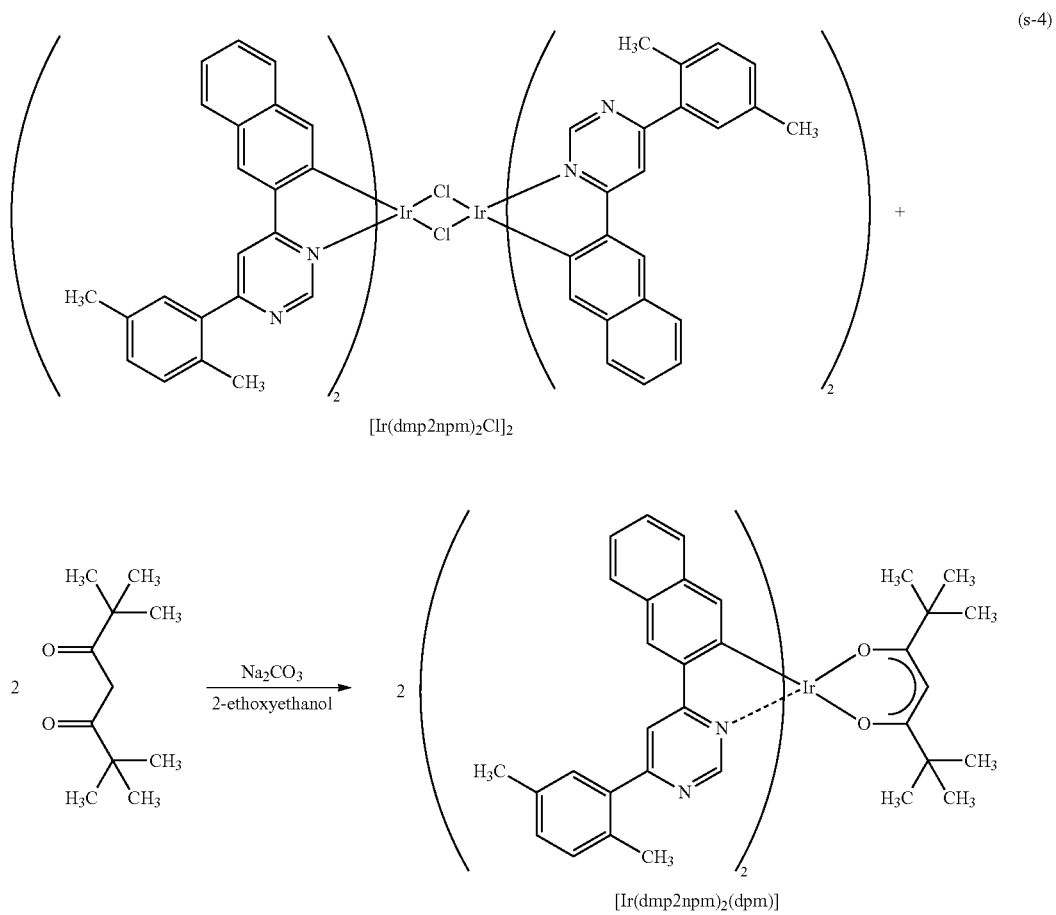

(s-4)

[Ir(dmp2npm)₂Cl]₂

[Ir(dmp2npm)₂(dpm)]

Figure 69:
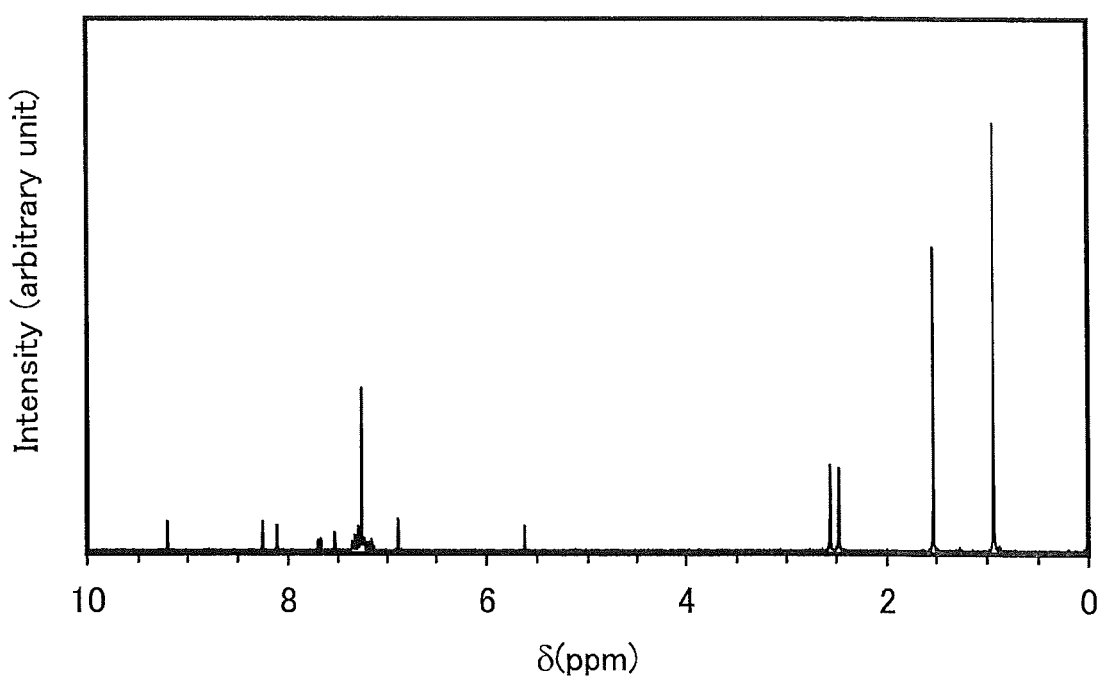
FIG. 69 shows a $^1$H NMR chart of an organometallic complex represented by a structural formula (201).

An analysis result by nuclear magnetic resonance spectrometry (¹H NMR) of the vermilion powder obtained is described below. The ¹H NMR chart is illustrated in FIG. 69. These results revealed that the organometallic complex [Ir(dmp2npm)₂(dpm)], which is one embodiment of the present invention represented by the structural formula (201), was obtained in Synthetic Example 17.

a thick line represents the emission spectrum. Note that the absorption spectrum in FIG. 70 is a result obtained by subtraction of the absorption spectrum of only dichloromethane that was put in a quartz cell from the measured absorption spectrum of the dichloromethane solution (0.067 mmol/L) in a quartz cell.

As shown in FIG. 70, the organometallic complex [Ir(dmp2npm)₂(dpm)], which is one embodiment of the present

EXAMPLE 25

In Example 25, a light-emitting element which is one embodiment of the present invention is described with reference to FIG. 14. Chemical formulas of materials used in this example are shown below. Note that the chemical formulas of the materials described above are omitted.

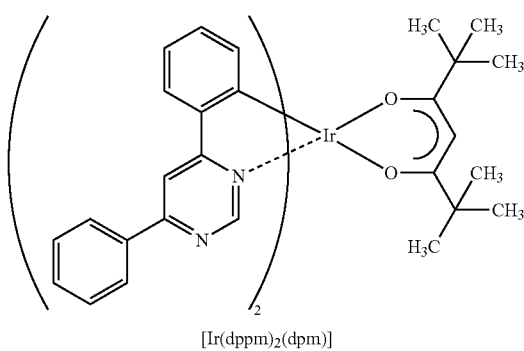

[Ir(dppm)$_2$(dpm)]

A method of fabricating a light-emitting element 6 of this example is described below.

invention, has an emission peak at 625 nm, and red light was observed from the dichloromethane solution.

nm, and the weight ratio of BPAFLP to molybdenum oxide was adjusted to 4:2 (=BPAFLP:molybdenum oxide).

Next, a BPAFLP film was formed to a thickness of 20 nm on the hole-injection layer 1111, whereby a hole-transport layer 1112 was formed.

Further, 2mDBTPDBq-II, PCBA1BP, and bis(4,6-diphenylpyrimidinato)(dipivaloylmethanato)iridium(III) (abbreviation: [Ir(dppm)$_2$(dpm)]) synthesized in Example 12 were co-evaporated to form a light-emitting layer 1113 on the hole-transport layer 1112. The weight ratio of 2mDBTPDBq-II to PCBA1BP and [Ir(dppm)$_2$(dpm)] was adjusted to 0.8:0.2:0.025 (=2mDBTPDBq-II:PCBA1BP:[Ir(dppm)$_2$(dpm)]). The thickness of the light-emitting layer 1113 was set to 40 nm.

Next, a 2mDBTPDBq-II film was formed to a thickness of 10 nm on the light-emitting layer 1113, whereby a first electron-transport layer 1114a was formed.

Next, a BPhen film was formed to a thickness of 20 nm on the first electron-transport layer 1114a, whereby a second electron-transport layer 1114b was formed.

Further, a LiF film was formed to a thickness of 1 nm on the second electron-transport layer 1114b by evaporation, whereby an electron-injection layer 1115 was formed.

Lastly, an aluminum film was formed to a thickness of 200 nm by evaporation to for a second electrode 1103 functioning as a cathode. Thus, the light-emitting element 6 of this example was fabricated.

Note that in the above evaporation process, evaporation was all performed by a resistance heating method.

Table 11 shows an element structure of the light-emitting element 6 obtained as described above.

TABLE 11

| | First Electrode | Hole-injection Layer | Hole-transport Layer | Light-emitting Layer | First electron-Transport Layer | Second electron-Transport Layer | Electron-injection Layer | Second Electrode |
|---|---|---|---|---|---|---|---|---|
| Light-emitting Element 6 | ITSO 110 nm | BPAFLP:MoOx (=4:2) 40 nm | BPAFLP 20 nm | 2mDBTPDBq-II:PCBA1BP:[Ir(dppm)$_2$(dpm)] (=0.8:0.2:0.025) 40 nm | 2mDBTPDBq-II 10 nm | BPhen 20 nm | LF 1 nm | Al 200 nm |

(Light-Emitting Element 6)

First, an ITSO film was formed over a glass substrate 1100 by a sputtering method, so that a first electrode 1101 functioning as an anode was formed. The thickness was 110 nm and the electrode area was 2 mm×2 mm In pretreatment for forming the light-emitting element on the substrate 1100, UV ozone treatment was performed for 370 seconds after washing of a surface of the substrate with water and baking that was performed at 200° C. for 1 hour.

After that, the substrate 1100 was transferred into a vacuum evaporation apparatus where the pressure was reduced to approximately 10$^{-4}$ Pa, and subjected to vacuum baking at 170° C. for 30 minutes in a heating chamber of the vacuum evaporation apparatus, and then the substrate 1100 was cooled down for about 30 minutes.

Next, the substrate 1100 provided with the first electrode 1101 was fixed to a substrate holder in a vacuum evaporation apparatus so that a surface on which the first electrode 1101 was provided faced downward. The pressure in the vacuum evaporation apparatus was reduced to about 10$^{-4}$ Pa, and then BPAFLP and molybdenum(VI) oxide were co-evaporated to form a hole-injection layer 1111 on the first electrode 1101. The thickness of the hole-injection layer 1111 was set to 40

In a glove box containing a nitrogen atmosphere, the light-emitting element 6 was sealed so as not to be exposed to the air. After that, operation characteristics of the light-emitting element 6 were measured. Note that the measurements were carried out at room temperature (in an atmosphere kept at 25° C.).

Figure 71:
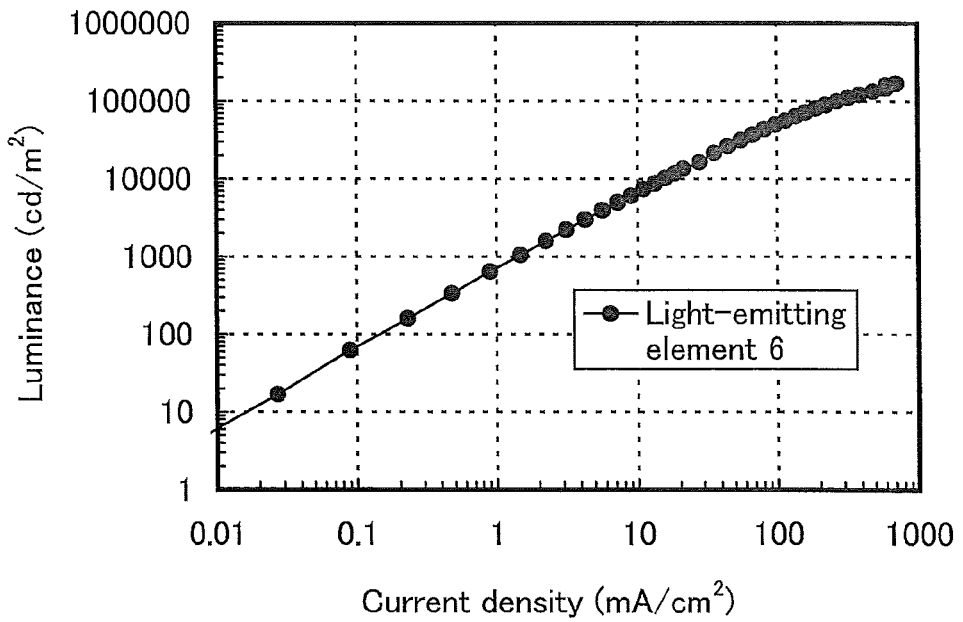
FIG. 71 shows current density vs. luminance characteristics of a light-emitting element 6.
Figure 72:
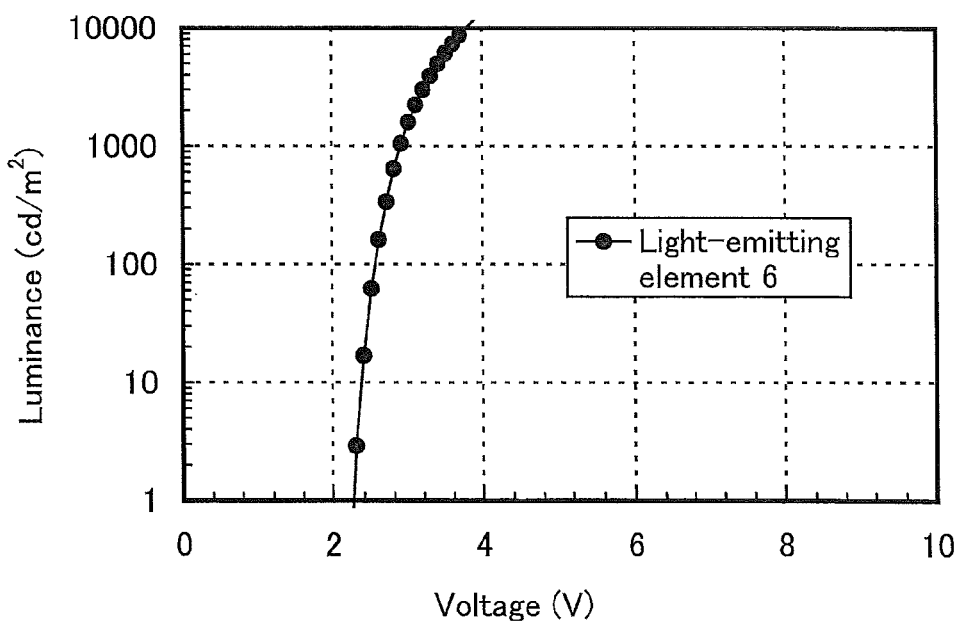
FIG. 72 shows voltage vs luminance characteristics of the light-emitting element 6.
Figure 73:
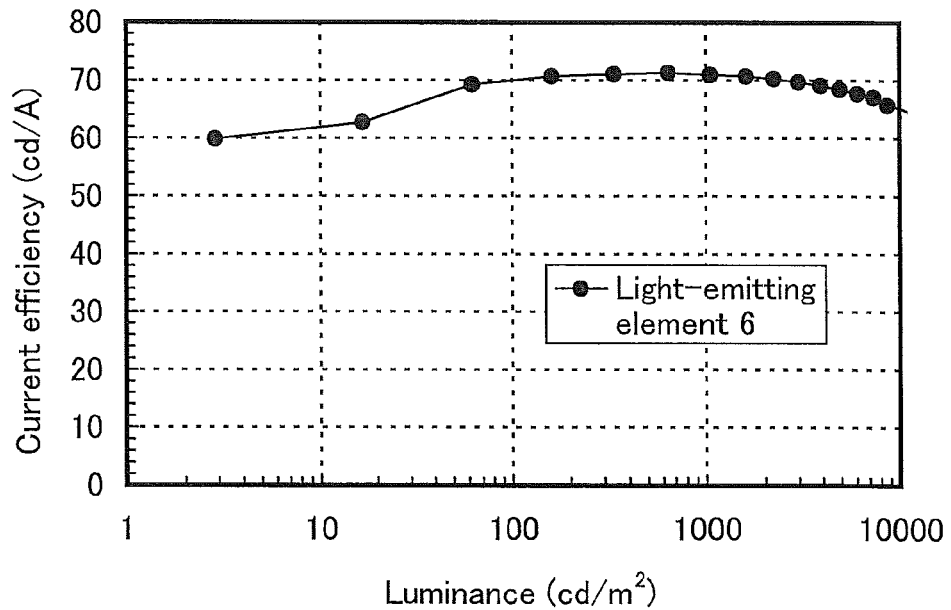
FIG. 73 shows luminance vs. current efficiency characteristics of the light-emitting element 6.

FIG. 71 shows current density vs. luminance characteristics of the light-emitting element 6. In FIG. 71, the horizontal axis represents current density (mA/cm$^2$) and the vertical axis represents luminance (cd/m$^2$). FIG. 72 shows voltage vs. luminance characteristics thereof. In FIG. 72, the horizontal axis represents voltage (V) and the vertical axis represents luminance (cd/m$^2$). FIG. 73 shows luminance vs. current efficiency characteristics thereof. In FIG. 73, the horizontal axis represents luminance (cd/m$^2$) and the vertical axis represents current efficiency (cd/A). Further, Table 12 shows voltage (V), current density (mA/cm$^2$), CIE chromaticity coordinates (x, y), current efficiency (cd/A), power efficiency (lm/W), and external quantum efficiency (%) of the light-emitting element 6 at a luminance of 1100 cd/m$^2$.

TABLE 12

|  | Voltage (V) | Current Density (mA/cm²) | Chromaticity (x, y) | Current Efficiency (cd/A) | Power Efficiency (lm/W) | External Quantum Efficiency (%) |
|---|---|---|---|---|---|---|
| Light-emitting Element 6 | 2.9 | 1.5 | (0.55, 0.45) | 71 | 77 | 27 |

Figure 74:
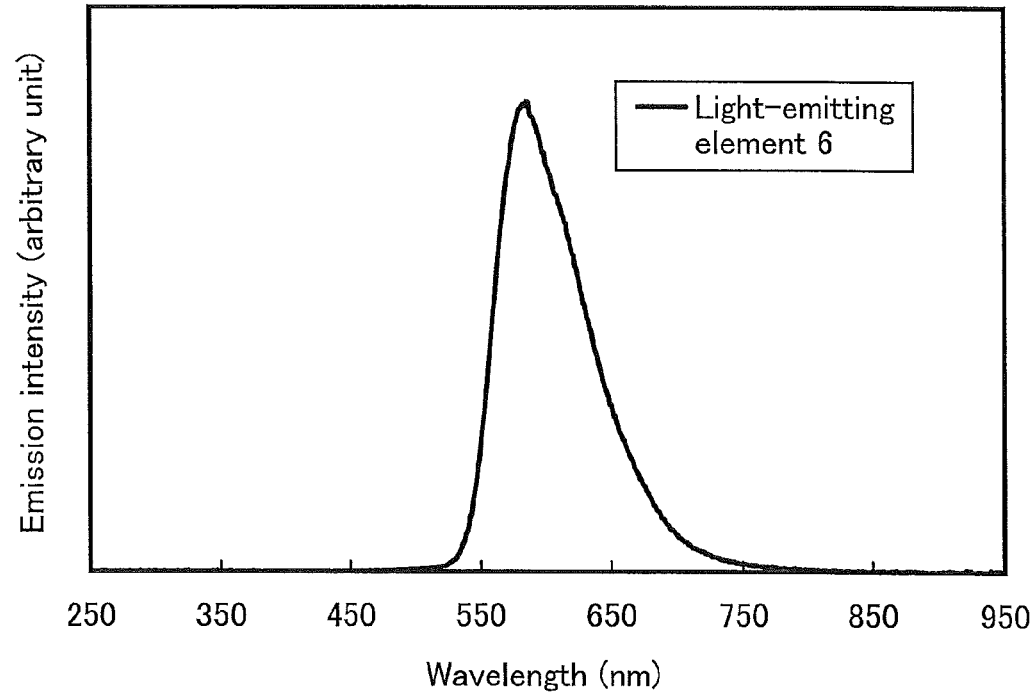
FIG. 74 shows an emission spectrum of the light-emitting element 6.

FIG. 74 shows an emission spectrum of the light-emitting element 6 which was obtained by applying a current of 0.1 mA. In FIG. 74, the horizontal axis represents wavelength (nm) and the vertical axis represents light emission intensity (arbitrary unit). As shown in FIG. 74, the emission spectrum of the light-emitting element 6 has a peak at 586 nm. In addition, as shown in Table 12, the CIE chromaticity coordinates of the light-emitting element 6 were (x, y)=(0.55, 0.45) at a luminance of 1100 cd/m². The results show that orange light emission originating from [Ir(dppm)₂(dpm)] was obtained from the light-emitting element 6.

Table 12, FIG. 71, FIG. 72, and FIG. 73 indicate that the light-emitting element 6 has high emission efficiency.

The above results suggest that an element with high emission efficiency can be realized by using the organometallic complex which is one embodiment of the present invention as a light-emitting material.

Figure 75:
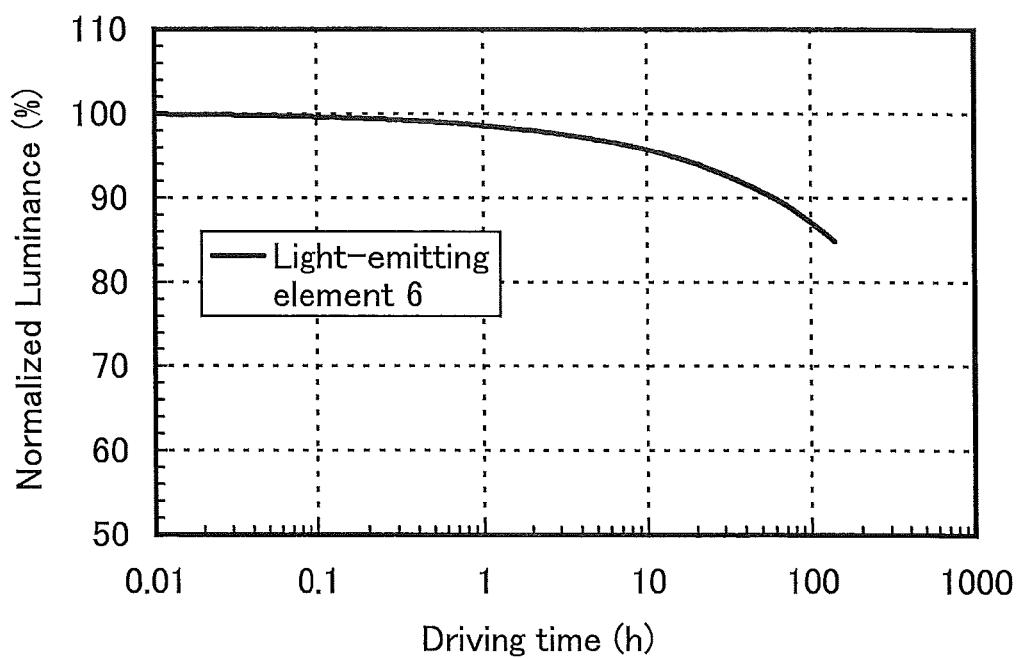
FIG. 75 shows results obtained by reliability testing of the light-emitting element 6.

Next, reliability testing of the light-emitting element 6 was carried out. Results of the reliability testing are shown in FIG. 75. In FIG. 75, the vertical axis represents normalized luminance (%) on the assumption that an initial luminance is 100%, and the horizontal axis represents driving time (h) of the element.

In the reliability testing, the light-emitting element 6 was driven under the conditions where the initial luminance was set to 5000 cd/m² and the current density was constant.

The light-emitting element 6 kept 85% of the initial luminance after the driving for 140 hours.

The above results suggest that an element having high reliability can be realized by using an organometallic complex which is one embodiment of the present invention as a light-emitting material.

EXAMPLE 26

In Example 26, a light-emitting element which is one embodiment of the present invention is described with reference to FIG. 14. Chemical formulas of materials used in this example are shown below. Note that the chemical formulas of the materials described above are omitted.

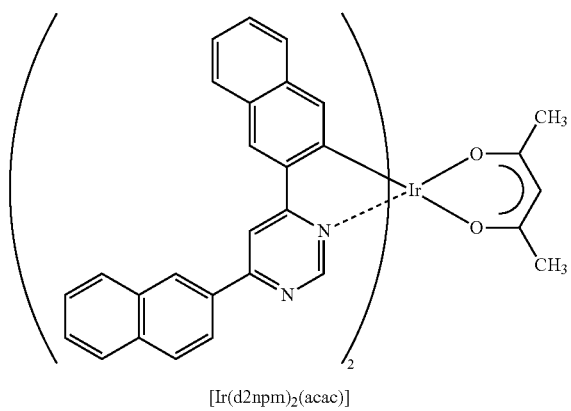

[Ir(d2npm)₂(acac)]

-continued

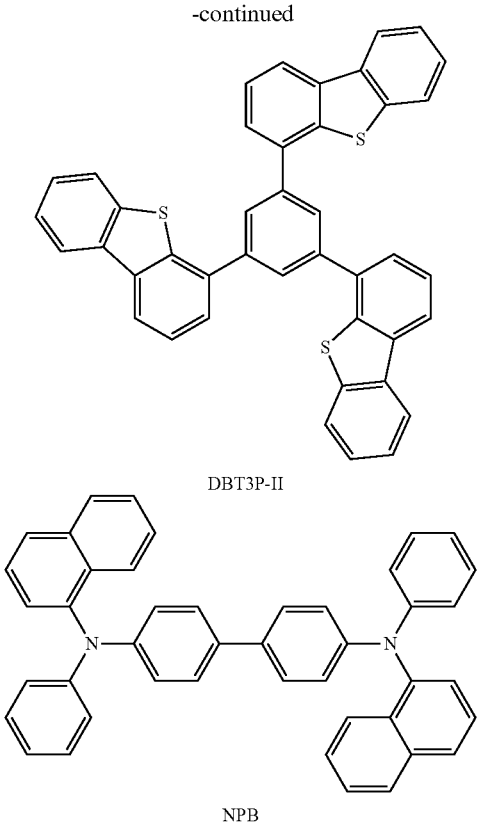

DBT3P-II

NPB

A method of fabricating a light-emitting element 7 of this example is described below.

(Light-Emitting Element 7)

First, an ITSO film was formed over a glass substrate 1100 by a sputtering method, so that a first electrode 1101 functioning as an anode was formed. The thickness was 110 nm and the electrode area was 2 mm×2 mm.

In pretreatment for forming the light-emitting element on the substrate 1100, UV ozone treatment was performed for 370 seconds after washing of a surface of the substrate with water and baking that was performed at 200° C. for 1 hour.

After that, the substrate 1100 was transferred into a vacuum evaporation apparatus where the pressure was reduced to approximately $10^{-4}$ Pa, and subjected to vacuum baking at 170° C. for 30 minutes in a heating chamber of the vacuum evaporation apparatus, and then the substrate 1100 was cooled down for about 30 minutes.

Next, the substrate 1100 provided with the first electrode 1101 was fixed to a substrate holder in a vacuum evaporation apparatus so that a surface on which the first electrode 1101 was provided faced downward. The pressure in the vacuum evaporation apparatus was reduced to about $10^{-4}$ Pa, and then 1,3,5-tri(dibenzothiophen-4-yl)-benzene (abbreviation:

DBT3P-II) and molybdenum(VI) oxide were co-evaporated to form a hole-injection layer 1111 on the first electrode 1101. The thickness of the hole-injection layer 1111 was set to 40 nm, and the weight ratio of DBT3P-II to molybdenum oxide was adjusted to 4:2 (=DBT3P-II:molybdenum oxide).

Next, a BPAFLP film was formed to a thickness of 20 nm on the hole-injection layer 1111, whereby a hole-transport layer 1112 was formed.

Further, 2mDBTPDBq-II, 4,4'-bis[N-(1-naphthyl)-N-phenylamino]biphenyl (abbreviation: NPB), and (acetylacetonato)bis[4,6-di(naphthalen-2-yl)pyrimidinato] iridium(III) (abbreviation: [Ir(d2npm)$_2$(acac)]) synthesized in Example 13 were co-evaporated to form a light-emitting layer 1113 on the hole-transport layer 1112. The weight ratio of 2mDBTPDBq-II to NPB and [Ir(d2npm)$_2$(acac)] was adjusted to 0.8: 0.2:0.025 (=2mDBTPDBq-II:NPB:[Ir(d2npm)$_2$(acac)]). The thickness of the light-emitting layer 1113 was set to 40 nm Next, a 2mDBTPDBq-II film was formed to a thickness of 10 nm on the light-emitting layer 1113, whereby a first electron-transport layer 1114a was formed.

Next, a BPhen film was formed to a thickness of 20 nm on the first electron-transport layer 1114a, whereby a second electron-transport layer 1114b was formed.

Further, a LiF film was formed to a thickness of 1 nm on the second electron-transport layer 1114b by evaporation, whereby an electron-injection layer 1115 was foliated.

Lastly, an aluminum film was formed to a thickness of 200 nm by evaporation to form a second electrode 1103 functioning as a cathode. Thus, the light-emitting element 7 of this example was fabricated.

Note that in the above evaporation process, evaporation was all performed by a resistance heating method.

Table 13 shows an element structure of the light-emitting element 7 obtained as described above.

TABLE 13

| | First Electrode | Hole-injection Layer | Hole-transport Layer | Light-emitting Layer | First electron-Transport Layer | Second electron-Transport Layer | Electron-injection Layer | Second Electrode |
|---|---|---|---|---|---|---|---|---|
| Light-emitting Element 7 | ITSO 110 nm | DBT3P-II: MoOx (=4:2) 40 nm | BPAFLP 20 nm | 2mDBTPDBq-II: NPB: [Ir(d2npm)$_2$(acac)] (=0.8:0.2:0.025) 40 nm | 2mDBTPDBq-II 10 nm | BPhen 20 nm | LiF 1 nm | Al 200 nm |

In a glove box containing a nitrogen atmosphere, the light-emitting element 7 was sealed so as not to be exposed to the air. After that, operation characteristics of the light-emitting element 7 were measured. Note that the measurements were carried out at room temperature (in an atmosphere kept at 25° C.).

Figure 76:
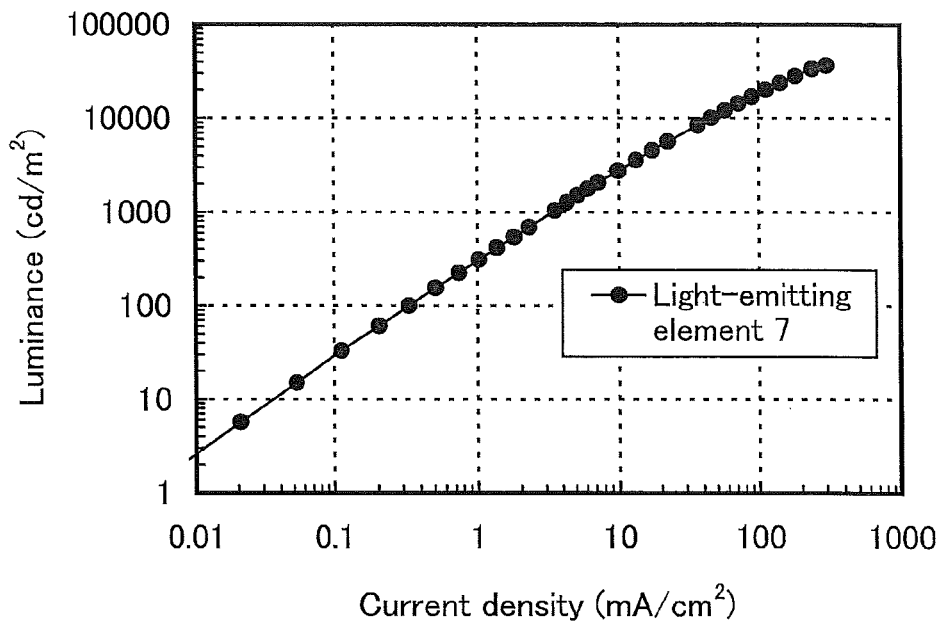
FIG. 76 shows current density vs. luminance characteristics of a light-emitting element 7.
Figure 77:
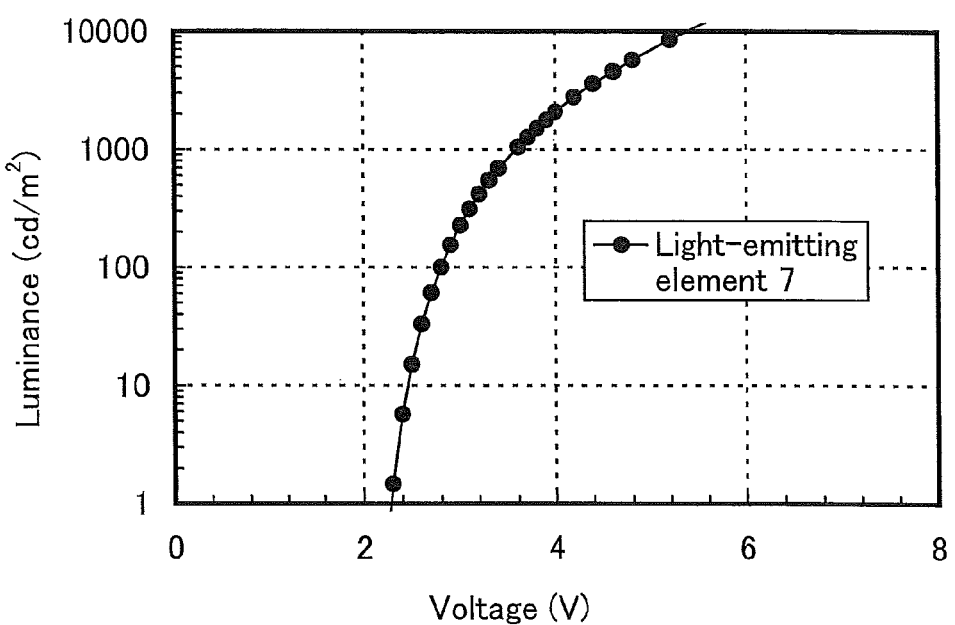
FIG. 77 shows voltage vs. luminance characteristics of the light-emitting element 7.
Figure 78:
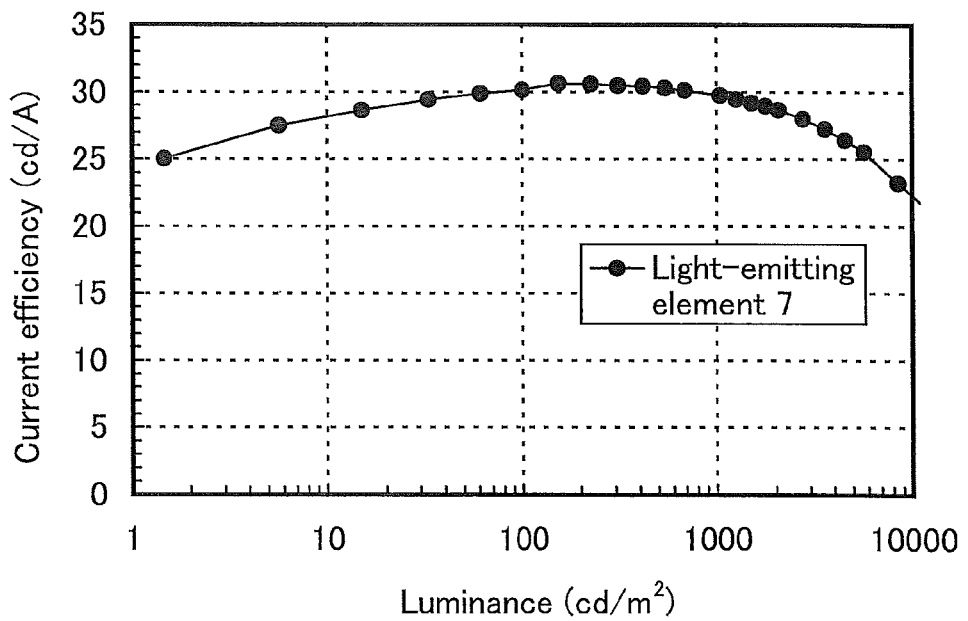
FIG. 78 shows luminance vs. current efficiency characteristics of the light-emitting element 7.

FIG. 76 shows current density vs. luminance characteristics of the light-emitting element 7. In FIG. 76, the horizontal axis represents current density (mA/cm$^2$) and the vertical axis represents luminance (cd/m$^2$). FIG. 77 shows voltage vs. luminance characteristics thereof. In FIG. 77, the horizontal axis represents voltage (V) and the vertical axis represents luminance (cd/m$^2$). FIG. 78 shows luminance vs. current efficiency characteristics thereof. In FIG. 78, the horizontal axis represents luminance (cd/m$^2$) and the vertical axis represents current efficiency (cd/A). Further, Table 14 shows voltage (V), current density (mA/cm$^2$), CIE chromaticity coordinates (x, y), current efficiency (cd/A), power efficiency (lm/W), and external quantum efficiency (%) of the light-emitting element 7 at a luminance of 1000 cd/m$^2$.

TABLE 14

| | Voltage (V) | Current Density (mA/cm$^2$) | Chromaticity (x, y) | Current Efficiency (cd/A) | Power Efficiency (lm/W) | External Quantum Efficiency (%) |
|---|---|---|---|---|---|---|
| Light-emitting Element 7 | 3.6 | 3.5 | (0.64, 0.36) | 30 | 26 | 21 |

Figure 79:
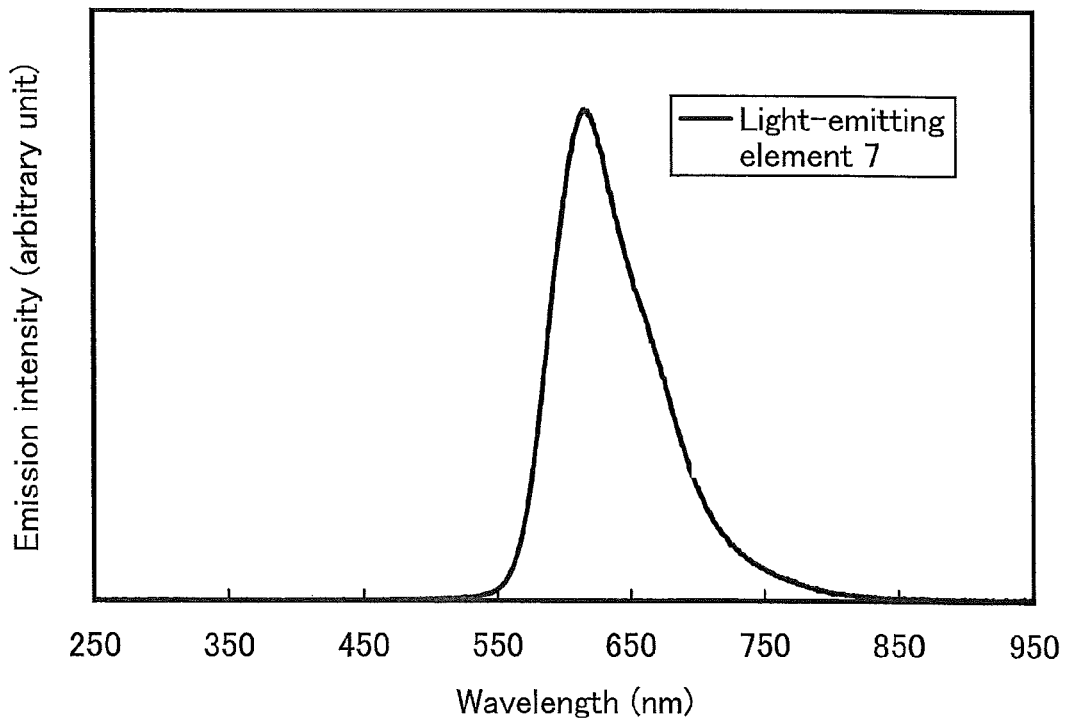
FIG. 79 shows an emission spectrum of the light-emitting element 7.

FIG. 79 shows an emission spectrum of the light-emitting element 7 which was obtained by applying a current of 0.1 mA. In FIG. 79, the horizontal axis represents wavelength (nm) and the vertical axis represents light emission intensity (arbitrary unit). As shown in FIG. 79, the emission spectrum of the light-emitting element 7 has a peak at 616 nm. In addition, as shown in Table 14, the CIE chromaticity coordinates of the light-emitting element 7 were (x, y)=(0.64, 0.36) at a luminance of 1000 cd/m$^2$. The results show that red light emission originating from [Ir(d2npm)$_2$(acac)] was obtained from the light-emitting element 7.

Table 14, FIG. 76, FIG. 77, and FIG. 78 indicate that the light-emitting element 7 has high emission efficiency.

The above results suggest that an element with high emission efficiency can be realized by using the organometallic complex which is one embodiment of the present invention as a light-emitting material.

Figure 80:
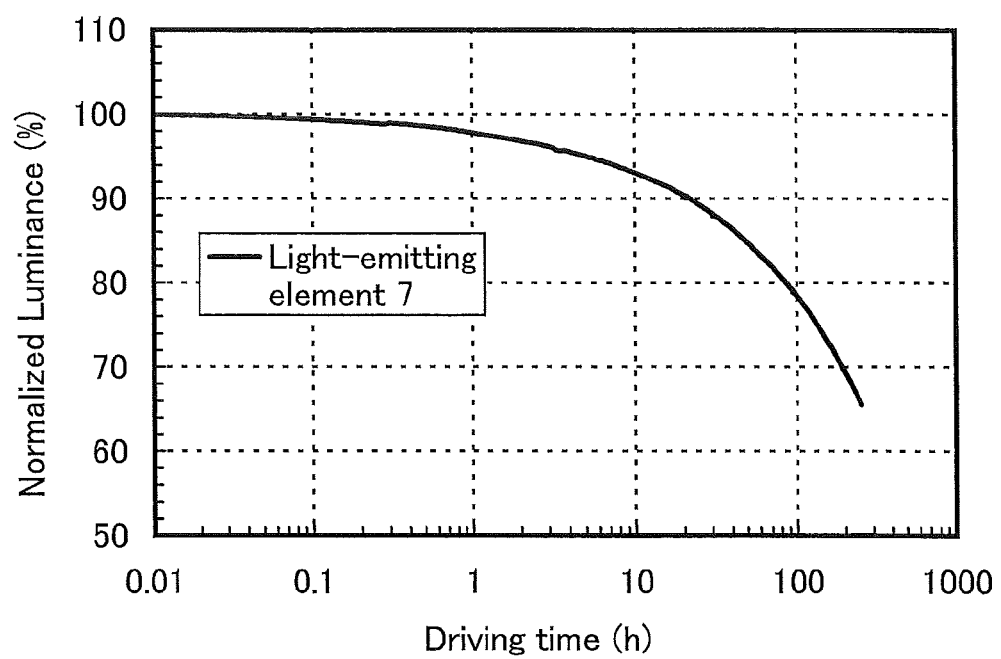
FIG. 80 shows results obtained by reliability testing of the light-emitting element 7.

Next, reliability testing of the light-emitting element 7 was carried out. Results of the reliability testing are shown in FIG. 80. In FIG. 80, the vertical axis represents normalized luminance (%) on the assumption that an initial luminance is 100%, and the horizontal axis represents driving time (h) of the element.

In the reliability testing, the light-emitting element 7 was driven under the conditions where the initial luminance was set to 5000 cd/m$^2$ and the current density was constant.

The light-emitting element 7 kept 66% of the initial luminance after the driving for 250 hours.

The above results suggest that an element having high reliability can be realized by using an organometallic complex which is one embodiment of the present invention as a light-emitting material.

EXAMPLE 27

In Example 27, a light-emitting element which is one embodiment of the present invention is described with reference to FIG. 14. Chemical formulas of materials used in this example are shown below. Note that the chemical formulas of the materials described above are omitted.

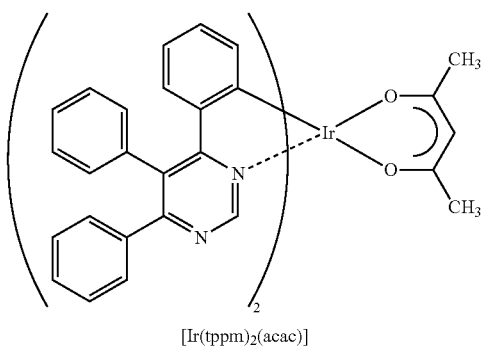

[Ir(tppm)₂(acac)]

A method of fabricating a light-emitting element 8 of this example is described below.

(Light-Emitting Element 8)

The light-emitting element 8 was fabricated in a manner similar to that in the light-emitting element 7 described in Example 26 except for a light-emitting layer 1113. The light-emitting layer 1113 of the light-emitting element 8 is described below.

The light-emitting layer 1113 of the light-emitting element 8 was formed by co-evaporation of 2mDBTPDBq-II, NPB, and (acetylacetonato)bis(4,5,6-triphenylpyrimidinato)iridium (III) (abbreviation: [Ir(tppm)₂(acac)]) synthesized in Example 17. The weight ratio of 2mDBTPDBq-II to NPB and [Ir(tppm)₂(acac)] was adjusted to 0.8:0.2:0.025 (=2mDBTP-DBq-II:NPB:[Ir(tppm)₂(acac)]). The thickness of the light-emitting layer 1113 was set to 40 nm.

Table 15 shows an element structure of the light-emitting element 8 obtained as described above.

TABLE 15

| | First Electrode | Hole-injection Layer | Hole-transport Layer | Light-emitting Layer | First electron-Transport Layer | Second electron-Transport Layer | Electron-injection Layer | Second Electrode |
|---|---|---|---|---|---|---|---|---|
| Light-emitting Element 8 | ITSO 110 nm | DBT3P-II:MoOx (=4:2) 40 nm | BPAFLP 20 nm | 2mDBTPDBq-II:NPB:[Ir(tppm)₂(acac)] (=0.8:0.2:0.025) 40 nm | 2mDBTPDBq-II 10 nm | BPhen 20 nm | LiF 1 nm | Al 200 nm |

In a glove box containing a nitrogen atmosphere, the light-emitting element 8 was sealed so as not to be exposed to the air. After that, operation characteristics of the light-emitting element 8 were measured. Note that the measurements were carried out at room temperature (in an atmosphere kept at 25° C.).

Figure 81:
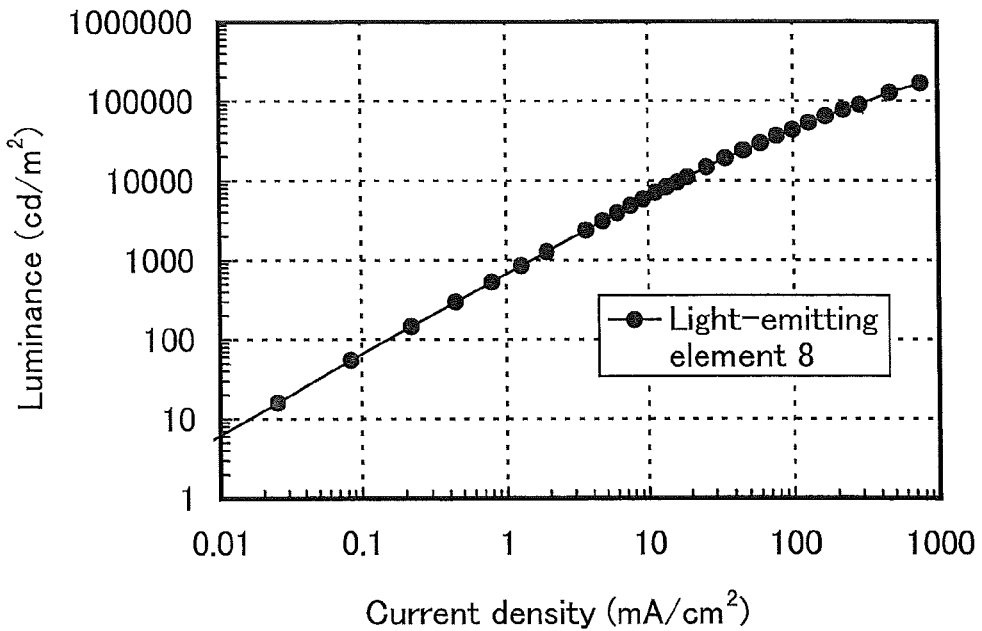
FIG. 81 shows current density vs. luminance characteristics of a light-emitting element 8.
Figure 82:
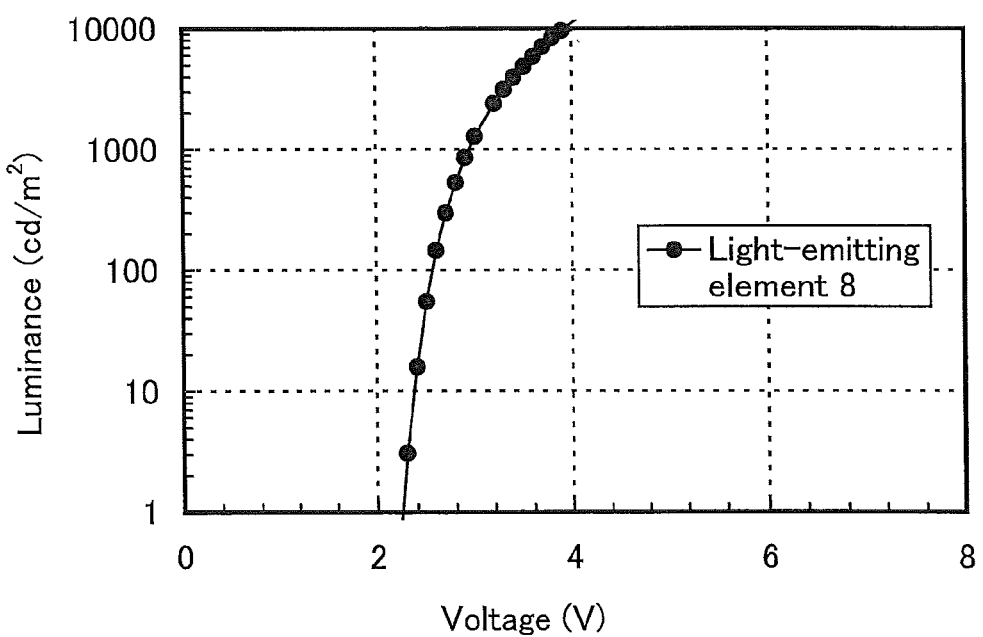
FIG. 82 shows voltage vs. luminance characteristics of the light-emitting element 8.
Figure 83:
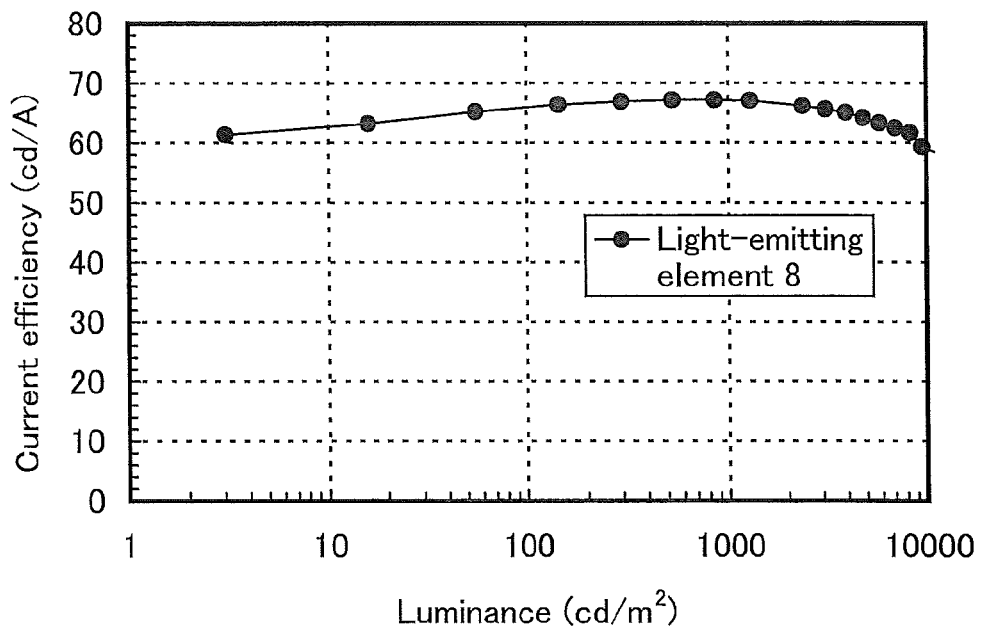
FIG. 83 shows luminance vs. current efficiency characteristics of the light-emitting element 8.
Figure 85:
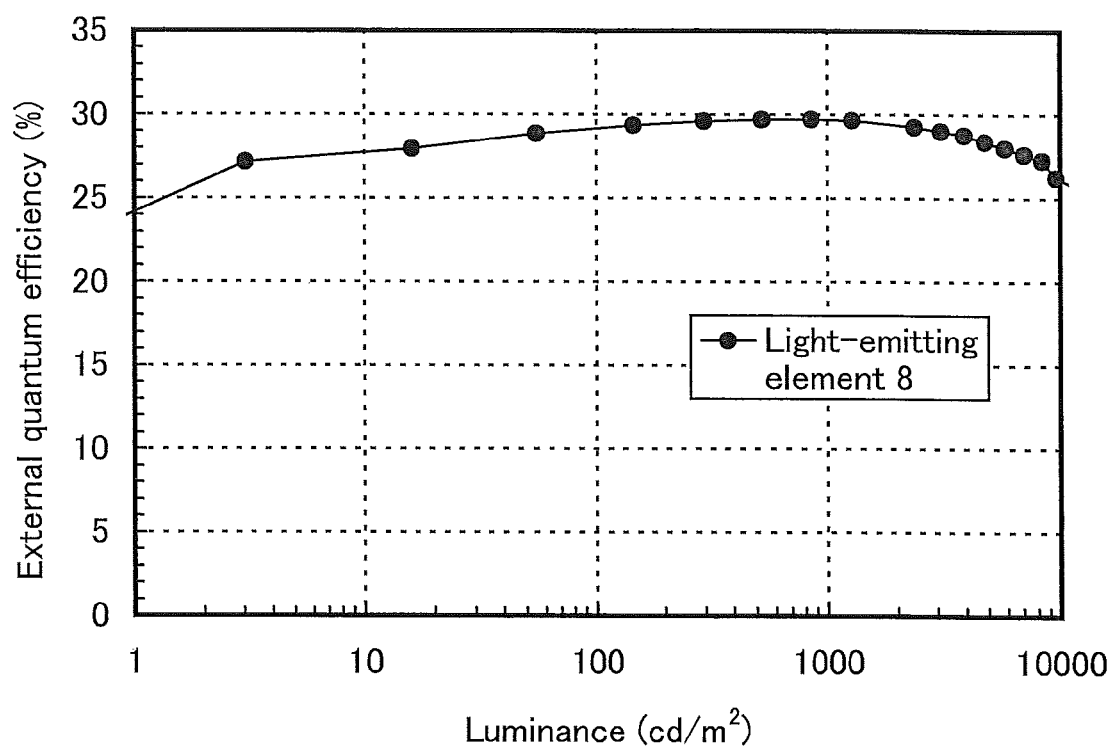
FIG. 85 shows luminance vs. external quantum efficiency characteristics of the light-emitting element 8.

FIG. 81 shows current density vs. luminance characteristics of the light-emitting element 8. In FIG. 81, the horizontal axis represents current density (mA/cm²) and the vertical axis represents luminance (cd/m²). FIG. 82 shows voltage vs. luminance characteristics thereof. In FIG. 82, the horizontal axis represents voltage (V) and the vertical axis represents luminance (cd/m²). FIG. 83 shows luminance vs. current efficiency characteristics thereof. In FIG. 83, the horizontal axis represents luminance (cd/m²) and the vertical axis represents current efficiency (cd/A). In addition, FIG. 85 shows luminance vs. external quantum efficiency characteristics thereof. In FIG. 85, the horizontal axis represents luminance (cd/m²) and the vertical axis represents external quantum efficiency (%).

Further, Table 16 shows voltage (V), current density (mA/cm²), CIE chromaticity coordinates (x, y), current efficiency (cd/A), power efficiency (lm/W), and external quantum efficiency (%) of the light-emitting element 8 at a luminance of 850 cd/m².

TABLE 16

| | Voltage (V) | Current Density (mA/cm²) | Chromaticity (x, y) | Current Efficiency (cd/A) | Power Efficiency (lm/W) | External Quantum Efficiency (%) |
|---|---|---|---|---|---|---|
| Light-emitting Element 8 | 2.9 | 1.3 | (0.59, 0.41) | 67 | 73 | 30 |

Figure 84:
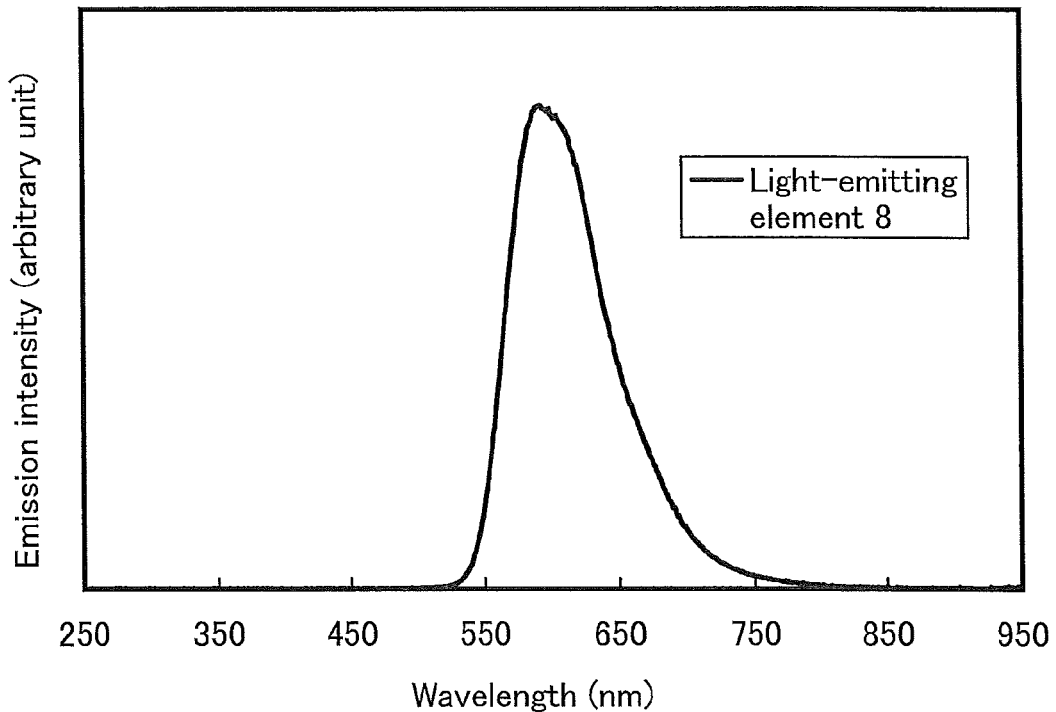
FIG. 84 shows an emission spectrum of the light-emitting element 8.

FIG. 84 shows an emission spectrum of the light-emitting element 8 which was obtained by applying a current of 0.1 mA. In FIG. 84, the horizontal axis represents wavelength (nm) and the vertical axis represents light emission intensity (arbitrary unit). As shown in FIG. 84, the emission spectrum of the light-emitting element 8 has a peak at 593 nm. In addition, as shown in Table 16, the CIE chromaticity coordinates of the light-emitting element 8 were (x, y)=(0.59, 0.41) at a luminance of 850 cd/m². The results show that orange light emission originating from [Ir(tppm)₂(acac)] was obtained from the light-emitting element 8.

FIG. 81, FIG. 82, FIG. 83, FIG. 85, and Table 16 indicate that the light-emitting element 8 has high emission efficiency. In particular, the light-emitting element 8 has an extremely high external quantum efficiency at a luminance of 850 cd/m², which is 30%. Note that it is said that the light extraction efficiency of an organic EL element is approximately 20% to 30%, considering light absorption by upper and lower electrodes (the light extraction efficiency is considered to be reduced by approximately 10%) or the like, the limit of the external quantum efficiency can be approximately 25% at most. However, the results of the external quantum efficiency this time is over the limit, indicating that the conventional theoretical value of the light extraction efficiency was wrong. That is, by using the organometallic complex which is one embodiment of the present invention, a novel light-emitting element with such a high efficiency can be realized, so that it is possible to indicate the theoretical value of the light extraction efficiency is wrong.

The above results suggest that an element with high emission efficiency can be realized by using the organometallic complex which is one embodiment of the present invention as a light-emitting material.

Figure 86:
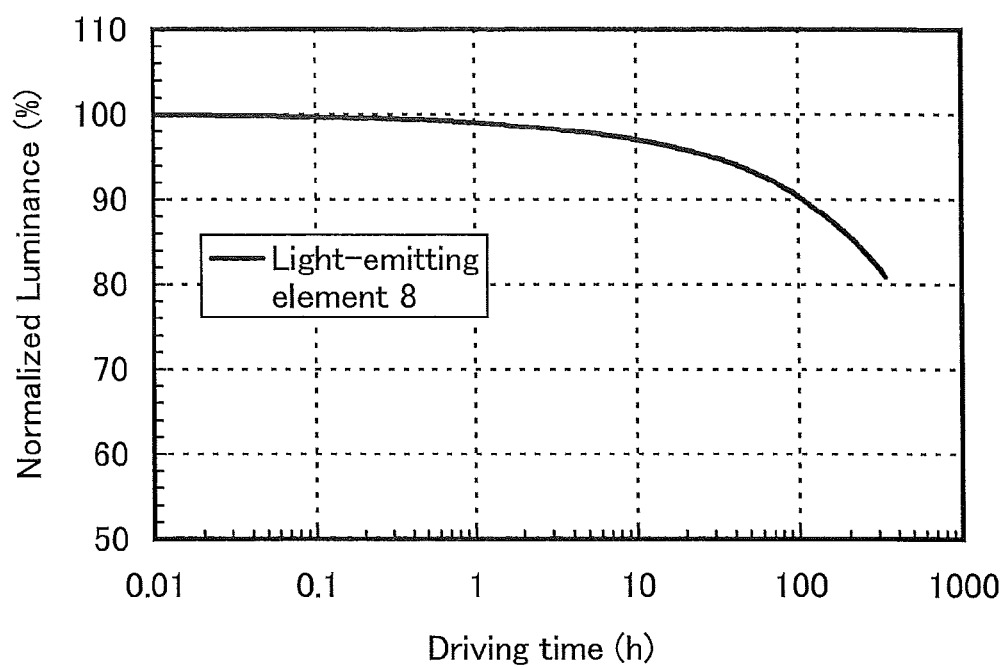
FIG. 86 shows results obtained by reliability testing of the light-emitting element 8.

Next, reliability testing of the light-emitting element 8 was carried out. Results of the reliability testing are shown in FIG. 86. In FIG. 86, the vertical axis represents normalized luminance (%) on the assumption that an initial luminance is 100%, and the horizontal axis represents driving time (h) of the element.

In the reliability testing, the light-emitting element 8 was driven under the conditions where the initial luminance was set to 5000 cd/m² and the current density was constant.

The light-emitting element 8 kept 81% of the initial luminance after the driving for 340 hours.

The above results suggest that an element having high reliability can be realized by using an organometallic complex which is one embodiment of the present invention as a light-emitting material.

EXAMPLE 28

In Example 28, a light-emitting element which is one embodiment of the present invention is described with reference to FIG. 14. Chemical formulas of materials used in this example are shown below. Note that the chemical formulas of the materials described above are omitted.

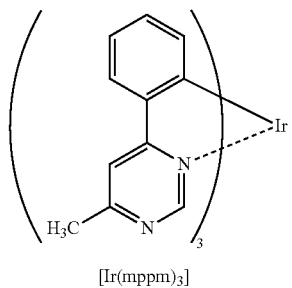

[Ir(mppm)$_3$]

A method of fabricating a light-emitting element 9 of this example is described below.
(Light-Emitting Element 9)

The light-emitting element 9 was fabricated in a manner similar to that in the light-emitting element 7 described in Example 26 except for a light-emitting layer 1113. The light-emitting layer 1113 of the light-emitting element 9 is described below.

Figure 88:
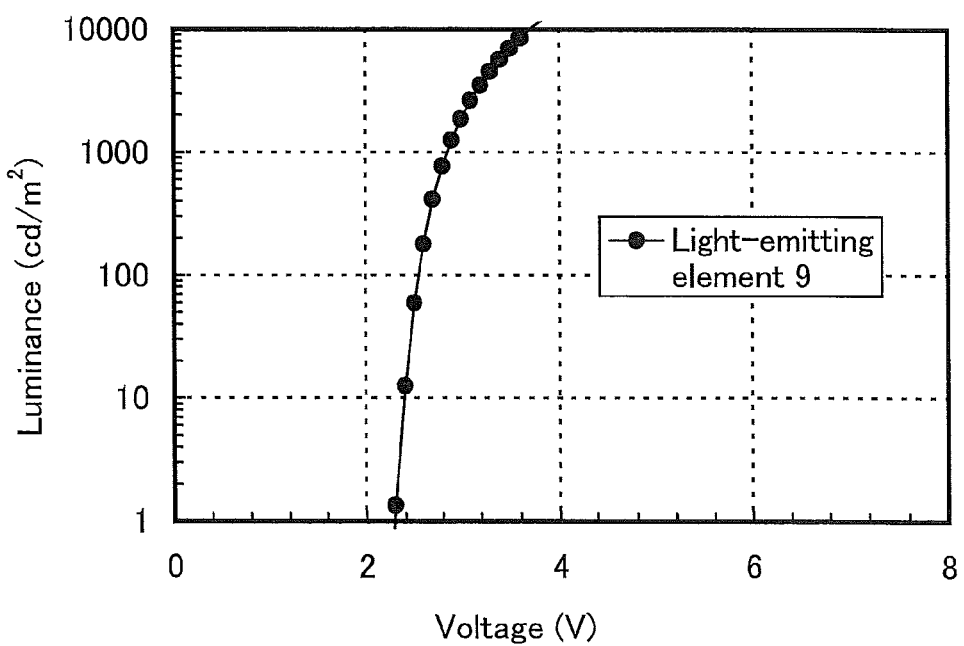
FIG. 88 shows voltage vs. luminance characteristics of the light-emitting element 9.
Figure 89:
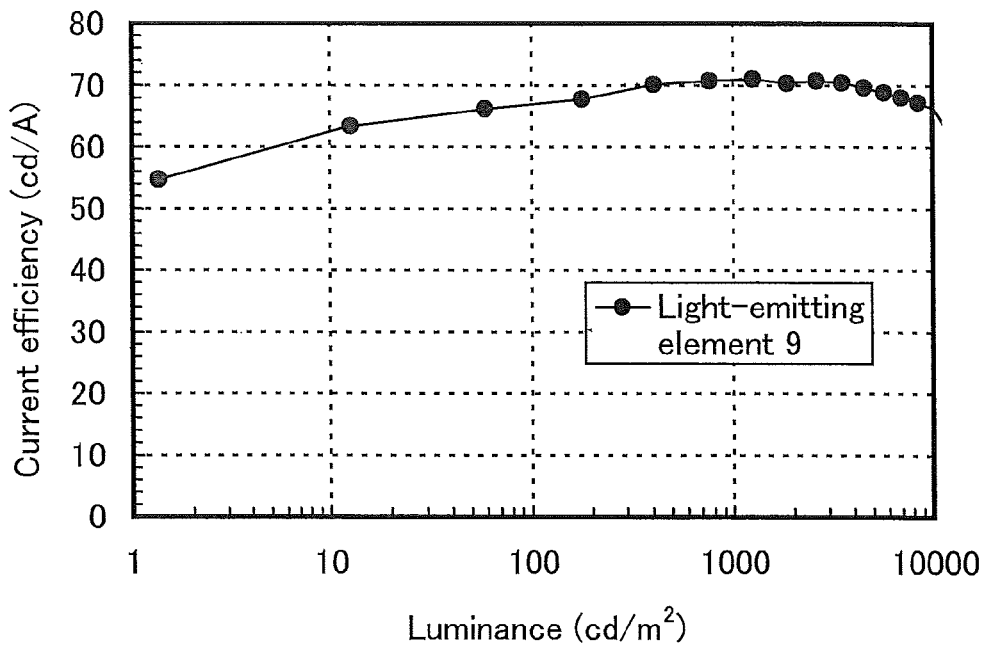
FIG. 89 shows luminance vs. current efficiency characteristics of the light-emitting element 9.

The light-emitting layer 1113 of the light-emitting element 9 was formed by co-evaporation of 2mDBTPDBq-II, PCBA1BP, and tris(4-methyl-6-phenylpyrimidinato)iridium (III) (abbreviation: [Ir(mppm)$_3$]) synthesized in Example 18. The weight ratio of 2mDBTPDBq-II to PCBA1BP and [Ir(mppm)$_3$] was adjusted to 0.8:0.2:0.05 (=2mDBTPDBq-II: PCBA1BP:[ft(mppm)$_3$]). The thickness of the light-emitting layer 1113 was set to 40 nm Table 17 shows an element structure of the light-emitting element 9 obtained as described above.

represents luminance (cd/m$^2$). FIG. 88 shows voltage vs. luminance characteristics thereof. In FIG. 88, the horizontal axis represents voltage (V) and the vertical axis represents luminance (cd/m$^2$). FIG. 89 shows luminance vs. current efficiency characteristics thereof. In FIG. 89, the horizontal axis represents luminance (cd/m$^2$) and the vertical axis represents current efficiency (cd/A). Further, Table 18 shows voltage (V), current density (mA/cm$^2$), CIE chromaticity coordinates (x, y), current efficiency (cd/A), power efficiency (lm/W), and external quantum efficiency (%) of the light-emitting element 9 at a luminance of 770 cd/m$^2$.

TABLE 18

| | Voltage (V) | Current Density (mA/cm$^2$) | Chromaticity (x, y) | Current Efficiency (cd/A) | Power Efficiency (lm/W) | External Quantum Efficiency (%) |
|---|---|---|---|---|---|---|
| Light-emitting Element 9 | 2.8 | 1.1 | (0.41, 0.58) | 71 | 79 | 20 |

Figure 90:
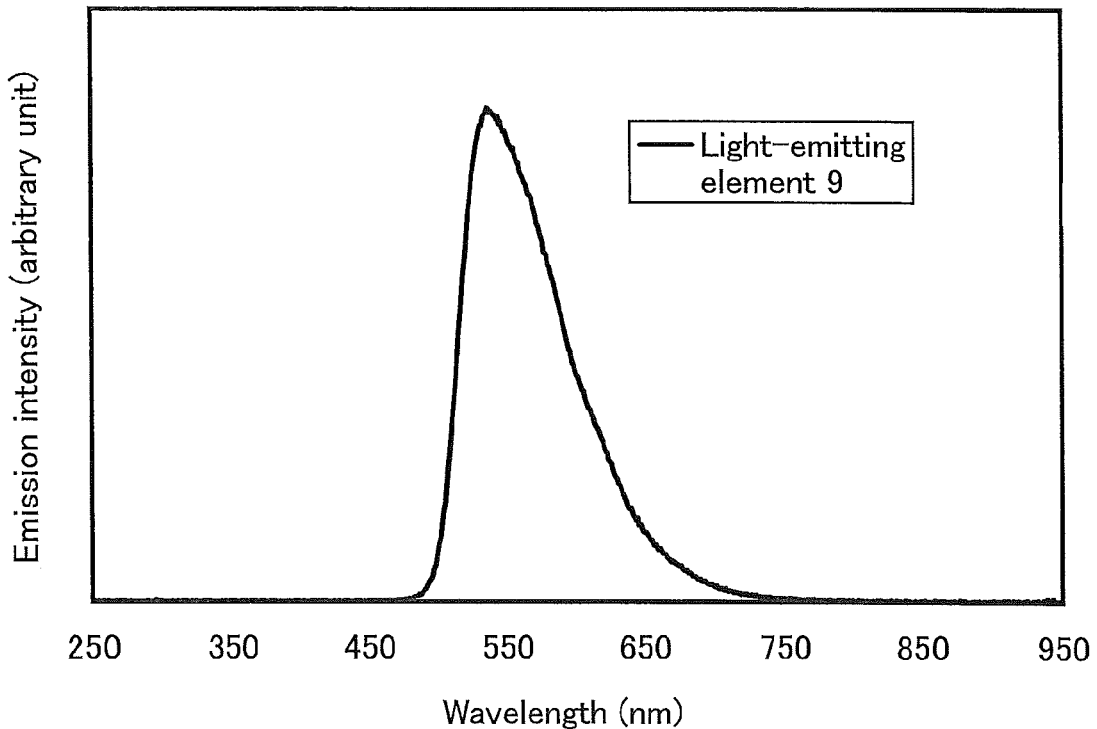
FIG. 90 shows an emission spectrum of the light-emitting element 9.

FIG. 90 shows an emission spectrum of the light-emitting element 9 which was obtained by applying a current of 0.1 mA. In FIG. 90, the horizontal axis represents wavelength (nm) and the vertical axis represents light emission intensity (arbitrary unit). As shown in FIG. 90, the emission spectrum of the light-emitting element 9 has a peak at 536 nm. In addition, as shown in Table 18, the CIE chromaticity coordinates of the light-emitting element 9 were (x, y)=(0.41, 0.58) at a luminance of 770 cd/m$^2$. The results show that yellow green light emission originating from [Ir(mppm)$_3$] was obtained from the light-emitting element 9.

Figure 87:
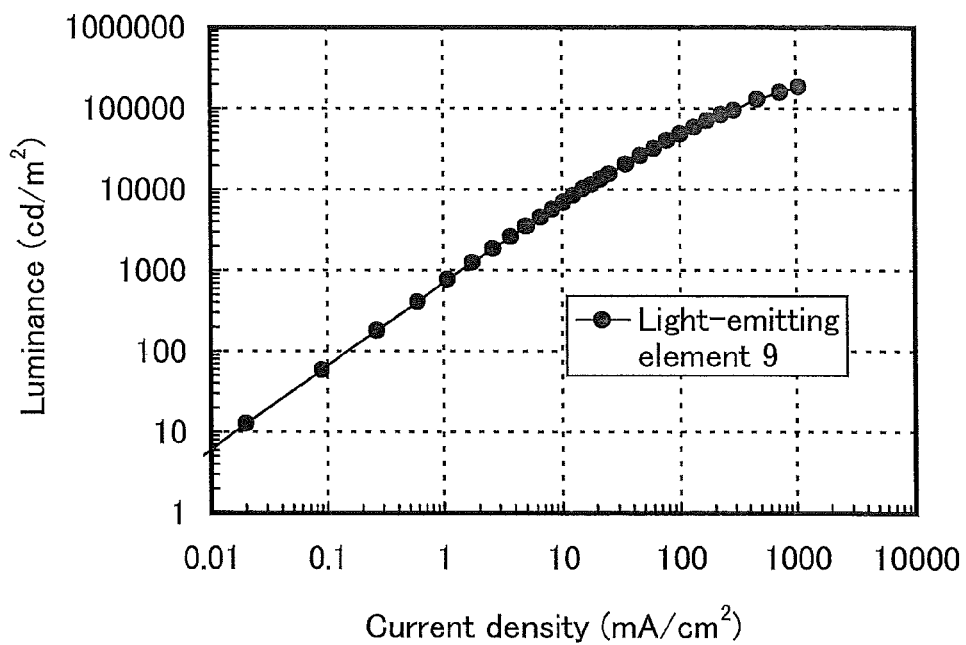
FIG. 87 shows current density vs. luminance characteristics of a light-emitting element 9.

Table 18, FIG. 87, FIG. 88, and FIG. 89 indicate that the light-emitting element 9 has high emission efficiency.

The above results suggest that an element with high emission efficiency can be realized by using the organometallic complex which is one embodiment of the present invention as a light-emitting material.

Figure 91:
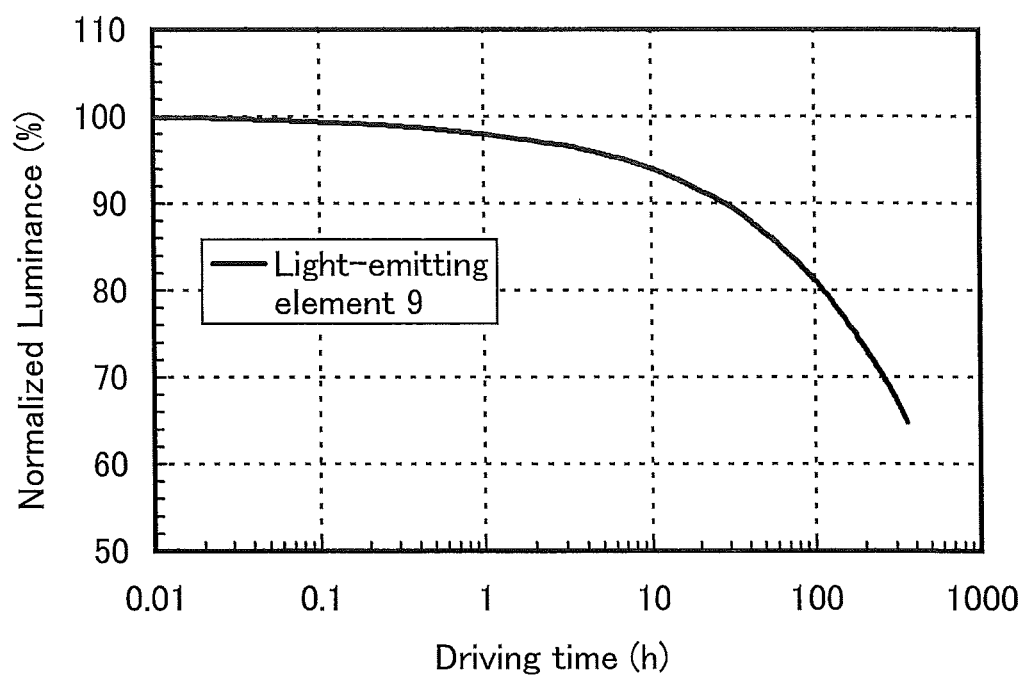
FIG. 91 shows results obtained by reliability testing of the light-emitting element 9.

Next, reliability testing of the light-emitting element 9 was carried out. Results of the reliability testing are shown in FIG. 91. In FIG. 91, the vertical axis represents normalized luminance (%) on the assumption that an initial luminance is 100%, and the horizontal axis represents driving time (h) of the element.

TABLE 17

| | First Electrode | Hole-injection Layer | Hole-transport Layer | Light-emitting Layer | First electron-Transport Layer | Second electron-Transport Layer | Electron-injection Layer | Second Electrode |
|---|---|---|---|---|---|---|---|---|
| Light-emitting Element 9 | ITSO 110 nm | DBT3P-II:MoOx (=4:2) 40 nm | BPAFLP 20 nm | 2mDBTPDBq-II:PCBA1BP:[Ir(mppm)$_3$] (=0.8:0.2:0.05) 40 nm | 2mDBTPDBq-II 10 nm | BPhen 20 nm | LiF 1 nm | Al 200 nm |

In a glove box containing a nitrogen atmosphere, the light-emitting element 9 was sealed so as not to be exposed to the air. After that, operation characteristics of the light-emitting element 9 were measured. Note that the measurements were carried out at room temperature (in an atmosphere kept at 25° C.).

FIG. 87 shows current density vs. luminance characteristics of the light-emitting element 9. In FIG. 87, the horizontal axis represents current density (mA/cm$^2$) and the vertical axis In the reliability testing, the light-emitting element 9 was driven under the conditions where the initial luminance was set to 5000 cd/m$^2$ and the current density was constant.

The light-emitting element 9 kept 65% of the initial luminance after the driving for 360 hours.

The above results suggest that an element having high reliability can be realized by using an organometallic complex which is one embodiment of the present invention as a light-emitting material.

EXAMPLE 29

In Example 29, a light-emitting element which is one embodiment of the present invention is described with reference to FIG. 14. Chemical formulas of materials used in this example are shown below. Note that the chemical formulas of the materials described above are omitted.

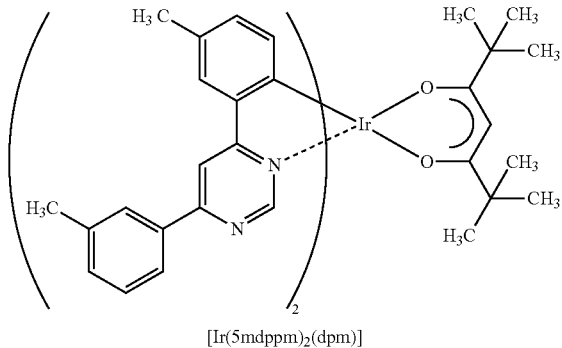

[Ir(5mdppm)₂(dpm)]

A method of fabricating a light-emitting element 10 of this example is described below.
(Light-Emitting Element 10)

The light-emitting element 10 was fabricated in a manner similar to that in the light-emitting element 7 described in Example 26 except for a light-emitting layer 1113. The light-emitting layer 1113 of the light-emitting element 10 is described below.

The light-emitting layer 1113 of the light-emitting element 10 was formed by co-evaporation of 2mDBTPDBq-II, NPB, and bis[4,6-bis(3-methylphenyl)pyrimidinato](dipivaloyl-methanato)iridium(III) (abbreviation: [Ir(5mdppm)₂(dpm)]) synthesized in Example 19. The weight ratio of 2mDBTP-DBq-II to NPB and [Ir(5mdppm)₂(dpm)] was adjusted to 0.8:0.2:0.05 (=2mDBTPDBq-II:NPB:[ft(5mdppm)₂(dpm)]). The thickness of the light-emitting layer 1113 was set to 40 nm.

Table 19 shows an element structure of the light-emitting element 10 obtained as described above.

In a glove box containing a nitrogen atmosphere, the light-emitting element 10 was sealed so as not to be exposed to the air. After that, operation characteristics of the light-emitting element 10 were measured. Note that the measurements were carried out at room temperature (in an atmosphere kept at 25° C.).

Figure 92:
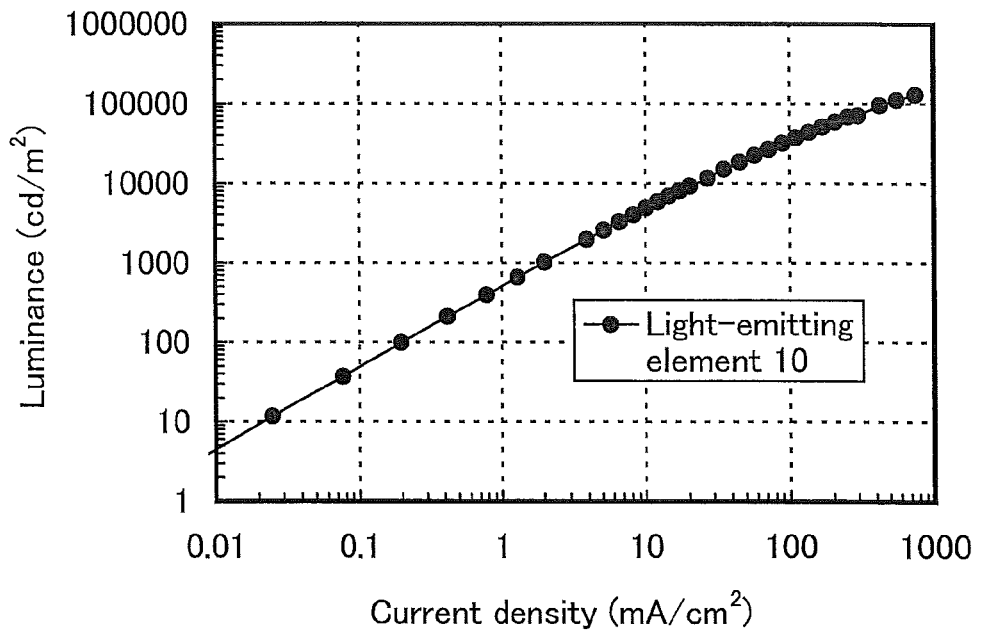
FIG. 92 shows current density vs. luminance characteristics of a light-emitting element 10.
Figure 93:
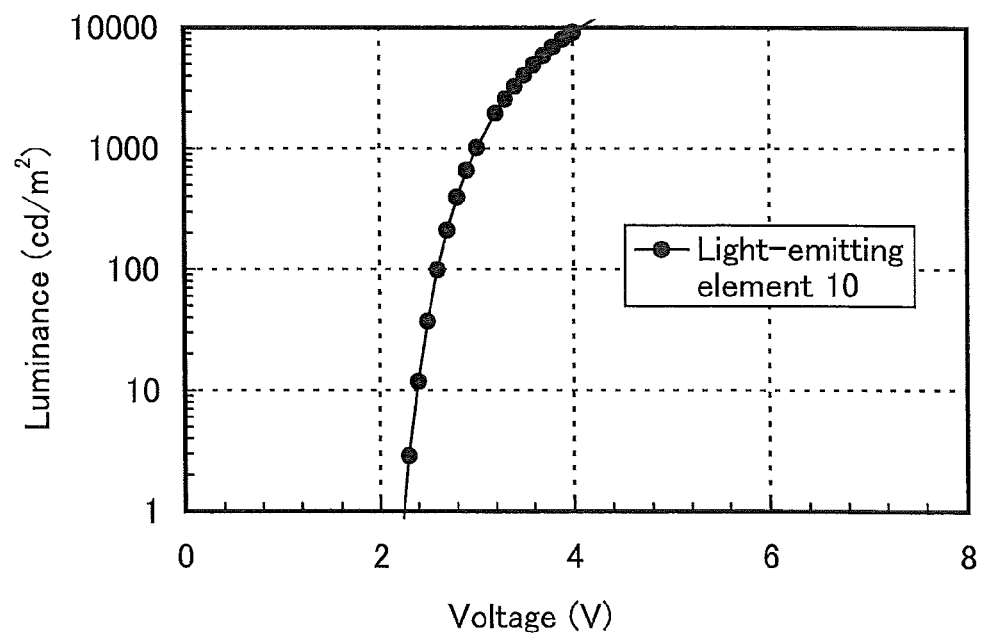
FIG. 93 shows voltage vs. luminance characteristics of the light-emitting element 10.
Figure 94:
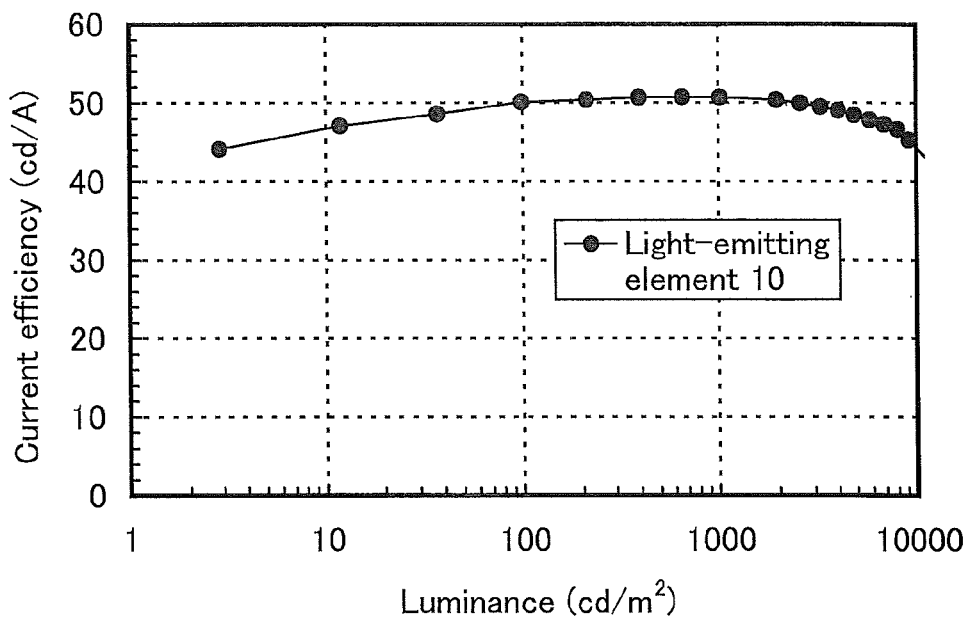
FIG. 94 shows luminance vs. current efficiency characteristics of the light-emitting element 10.
Figure 96:
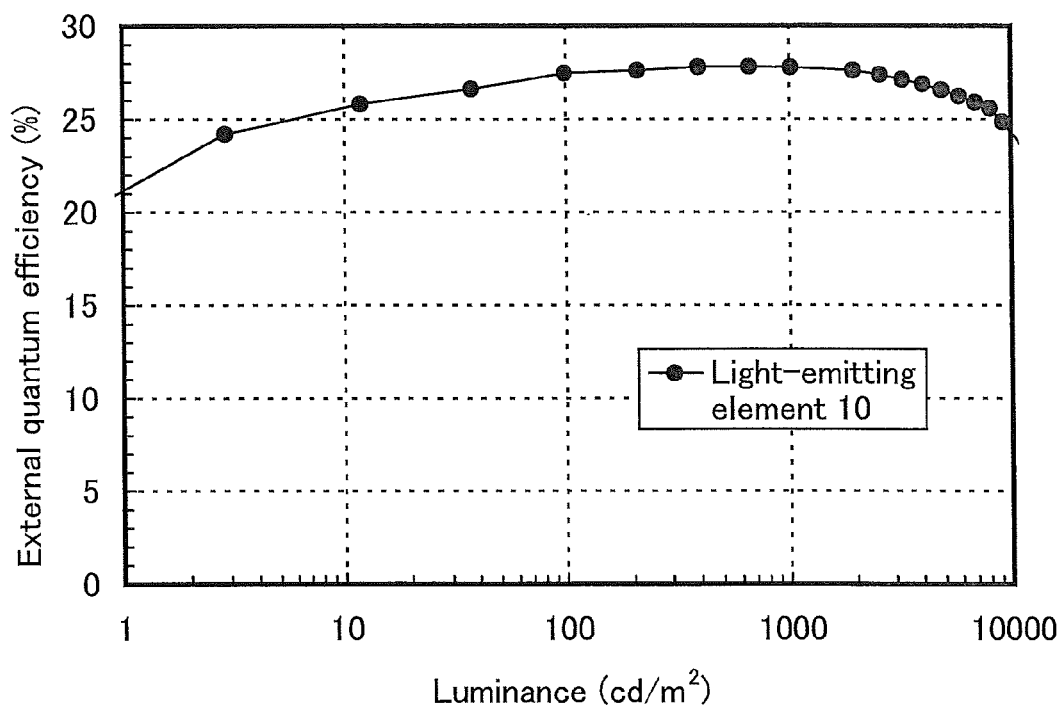
FIG. 96 shows luminance vs. external quantum efficiency characteristics of the light-emitting element 10.

FIG. 92 shows current density vs. luminance characteristics of the light-emitting element 10. In FIG. 92, the horizontal axis represents current density (mA/cm²) and the vertical axis represents luminance (cd/m²). FIG. 93 shows voltage vs. luminance characteristics thereof. In FIG. 93, the horizontal axis represents voltage (V) and the vertical axis represents luminance (cd/m²). FIG. 94 shows luminance vs. current efficiency characteristics thereof. In FIG. 94, the horizontal axis represents luminance (cd/m²) and the vertical axis represents current efficiency (cd/A). In addition, FIG. 96 shows luminance vs. external quantum efficiency characteristics thereof. In FIG. 96, the horizontal axis represents luminance (cd/m²) and the vertical axis represents external quantum efficiency (%).

Further, Table 20 shows voltage (V), current density (mA/cm²), CIF, chromaticity coordinates (x, y), current efficiency (cd/A), power efficiency (lm/W), and external quantum efficiency (%) of the light-emitting element 10 at a luminance of 1000 cd/m².

TABLE 20

| | Voltage (V) | Current Density (mA/cm²) | Chromaticity (x, y) | Current Efficiency (cd/A) | Power Efficiency (lm/W) | External Quantum Efficiency (%) |
|---|---|---|---|---|---|---|
| Light-emitting Element 10 | 3.0 | 2.0 | (0.62, 0.38) | 51 | 53 | 28 |

Figure 95:
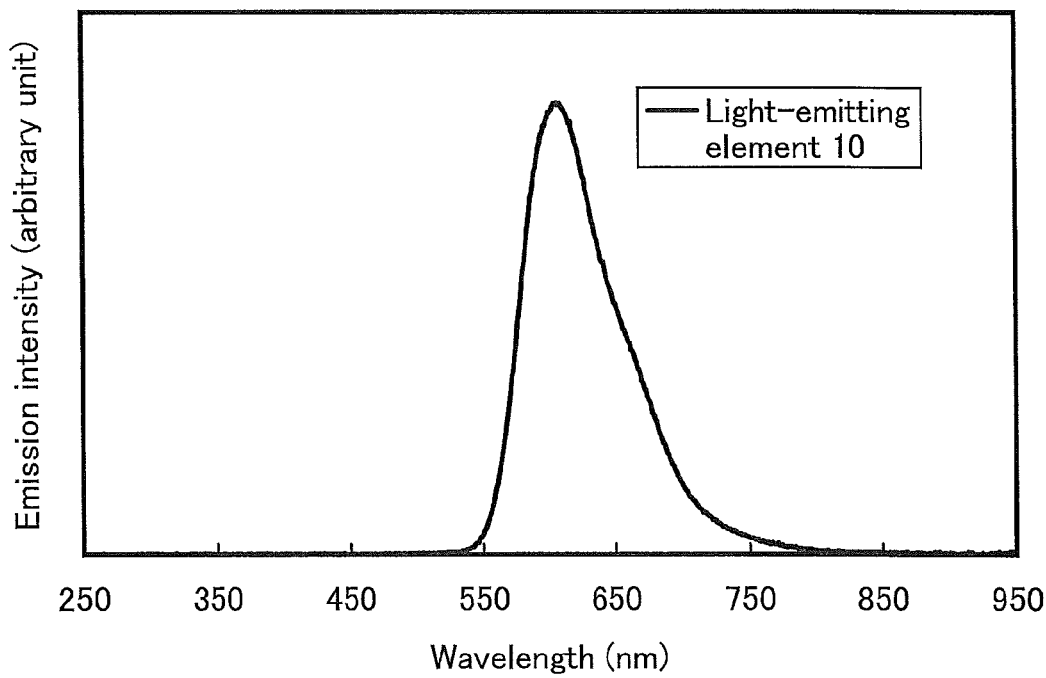
FIG. 95 shows an emission spectrum of the light-emitting element 10.

FIG. 95 shows an emission spectrum of the light-emitting element 10 which was obtained by applying a current of 0.1 mA. In FIG. 95, the horizontal axis represents wavelength (nm) and the vertical axis represents light emission intensity (arbitrary unit). As shown in FIG. 95, the emission spectrum of the light-emitting element 10 has a peak at 606 nm. In addition, as shown in Table 20, the CIE chromaticity coordinates of the light-emitting element 10 were (x, y)=(0.62, 0.38) at a luminance of 1000 cd/m². The results show that orange light emission originating from [Ir(5mdppm)₂(dpm)] was obtained from the light-emitting element 10.

FIG. 92, FIG. 93, FIG. 94, FIG. 96, and Table 20 indicate that the light-emitting element 10 has high emission efficiency. In particular, the light-emitting element 10 has an extremely high external quantum efficiency at a luminance of 1000 cd/m², which is 28%. Note that it is said that the light

TABLE 19

| | First Electrode | Hole-injection Layer | Hole-transport Layer | Light-emitting Layer | | First electron-Transport Layer | Second electron-Transport Layer | Electron-injection Layer | Second Electrode |
|---|---|---|---|---|---|---|---|---|---|
| Light-emitting Element 10 | ITSO 110 nm | DBT3P-II:MoOx (=4:2) 40 nm | BPAFLP 20 nm | 2mDBTPDBq-II:NPB:[Ir(5m dppm)₂(dpm)] (=0.8:0.2:0.05) 40 nm | | 2mDBTPDBq-II 10 nm | BPhen 20 nm | LiF 1 nm | Al 200 nm | extraction efficiency of an organic EL element is approximately 20% to 30%, considering light absorption by upper and lower electrodes (the light extraction efficiency is considered to be reduced by approximately 10%) or the like, the limit of the external quantum efficiency can be approximately 25% at most. However, the results of the external quantum efficiency this time is over the limit, indicating that the conventional theoretical value of the light extraction efficiency was wrong. That is, by using the organometallic complex which is one embodiment of the present invention, a novel light-emitting element with such a high efficiency can be realized, so that it is possible to indicate the theoretical value of the light extraction efficiency is wrong.

The above results suggest that an element with high emission efficiency can be realized by using the organometallic complex which is one embodiment of the present invention as a light-emitting material.

Figure 97:
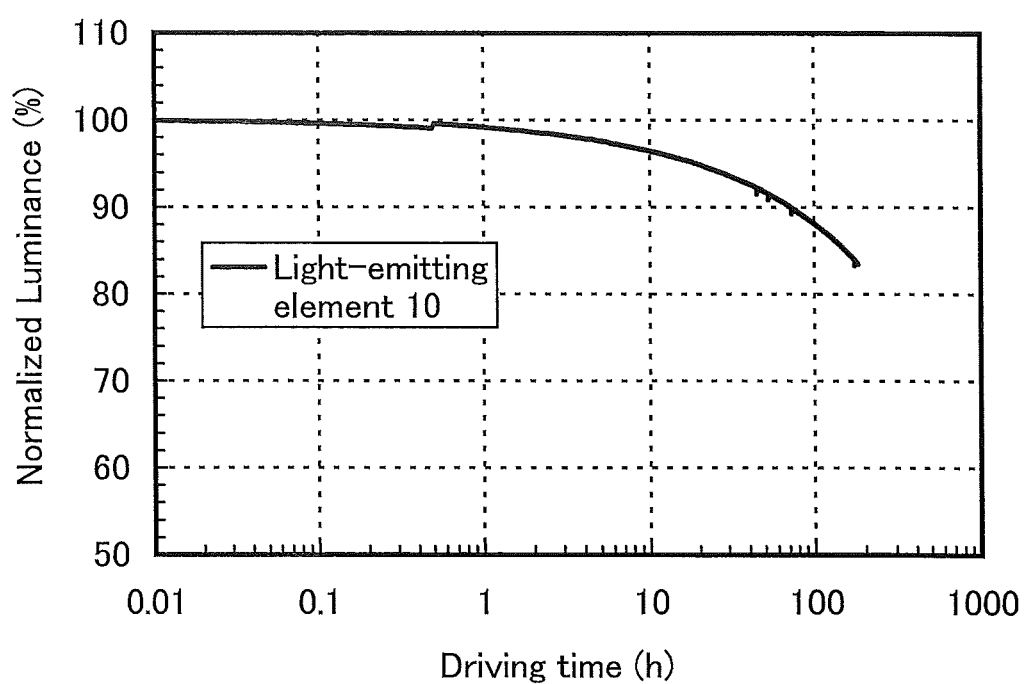
FIG. 97 shows results obtained by reliability testing of the light-emitting element 10.

Next, reliability testing of the light-emitting element 10 was carried out. Results of the reliability testing are shown in FIG. 97. In FIG. 97, the vertical axis represents normalized luminance (%) on the assumption that an initial luminance is 100%, and the horizontal axis represents driving time (h) of the element.

The light-emitting layer 1113 of the light-emitting element 11 was formed by co-evaporation of 2mDBTPDBq-II, NPB, and (diisobutyrylmethanato)bis[4,6-bis(3-methylphenyl)pyrimidinato] iridium(III) (abbreviation: [Ir(5mdppm)$_2$(dibm)]) synthesized in Example 20. The weight ratio of 2mDBTPDBq-II to NPB and [Ir(5mdppm)$_2$(dibm)] was adjusted to 0.8:0.2:0.05 (=2mDBTPDBq-II:NPB:[ft(5mdppm)$_2$(dibm)]). The thickness of the light-emitting layer 1113 was set to 40 nm.

Table 21 shows an element structure of the light-emitting element 11 obtained as described above.

TABLE 21

| | First Electrode | Hole-injection Layer | Hole-transport Layer | Light-emitting Layer | First electron-Transport Layer | Second electron-Transport Layer | Electron-injection Layer | Second Electrode |
|---|---|---|---|---|---|---|---|---|
| Light-emitting Element 11 | ITSO 110 nm | DBT3P-II:MoOx (=4:2) 40 nm | BPAFLP 20 nm | 2mDBTPDBq-II:NPB:[Ir(5m dppm)$_2$ (dibm)] (=0.8:02:0.05) 40 nm | 2mDBTPDBq-II 10 nm | BPhen 20 nm | LiF 1 nm | Al 200 nm |

In the reliability testing, the light-emitting element 10 was driven under the conditions where the initial luminance was set to 5000 cd/m$^2$ and the current density was constant.

The light-emitting element 10 kept 83% of the initial luminance after the driving for 180 hours.

The above results suggest that an element having high reliability can be realized by using an organometallic complex which is one embodiment of the present invention as a light-emitting material.

EXAMPLE 30

In Example 30, a light-emitting element which is one embodiment of the present invention is described with reference to FIG. 14. Chemical formulas of materials used in this example are shown below. Note that the chemical formulas of the materials described above are omitted.

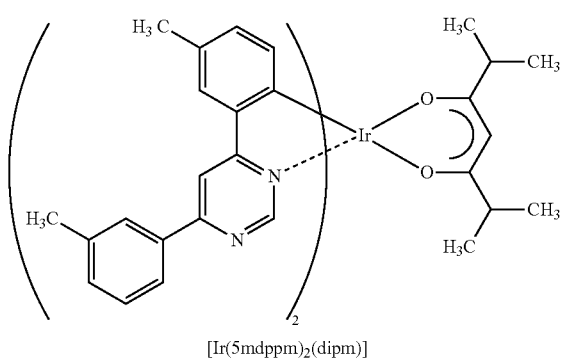

[Ir(5mdppm)$_2$(dipm)]

A method of fabricating a light-emitting element 11 of this example is described below.
(Light-Emitting Element 11)
The light-emitting element 11 was fabricated in a manner similar to that in the light-emitting element 7 described in Example 26 except for a light-emitting layer 1113. The light-emitting layer 1113 of the light-emitting element 11 is described below.

In a glove box containing a nitrogen atmosphere, the light-emitting element 11 was sealed so as not to be exposed to the air. After that, operation characteristics of the light-emitting element 11 were measured. Note that the measurements were carried out at room temperature (in an atmosphere kept at 25° C.).

Figure 98:
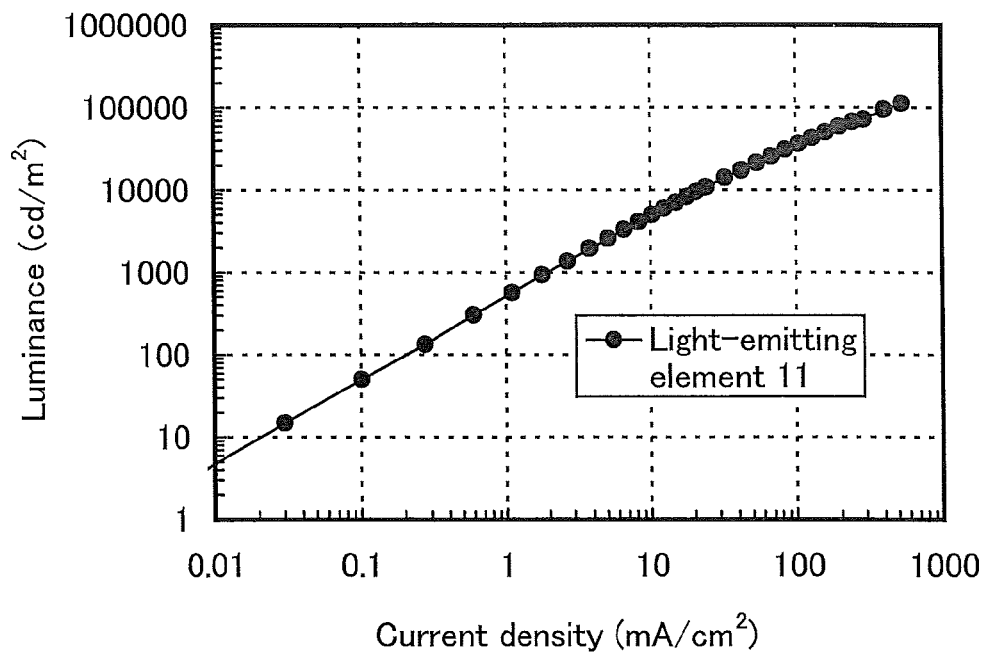
FIG. 98 shows current density vs. luminance characteristics of a light-emitting element 11.
Figure 99:
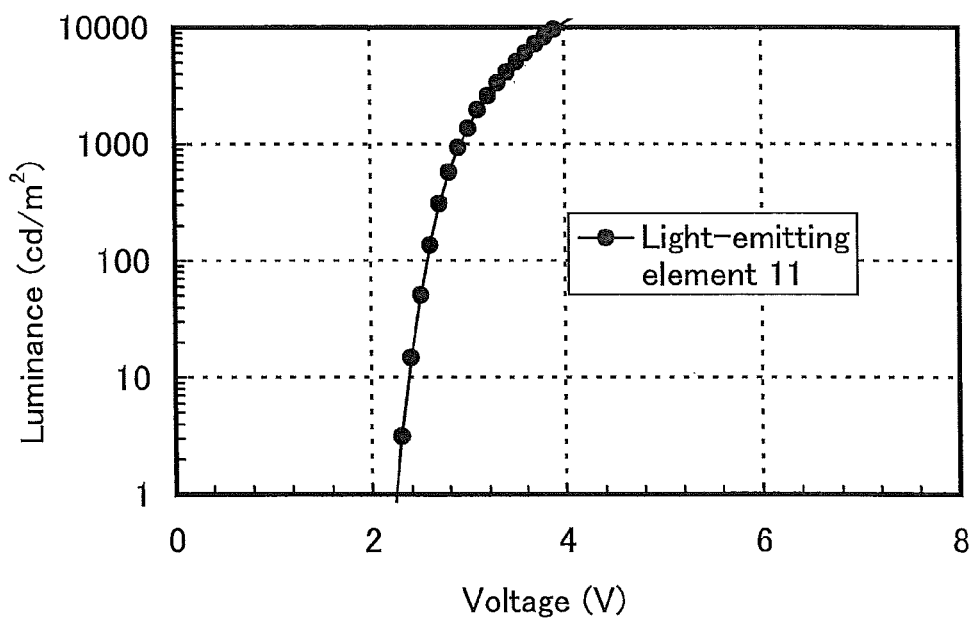
FIG. 99 shows voltage vs. luminance characteristics of the light-emitting element 11.
Figure 100:
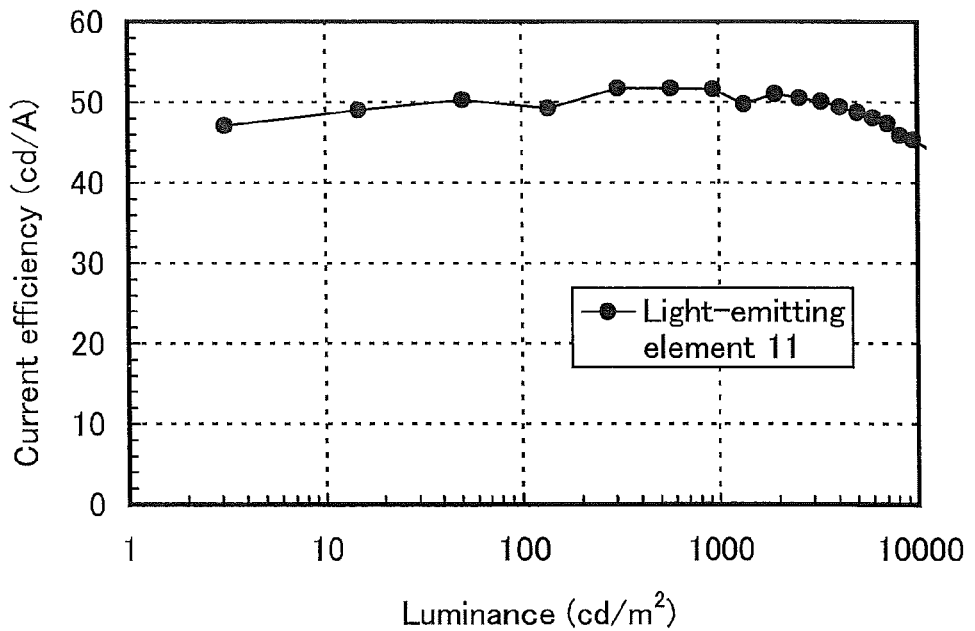
FIG. 100 shows luminance vs. current efficiency characteristics of the light-emitting element 11.
Figure 102:
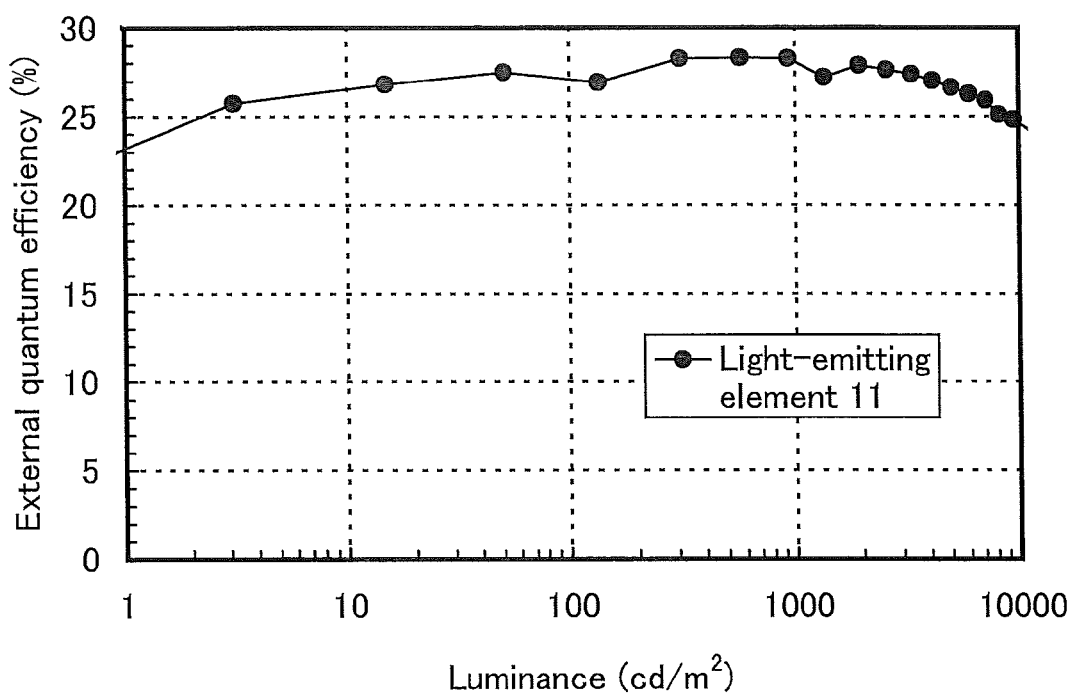
FIG. 102 shows luminance vs. external quantum efficiency characteristics of the light-emitting element 11.

FIG. 98 shows current density vs. luminance characteristics of the light-emitting element 11. In FIG. 98, the horizontal axis represents current density (mA/cm$^2$) and the vertical axis represents luminance (cd/m$^2$). FIG. 99 shows voltage vs. luminance characteristics thereof. In FIG. 99, the horizontal axis represents voltage (V) and the vertical axis represents luminance (cd/m$^2$). FIG. 100 shows luminance vs. current efficiency characteristics thereof. In FIG. 100, the horizontal axis represents luminance (cd/m$^2$) and the vertical axis represents current efficiency (cd/A). In addition, FIG. 102 shows luminance vs. external quantum efficiency characteristics thereof. In FIG. 102, the horizontal axis represents luminance (cd/m$^2$) and the vertical axis represents external quantum efficiency (%).

Further, Table 22 shows voltage (V), current density (mA/cm$^2$), CIE chromaticity coordinates (x, y), current efficiency (cd/A), power efficiency (lm/W), and external quantum efficiency (%) of the light-emitting element 11 at a luminance of 930 cd/m$^2$.

TABLE 22

| | Voltage (V) | Current Density (mA/cm$^2$) | Chromaticity (x, y) | Current Efficiency (cd/A) | Power Efficiency (lm/W) | External Quantum Efficiency (%) |
|---|---|---|---|---|---|---|
| Light-emitting Element 11 | 2.9 | 1.8 | (0.61, 0.38) | 52 | 56 | 28 |

Figure 101:
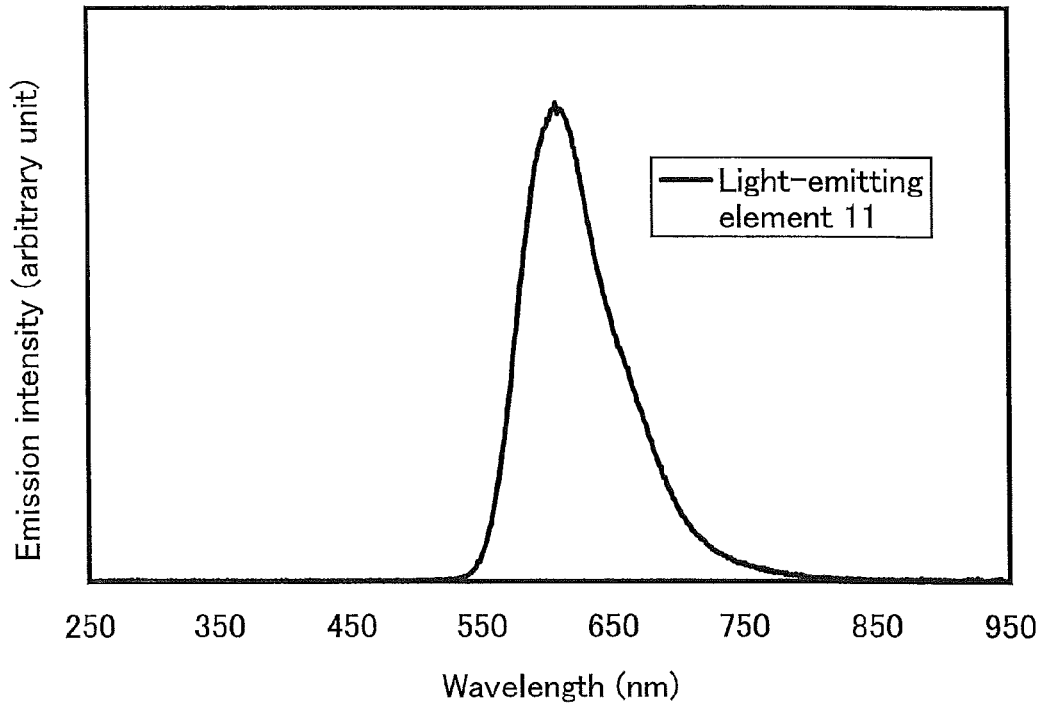
FIG. 101 shows an emission spectrum of the light-emitting element 11.

FIG. 101 shows an emission spectrum of the light-emitting element 11 which was obtained by applying a current of 0.1 mA. In FIG. 101, the horizontal axis represents wavelength (nm) and the vertical axis represents light emission intensity (arbitrary unit). As shown in FIG. 101, the emission spectrum of the light-emitting element 11 has a peak at 607 nm. In addition, as shown in Table 22, the CIE chromaticity coordinates of the light-emitting element 11 were (x, y)=(0.61, 0.38) at a luminance of 930 cd/m². The results show that orange light emission originating from [Ir(5mdppm)$_2$(dibm)] was obtained from the light-emitting element 11.

FIG. 98, FIG. 99, FIG. 100, FIG. 102, and Table 22 indicate that the light-emitting element 11 has high emission efficiency. In particular, the light-emitting element 11 has an extremely high external quantum efficiency at a luminance of 930 cd/m², which is 28%. Note that it is said that the light extraction efficiency of an organic EL element is approximately 20% to 30%, considering light absorption by upper and lower electrodes (the light extraction efficiency is considered to be reduced by approximately 10%) or the like, the limit of the external quantum efficiency can be approximately 25% at most. However, the results of the external quantum efficiency this time is over the limit, indicating that the conventional theoretical value of the light extraction efficiency was wrong. That is, by using the organometallic complex which is one embodiment of the present invention, a novel light-emitting element with such a high efficiency can be realized, so that it is possible to indicate the theoretical value of the light extraction efficiency is wrong.

The above results suggest that an element with high emission efficiency can be realized by using the organometallic complex which is one embodiment of the present invention as a light-emitting material.

Figure 103:
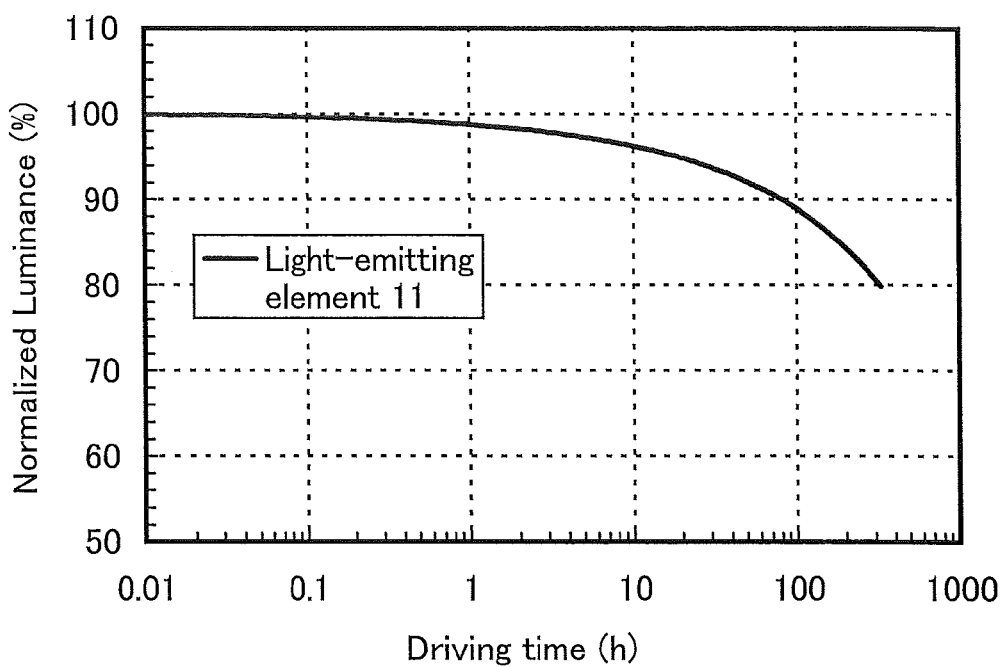
FIG. 103 shows results obtained by reliability testing of the light-emitting element 11.

Next, reliability testing of the light-emitting element 11 was carried out. Results of the reliability testing are shown in FIG. 103. In FIG. 103, the vertical axis represents normalized luminance (%) on the assumption that an initial luminance is 100%, and the horizontal axis represents driving time (h) of the element.

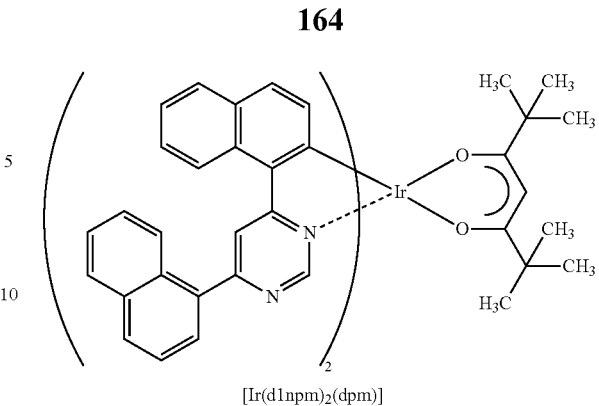

[Ir(d1npm)$_2$(dpm)]

A method of fabricating a light-emitting element 12 of this example is described below.
(Light-Emitting Element 12)

The light-emitting element 12 was fabricated in a manner similar to that in the light-emitting element 7 described in Example 26 except for a light-emitting layer 1113. The light-emitting layer 1113 of the light-emitting element 12 is described below.

The light-emitting layer 1113 of the light-emitting element 12 was formed by co-evaporation of 2mDBTPDBq-II, PCBA1BP, and bis[4,6-di(naphthalen-1-yl)pyrimidinato](dipivaloylmethanato)iridium(III) (abbreviation: [Ir(d1npm)$_2$(dpm)]) synthesized in Example 21. The weight ratio of 2mDBTPDBq-II to PCBA1BP and [Ir(d1npm)$_2$(dpm)] was adjusted to 0.8:0.2:0.05 (=2mDBTPDBq-II: PCBA1BP:[Ir(d1npm)$_2$(dpm)]). The thickness of the light-emitting layer 1113 was set to 40 nm.

Table 23 shows an element structure of the light-emitting element 12 obtained as described above.

TABLE 23

| | First Electrode | Hole-injection Layer | Hole-transport Layer | Light-emitting Layer | First electron-Transport Layer | Second electron-Transport Layer | Electron-injection Layer | Second Electrode |
|---|---|---|---|---|---|---|---|---|
| Light-emitting Element 12 | ITSO 110 nm | DBT3P-II:MoOx (=4:2) 40 nm | BPAFLP 20 nm | 2mDBTPDBq-II:PCBA1BP:[Ir(d1npm)$_2$(dpm)] (=0.8:0.2:0.05) 40 nm | 2mDBTPDBq-II 10 nm | BPhen 20 nm | LiF 1 nm | Al 200 nm |

In the reliability testing, the light-emitting element 11 was driven under the conditions where the initial luminance was set to 5000 cd/m² and the current density was constant.

The light-emitting element 11 kept 80% of the initial luminance after the driving for 330 hours.

The above results suggest that an element having high reliability can be realized by using an organometallic complex which is one embodiment of the present invention as a light-emitting material.

EXAMPLE 31

In Example 31, a light-emitting element which is one embodiment of the present invention is described with reference to FIG. 14. Chemical formulas of materials used in this example are shown below. Note that the chemical formulas of the materials described above are omitted.

In a glove box containing a nitrogen atmosphere, the light-emitting element 12 was sealed so as not to be exposed to the air. After that, operation characteristics of the light-emitting element 12 were measured. Note that the measurements were carried out at room temperature (in an atmosphere kept at 25° C.).

Figure 104:
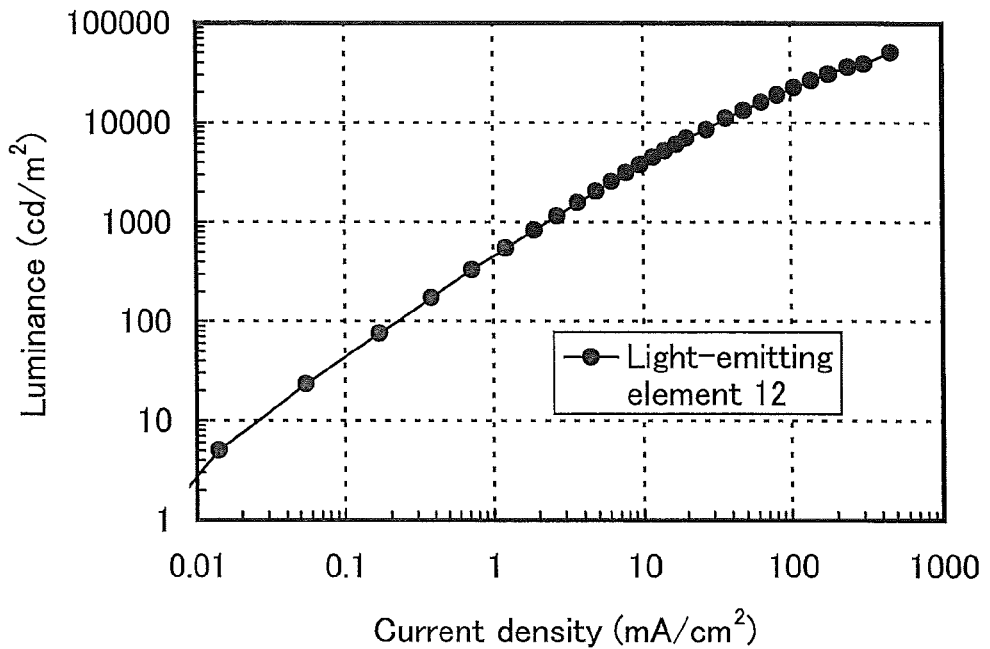
FIG. 104 shows current density vs. luminance characteristics of a light-emitting element 12.
Figure 105:
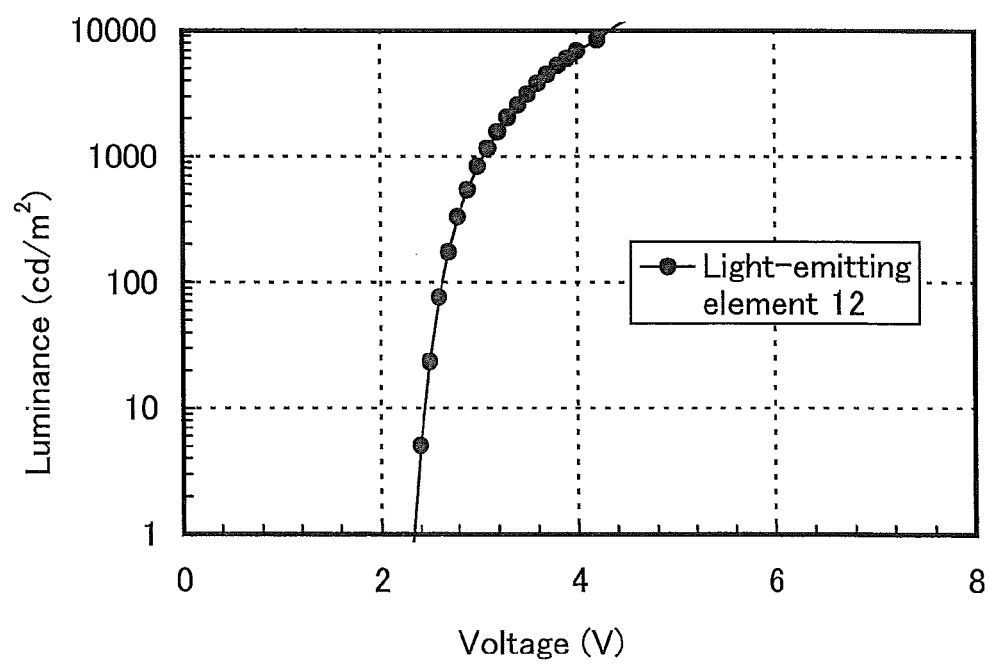
FIG. 105 shows voltage vs luminance characteristics of the light-emitting element 12.
Figure 106:
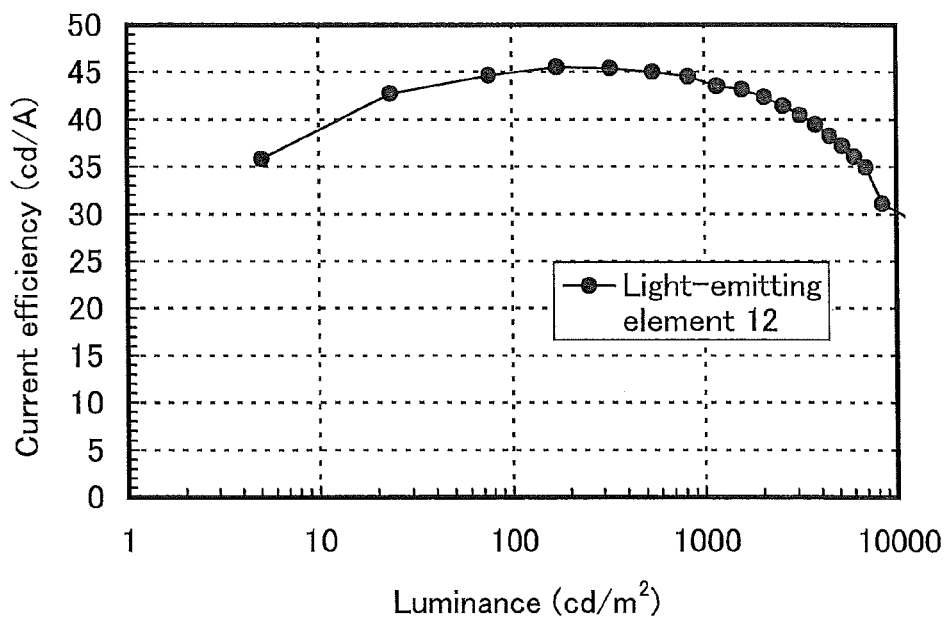
FIG. 106 shows luminance vs. current efficiency characteristics of the light-emitting element 12.

FIG. 104 shows current density vs. luminance characteristics of the light-emitting element 12. In FIG. 104, the horizontal axis represents current density (mA/cm²) and the vertical axis represents luminance (cd/m²). FIG. 105 shows voltage vs. luminance characteristics thereof. In FIG. 105, the horizontal axis represents voltage (V) and the vertical axis represents luminance (cd/m²). FIG. 106 shows luminance vs. current efficiency characteristics thereof. In FIG. 106, the horizontal axis represents luminance (cd/m²) and the vertical axis represents current efficiency (cd/A). Further, Table 24 shows voltage (V), current density (mA/cm²), CIE chromaticity coordinates (x, y), current efficiency (cd/A), power efficiency (lm/W), and external quantum efficiency (%) of the light-emitting element 12 at a luminance of 1200 cd/m².

TABLE 24

|  | Voltage (V) | Current Density (mA/cm²) | Chromaticity (x, y) | Current Efficiency (cd/A) | Power Efficiency (lm/W) | External Quantum Efficiency (%) |
|---|---|---|---|---|---|---|
| Light-emitting Element 12 | 3.1 | 2.7 | (0.63, 0.37) | 44 | 44 | 26 |

Figure 107:
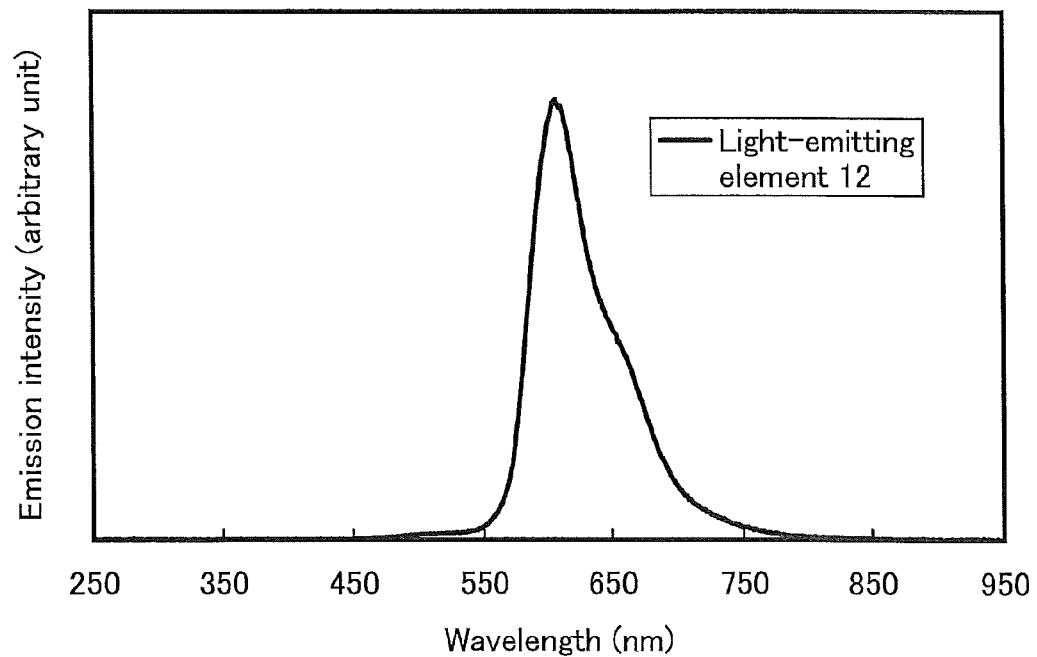
FIG. 107 shows an emission spectrum of the light-emitting element 12.

FIG. 107 shows an emission spectrum of the light-emitting element 12 which was obtained by applying a current of 0.1 mA. In FIG. 107, the horizontal axis represents wavelength (nm) and the vertical axis represents light emission intensity (arbitrary unit). As shown in FIG. 107, the emission spectrum of the light-emitting element 12 has a peak at 607 nm. In addition, as shown in Table 24, the CIE chromaticity coordinates of the light-emitting element 12 were (x, y) (0.63, 0.37) at a luminance of 1200 cd/m². The results show that red light emission originating from [Ir(d1npm)$_2$(dpm)] was obtained from the light-emitting element 12.

Table 24, FIG. 104, FIG. 105, and FIG. 106 indicate that the light-emitting element 12 has high emission efficiency.

The above results suggest that an element with high emission efficiency can be realized by using the organometallic complex which is one embodiment of the present invention as a light-emitting material.

Figure 108:
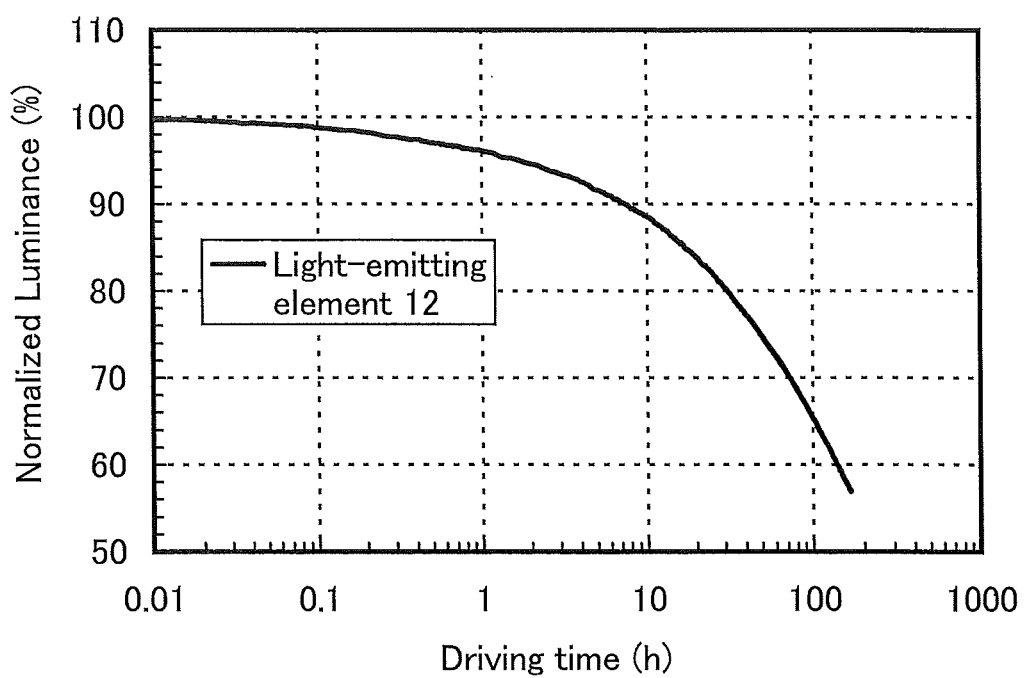
FIG. 108 shows results obtained by reliability testing of the light-emitting element 12.

Next, reliability testing of the light-emitting element 12 was carried out. Results of the reliability testing are shown in FIG. 108. In FIG. 108, the vertical axis represents normalized luminance (%) on the assumption that an initial luminance is 100%, and the horizontal axis represents driving time (h) of the element.

In the reliability testing, the light-emitting element 12 was driven under the conditions where the initial luminance was set to 5000 cd/m² and the current density was constant.

The light-emitting element 12 kept 57% of the initial luminance after the driving for 170 hours.

The above results suggest that an element having high reliability can be realized by using an organometallic complex which is one embodiment of the present invention as a light-emitting material.

EXAMPLE 32

In Example 32, a light-emitting element which is one embodiment of the present invention is described with reference to FIG. 14. Chemical formulas of materials used in this example are shown below. Note that the chemical formulas of the materials described above are omitted.

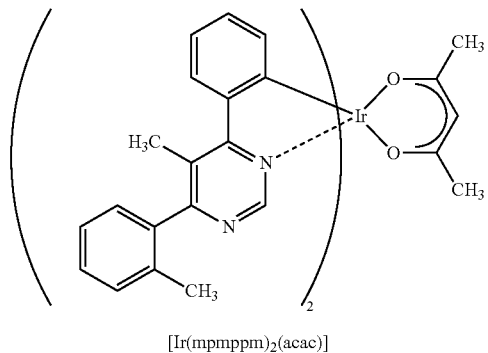

[Ir(mpmppm)$_2$(acac)]

A method of fabricating a light-emitting element 13 of this example is described below.

(Light-Emitting Element 13)

The light-emitting element 13 was fabricated in a manner similar to that in the light-emitting element 7 described in Example 26 except for a light-emitting layer 1113. The light-emitting layer 1113 of the light-emitting element 13 is described below.

The light-emitting layer 1113 of the light-emitting element 13 was formed by co-evaporation of 2mDBTPDBq-II, PCBA1BP, and (acetylacetonato)bis[6-(2-methylphenyl)-4-phenyl-5-methylpyrimidinato]iridium(III) (abbreviation: [Ir(mpmppm)$_2$(acac)]) synthesized in Example 22. The weight ratio of 2mDBTPDBq-II to PCBA1BP and [Ir(mpmppm)$_2$(acac)] was adjusted to 0.8:0.2:0.025 (=2mDBTPDBq-II: PCBA1BP:[Ir(mpmppm)$_2$(acac)]). The thickness of the light-emitting layer 1113 was set to 40 nm.

Table 25 shows an element structure of the light-emitting element 13 obtained as described above.

TABLE 25

|  | First Electrode | Hole-injection Layer | Hole-transport Layer | Light-emitting Layer | First electron-Transport Layer | Second electron-Transport Layer | Electron-injection Layer | Second Electrode |
|---|---|---|---|---|---|---|---|---|
| Light-emitting Element 13 | ITSO 110 nm | DBT3P-II:MoO$x$ (=4:2) 40 nm | BPAFLP 20 nm | 2mDBTPDBq-II:PCBA1BP:[Ir(mpmppm)$_2$(acac)] (=0.8:0.2:0.025) 40 nm | 2mDBTPDBq-II 10 nm | BPhen 20 nm | LiF 1 nm | Al 200 nm |

In a glove box containing a nitrogen atmosphere, the light-emitting element 13 was sealed so as not to be exposed to the air. After that, operation characteristics of the light-emitting element 13 were measured. Note that the measurements were carried out at room temperature (in an atmosphere kept at 25° C.).

Figure 109:
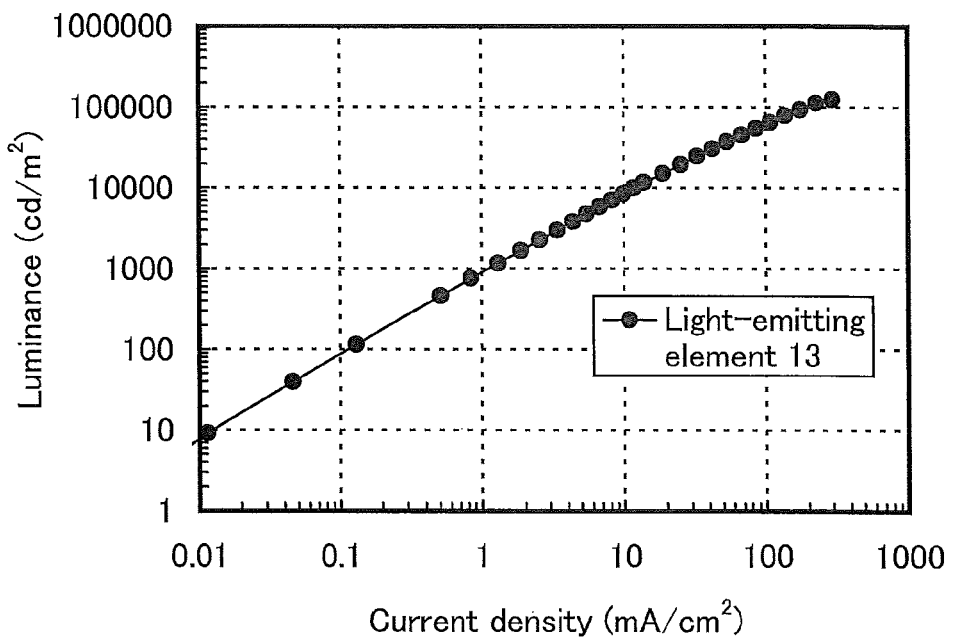
FIG. 109 shows current density vs. luminance characteristics of a light-emitting element 13.
Figure 110:
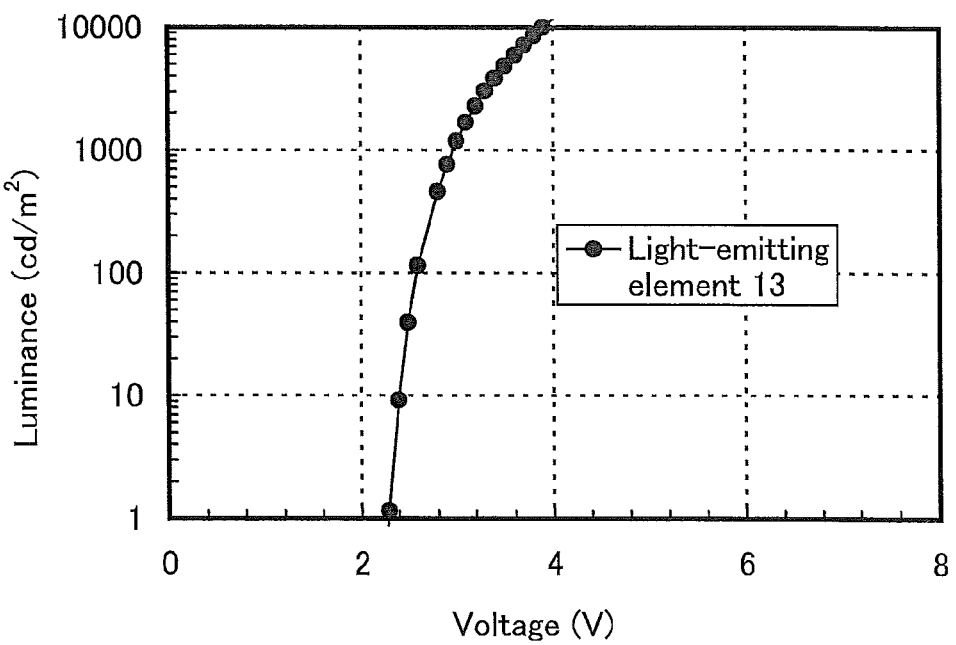
FIG. 110 shows voltage vs. luminance characteristics of the light-emitting element 13.
Figure 111:
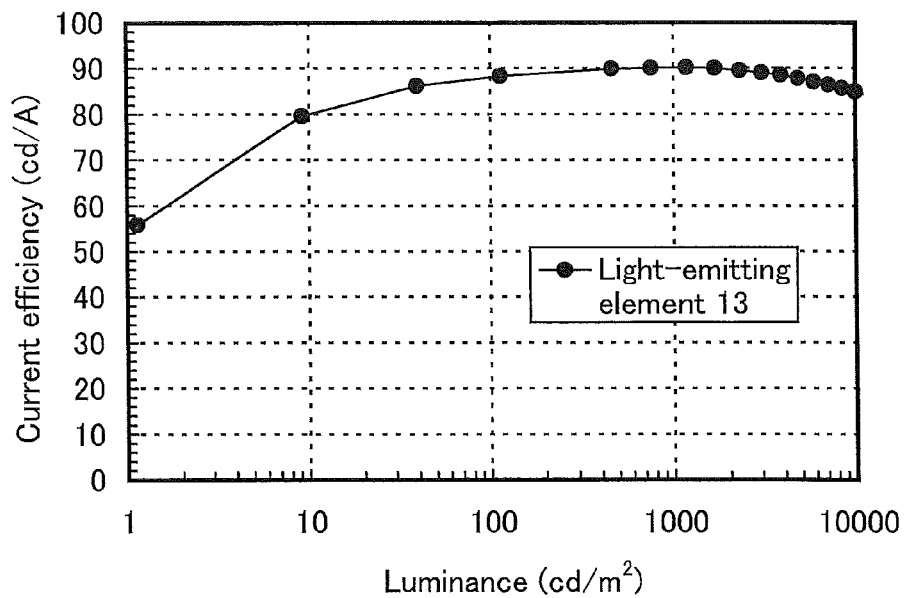
FIG. 111 shows luminance vs. current efficiency characteristics of the light-emitting element 13.
Figure 113:
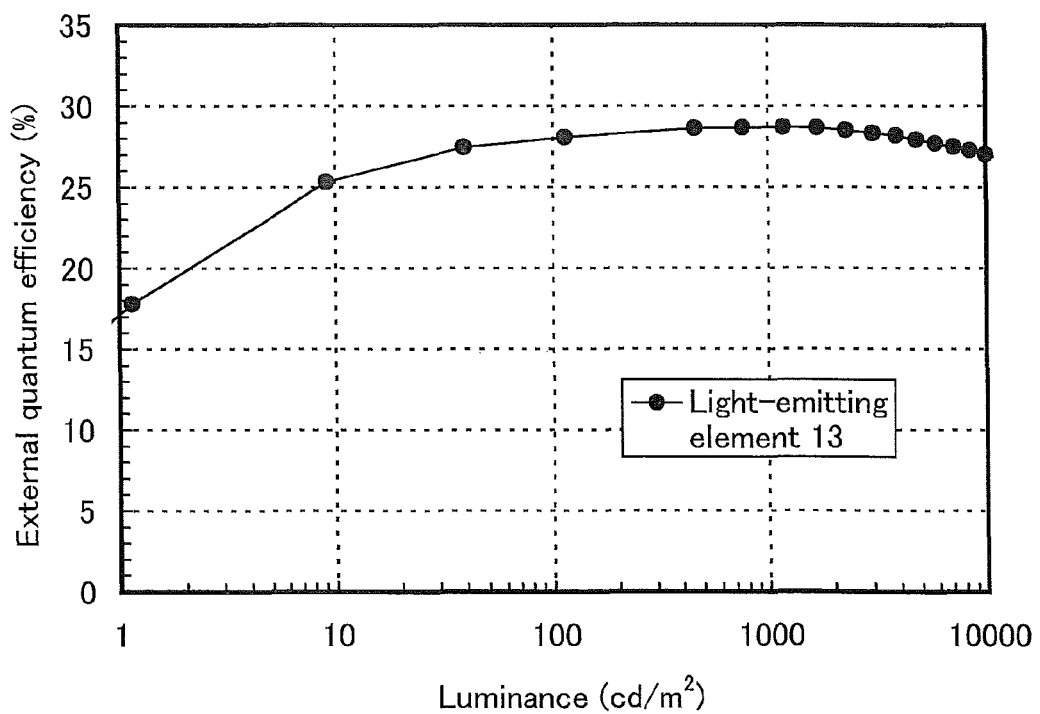
FIG. 113 shows luminance vs. external quantum efficiency characteristics of the light-emitting element 13.

FIG. 109 shows current density vs. luminance characteristics of the light-emitting element 13. In FIG. 109, the horizontal axis represents current density (mA/cm$^2$) and the vertical axis represents luminance (cd/m$^2$). FIG. 110 shows voltage vs. luminance characteristics thereof. In FIG. 110, the horizontal axis represents voltage (V) and the vertical axis represents luminance (cd/m$^2$). FIG. 111 shows luminance vs. current efficiency characteristics thereof. In FIG. 111, the horizontal axis represents luminance (cd/m$^2$) and the vertical axis represents current efficiency (cd/A). In addition, FIG. 113 shows luminance vs. external quantum efficiency characteristics thereof. In FIG. 113, the horizontal axis represents luminance (cd/m$^2$) and the vertical axis represents external quantum efficiency (%).

Further, Table 26 shows voltage (V), current density (mA/cm$^2$), CIE chromaticity coordinates (x, y), current efficiency (cd/A), power efficiency (1 m/W), and external quantum efficiency (%) of the light-emitting element 13 at a luminance of 1200 cd/m$^2$.

TABLE 26

| | Voltage (V) | Current Density (mA/cm$^2$) | Chromaticity (x, y) | Current Efficiency (cd/A) | Power Efficiency (lm/W) | External Quantum Efficiency (%) |
|---|---|---|---|---|---|---|
| Light-emitting Element 13 | 3.0 | 1.3 | (0.50, 0.49) | 90 | 94 | 29 |

Figure 112:
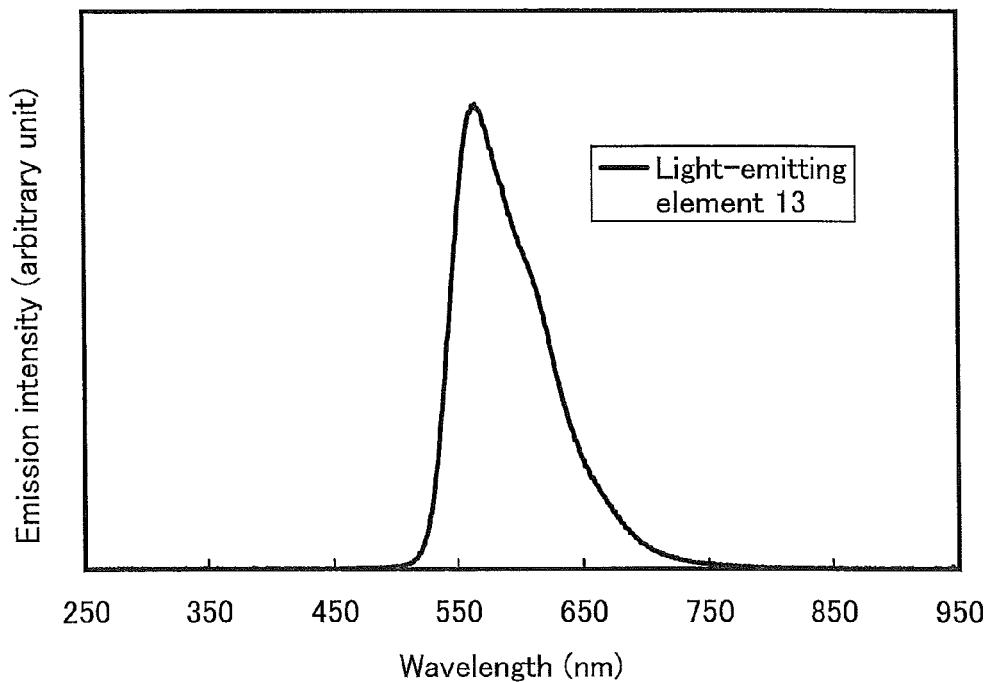
FIG. 112 shows an emission spectrum of the light-emitting element 13.

FIG. 112 shows an emission spectrum of the light-emitting element 13 which was obtained by applying a current of 0.1 mA. In FIG. 112, the horizontal axis represents wavelength (nm) and the vertical axis represents light emission intensity (arbitrary unit). As shown in FIG. 112, the emission spectrum of the light-emitting element 13 has a peak at 565 nm. In addition, as shown in Table 26, the CIE chromaticity coordinates of the light-emitting element 13 were (x, y) (0.50, 0.49) at a luminance of 1200 cd/m$^2$. The results show that yellow light emission originating from [Ir(mpmppm)$_2$(acac)] was obtained from the light-emitting element 13.

FIG. 109, FIG. 110, FIG. 111, FIG. 113, and Table 26 indicate that the light-emitting element 13 has high emission efficiency. In particular, the light-emitting element 13 has an extremely high external quantum efficiency at a luminance of 1200 cd/m$^2$, which is 29%. Note that it is said that the light extraction efficiency of an organic EL element is approximately 20% to 30%, considering light absorption by upper and lower electrodes (the light extraction efficiency is considered to be reduced by approximately 10%) or the like, the limit of the external quantum efficiency can be approximately 25% at most. However, the results of the external quantum efficiency this time is over the limit, indicating that the conventional theoretical value of the light extraction efficiency was wrong. That is, by using the organometallic complex which is one embodiment of the present invention, a novel light-emitting element with such a high efficiency can be realized, so that it is possible to indicate the theoretical value of the light extraction efficiency is wrong.

The above results suggest that an element with high emission efficiency can be realized by using the organometallic complex which is one embodiment of the present invention as a light-emitting material.

Figure 114:
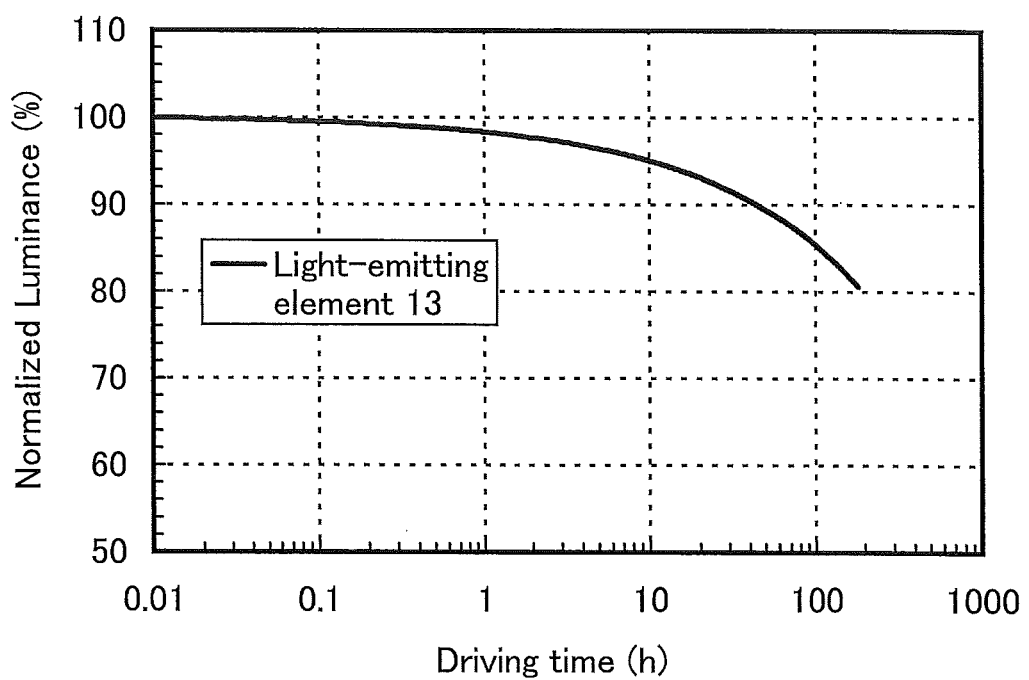
FIG. 114 shows results obtained by reliability testing of the light-emitting element 13.

Next, reliability testing of the light-emitting element 13 was carried out. Results of the reliability testing are shown in FIG. 114. In FIG. 114, the vertical axis represents normalized luminance (%) on the assumption that an initial luminance is 100%, and the horizontal axis represents driving time (h) of the element.

In the reliability testing, the light-emitting element 13 was driven under the conditions where the initial luminance was set to 5000 cd/m$^2$ and the current density was constant.

The light-emitting element 13 kept 81% of the initial luminance after the driving for 180 hours.

The above results suggest that an element having high reliability can be realized by using an organometallic complex which is one embodiment of the present invention as a light-emitting material.

EXAMPLE 33

In Example 33, a light-emitting element which is one embodiment of the present invention is described with reference to FIG. 14. Chemical formulas of materials used in this example are shown below. Note that the chemical formulas of the materials described above are omitted.

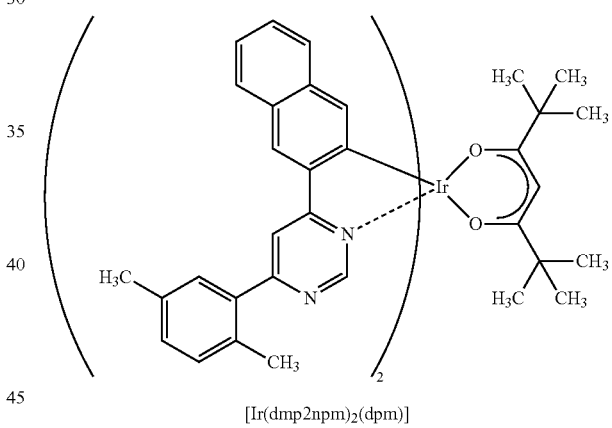

[Ir(dmp2npm)$_2$(dpm)]

A method of fabricating a light-emitting element 14 of this example is described below.

(Light-Emitting Element 14)

The light-emitting element 14 was fabricated in a manner similar to that in the light-emitting element 7 described in Example 26 except for a light-emitting layer 1113. The light-emitting layer 1113 of the light-emitting element 14 is described below.

The light-emitting layer 1113 of the light-emitting element 14 was formed by co-evaporation of 2mDBTPDBq-II, NPB, and bis[4-(2,5-dimethylphenyl)-6-(naphthalen-2-yl)pyrimidinato](dipivaloylmethanato)iridium(III) (abbreviation: [Ir(dmp2npm)$_2$(dpm)]) synthesized in Example 24. The weight ratio of 2mDBTPDBq-II to NPB and [Ir(dmp2npm)$_2$(dpm)] was adjusted to 0.8:0.2:0.025 (=2mDBTPDBq-II:NPB:[Ir(dmp2npm)$_2$(dpm)]). The thickness of the light-emitting layer 1113 was set to 40 nm.

Table 27 shows an element structure of the light-emitting element 14 obtained as described above.

TABLE 27

|  | First Electrode | Hole-injection Layer | Hole-transport Layer | Light-emitting Layer | First electron-Transport Layer | Second electron-Transport Layer | Electron-injection Layer | Second Electrode |
|---|---|---|---|---|---|---|---|---|
| Light-emitting Element 14 | ITSO 110 nm | DBT3P-II:MoOx (=4:2) 40 nm | BPAFLP 20 nm | 2mDBTPDBq-II:NPB:[Ir(dmp2npm)$_2$(dpm)] (=0.8:0.2:0.025) 40 nm | 2mDBTPDBq-II 10 nm | BPhen 20 nm | LiF 1 nm | Al 200 nm |

In a glove box containing a nitrogen atmosphere, the light-emitting element 14 was sealed so as not to be exposed to the air. After that, operation characteristics of the light-emitting element 14 were measured. Note that the measurements were carried out at room temperature (in an atmosphere kept at 25° C.).

Figure 115:
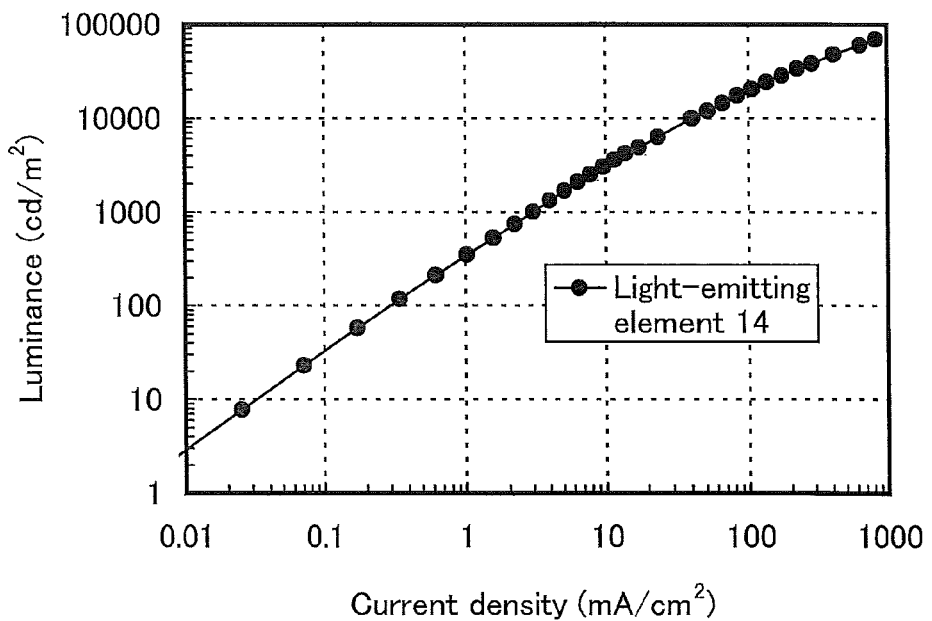
FIG. 115 shows current density vs. luminance characteristics of a light-emitting element 14.
Figure 116:
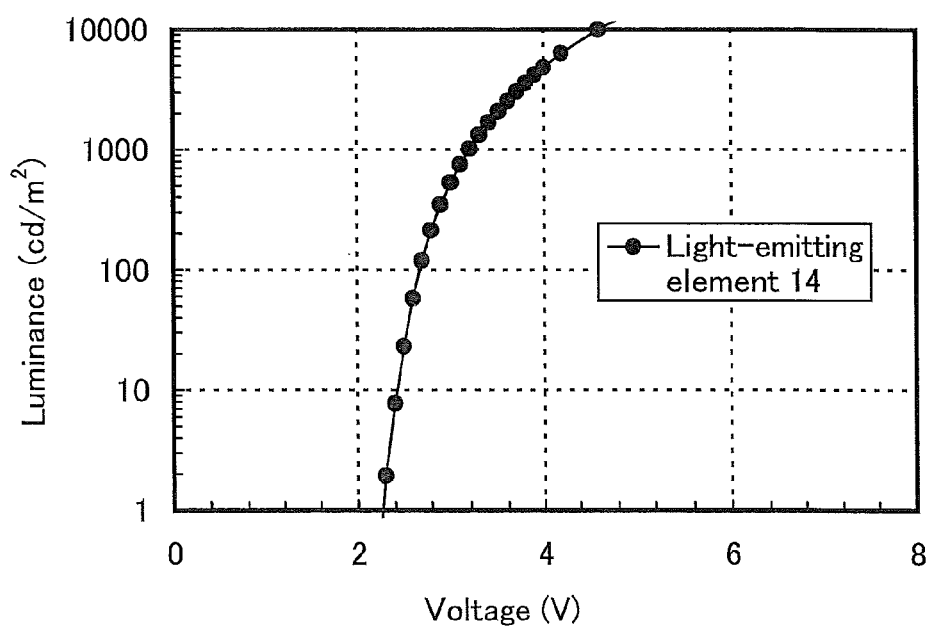
FIG. 116 shows voltage vs. luminance characteristics of the light-emitting element 14.
Figure 117:
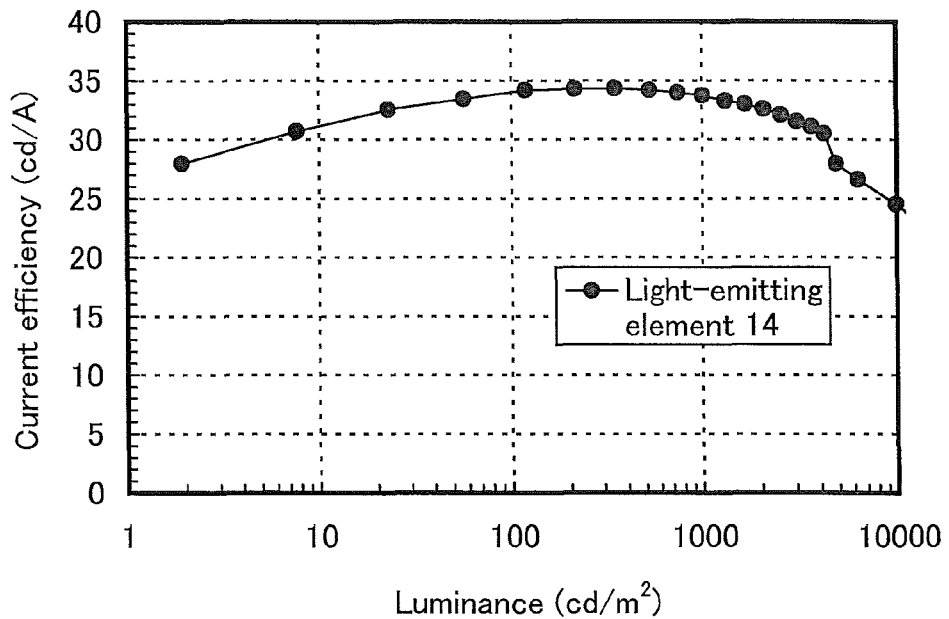
FIG. 117 shows luminance vs. current efficiency characteristics of the light-emitting element 14.

FIG. 115 shows current density vs. luminance characteristics of the light-emitting element 14. In FIG. 115, the horizontal axis represents current density (mA/cm$^2$) and the vertical axis represents luminance (cd/m$^2$). FIG. 116 shows voltage vs luminance characteristics thereof. In FIG. 116, the horizontal axis represents voltage (V) and the vertical axis represents luminance (cd/m$^2$). FIG. 117 shows luminance vs. current efficiency characteristics thereof. In FIG. 117, the horizontal axis represents luminance (cd/m$^2$) and the vertical axis represents current efficiency (cd/A). Further, Table 28 shows voltage (V), current density (mA/cm$^2$), CIE chromaticity coordinates (x, y), current efficiency (cd/A), power efficiency (lm/W), and external quantum efficiency (%) of the light-emitting element 14 at a luminance of 1000 cd/m$^2$.

TABLE 28

| | Voltage (V) | Current Density (mA/cm$^2$) | Chromaticity (x, y) | Current Efficiency (cd/A) | Power Efficiency (lm/W) | External Quantum Efficiency (%) |
|---|---|---|---|---|---|---|
| Light-emitting Element 14 | 3.2 | 3.0 | (0.63, 0.37) | 34 | 33 | 21 |

Figure 118:
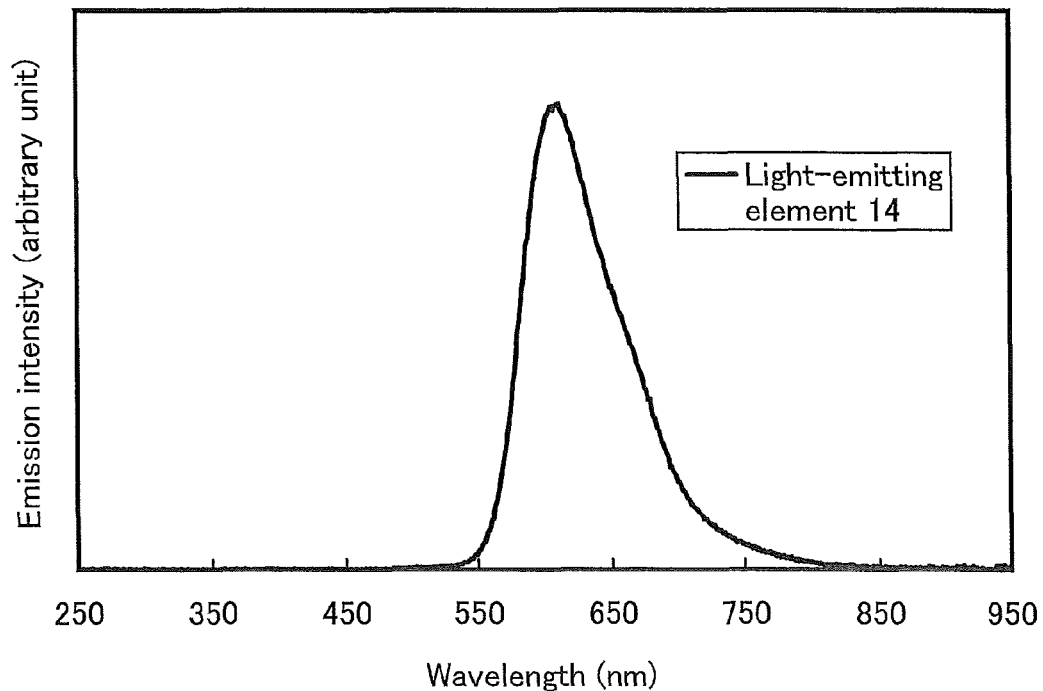
FIG. 118 shows an emission spectrum of the light-emitting element 14.

FIG. 118 shows an emission spectrum of the light-emitting element 14 which was obtained by applying a current of 0.1 mA. In FIG. 118, the horizontal axis represents wavelength (nm) and the vertical axis represents light emission intensity (arbitrary unit). As shown in FIG. 118, the emission spectrum of the light-emitting element 14 has a peak at 611 nm. In addition, as shown in Table 28, the CIE chromaticity coordinates of the light-emitting element 14 were (x, y)=(0.63, 0.37) at a luminance of 1000 cd/m$^2$. The results show that red light emission originating from [Ir(dmp2npm)$_2$(dpm)] was obtained from the light-emitting element 14.

Table 28, FIG. 115, FIG. 116, and FIG. 117 indicate that the light-emitting element 14 has high emission efficiency.

The above results suggest that an element with high emission efficiency can be realized by using the organometallic complex which is one embodiment of the present invention as a light-emitting material.

Figure 119:
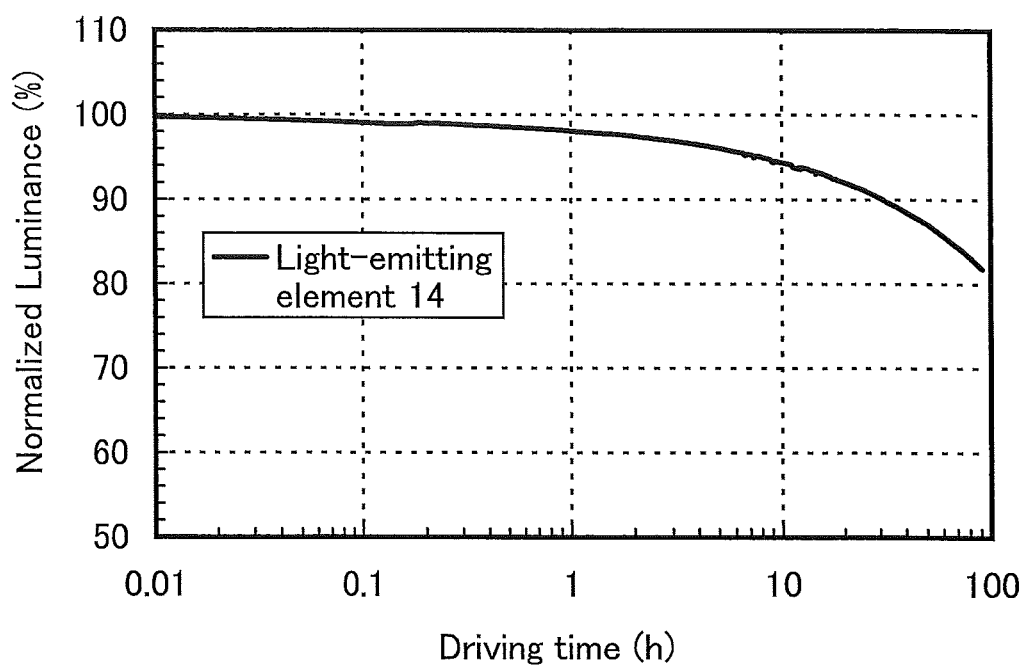
FIG. 119 shows results obtained by reliability testing of the light-emitting element 14.

Next, reliability testing of the light-emitting element 14 was carried out. Results of the reliability testing are shown in FIG. 119. In FIG. 119, the vertical axis represents normalized luminance (%) on the assumption that an initial luminance is 100%, and the horizontal axis represents driving time (h) of the element.

In the reliability testing, the light-emitting element 14 was driven under the conditions where the initial luminance was set to 5000 cd/m$^2$ and the current density was constant.

The light-emitting element 14 kept 82% of the initial luminance after the driving for 92 hours.

The above results suggest that an element having high reliability can be realized by using an organometallic complex which is one embodiment of the present invention as a light-emitting material.

Reference Example 1

A method of synthesizing 4-phenyl-4'-(9-phenylfluoren-9-yl)triphenylamine (abbreviation: BPAFLP) used in the above Examples is specifically described. A structure of BPAFLP is shown below.

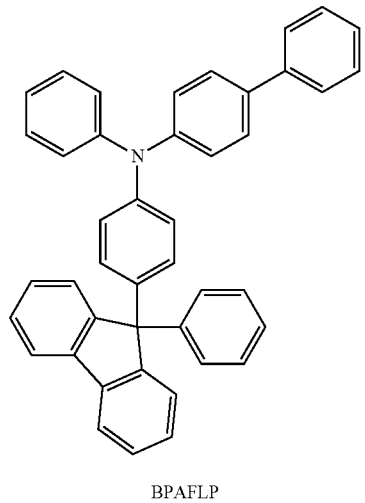 [SMILES: c1ccc(-c2ccc(N(c3ccccc3)c3ccc(C4(c5ccccc5)c5ccccc5-c5ccccc54)cc3)cc2)cc1]

BPAFLP

Step 1: Method of synthesizing
9-(4-bromophenyl)-9-phenylfluorene

In a 100-mL three-neck flask, 1.2 g (50 mmol) of magnesium was heated and stirred under reduced pressure for 30 minutes to be activated. After the three-neck flask was cooled to room temperature and was made to have a nitrogen atmosphere, several drops of dibromoethane were added, so that foam formation and heat generation were confirmed. After 12 g (50 mmol) of 2-bromobiphenyl dissolved in 10 mL of diethyl ether was slowly dropped into this mixture, the mixture was stirred and heated under reflux for 2.5 hours and made into a Grignard reagent.

Into a 500-mL three-neck flask were put 10 g (40 mmol) of 4-bromobenzophenone and 100 mL of diethyl ether. After the Grignard reagent which was synthesized in advance was slowly dropped into this mixture, the mixture was stirred and heated under reflux for 9 hours.

After reaction, this mixture solution was filtered to give a residue. The residue was dissolved in 150 mL of ethyl acetate, and 1N-hydrochloric acid was added to the mixture, which was then stirred for 2 hours until it was made acid. An organic layer of this liquid was washed with water, and magnesium sulfate was added to remove moisture. This suspension was filtered, and the obtained filtrate was concentrated to give a highly viscous substance.

Into a 500-mL recovery flask were put this highly viscous substance, 50 mL of glacial acetic acid, and 1.0 mL of hydrochloric acid. The mixture was stirred and heated at 130° C. for 1.5 hours under a nitrogen atmosphere to be reacted.

After reaction, this reaction mixture solution was filtered to give a residue. The residue was washed with water, an aqueous sodium hydroxide solution, water, and methanol in this order. After that, the mixture was dried to give 11 g of white powder in 69% yield, which was the objective substance. A synthesis scheme (x-1) of Step 1 is shown below.

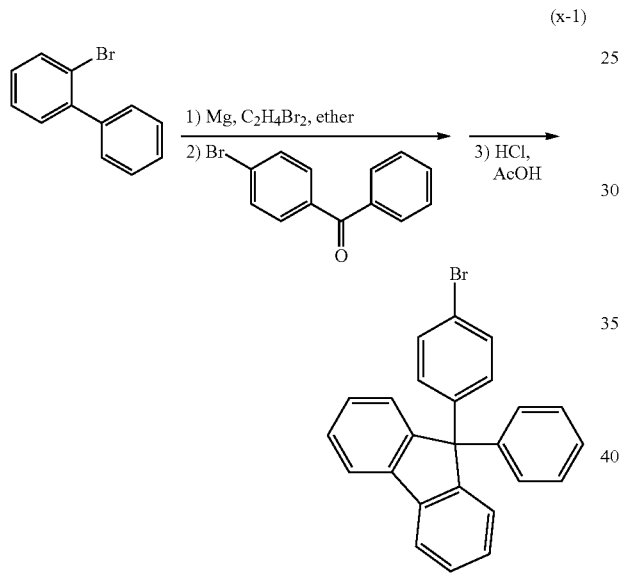

Step 2: Method of synthesizing 4-phenyl-4'-(9-phenylfluoren-9-yl)triphenylamine (abbreviation: BPAFLP)

Into a 100-mL three-neck flask were put 3.2 g (8.0 mmol) of 9-(4-bromophenyl)-9-phenylfluorene, 2.0 g (8.0 mmol) of 4-phenyl-diphenylamine, 1.0 g (10 mmol) of sodium tert-butoxide, and 23 mg (0.04 mmol) of bis(dibenzylideneacetone)palladium(0), and the air in the three-neck flask was replaced with nitrogen. Then, 20 mL of dehydrated xylene was added to this mixture. After the mixture was deaerated while being stirred under reduced pressure, 0.2 mL (0.1 mmol) of tri(tert-butyl)phosphine (10 wt % hexane solution) was added thereto. This mixture was heated and stirred under a nitrogen atmosphere at 110° C. for 2 hours to be reacted.

After reaction, 200 mL of toluene was added to the reaction mixture solution, and the resulting suspension was filtered through Florisil and Celite. The obtained filtrate was concentrated, and purification was carried out by silica gel column chromatography using toluene and hexane as a developing solvent in a ratio of 1:4. The obtained fraction was concentrated, and acetone and methanol were added to the mixture. The mixture was irradiated with ultrasonic waves and then recrystallized to give 4.1 g of white powder in 92% yield, which was the objective substance. A synthesis scheme (x-2) of Step 2 is shown below.

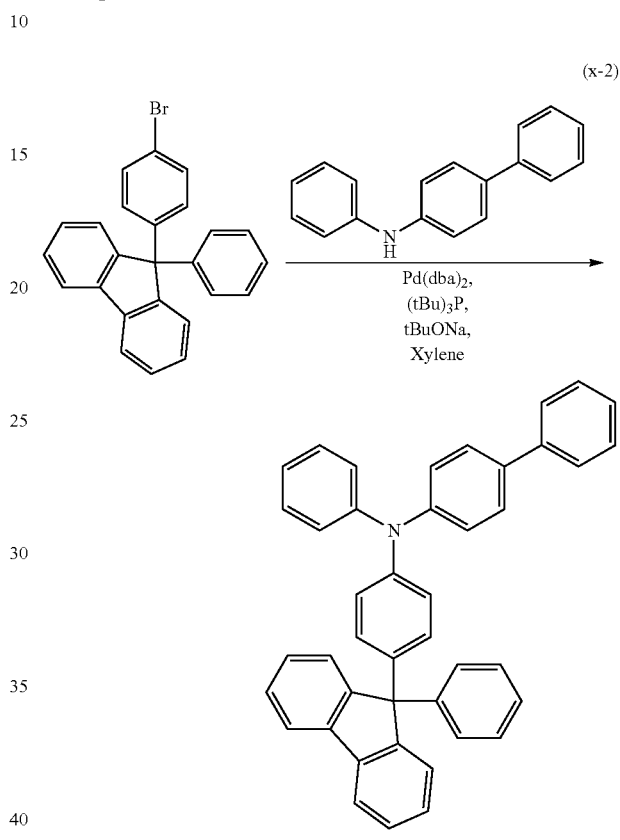

An Rf value of the objective substance by a silica gel thin layer chromatography (TLC) using ethyl acetate and hexane as a developing solvent in a ratio of 1:10 was 0.41, that of 9-(4-bromophenyl)-9-phenylfluorene was 0.51, and that of 4-phenyl-diphenylamine was 0.27.

The compound obtained in Step 2 above was measured by a nuclear magnetic resonance spectrometry ($^1$H NMR). The measurement data are shown below. The measurement results revealed that the obtained compound was BPAFLP (abbreviation), which is a fluorene derivative.

$^1$H NMR (CDCl$_3$, 300 MHz): δ (ppm)=6.63-7.02 (m, 3H), 7.06-7.11 (m, 6H), 7.19-7.45 (m, 18H), 7.53-7.55 (m, 2H), 7.75 (d, J=6.9, 2H).

Reference Example 2

A method of synthesizing 2-[3-(dibenzothiophen-4-yl)phenyl]dibenzo [f,h]quinoxaline (abbreviation: 2mDBTP-DBq-II) used in Examples is described.

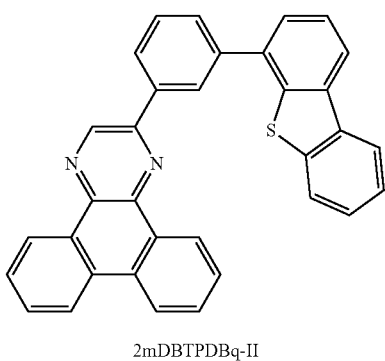 [SMILES: c1cc(-c2cnc3c4ccccc4c4ccccc4c3n2)cc(-c2cccc3c2sc2ccccc23)c1]

2mDBTPDBq-II

Synthesis of 2-[3-(dibenzothiophen-4-yl)phenyl] dibenzo[f,h]quinoxaline (abbreviation: 2mDBTP-DBq-II)

A synthesis scheme (y-1) of 2-[3-(dibenzothiophen-4-yl)phenyl]dibenzo[f,h]quinoxaline (abbreviation: 2mDBTP-DBq-II) is shown below.

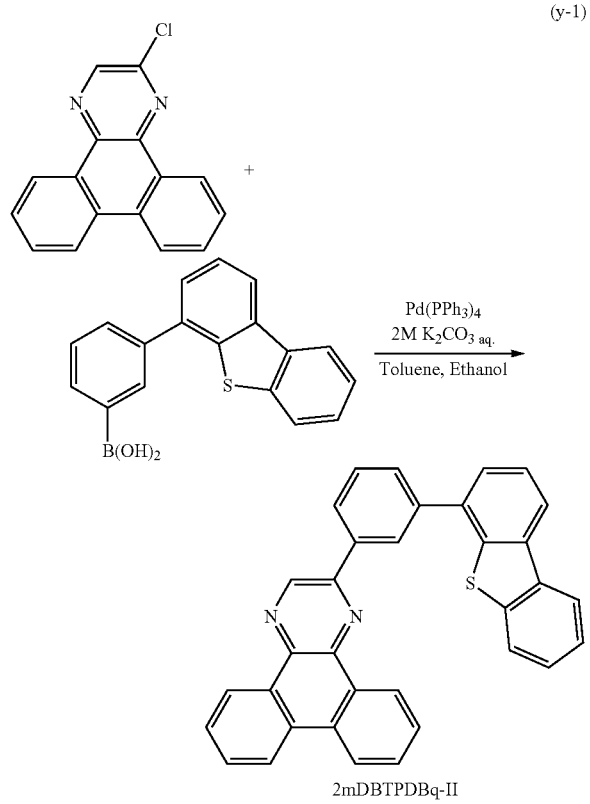

(y-1)

2mDBTPDBq-II

In a 2-L three-neck flask were put 5.3 g (20 mmol) of 2-chlorodibenzo[f,h]quinoxaline, 6.1 g (20 mmol) of 3-(dibenzothiophen-4-yl)phenylboronic acid, 460 mg (0.4 mmol) of tetrakis(triphenylphosphine)palladium(0), 300 mL of toluene, 20 mL of ethanol, and 20 mL of a 2M aqueous potassium carbonate solution. The mixture was degassed by being stirred under reduced pressure, and the air in the three-neck flask was replaced with nitrogen. This mixture was stirred under a nitrogen stream at 100° C. for 7.5 hours. After cooled to room temperature, the obtained mixture was filtered to give a white residue. The obtained residue was washed with water and ethanol in this order, and then dried. The obtained solid was dissolved in about 600 mL of hot toluene, followed by suction filtration through Celite and Florisil, whereby a clear colorless filtrate was obtained. The obtained filtrate was concentrated and purified by silica gel column chromatography using about 700 mL of silica gel. The chromatography was carried out using hot toluene as a developing solvent. Acetone and ethanol were added to the solid obtained here, followed by irradiation with ultrasonic waves. Then, the generated suspended solid was collected by filtration and the obtained solid was dried to give 7.85 g of white powder in 80% yield.

The above objective substance was relatively soluble in hot toluene, but was a material that was easy to precipitate when cooled. Further, the substance was poorly soluble in other organic solvents such as acetone and ethanol. Hence, the utilization of these different degrees of solubility resulted in a high-yield synthesis by a simple method as above. Specifically, after the reaction finished, the mixture was returned to room temperature and the precipitated solid was collected by filtration, whereby most impurities were able to be easily removed. Further, by the column chromatography with hot toluene as a developing solvent, the objective substance, which is easy to precipitate, was able to be readily purified.

By a train sublimation method, 4.0 g of the obtained white powder was purified. In the purification, the white powder was heated at 300° C. under a pressure of 5.0 Pa with a flow rate of argon gas of 5 mL/min. After the purification, the objective substance was obtained in a yield of 88% as 3.5 g of white powder.

A nuclear magnetic resonance spectrometry ($^1$H NMR) identified this compound as 2-[3-(dibenzothiophen-4-yl)phenyl]dibenzo[f,h] quinoxaline (abbreviation: 2mDBTPDBq-II), which was the objective substance.

$^1$H NMR data of the obtained substance are shown below.

$^1$H NMR (CDCl$_3$, 300 MHz): δ (ppm)=7.45-7.52 (m, 2H), 7.59-7.65 (m, 2H), 7.71-7.91 (m, 7H), 8.20-8.25 (m, 2H), 8.41 (d, J=7.8 Hz, 1H), 8.65 (d, J=7.5 Hz, 2H), 8.77-8.78 (m, 1H), 9.23 (dd, J=7.2 Hz, 1.5 Hz, 1H), 9.42 (dd, J=7.8 Hz, 1.5 Hz, 1H), 9.48 (s, 1H).

Reference Example 3

A method of synthesizing N,N'-bis(3-methylphenyl)-N,N'-bis[3-(9-phenyl-9H-fluoren-9-yl)phenyl]-pyrene-1,6-diamine (abbreviation: 1,6mMemFLPAPrn)] used in Examples is specifically described. A structure of 1,6mMemFLPAPrn is illustrated below.

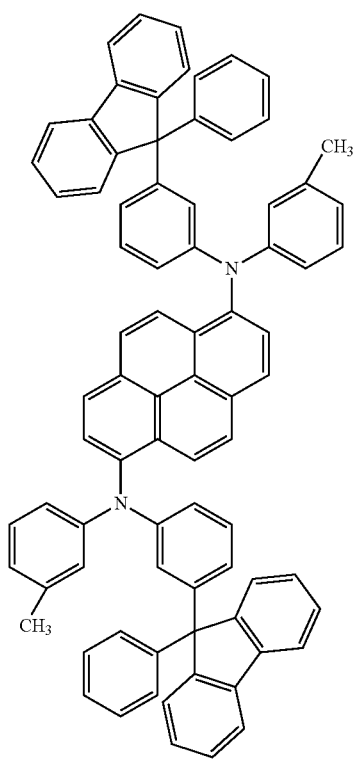

1,6mMemFLPAPrn

Step 1: Method of synthesizing 3-methylphenyl-3-(9-phenyl-9H-fluoren-9-yl)phenylamine (abbreviation: mMemFLPA)

Into a 200-mL three-neck flask were put 3.2 g (8.1 mmol) of 9-(3-bromophenyl)-9-phenylfluorene and 2.3 g (24.1 mmol) of sodium tert-butoxide, and the air in the flask was replaced with nitrogen. To this mixture were added 40.0 mL of toluene, 0.9 mL (8.3 mmol) of m-toluidine, and 0.2 mL of a 10% hexane solution of tri(tert-butyl)phosphine. The temperature of this mixture was set to 60° C., and 44.5 mg (0.1 mmol) of bis(dibenzylideneacetone)palladium(0) was added to the mixture. The temperature of the mixture was raised to 80° C., followed by stirring for 2.0 hours. After the stirring, suction filtration was carried out through Florisil, Celite, and alumina to obtain a filtrate. The filtrate was concentrated to give a solid, which was then purified by silica gel column chromatography using hexane and toluene as a developing solvent in a ratio of 1:1, and recrystallization with a mixed solvent of toluene and hexane was performed, so that 2.8 g of a white solid was obtained in 82% yield. A synthesis scheme (z-1) of Step 1 is shown below.

(z-1)

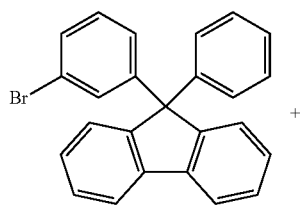

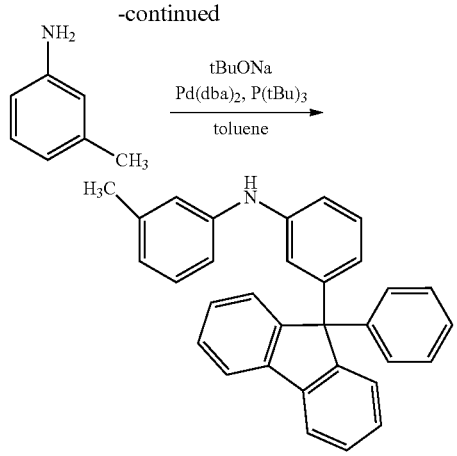

Step 2: Method of synthesizing N,N'-bis(3-methylphenyl)-N,N'-bis[3-(9-phenyl-9H-fluoren-9-yl)phenyl]-pyrene-1,6-dia mine (abbreviation: 1,6mMemFLPAPrn)

Into a 100-mL three-neck flask were put 0.6 g (1.7 mmol) of 1,6-dibromopyrene, 1.4 g (3.4 mmol) of 3-methylphenyl-3-(9-phenyl-9H-fluoren-9-yl)phenylamine, and 0.5 g (5.1 mmol) of sodium tert-butoxide, and the air in the flask was replaced with nitrogen. To this mixture were added 21.0 mL of toluene and 0.2 mL of a 10% hexane solution of tri(tert-butyl)phosphine. The temperature of this mixture was set to 60° C., and 34.9 mg (0.1 mmol) of bis(dibenzylideneacetone)palladium(0) was added to the mixture. The temperature of this mixture was raised to 80° C., followed by stirring for 3.0 hours. After the stirring, 400 mL of toluene was added to the mixture, and the mixture was heated. While the mixture was kept hot, it was suction-filtered through Florisil, Celite, and alumina to give a filtrate. The obtained filtrate was concentrated to give a solid, which was then purified by silica gel column chromatography using hexane and toluene as a developing solvent in a ratio of 3:2 to give a yellow solid. The obtained yellow solid was recrystallized with a mixed solvent of toluene and hexane, so that 1.2 g of a yellow solid, which was an objective substance, was obtained in 67% yield.

By a train sublimation method, 1.0 g of the obtained yellow solid was purified. In the purification, the yellow solid was heated at 317° C. under a pressure of 2.2 Pa with a flow rate of an argon gas of 5.0 mL/min. After the purification, 1.0 g of a yellow solid, which was the objective substance, was obtained in 93% yield. A synthesis scheme (z-2) of Step 2 is shown below.

(z-2)

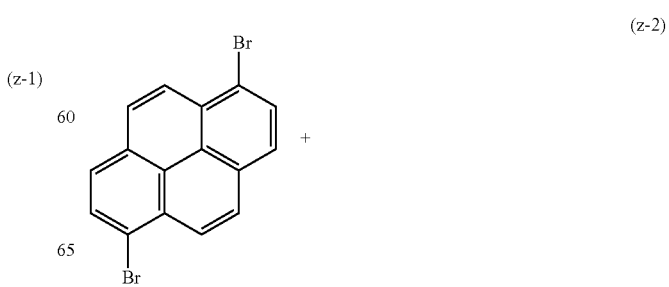

-continued

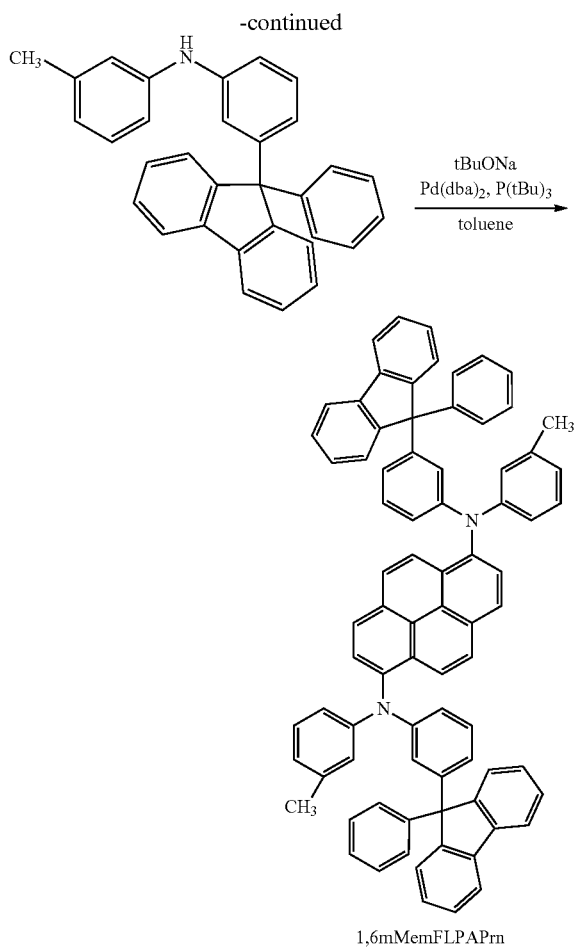

1,6mMemFLPAPrn

A nuclear magnetic resonance (NMR) method identified this compound as N,N'-bis(3-methylphenyl)-N,N'-bis[3-(9-phenyl-9H-fluoren-9-yl)phenyl]-pyrene-1,6-dia mine (abbreviation: 1,6mMemFLPAPrn), which was the objective substance.

$^1$H NMR data of the obtained compound are shown below.

$^1$H NMR (CDCl$_3$, 300 MHz): δ=2.21 (s, 6H), 6.67 (d, J=7.2 Hz, 2H), 6.74 (d, J=7.2 Hz, 2H), 7.17-7.23 (m, 34H), 7.62 (d, J=7.8 Hz, 4H), 7.74 (d, J=7.8 Hz, 2H), 7.86 (d, J=9.0 Hz, 2H), 8.04 (d, J=8.7 Hz, 4H)

REFERENCE NUMERALS

101: first electrode, 102: EL layer, 103: second electrode, 111: hole-injection layer, 112: hole-transport layer, 113: light-emitting layer, 114: electron-transport layer, 115: electron-injection layer, 213: first light-emitting layer, 214: separation layer, 215: second light-emitting layer, 305: charge generation layer, 401: substrate, 402: insulating layer, 403: first electrode, 404: partition, 405: opening, 406: partition, 407: EL layer, 408: second electrode, 501: substrate, 503: scanning line, 505: region, 506: partition, 508: data line, 509: connection wiring, 510: input terminal, 512: input terminal, 601: element substrate, 602: pixel portion, 603: driver circuit portion, 604: driver circuit portion, 605: sealing material, 606: sealing substrate, 607: lead wiring, 608: FPC, 609: n-channel TFT, 610: p-channel TFT, 611: switching TFT, 612: current control TFT, 613: anode, 614: insulator, 615: EL layer, 616: cathode, 617: light-emitting element, 618: space, 700: first EL layer, 701: second EL layer, 801: lighting device, 802: lighting device, 803: desk lamp, 511a: FPC, 511b: FPC, 1100: substrate, 1101: first electrode, 1103: second electrode, 1111: hole-injection layer, 1111a: first hole-injection layer, 1111b: second hole-injection layer, 1111c: third hole-injection layer, 1112: hole-transport layer, 1112a: first hole-transport layer, 1112b: second hole-transport layer, 1112c: third hole-transport layer, 1113: light-emitting layer, 1113a: first light-emitting layer, 1113b: second light-emitting layer, 1113c: third light-emitting layer, 1114a: first electron-transport layer, 1114b: second electron-transport layer, 1114c: third electron-transport layer, 1115: electron-injection layer, 1115a: first electron-injection layer, 1115b: second electron-injection layer, 1115c: third electron-injection layer, 7100: television device, 7101: housing, 7103: display portion, 7105: stand, 7107: display portion, 7109: operation key, 7110: remote controller, 7201: main body, 7202: housing, 7203: display portion, 7204: keyboard, 7205: external connection port, 7206: pointing device, 7301: housing, 7302: housing, 7303: joint portion, 7304: display portion, 7305: display portion, 7306: speaker portion, 7307: recording medium insertion portion, 7308: LED lamp, 7309: operation key, 7310: connection terminal, 7311: sensor, 7312: microphone, 7400: mobile phone, 7401: housing, 7402: display portion, 7403: operation button, 7404: external connection port, 7405: speaker, 7406: microphone, 7501: lighting portion, 7502: shade, 7503: adjustable arm, 7504: support, 7505: base, 7506: power supply switch, 9501: lighting portion, 9503: support, 9505: support case, 9900: lighting device.

This application is based on Japanese Patent Application serial no. 2010-238001 filed with Japan Patent Office on Oct. 22, 2010, and 2010-291881 filed with Japan Patent Office on Dec. 28, 2010, the entire contents of which are hereby incorporated by reference.

The invention claimed is:

1. A light-emitting element comprising an organometallic complex between a pair of electrodes, wherein the organometallic complex comprises a structure represented by a formula (G1),

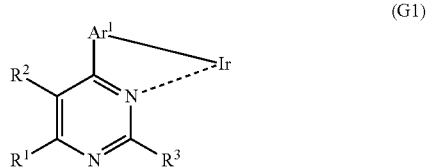

(G1)

wherein R$^1$ represents an alkyl group having 1 to 4 carbon atoms or a substituted or unsubstituted aryl group having 6 to 10 carbon atoms, wherein the substituted aryl group having 6 to 10 carbon atoms is substituted by one or more alkyl groups each having 1 to 4 carbon atoms, one or more alkoxy groups each having 1 to 4 carbon atoms, one or more alkylthio groups each having 1 to 4 carbon atoms, one or more aryl groups each having 6 to 10 carbon atoms, one or more halogen groups, or one or more haloalkyl groups each having 1 to 4 carbon atoms, wherein R$^2$ represents any of hydrogen, an alkyl group having 1 to 4 carbon atoms, and a substituted or unsubstituted phenyl group, wherein the substituted phenyl group is substituted by one or more alkyl groups each having 1 to 4 carbon atoms, one or more alkoxy groups each having 1 to 4 carbon atoms, one or more alkylthio groups each having 1 to 4 carbon atoms, one or more aryl groups each having 6 to 10 carbon atoms, one or more halogen groups, or one or more haloalkyl groups each having 1 to 4 carbon atoms, wherein $R^3$ represents hydrogen or an alkyl group having 1 to 4 carbon atoms, wherein $Ar^1$ represents a substituted or unsubstituted arylene group having 6 to 10 carbon atoms, and wherein the substituted arylene group having 6 to 10 carbon atoms is substituted by one or more alkyl groups each having 1 to 4 carbon atoms, one or more alkoxy groups each having 1 to 4 carbon atoms, one or more alkylthio groups each having 1 to 4 carbon atoms, one or more aryl groups each having 6 to 10 carbon atoms, one or more halogen groups, or one or more haloalkyl groups each having 1 to 4 carbon atoms.

2. The light-emitting element according to claim 1, wherein the structure is represented by a formula (G2), and

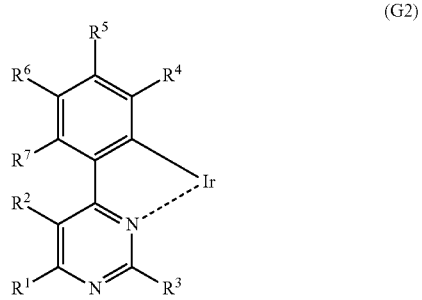

(G2)

wherein $R^4$, $R^5$, $R^6$, and $R^7$ individually represent any of hydrogen, an alkyl group having 1 to 4 carbon atoms, an alkoxy group having 1 to 4 carbon atoms, an alkylthio group having 1 to 4 carbon atoms, halogen, a haloalkyl group having 1 to 4 carbon atoms, and a substituted or unsubstituted aryl group having 6 to 10 carbon atoms, and wherein, with respect to $R^4$, $R^5$, $R^6$, and $R^7$, the substituted aryl group having 6 to 10 carbon atoms is substituted by one or more alkyl groups each having 1 to 4 carbon atoms, one or more alkoxy groups each having 1 to 4 carbon atoms, one or more alkylthio groups each having 1 to 4 carbon atoms, one or more aryl groups each having 6 to 10 carbon atoms, one or more halogen groups, or one or more haloalkyl groups having 1 to 4 carbon atoms.

3. The light-emitting element according to claim 1, wherein the structure represented by a formula (G3), and

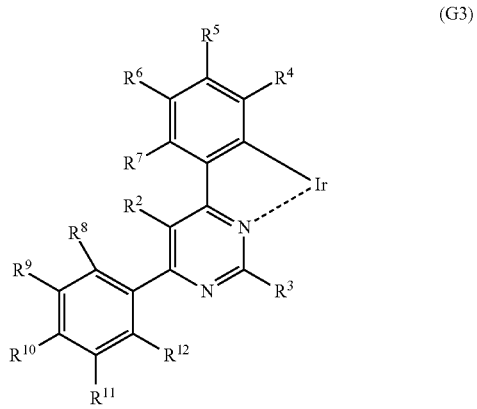

(G3)

wherein $R^4$, $R^5$, $R^6$, $R^7$, $R^8$, $R^9$, $R^{10}$, $R^{11}$, and $R^{12}$ individually represent any of hydrogen, an alkyl group having 1 to 4 carbon atoms, an alkoxy group having 1 to 4 carbon atoms, an alkylthio group having 1 to 4 carbon atoms, halogen, a haloalkyl group having 1 to 4 carbon atoms, and a substituted or unsubstituted aryl group having 6 to 10 carbon atoms, and wherein, with respect to $R^4$, $R^5$, $R^6$, $R^7$, $R^8$, $R^9$, $R^{10}$, $R^{11}$, and $R^{12}$, the substituted aryl group having 6 to 10 carbon atoms is substituted by one or more alkyl groups each having 1 to 4 carbon atoms, one or more alkoxy groups each having 1 to 4 carbon atoms, one or more alkylthio groups each having 1 to 4 carbon atoms, one or more aryl groups each having 6 to 10 carbon atoms, one or more halogen groups, or one or more haloalkyl groups each having 1 to 4 carbon atoms.

4. A light-emitting device comprising the light-emitting element according to claim 1.

5. An electronic device comprising the light-emitting device according to claim 4 in a display portion.

6. A lighting device comprising the light-emitting device according to claim 4 in a light-emitting portion.

7. A light-emitting element comprising an organometallic complex between a pair of electrodes, wherein the organometallic complex is represented by a formula (G4),

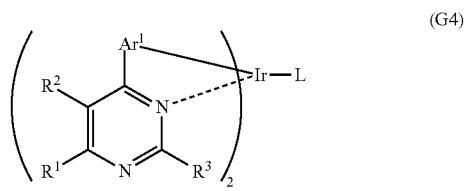

(G4)

wherein $R^1$ represents an alkyl group having 1 to 4 carbon atoms or a substituted or unsubstituted aryl group having 6 to 10 carbon atoms, wherein the substituted aryl group having 6 to 10 carbon atoms is substituted by one or more alkyl groups each having 1 to 4 carbon atoms, one or more alkoxy groups each having 1 to 4 carbon atoms, one or more alkylthio groups each having 1 to 4 carbon atoms, one or more aryl groups each having 6 to 10 carbon atoms, one or more halogen groups, or one or more haloalkyl groups each having 1 to 4 carbon atoms, wherein $R^2$ represents any of hydrogen, an alkyl group having 1 to 4 carbon atoms, and a substituted or unsubstituted phenyl group, wherein the substituted phenyl group is substituted by one or more alkyl groups each having 1 to 4 carbon atoms, one or more alkoxy groups each having 1 to 4 carbon atoms, one or more alkylthio groups each having 1 to 4 carbon atoms, one or more aryl groups each having 6 to 10 carbon atoms, one or more halogen groups, or one or more haloalkyl groups each having 1 to 4 carbon atoms, wherein $R^3$ represents hydrogen or an alkyl group having 1 to 4 carbon atoms, and wherein $Ar^1$ represents a substituted or unsubstituted arylene group having 6 to 10 carbon atoms, wherein the substituted arylene group having 6 to 10 carbon atoms is substituted by one or more alkyl groups each having 1 to 4 carbon atoms, one or more alkoxy groups each having 1 to 4 carbon atoms, one or more alkylthio groups each having 1 to 4 carbon atoms, one or more aryl groups each having 6 to 10 carbon atoms, one or more halogen groups, or one or more haloalkyl groups each having 1 to 4 carbon atoms, wherein L is any one of formulas (L1), (L2), (L3), (L4), (L5), (L6), and (L7), (L1)

[Structure showing R$^{71}$, R$^{72}$, R$^{73}$ on a diketonate ligand]

(L2)

[Structure showing pyridine carboxylate with R$^{74}$, R$^{75}$, R$^{76}$, R$^{77}$]

(L3)

[Structure showing R$^{78}$, R$^{79}$, R$^{80}$, R$^{81}$, R$^{82}$ on a salicylaldiminate]

(L4)

[Structure showing R$^{83}$, R$^{84}$, R$^{85}$, R$^{86}$ on a salicylaldehyde]

(L5)

[Structure showing R$^{87}$, R$^{88}$, R$^{89}$, R$^{90}$ on pyridine with A$^1$, A$^2$, A$^3$]

(L6)

[Structure showing tetrakis(pyrazolyl)borate with R$^{91}$–R$^{102}$]

(L7)

[Structure showing R$^{103}$, R$^{104}$, R$^{105}$, R$^{106}$, R$^{107}$, R$^{108}$, R$^{109}$ on phenylpyrimidine]

wherein R$^{71}$, R$^{72}$, R$^{73}$, R$^{74}$, R$^{75}$, R$^{76}$, R$^{77}$, R$^{78}$, R$^{79}$, R$^{80}$, R$^{81}$, R$^{82}$, R$^{83}$, R$^{84}$, R$^{85}$, R$^{86}$, R$^{87}$, R$^{88}$, R$^{89}$, R$^{90}$, R$^{91}$, R$^{92}$, R$^{93}$, R$^{94}$, R$^{95}$, R$^{96}$, R$^{97}$, R$^{98}$, R$^{99}$, R$^{100}$, R$^{101}$, R$^{102}$, R$^{103}$, R$^{104}$, R$^{105}$, R$^{106}$, R$^{107}$, R$^{108}$, and R$^{109}$ individually represent any of hydrogen, an alkyl group having 1 to 4 carbon atoms, a halogen, a vinyl group, a haloalkyl group having 1 to 4 carbon atoms, an alkoxy group having 1 to 4 carbon atoms, and an alkylthio group having 1 to 4 carbon atoms, wherein A$^1$, A$^2$, and A$^3$ individually represent any of nitrogen, sp$^2$ hybridized carbon bonded to hydrogen, and sp$^2$ hybridized carbon bonded to a substituent R, and wherein the substituent R represents any of an alkyl group having 1 to 4 carbon atoms, a halogen, a haloalkyl group having 1 to 4 carbon atoms, and a phenyl group.

8. The light-emitting element according to claim 7, wherein the organometallic complex is represented by a formula (G5), and (G5)

[Structure showing Ir complex with R$^1$–R$^7$ substituents and ligand L, with subscript 2]

wherein R$^4$, R$^5$, R$^6$, and R$^7$ individually represent any of hydrogen, an alkyl group having 1 to 4 carbon atoms, an alkoxy group having 1 to 4 carbon atoms, an alkylthio group having 1 to 4 carbon atoms, halogen, a haloalkyl group having 1 to 4 carbon atoms, and a substituted or unsubstituted aryl group having 6 to 10 carbon atoms, and wherein, with respect to R$^4$, R$^5$, R$^6$, and R$^7$, the substituted aryl group having 6 to 10 carbon atoms is substituted by one or more alkyl groups each having 1 to 4 carbon atoms, one or more alkoxy groups each having 1 to 4 carbon atoms, one or more alkylthio groups each having 1 to 4 carbon atoms, one or more aryl groups each having 6 to 10 carbon atoms, one or more halogen groups, or one or more haloalkyl groups each having 1 to 4 carbon atoms.

9. The light-emitting element according to claim 7, wherein the organometallic complex is represented by a formula (G6), and

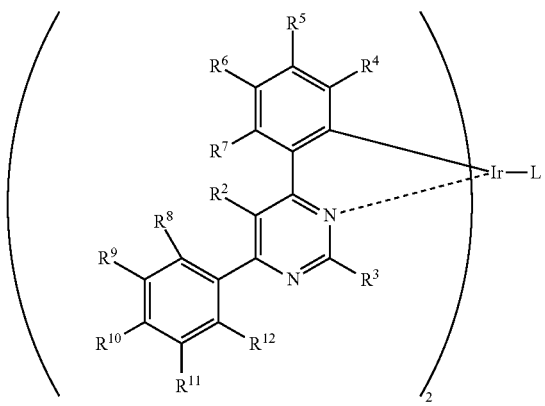

wherein $R^4$, $R^5$, $R^6$, $R^7$, $R^8$, $R^9$, $R^{10}$, $R^{12}$, and $R^{12}$ individually represent any of hydrogen, an alkyl group having 1 to 4 carbon atoms, an alkoxy group having 1 to 4 carbon atoms, an alkylthio group having 1 to 4 carbon atoms, halogen, a haloalkyl group having 1 to 4 carbon atoms, and a substituted or unsubstituted aryl group having 6 to 10 carbon atoms, and wherein, with respect to $R^4$, $R^5$, $R_6$, $R_7$, $R_8$, $R_9$, $R^{10}$, $R_{11}$, and $R^{12}$, the substituted aryl group having 6 to 10 carbon atoms is substituted by one or more alkyl groups each having 1 to 4 carbon atoms, one or more alkoxy groups each having 1 to 4 carbon atoms, one or more alkylthio groups each having 1 to 4 carbon atoms, one or more aryl groups each having 6 to 10 carbon atoms, one or more halogen groups, or one or more haloalkyl groups each having 1 to 4 carbon atoms.

10. A light-emitting device comprising the light-emitting element according to claim 7.

11. An electronic device comprising the light-emitting device according to claim 10 in a display portion.

12. A lighting device comprising the light-emitting device according to claim 10 in a light-emitting portion.

13. A light-emitting element comprising an organometallic complex between a pair of electrodes, wherein the organometallic complex is represented by a formula (G7),

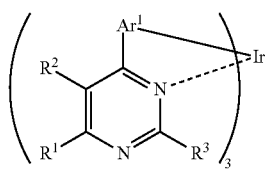

wherein $R^l$ represents an alkyl group having 1 to 4 carbon atoms or a substituted or unsubstituted aryl group having 6 to 10 carbon atoms, wherein the substituted aryl group having 6 to 10 carbon atoms is substituted by one or more alkyl groups each having 1 to 4 carbon atoms, one or more alkoxy groups each having 1 to 4 carbon atoms, one or more alkylthio groups each having 1 to 4 carbon atoms, one or more aryl groups each having 6 to 10 carbon atoms, one or more halogen groups, or one or more haloalkyl groups each having 1 to 4 carbon atoms, wherein $R^2$ represents any of hydrogen, an alkyl group having 1 to 4 carbon atoms, and a substituted or unsubstituted phenyl group, wherein the substituted phenyl group is substituted by one or more alkyl groups each having 1 to 4 carbon atoms, one or more alkoxy groups each having 1 to 4 carbon atoms, one or more alkylthio groups each having 1 to 4 carbon atoms, one or more aryl groups each having 6 to 10 carbon atoms, one or more halogen groups, or one or more haloalkyl groups each having 1 to 4 carbon atoms, wherein $R^3$ represents hydrogen or an alkyl group having 1 to 4 carbon atoms, wherein $Ar^1$ represents a substituted or unsubstituted arylene group having 6 to 10 carbon atoms, and wherein the substituted arylene group having 6 to 10 carbon atoms is substituted by one or more alkyl groups each having 1 to 4 carbon atoms, one or more alkoxy groups each having 1 to 4 carbon atoms, one or more alkylthio groups each having 1 to 4 carbon atoms, one or more aryl groups each having 6 to 10 carbon atoms, one or more halogen groups, or one or more haloalkyl groups each having 1 to 4 carbon atoms.

14. The light-emitting element according to claim 13, wherein the organometallic complex is represented by a formula (G8), and

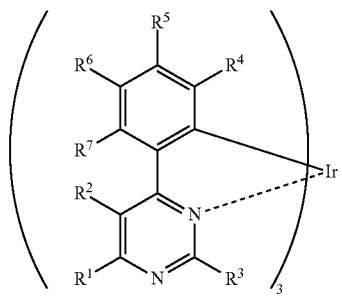

wherein $R^4$, $R^5$, $R^6$, and $R^7$ individually represent any of hydrogen, an alkyl group having 1 to 4 carbon atoms, an alkoxy group having 1 to 4 carbon atoms, an alkylthio group having 1 to 4 carbon atoms, halogen, a haloalkyl group having 1 to 4 carbon atoms, and a substituted or unsubstituted aryl group having 6 to 10 carbon atoms, and wherein the substituted aryl group having 6 to 10 carbon atoms is substituted by one or more alkyl groups each having 1 to 4 carbon atoms, one or more alkoxy groups each having 1 to 4 carbon atoms, one or more alkylthio groups each having 1 to 4 carbon atoms, one or more aryl groups each having 6 to 10 carbon atoms, one or more halogen groups, or one or more haloalkyl groups each having 1 to 4 carbon atoms.

15. The light-emitting element according to claim 13, wherein the organometallic complex is represented by a formula (G9), and

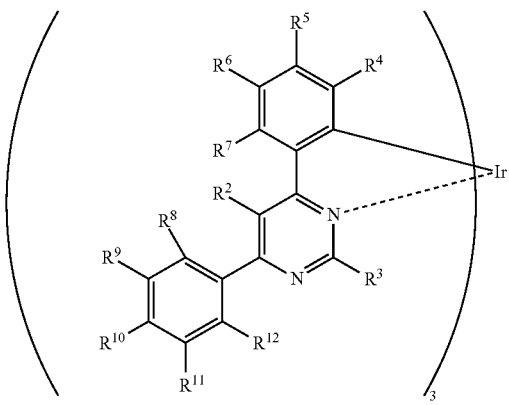

(G9)

wherein $R^4$, $R^5$, $R^6$, $R^7$, $R^8$, $R^9$, $R^{11}$, and $R^{12}$ individually represent any of hydrogen, an alkyl group having 1 to 4 carbon atoms, an alkoxy group having 1 to 4 carbon atoms, an alkylthio group having 1 to 4 carbon atoms, halogen, a haloalkyl group having 1 to 4 carbon atoms, and a substituted or unsubstituted aryl group having 6 to 10 carbon atoms, and wherein the substituted aryl group having 6 to 10 carbon atoms is substituted by one or more alkyl groups each having 1 to 4 carbon atoms, one or more alkoxy groups each having 1 to 4 carbon atoms, one or more alkylthio groups each having 1 to 4 carbon atoms, one or more aryl groups each having 6 to 10 carbon atoms, one or more halogen groups, or one or more haloalkyl groups each having 1 to 4 carbon atoms.

16. A light-emitting device comprising the light-emitting element according to claim 13.

17. An electronic device comprising the light-emitting device according to claim 16 in a display portion.

18. A lighting device comprising the light-emitting device according to claim 16 in a light-emitting portion.

* * * * *

UNITED STATES PATENT AND TRADEMARK OFFICE
CERTIFICATE OF CORRECTION

| | |
|---|---|
| PATENT NO. | : 9,184,398 B2 |
| APPLICATION NO. | : 14/584362 |
| DATED | : November 10, 2015 |
| INVENTOR(S) | : Hideko Inoue et al. |

It is certified that error appears in the above-identified patent and that said Letters Patent is hereby corrected as shown below:

In the Specification:

Column 4, Line 58; Change "formula represents" to --formula, L represents--.

Column 11, Line 16; Change "voltage vs luminance" to --voltage vs. luminance--.

Column 12, Line 15; Change "voltage vs luminance" to --voltage vs. luminance--.

Column 14, Line 51; Change "test-butoxy" to --tert-butoxy--.

Column 22, Line 32; Change "arylpyrimidine, derivative" to --arylpyrimidine derivative--.

Column 23, Line 18; Change "Binuclear" to --dinuclear--.

Column 24, Line 43; Change "(i.e., R')" to --(i.e., $R^1$)--.

Column 27, Line 38; Change "formula" to --formulas--.

Column 53, Line 3; Change "anthrylphenyl]" to --anthryl)phenyl]--.

Column 53, Line 10; Change "(4-phenylphenyflanthracene" to --(4-phenylphenyl)anthracene--.

Column 60, Line 4; Change "partition. 404 having, the" to --partition 404 having the--.

Column 62, Line 20; Change "3 μn)" to --3 μm)--.

Column 71, Line 14; Change "complex. [Ir" to --complex [Ir--.

Column 73, Line 14; Change "name. tris[" to --name: tris[--.

Column 73, Line 42; Change "distilled of and" to --distilled off and--.

Column 80, Line 4; Change "found" to --formed--.

Column 83, Line 26; Change "fainted" to --formed--.

Column 86, Line 14; Change "foamed" to --formed--.

Column 88, Line 25; Change "[2,4-pentanedionato" to --(2,4-pentanedionato--.

Column 88, Line 26; Change "(I II)" to --(III)--.

Column 89, Line 35; Change "[h(tBuppm)$_2$Cl]$_2$" to --[Ir(tBuppm)$_2$Cl]$_2$--.

Signed and Sealed this
Twenty-sixth Day of April, 2016

Michelle K. Lee
*Director of the United States Patent and Trademark Office*

CERTIFICATE OF CORRECTION (continued)
U.S. Pat. No. 9,184,398 B2

In the Specification:

Column 91, Line 14; Change "[ft(tBuppm)$_2$(acac)]" to --[Ir(tBuppm)$_2$(acac)]--.

Column 92, Line 59; Change "Ruined" to --formed--.

Column 96, Line 43; Change "1e Pa, and" to --10$^{-4}$ Pa, and--.

Column 96, Line 65; Change "dia mine" to --diamine--.

Column 97, Line 23; Change "[ft(dpppm)$_2$" to --[Ir(dpppm)$_2$--.

Column 100, Line 41; Change "phe nyl" to --phenyl--.

Column 101, Line 65; Change "δ (CDC1$_3$):" to --δ (CDC1$_3$):--.

Column 104, Line 60; Change "(ftCl$_3$·H$_2$O)" to --(IrCl$_3$·H$_2$O)--.

Column 112, Line 62; Change "4-yl-KC}" to --4-yl-$k$C}--.

Column 112, Lines 62-63; Change "pentanedi onato" to --pentanedionato--.

Column 123, Line 43; Change "scheme (1-1) of" to --scheme (I-1) of--.

Column 124, Line 14; Change "scheme (1-2)" to --scheme (I-2)--.

Column 124, Line 67; Change "scheme (1-3)" to --scheme (I-3)--.

Column 128, Line 13; Change "(F5920," to --(FS920,--.

Column 131, Line 3; Change "(dpm)]" to --(dpm)])--.

Column 132, Line 9; Change "(s, 11-1)," to --(s, 1H),--.

Column 133, Line 13; Change "[ft(5md-" to --[Ir(5md- --.

Column 135, Line 22; Change "(6.081 mmol/L)" to --(0.081 mmol/L)--.

Column 144, Line 2; Change "pyrimi dinyl" to --pyrimidinyl--.

Column 147, Line 3; Change "iridi um" to --iridium--.

Column 150, Line 25; Change "to for a" to --to form a--.

Column 153, Line 17; Change "40 nm" to --40 nm.--.

Column 153, Line 26; Change "foliated." to --formed.--.

Column 157, Line 43; Change "[ft(mppm)$_3$])." to --[Ir(mppm)$_3$]).--.

Column 157, Line 44; Change "40 nm" to --40 nm.--.

Column 159, Line 38; Change "[ft(5mdppm)$_2$" to --[Ir(5mdppm)$_2$--.

Column 160, Line 11; Change "CIF, chromaticity" to --CIF chromaticity--.

Column 162, Line 7; Change "[ft(5md-" to --[Ir(5md- --.

Column 167, Line 23; Change "(1 m/W)," to --(1m/W),--.

Column 168, Line 60; Change "iridi um" to --iridium--.

Column 169, Line 23; Change "voltage vs luminance" to --voltage vs. luminance--.

Column 174, Line 64; Change "1,6-dia" to --1,6-dia- --.

Column 176, Line 23; Change "dia mine" to --diamine--.

CERTIFICATE OF CORRECTION (continued)
U.S. Pat. No. 9,184,398 B2

In the Specification:

Column 177, Line 40; Change "dia mine" to --diamine--.

In the Claims:

Column 179, Line 4, Claim 1; Change "1to 4" to --1 to 4--.
Column 179, Line 44, Claim 2; Change "groups having" to --groups each having--.
Column 182, Line 22, Claim 7; Change "1to 4" to --1 to 4--.
Column 183, Line 29, Claim 9; Change "10carbon" to --10 carbon--.
Column 185, Line 20, Claim 15; Change "$R^9$, $R^{11}$, and $R^{12}$" to --$R^9$, $R^{10}$, $R^{11}$, and $R^{12}$--.